(12) United States Patent
Jang et al.

(10) Patent No.: US 10,629,819 B2
(45) Date of Patent: Apr. 21, 2020

(54) COMPOUND FOR ORGANIC ELECTRONIC ELEMENT, ORGANIC ELECTRICAL ELEMENT USING COMPOUND, AND ELECTRONIC DEVICE COMPRISING SAME

(71) Applicant: DUK SAN NEOLUX CO., LTD, Cheonan-si, Chungcheongnam-do (KR)

(72) Inventors: Jae Wan Jang, Cheonan-si (KR); Ho Young Jung, Cheonan-si (KR); Seul-gi Kim, Daejeon (KR); Won Sam Kim, Hwaseong-si (KR); Ji Hun Byun, Cheonan-si (KR); Jung Hwan Park, Hwaseong-si (KR); Sun Phil Hwang, Ansan-si (KR)

(73) Assignee: Duk San Neolux Co., Ltd, Cheonan-si (KR)

( * ) Notice: Subject to any disclaimer, the term of this patent is extended or adjusted under 35 U.S.C. 154(b) by 0 days.

(21) Appl. No.: 16/207,558

(22) Filed: Dec. 3, 2018

(65) Prior Publication Data
US 2019/0103561 A1 Apr. 4, 2019

Related U.S. Application Data

(63) Continuation of application No. 15/507,036, filed as application No. PCT/KR2015/008443 on Aug. 12, 2015.

(30) Foreign Application Priority Data

Aug. 29, 2014 (KR) .................. 10-2014-0114083

(51) Int. Cl.
| | |
|---|---|
| *H01L 51/54* | (2006.01) |
| *C09K 11/06* | (2006.01) |
| *H01L 51/00* | (2006.01) |
| *H01L 51/50* | (2006.01) |
| *H05B 33/20* | (2006.01) |
| *C07B 59/00* | (2006.01) |
| *C07D 495/14* | (2006.01) |
| *C07D 495/22* | (2006.01) |
| *C07D 519/00* | (2006.01) |

(52) U.S. Cl.
CPC ........ *H01L 51/0071* (2013.01); *C07B 59/002* (2013.01); *C07D 495/14* (2013.01); *C07D 495/22* (2013.01); *C07D 519/00* (2013.01); *C09K 11/06* (2013.01); *H01L 51/0058* (2013.01); *H01L 51/0067* (2013.01); *H01L 51/0072* (2013.01); *H01L 51/0073* (2013.01); *H01L 51/0074* (2013.01); *H01L 51/50* (2013.01); *H05B 33/20* (2013.01); *C07B 2200/05* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0052* (2013.01); *H01L 51/0081* (2013.01); *H01L 51/0085* (2013.01); *H01L 51/5016* (2013.01); *Y02E 10/549* (2013.01)

(58) Field of Classification Search
CPC . C09K 11/06; C09K 2211/00; C09K 2211/10; C09K 2211/1007; C09K 2211/1011; C09K 2211/1092; C09K 2211/1029; C09K 2211/1044; C09K 2211/1088; C09K 2211/1059; C07B 2200/05; C07B 59/002; C07D 495/14; C07D 495/22; C07D 519/00; H01L 51/0032; H01L 51/005; H01L 51/0052; H01L 51/0058; H01L 51/0067; H01L 51/0071; H01L 51/0072; H01L 51/0073; H01L 51/0074; H01L 51/50; H01L 51/5012; H01L 51/5016
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | |
|---|---|---|
| 8,334,058 B2 | 12/2012 | Heil et al. |
| 8,507,904 B2 | 8/2013 | Kim et al. |
| 9,017,828 B2 | 4/2015 | Kim et al. |
| 9,079,920 B2 | 7/2015 | Park et al. |
| 9,290,513 B2 | 3/2016 | Park et al. |
| 2012/0168734 A1 | 7/2012 | Park et al. |
| 2013/0334518 A1 | 12/2013 | Park et al. |
| 2014/0027747 A1 | 1/2014 | Mun et al. |
| 2014/0225046 A1 | 8/2014 | Jatsch et al. |
| 2014/0326987 A1 | 11/2014 | Park et al. |

(Continued)

FOREIGN PATENT DOCUMENTS

| | | |
|---|---|---|
| JP | 2010230312 A | 10/2010 |
| KR | 10-2007-0765078 | 10/2007 |

(Continued)

OTHER PUBLICATIONS

Machine translation of KR2011-0066766. (Year: 2011).*

(Continued)

*Primary Examiner* — Andrew K Bohaty
(74) *Attorney, Agent, or Firm* — Harness, Dickey & Pierce, P.L.C.

(57) ABSTRACT

The objective of the present invention is to provide: a compound capable of ensuring high light-emitting efficiency and low driving voltage of an element, and increasing the lifespan thereof; an organic electrical element using compound; and an electronic device comprising the same.

8 Claims, 1 Drawing Sheet

(56) References Cited

U.S. PATENT DOCUMENTS

| | | | |
|---|---|---|---|
| 2015/0228909 A1 | 8/2015 | Kim et al. | |
| 2015/0307514 A1 | 10/2015 | Park et al. | |
| 2016/0005981 A1 | 1/2016 | Kim et al. | |

FOREIGN PATENT DOCUMENTS

| | | | | |
|---|---|---|---|---|
| KR | 10-2008-0813385 | | 3/2008 | |
| KR | 10-2010-0938796 | | 1/2010 | |
| KR | 10-2011-0016288 A | | 2/2011 | |
| KR | 20110066766 A | * | 6/2011 | |
| KR | 10-2012-1108398 | | 1/2012 | |
| KR | 10-2012-1108512 | | 1/2012 | |
| KR | 10-2011-0043439 | | 11/2012 | |
| KR | 10-2014-0009838 A | | 1/2014 | |
| KR | 10-2014-0069199 A | | 6/2014 | |
| KR | 10-2014-1418146 | | 7/2014 | |
| KR | 10-2015-0095186 A | | 8/2015 | |
| KR | 10-2013-0071547 | | 9/2015 | |
| KR | 10-2016-0028737 A | | 3/2016 | |
| KR | 10-2012-0140557 | | 9/2016 | |
| WO | WO-2013041176 A1 | | 3/2013 | |
| WO | WO-2013081315 A1 | | 6/2013 | |

OTHER PUBLICATIONS

International Search Report (in English and Korean) and Written Opinion of the ISA (in Korean) for PCT/KR2015/008443, ISA/KR, Daejeon, dated Jun. 14, 2016.

* cited by examiner

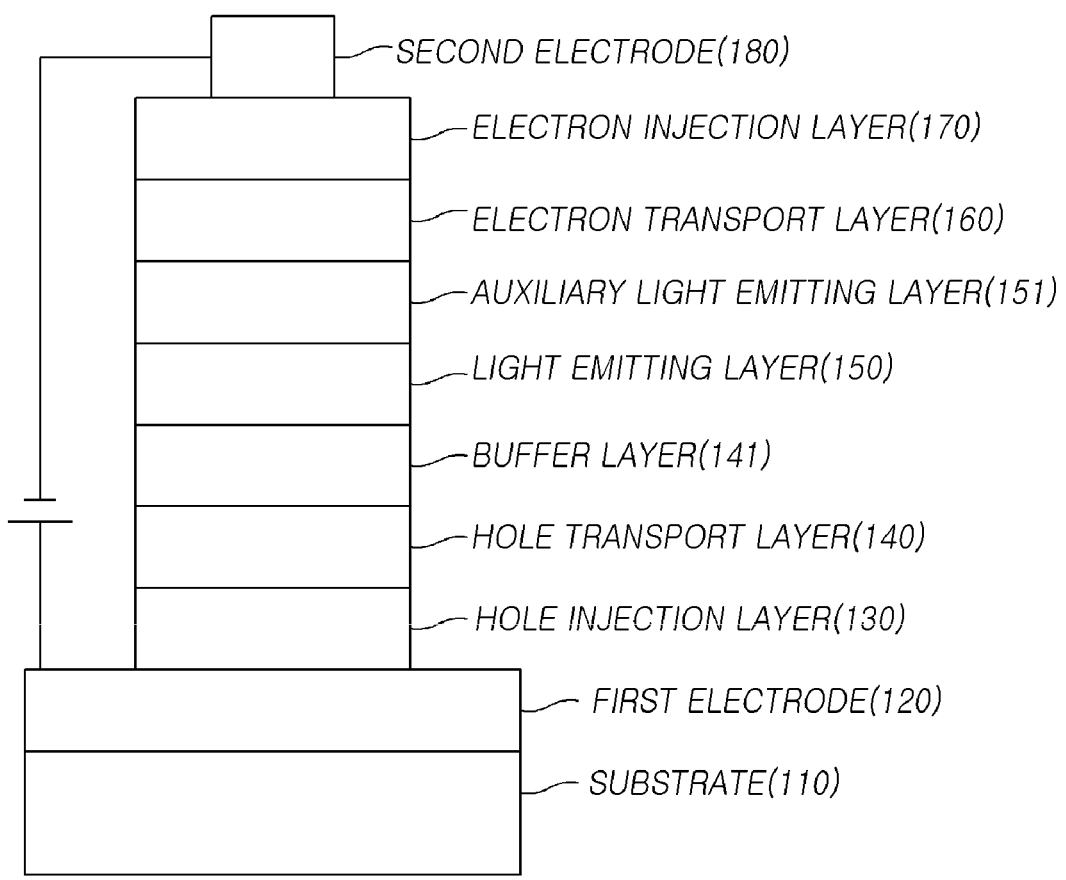

COMPOUND FOR ORGANIC ELECTRONIC ELEMENT, ORGANIC ELECTRICAL ELEMENT USING COMPOUND, AND ELECTRONIC DEVICE COMPRISING SAME

CROSS-REFERENCE TO RELATED APPLICATIONS

This application is a continuation of U.S. patent application Ser. No. 15/507,036 filed on Feb. 27, 2017, which is a U.S. National Phase Application under 35 U.S.C. 371 of International Application No. PCT/KR2015/008443 filed on Aug. 12, 2015 and published in Korean as WO 2016/032150 on Mar. 3, 2016. This application is based on and claims the benefit of priority from Korean Patent Application No. 10-2014-0114083 filed on Aug. 29, 2014. The entire disclosures of all of the above applications are incorporated herein by reference.

TECHNICAL FIELD

The present invention relates to a compound for an organic electronic element, an organic electronic element using the same, and an electronic device comprising the same.

BACKGROUND ART

In general, an organic light emitting phenomenon refers to a phenomenon in which electric energy is converted into light energy of an organic material using an organic material. An organic electronic element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electronic element, and for example, may include a hole injection layer, a hole transport layer, a light emitting layer, an electron transport layer, an electron injection layer, or the like.

A material used as an organic material layer in an organic electronic element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

When only one material is used as a light emitting material, there occur problems of shift of a maximum luminescence wavelength to a longer wavelength due to intermolecular interactions and lowering of the efficiency of a corresponding element due to the deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more and more as the size of display becomes larger and larger in the portable display market. Therefore, the power consumption is a very important factor in the portable display with a limited power source of the battery, and efficiency and lifetime issue also is solved.

Efficiency, lifetime, driving voltage, and the like are correlated with each other. For example, if efficiency is increased, then driving voltage is relatively lowered, and the crystallization of an organic material due to Joule heating generated during operation is reduced as driving voltage is lowered, as a result of which lifetime shows a tendency to increase. However, efficiency cannot be maximized only by simply improving the organic material layer. This is because long lifetime and high efficiency can be simultaneously achieved when an optimal combination of energy levels and T1 values, inherent material properties (mobility, interfacial properties, etc.), and the like among the respective layers included in the organic material layer is given.

That is, in order to allow the organic electronic element to sufficiently exhibit excellent characteristics, most of all, materials constituting an organic material layer in the element, for examples, a hole injection material, a hole transport material, a light emitting material, an electron transport material, an electron injection material, and the like need to be supported by stable and efficient materials, but the development of stable and efficient materials for the organic material layer for an organic electronic element is not sufficiently achieved. Therefore, the development of new materials is continuously required, and especially, the development of an electron transport material and a light emitting material is urgently required.

Polycyclic compounds containing heteroatoms are very different from each other with respect to characteristics resulting from the material structure, and thus are applied, as OLED materials, to various layers.

Especially, such compounds are different from each other with band gaps (HOMO, LUMO), electric characteristics, chemical characteristics, physical properties, and the like, and therefore, the application thereof to various OLED layers has been developed (application to HTL or phosphorescent host: U.S. Pat. No. 8,334,058, KR 1108398; and application to ETL: KR 0813385, KR 0765078). Recently, the development of OLED materials with respect to the kind, number, and position of heteroatoms of pentacyclic compounds have been actively developed (KR 1418146, KR 0938796, KR 2011-0043439, KR2012-0140557, KR 2013-0071547, JP 2010-230312, etc.).

DETAILED DESCRIPTION OF THE INVENTION

Technical Problem

In order to solve the above-mentioned problems occurring in the prior art, an object of the present invention is to provide a compound capable of achieving high luminous efficiency, a low driving voltage, and an improved lifetime of an element, an organic electronic element using the same, and an electronic device comprising the same.

The present company has been developing hepta-cyclic compound-related materials using the characteristics of the polycyclic compounds since 2009 (KR 1108512, U.S. Ser. No. 13/390,043). However, the hepta-cyclic compounds have a relatively low lifetime in spite of favorable efficiency, and thus the application thereof to current OLED panels is very difficult. Therefore, the present invention has a structure with seven rings, which is the same as in KR 1108512, but materials with high-efficiency and long-lifetime have been developed by varying the fused position constituting the penta-cyclic compounds and the kind and arrangement of heteroatoms.

Technical Solution

In accordance with an aspect of the present invention, there is provided a compound represented by the following formula.

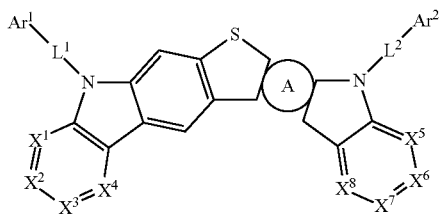

In another aspect of the present invention, there are provided an organic electronic element using the compound represented by the above formula, and an electronic device comprising the same.

Advantageous Effects

The use of the compound according to the present invention can achieve high luminous efficiency and a low driving voltage of an element and significantly improving an improved lifetime of an element.

BRIEF DESCRIPTION OF THE DRAWINGS

The FIGURE illustrates an example of an organic light emitting diode according to the present invention.

MODE FOR CARRYING OUT THE INVENTION

Hereinafter, some embodiments of the present invention will be described in detail with reference to the accompanying illustrative drawings In designation of reference numerals to components in respective drawings, it should be noted that the same elements would be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b), or the like may be used herein when describing components of the present invention. Each of these terminologies is not used to define an essence, order, or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine (F), bromine (Br), chlorine (Cl), and iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl group" or "halogen alkyl group" as used herein means an alkyl group substituted with halogen.

The term "heteroalkyl group" as used herein means an alkyl group of which at least one of carbon atoms is substituted with a hetero atom.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an alkyl group to which oxygen radical is attached, but not limited to, and, unless otherwise stated, has 1 to 60 carbon atoms.

The term "alkenoxyl group", "alkenoxy group", "alkenyloxyl group", or "alkenyloxy group" as used herein means an alkenyl group to which oxygen radical is attached, but not limited to, and, unless otherwise stated, has 2 to 60 carbon atoms.

The term "aryloxyl group" or "aryloxy group" as used herein means an aryl group to which oxygen radical is attached to, but not limited to, and has 6 to 60 carbon atoms.

Unless otherwise stated, the terms "aryl group" and "arylene group" each have 6 to 60 carbon atoms, but not limited thereto. The aryl group or arylene group herein means a monocyclic or polycyclic aromatic group, and includes an aromatic ring that is formed in conjunction with an adjacent substituent linked thereto or participating in the reaction. Examples of the aryl group may include a phenyl group, a biphenylyl group, a terphenylyl group, a naphthyl group, an anthracenyl group, a fluorene group, a spirofluorene group, and a spirobifluorene group.

The prefix "aryl" or "ar" means a radical substituted with an aryl group. For example, an arylalkyl group may be an alkyl group substituted with an aryl group, and an arylalkenyl group may be an alkenyl group substituted with an aryl group, and a radical substituted with an aryl group has a number of carbon atoms defined as herein.

Also, when prefixes are named subsequently, it means that substituents are listed in the order described first. For example, an arylalkoxy group means an alkoxy group substituted with an aryl group, an alkoxylcarbonyl group means a carbonyl group substituted with an alkoxyl group, and an arylcarbonylalkenyl group also means an alkenyl group substituted with an arylcarbonyl group, wherein the arylcarbonyl group may be a carbonyl group substituted with an aryl group.

Unless otherwise stated, the term "heteroalkyl" as used herein means alkyl containing one or more heteroatoms.

Unless otherwise stated, the term "heteroaryl group" or "heteroarylene group" as used herein means, but not limited to, an aryl or arylene group having 2 to 60 carbon atoms and containing one or more heteroatoms, includes at least one of monocyclic and polycyclic rings, and may also be formed in conjunction with an adjacent group.

Unless otherwise stated, the term "heterocyclic group" as used herein contains one or more heteroatoms, has 2 to 60 carbon atoms, includes at least one of homocyclic and heterocyclic rings, and may also be formed in conjunction with an adjacent group.

Unless otherwise stated, the term "heteroatom" as used herein represents N, O, S, P, or Si.

In addition, the "heterocyclic group" also may include a ring containing SO2 instead of carbon forming the ring. For examples, the "heterocyclic group" includes the following compound.

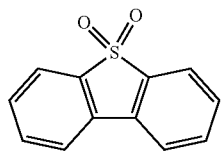 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the formulas used in the present invention are defined as in the index definition of the substituent of the following Formula.

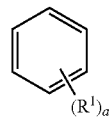

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$'s may be the same and different, and are linked to the benzene ring as follows. When a is an integer of 4 to 6, the substituents $R^1$'s may be the same and different, and are linked to the benzene ring in a similar manner to that when a is an integer of 2 or 3, hydrogen atoms linked to carbon constituents of the benzene ring being not represented as usual.

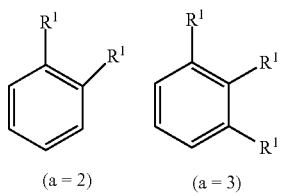

The FIGURE illustrates an organic electronic element according to an embodiment of the present invention.

Referring to the FIGURE, an organic electronic element 100 according to an embodiment of the present invention includes a first electrode 120 formed on a substrate 110, a second electrode 180, and an organic material layer between the first electrode 120 and the second electrode 180, which contains the compound of the present invention. Here, the first electrode 120 may be an anode (positive electrode), and the second electrode 180 may be a cathode (negative electrode). In the case of an inverted organic electronic element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an auxiliary light emitting layer 151, a buffer layer 141, etc., and the electron transport layer 160 and the like may serve as the hole blocking layer.

Although not shown, the organic electronic element according to an embodiment of the present invention may further include a protective layer or a light efficiency improving layer (capping layer) formed on at least one of the sides the first and second electrodes, which is a side opposite to the organic material layer.

The compound of the present invention employed in the organic material layer may be used as a host material, a dopant material, or a light efficiency layer material in the hole injection layer 130, the hole transport layer 140, the electron transport layer 160, the electron injection layer 170, the auxiliary light emitting layer 151, or the light emitting layer 150. Preferably, the compound of the present invention may be used for the hole transport layer 140 and the auxiliary light emitting layer 151.

Since depending on the type and position of a substituent to be attached, a band gap, electrical properties, interfacial properties, and the like may vary even in the same core, it is very important what the types of core and a combination of substituent attached to the core are. Specially, long lifetime and high efficiency can be simultaneously achieved when an optimal combination of energy levels and T1 values, inherent material properties (mobility, interfacial properties, etc.), and the like among the respective layers included in the organic material layer is given.

Accordingly, in the present invention, energy levels and T1 values and inherent material properties (mobility, interfacial properties, etc.), and the like among the respective layers included in the organic material layer are optimized by forming a light emitting layer using the compound represented by formula 1, and thus the lifetime and efficiency of the organic electronic element can be improved at the same time.

An organic light emitting diode according to an embodiment of the present invention may be manufactured using a physical vapor deposition (PVD) method. For example, the organic electronic element may be manufactured by depositing a metal, a metal oxide having conducive, or an alloy thereof, on the substrate to form the anode 120, forming on the organic material layer including the hole injection layer 130, the hole transport layer 140, the auxiliary light emitting layer 151, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electronic element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a color conversion material (CCM) structure in which electroluminescence from a blue (B) organic light emitting layer, and photoluminescence from an inorganic luminescent using the electroluminescence are combined. The present invention is applicable to these WOLEDs.

Further, the organic electronic element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electronic element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

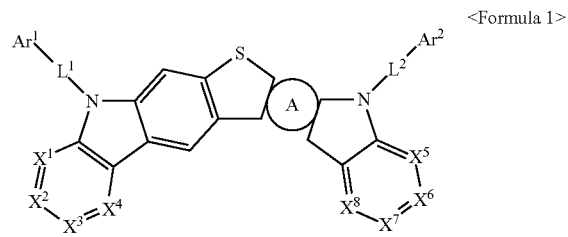

<Formula 1>

In Formula 1, $Ar^1$ and $Ar^2$ each may be independently selected from the group consisting of a $C_6$-$C_{60}$ aryl group, a fluorenyl group, a fused ring group of a $C_3$-$C_{60}$ aliphatic group and a $C_6$-$C_{60}$ aromatic group, a $C_2$-$C_{60}$ heterocyclic group containing at least one heteroatom of O, N, S, Si, and P, a $C_1$-$C_{50}$ alkyl group, and —N(R') (R").

Here, R' and R" each may be independently selected from the group consisting of a $C_6$-$C_{60}$ aryl group, a fluorenyl group, a $C_2$-$C_{60}$ heterocyclic group containing at least one heteroatom of O, N, S, Si, and P, and a $C_1$-$C_{50}$ alkyl group.

$L^1$ and $L^2$ each may be selected from the group consisting of a single bond, a $C_6$-$C_{60}$ arylene group, a fluorenylene group, a $C_2$-$C_{60}$ bivalent heterocyclic group containing at least one heteroatom of O, N, S, Si, and P, a fused ring group of a $C_3$-$C_{60}$ bivalent aliphatic group and a $C_6$-$C_{60}$ bivalent aromatic group, and a bivalent aliphatic hydrocarbon group. Here, each of them (excluding the single bond) may be substituted with at least one substituent selected from the group consisting of deuterium, a nitro group, a nitrile group, a halogen group, a $C_1$-$C_{20}$ alkyl group, a $C_6$-$C_{20}$ aryl group, a $C_2$-$C_{20}$ heterocyclic group, a $C_1$-$C_{20}$ alkoxy group, and an amino group.

$X^1$ to $X^8$ each are independently $CR^1$ or N.

$R^1$ may be selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a fused ring group of a $C_6$-$C_{60}$ aromatic group and a $C_3$-$C_{60}$ aliphatic group, a $C_1$-$C_{50}$ alkyl group, a $C_2$-$C_{20}$ alkenyl group, a $C_1$-$C_{30}$ alkoxy group, and a $C_6$-$C_{30}$ aryloxy group.

Alternatively, in the presence of a plurality of $R^1$'s, the plurality of $R^1$'s may be different from or the same as each other and adjacent $R^1$'s may be linked to each other to form at least one ring (provided that $R^1$ forming no ring is the same as defined in i) above). Here, $R^1$ forming no ring may be the same as defined in above. The ring formed herein may be a $C_3$-$C_{60}$ aliphatic ring or a $C_6$-$C_{60}$ aromatic ring, a $C_2$-$C_{60}$ heterocyclic ring, a $C_3$-$C_{60}$ alicyclic ring, or a fused ring formed of a combination thereof, and may be a saturated or unsaturated ring as well as a monocyclic or polycyclic ring.

For example, when $Ar^1$, $Ar^2$, R', R", $L^1$, $L^2$, and $R^1$ are an aryl group or an arylene group, $Ar^1$, $Ar^2$, R', R", $L^1$, $L^2$, and $R^1$ each are independently a phenyl group or phenylene group, a biphenyl group or biphenyl group, a terphenyl group or terphenylene group, a naphthyl group or naphthylene group, or a phenanthryl group or phenanthrylene group.

Ring A is a $C_6$-$C_{20}$ aromatic group condensed with two adjacent rings (thiophene and pyrrole). Here, the $C_6$-$C_{20}$ aromatic group of ring A may be substituted with at least one group selected from the group consisting of deuterium, halogen, a $C_6$-$C_{60}$ aryl group, a fluorenyl group, a $C_2$-$C_{60}$ heterocyclic group containing at least one heteroatom of O, N, S, Si, and P, a halogen group, a $C_1$-$C_{50}$ alkyl group, a fused ring group of a $C_6$-$C_{60}$ aromatic group and a $C_3$-$C_{60}$ aliphatic group, a $C_2$-$C_{20}$ alkenyl group, a $C_1$-$C_{30}$ alkoxy group, and a $C_6$-$C_{30}$ aryloxy group. In the presence of a plurality of substituents, the plurality of substituents may be different from or the same as each other and adjacent substituents may be linked to each other to form at least one ring. The ring formed herein may be a $C_3$-$C_{60}$ aliphatic ring or a $C_6$-$C_{60}$ aromatic ring, a $C_2$-$C_{60}$ heterocyclic ring, a $C_3$-$C_{60}$ alicyclic ring, or a fused ring formed of a combination thereof, and may be a saturated or unsaturated ring as well as a monocyclic or polycyclic ring.

Here, the $C_6$-$C_{20}$ aromatic group of ring A may be benzene, naphthalene, or phenanthrene, but is not limited thereto.

Specifically, ring A in Formula 1 above may be represented by one of the formulas A1 to A6 below.

A1

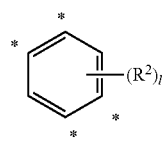

A2

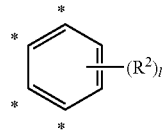

A3

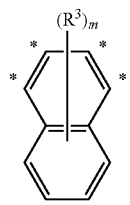

A4

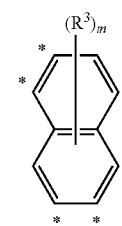

A5

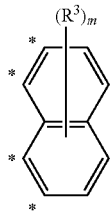

A6

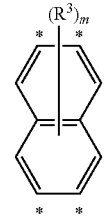

In A1 to A6, *'s are binding positions at which any one side of each of rings (thiophene and pyrrole) adjacent to ring A is shared and condensed.

Here, l is an integer of 0 to 2, and m is an integer of 0 to 4.

$R^2$ and $R^2$ may be selected from the group consisting of deuterium, halogen, a $C_6$-$C_{60}$ aryl group, a fluorenyl group, a $C_2$-$C_{60}$ heterocyclic group containing at least one heteroatom of O, N, S, Si, and P, a halogen group, a $C_1$~$C_{50}$ alkyl group, a fused ring group of a $C_6$-$C_{60}$ aromatic group and a $C_3$-$C_{60}$ aliphatic group, a $C_2$-$C_{20}$ alkenyl group, a $C_1$-$C_{30}$ alkoxy group, and a $C_6$-$C_{30}$ aryloxy group.

Alternatively, in the presence of a plurality of $R^2$'s and $R^3$'s, the plurality of $R^2$'s or $R^3$'s are different from or the same as each other and adjacent $R^2$'s or $R^3$'s may be linked to each other to form at least one ring. Here, $R^2$ and $R^3$ forming no ring each may be the same as defined above. The ring formed herein may be a $C_3$-$C_{60}$ aliphatic ring or a $C_6$-$C_{60}$ aromatic ring, a $C_2$-$C_{60}$ hetero ring, a $C_3$-$C_{60}$ alicyclic ring, or a fused ring formed of a combination thereof, and may be a saturated or unsaturated ring as well as a monocyclic or polycyclic ring.

Specifically, the compound represented by Formula 1 above may be represented by one of the formulas below.

<Formula 2>

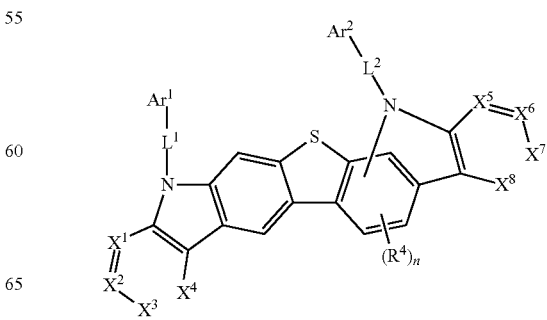

-continued

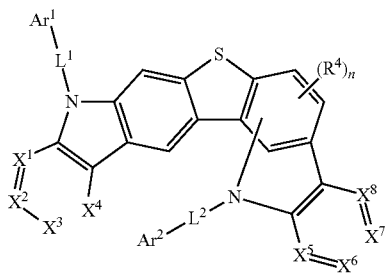
<Formula 3>

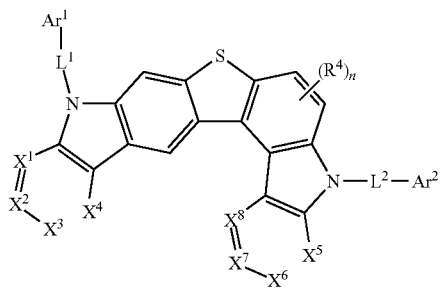
<Formula 4>

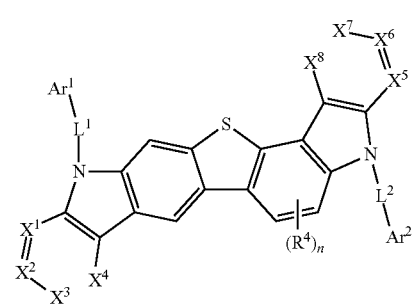
<Formula 5>

In Formula 2 to 5, $X^1$ to $X^8$, $Ar^1$, $Ar^2$, $L^1$, and $L^2$ each may be the same as defined in Formula 1 above.

Here, m is an integer of 0 to 2.

$R^4$ may be selected from the group consisting of deuterium, halogen, a $C_6$-$C_{60}$ aryl group, a fluorenyl group, a $C_2$-$C_{60}$ heterocyclic group containing at least one heteroatom of O, N, S, Si, and P, a halogen group, a $C_1$-$C_{50}$ alkyl group, a fused ring group of a $C_6$-$C_{60}$ aromatic group and a $C_3$-$C_{60}$ aliphatic group, a $C_2$-$C_{20}$ alkenyl group, a $C_1$-$C_{30}$ alkoxy group, and a $C_6$-$C_{30}$ aryloxy group.

Alternatively, in the presence of a plurality of $R^4$'s, the plurality of $R^4$'s each may be different from or the same as each other and adjacent $R^4$'s may be linked to each other to form at least one ring. Here, $R^4$ forming no ring each may be the same as defined above. The ring formed herein may be a $C_3$-$C_{60}$ aliphatic ring group or a $C_6$-$C_{60}$ aromatic ring, a $C_2$-$C_{60}$ heterocyclic ring, a $C_3$-$C_{60}$ alicyclic group, or a fused ring formed of a combination thereof, and may be a saturated or unsaturated ring as well as a monocyclic or polycyclic ring.

In formulas 1 to 5, the aryl group, fluorenyl group, heterocyclic group, fused ring group, alkyl group, alkenyl group, alkoxy group, and aryloxy group each may be substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, a $C_8$-$C_{20}$ arylalkenyl group, and —N($R^a$)($R^b$).

$R^a$ and $R^b$ each may be independently selected from the group consisting of a $C_6$-$C_{60}$ aryl group, a fluorenyl group, a $C_2$-$C_{60}$ heterocyclic group containing at least one heteroatom of O, N, S, Si, and P, and a $C_1$-$C_{50}$ alkyl group.

Here, the aryl group may be an aryl group having 6-60 carbon atoms, preferably 6-40 carbon atoms, and more preferably 6-30 carbon atoms;

the heterocyclic group may be a heterocyclic group having 2-60 carbon atoms, preferably 2-30 carbon atoms, and more preferably 2-20 carbon atoms; and the alkyl group may be an alkyl group having 1-50 carbon atoms, preferably 1-30 carbon atoms, more preferably 1-20 carbon atoms, and especially preferably 1-10 carbon atoms.

Specifically, the compound represented by Formula 1 above may be represented by one of the formulas below.

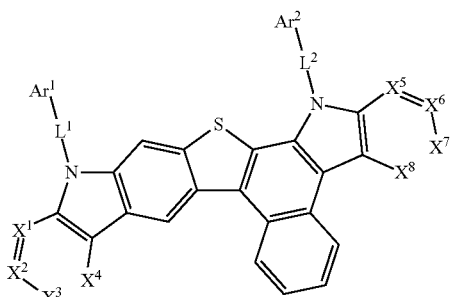
<Formula 6>

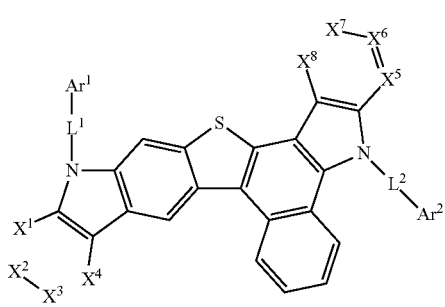
<Formula 7>

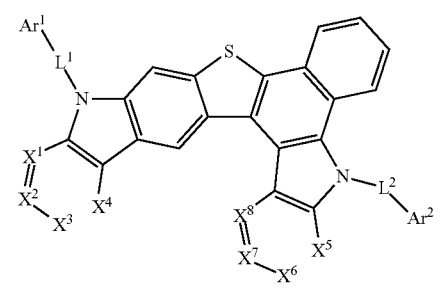
<Formula 8>

-continued
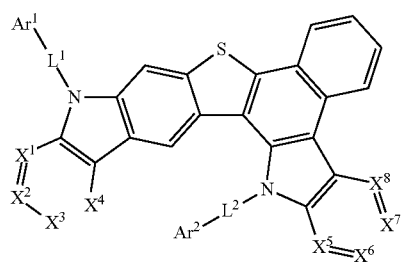
<Formula 9>
In Formula 6 to 9,
$X^1$ to $X^8$, $Ar^1$, $Ar^2$, $L^1$, and $L^2$ may be the same as $X^1$ to $X^8$, $Ar^1$, $Ar^2$, $L^1$, and $L^2$ defined in Formula 1 above.
More specifically, the compounds represented by Formulas 1 to 9 may be one of the following compounds.
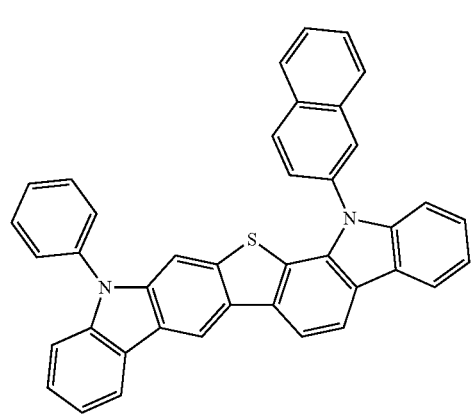
P-1
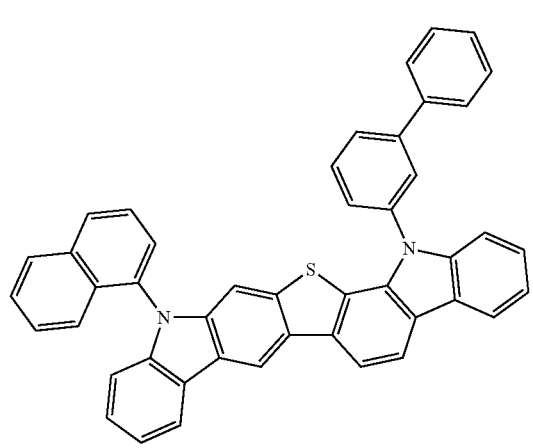
P-2
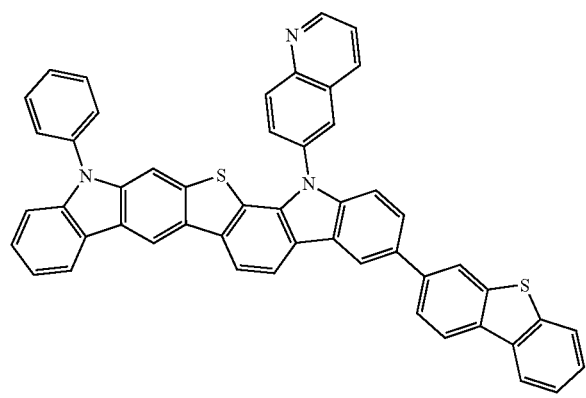
P-3
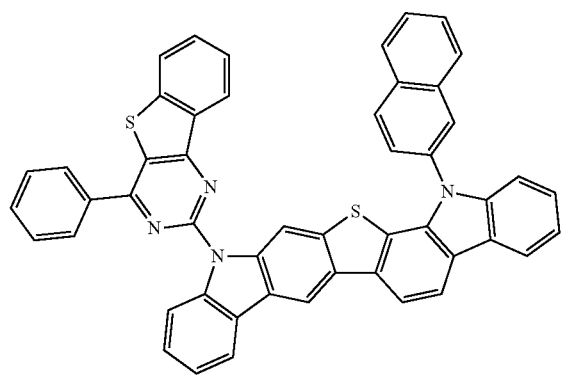
P-4

-continued
P-5
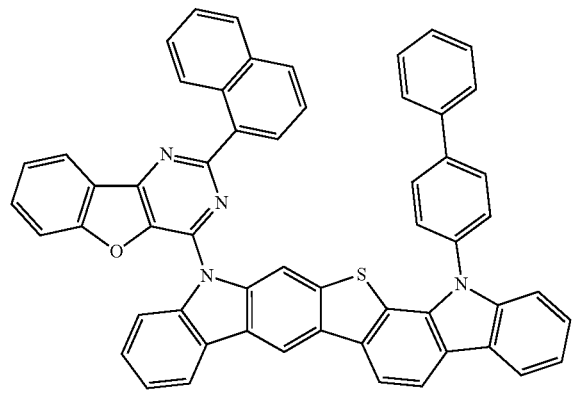
P-6
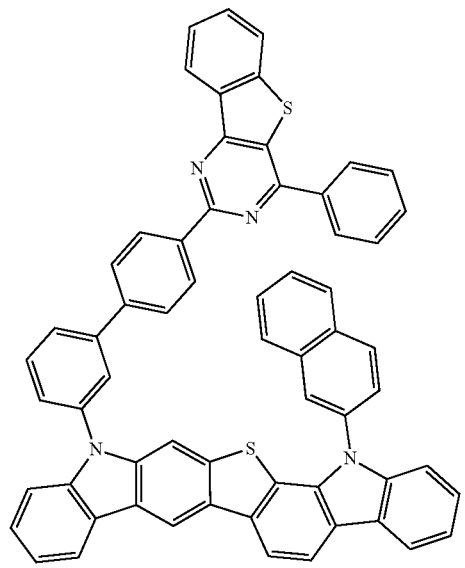
P-7
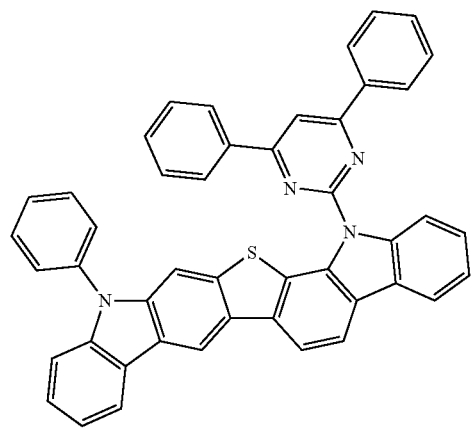
P-8
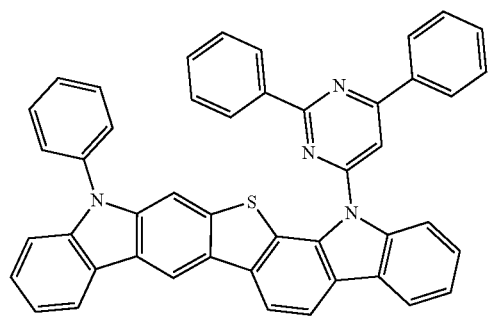
P-9
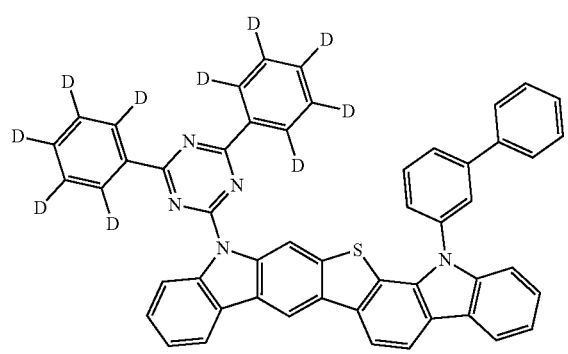
P-10
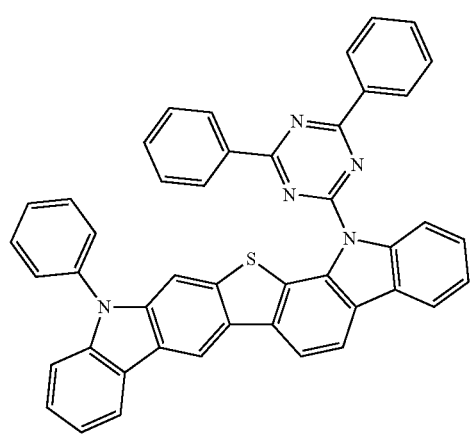

-continued
P-11
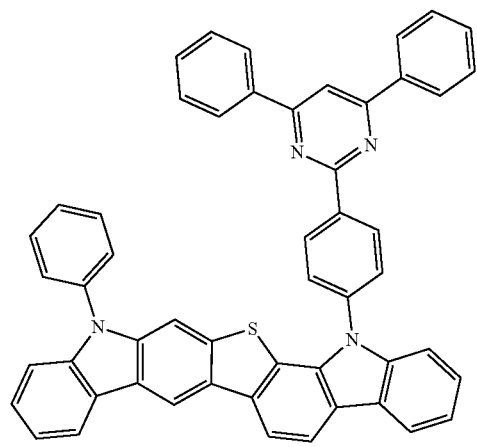
P-12
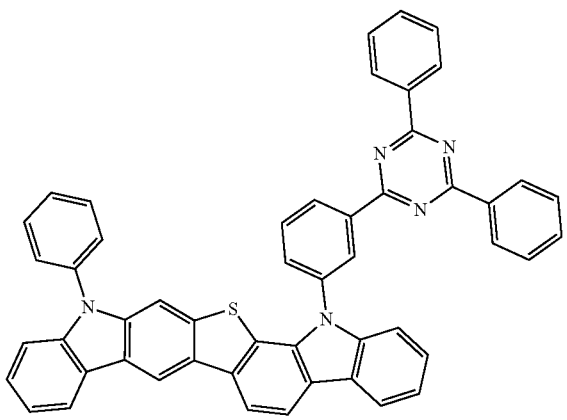
P-13
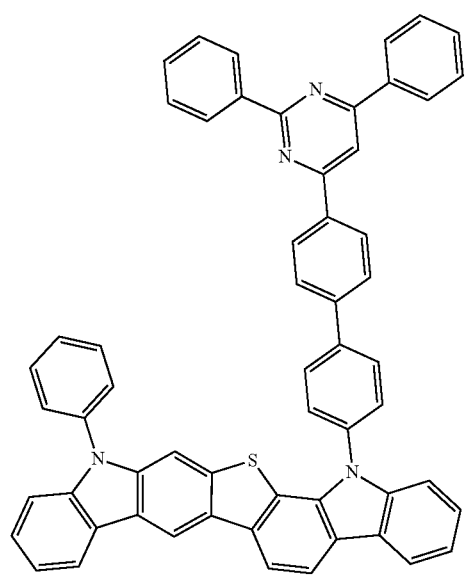
P-14
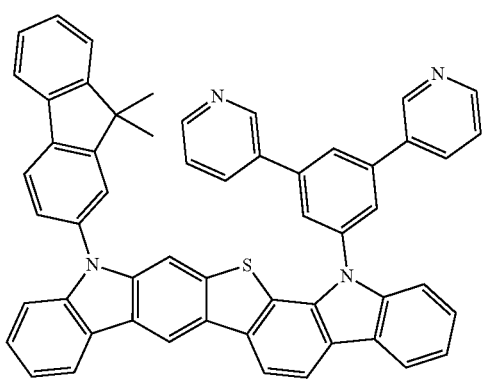
P-15
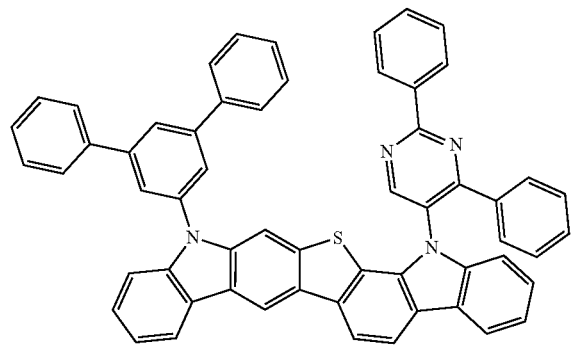
P-16
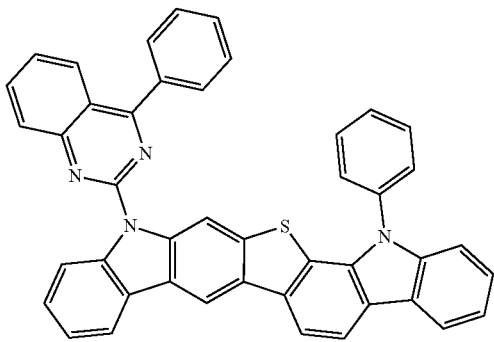

-continued
P-17
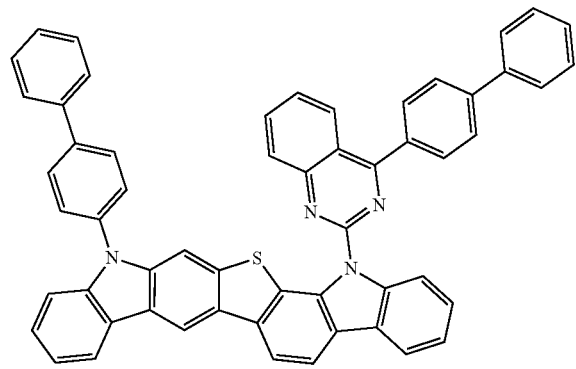
P-18
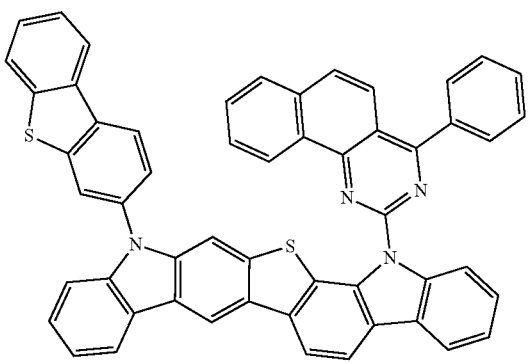
P-19
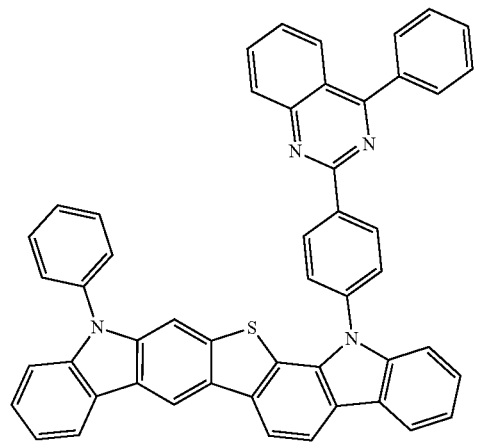
P-20
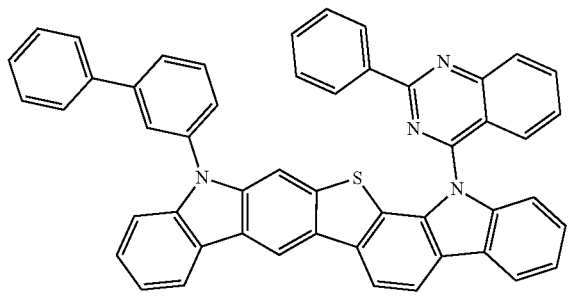
P-21
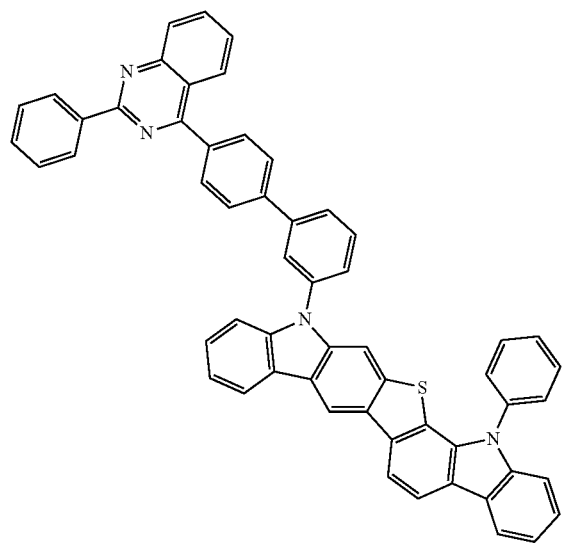
P-22
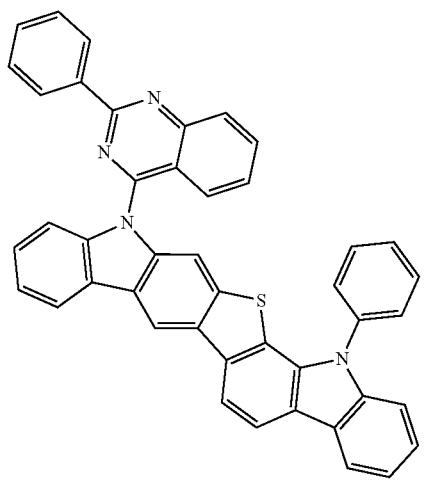

-continued
P-23
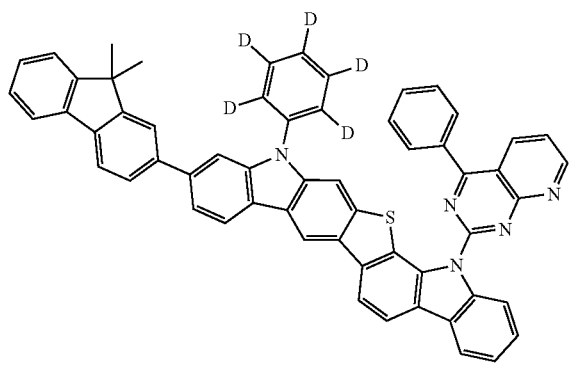
P-24
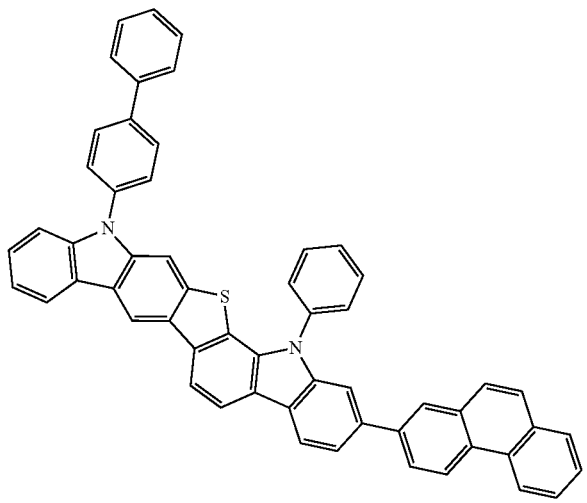
P-25
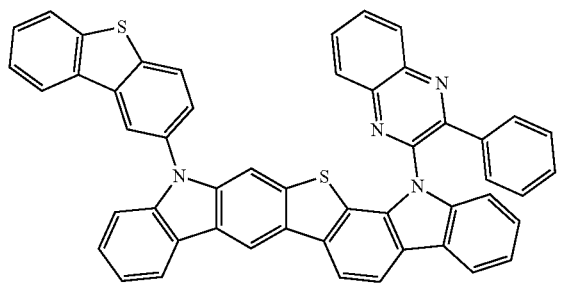
P-26
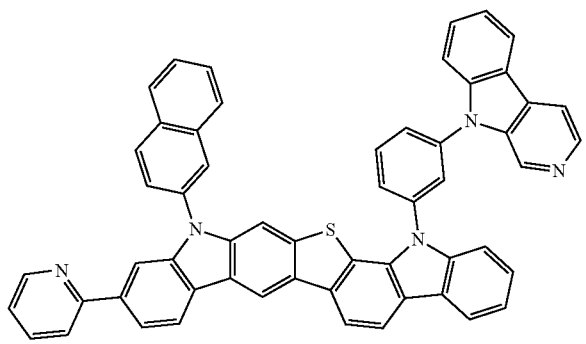
P-27
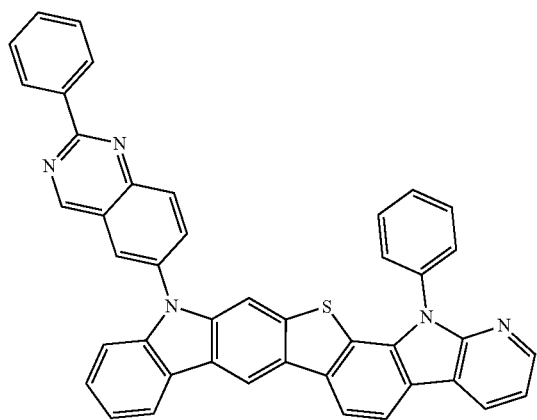
P-28
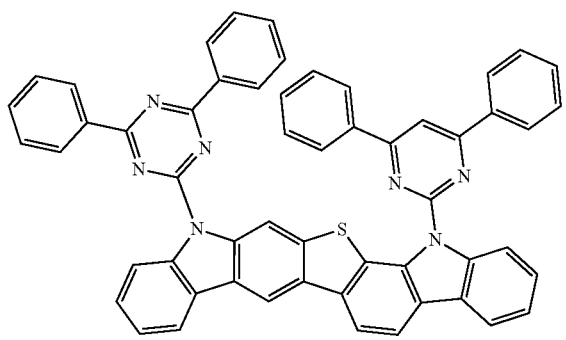

-continued
P-29
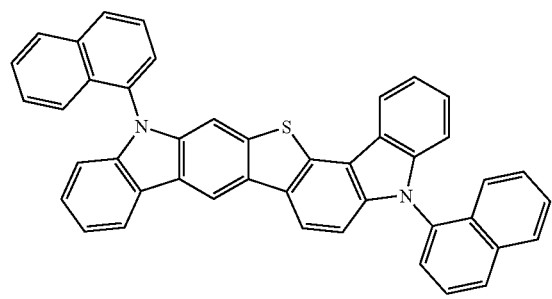
P-30
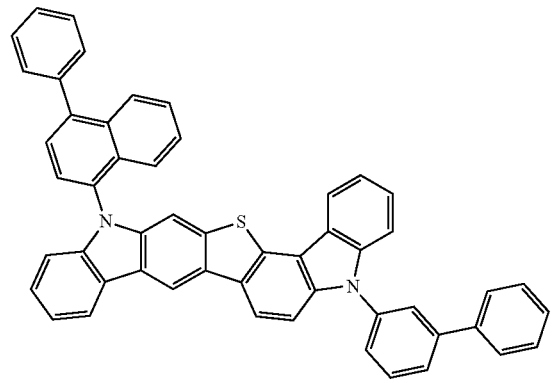
P-31
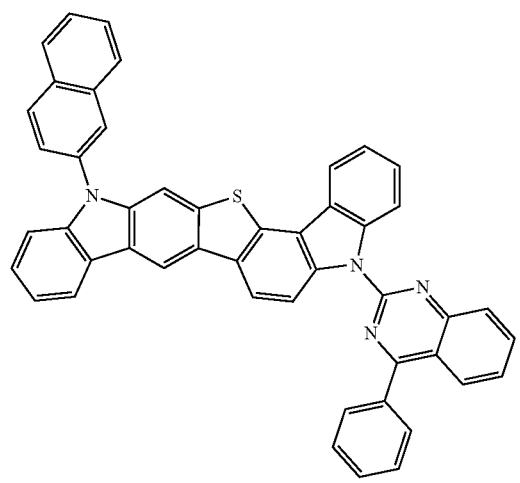
P-32
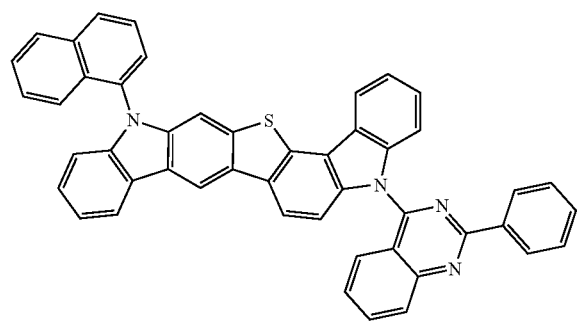
P-33
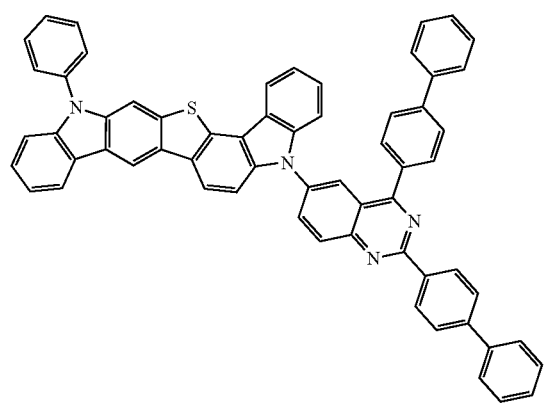
P-34
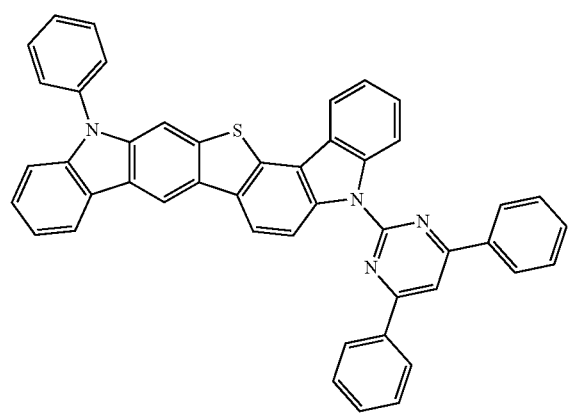

-continued
P-35
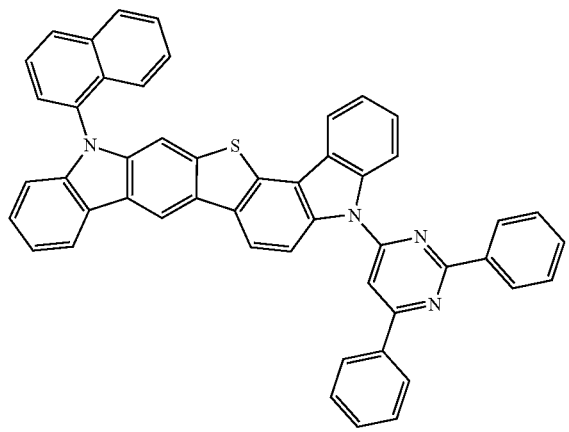
P-36
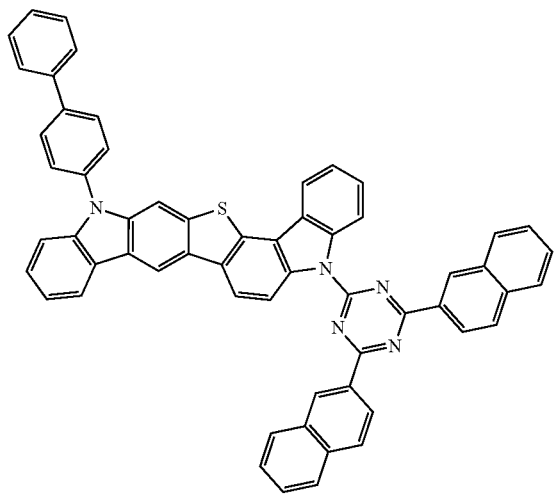
P-37
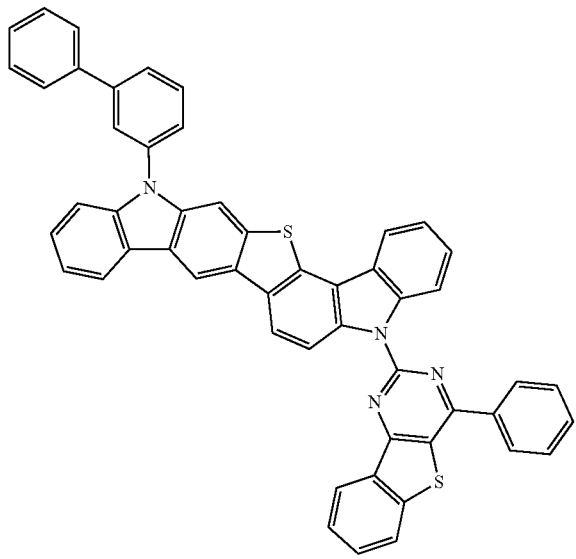
P-38
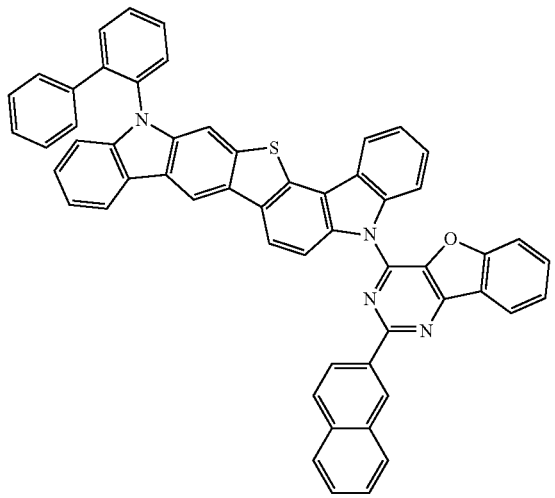
P-39
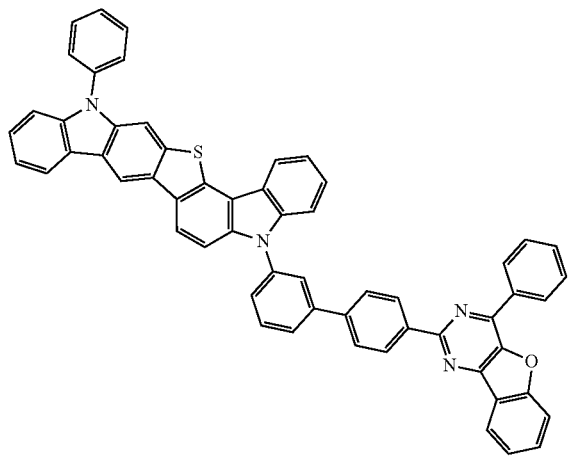
P-40
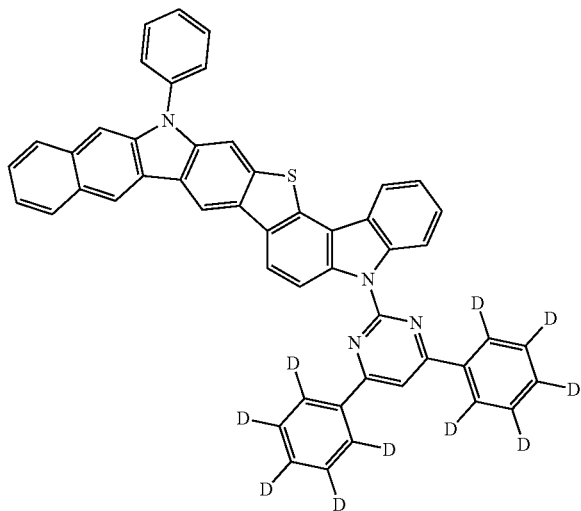

P-41
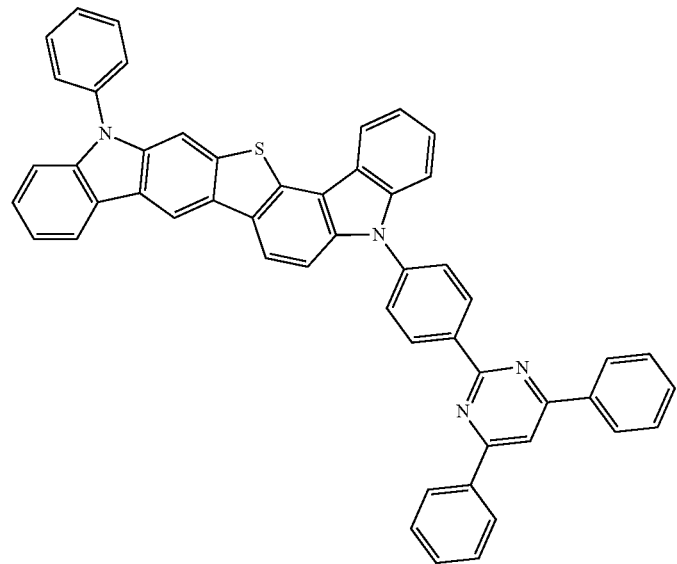
P-42
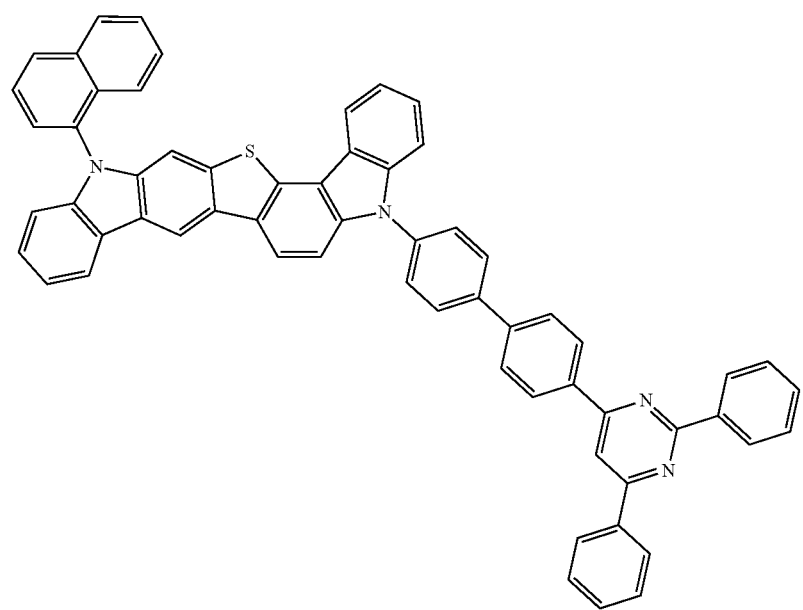

-continued
P-43
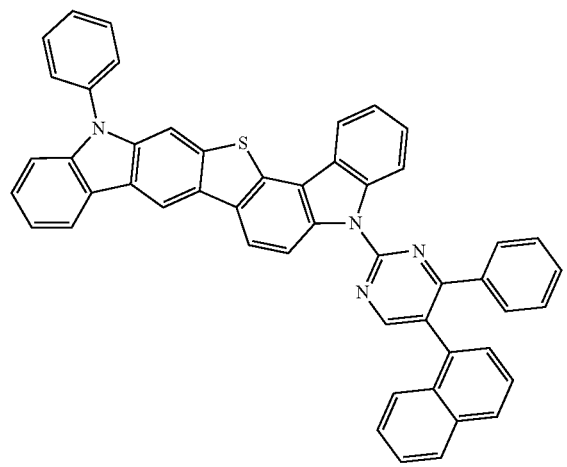
P-44
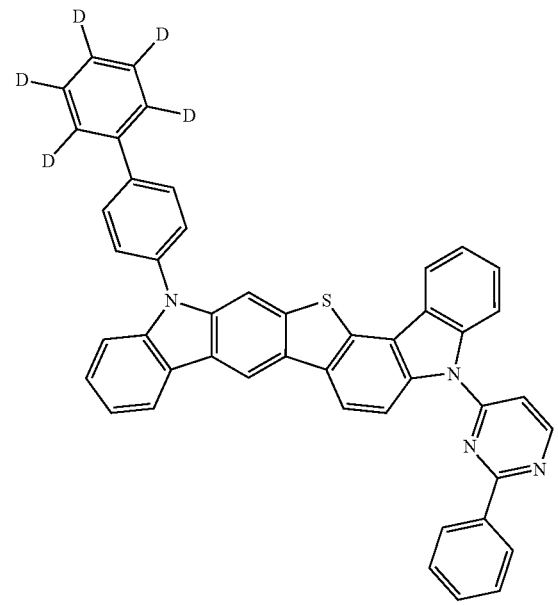
P-45
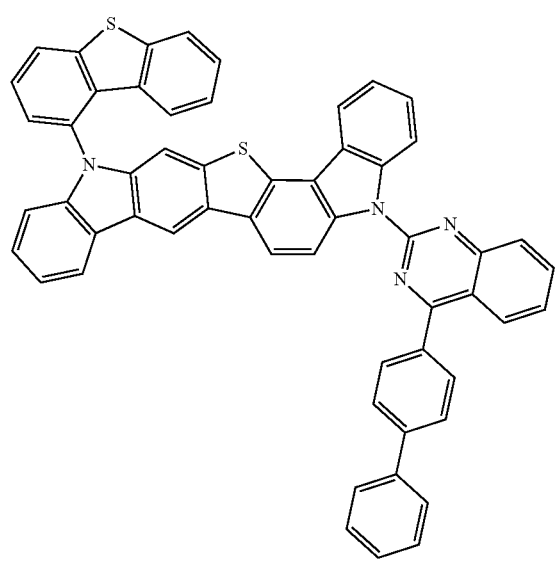
P-46
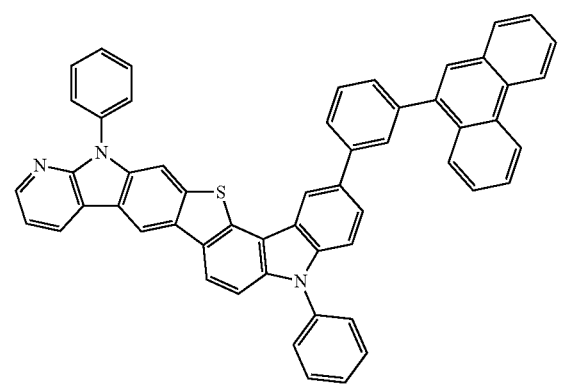

-continued
P-47
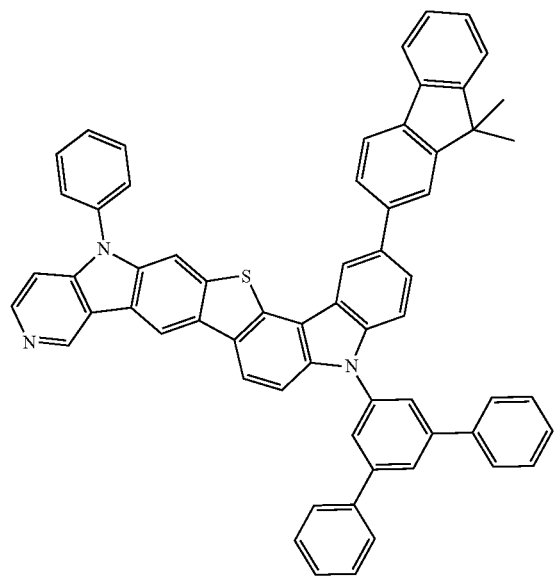
P-48
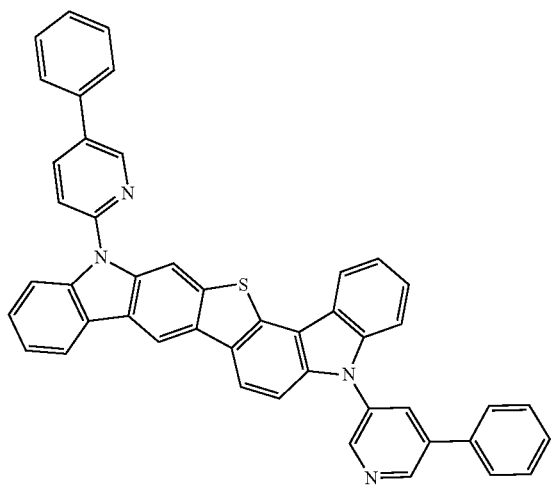
P-49
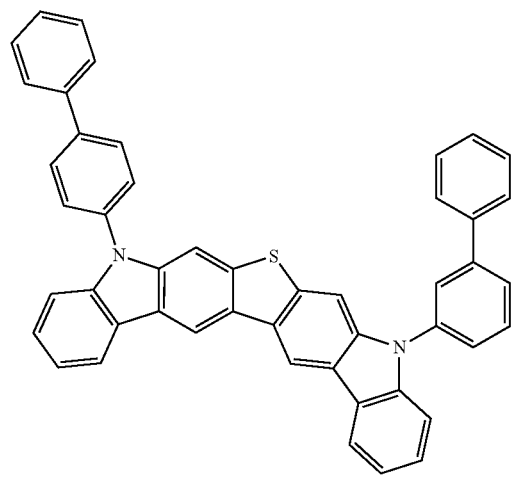
P-50
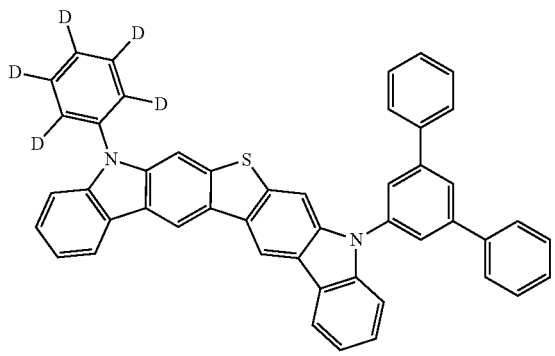
P-51
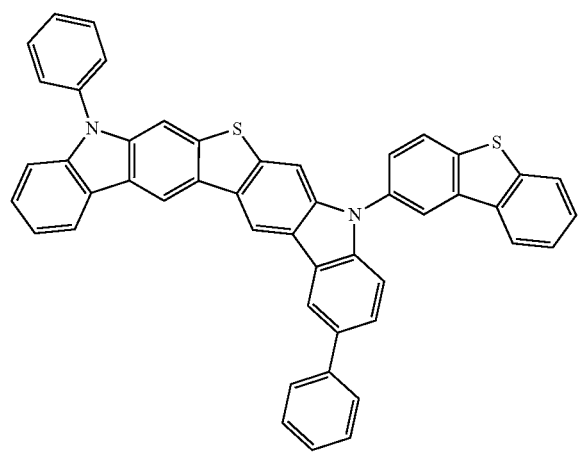
P-52
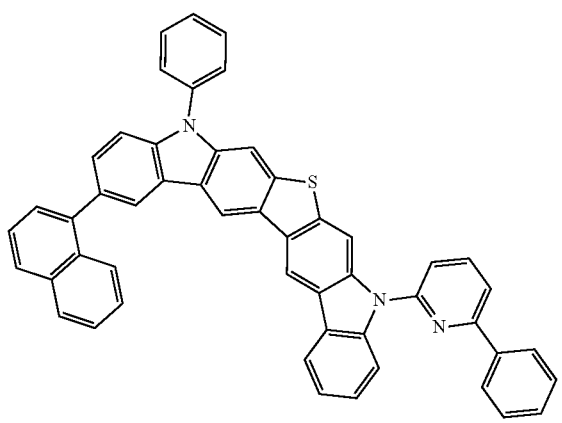

P-53
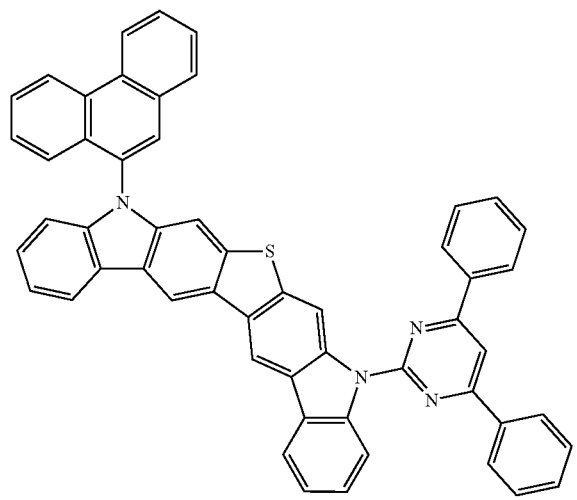
P-54
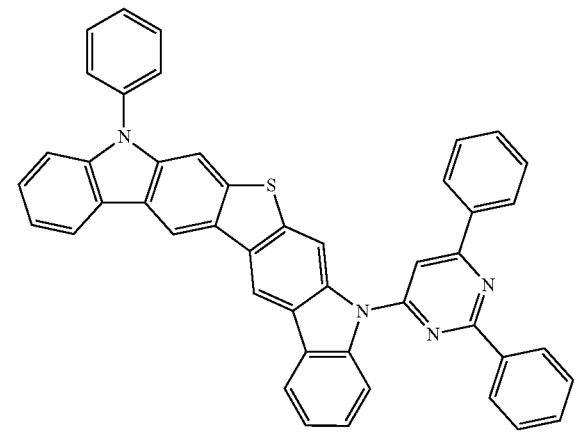
P-55
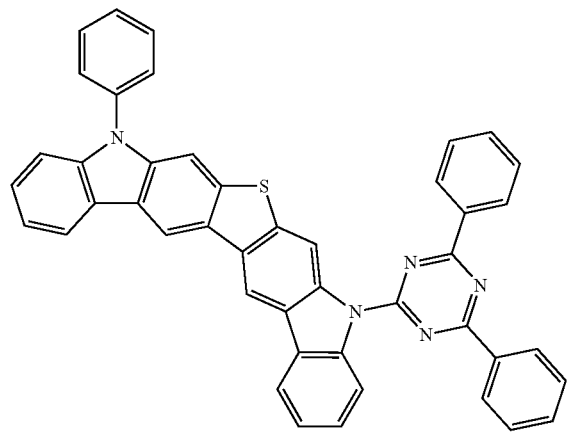
P-56
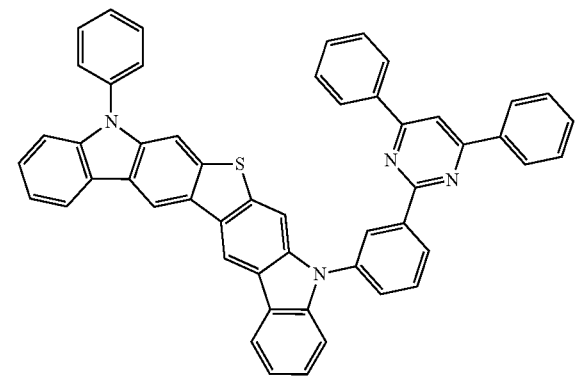
P-57
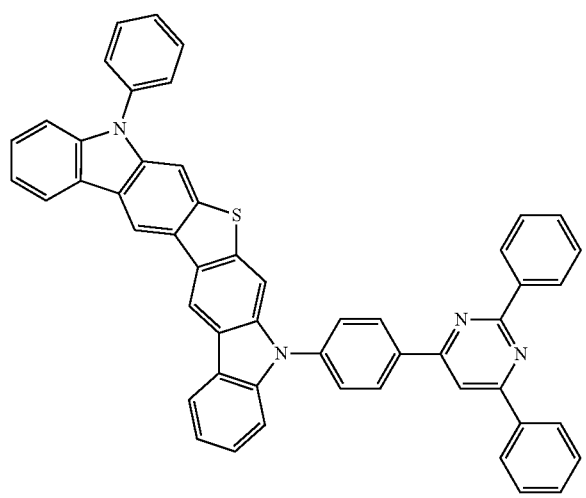
P-58
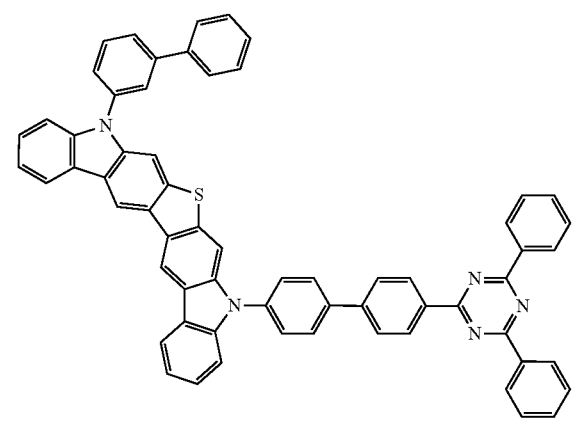

-continued
P-59
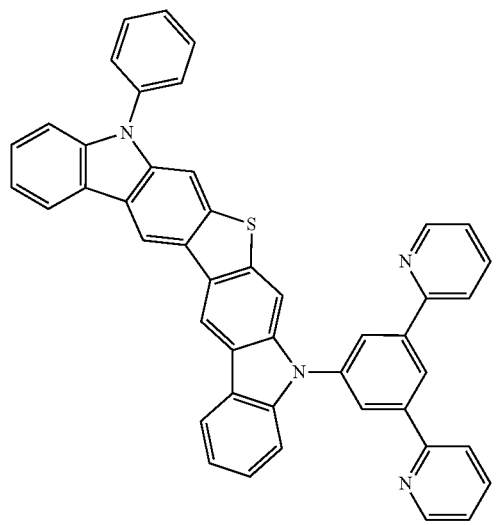
P-60
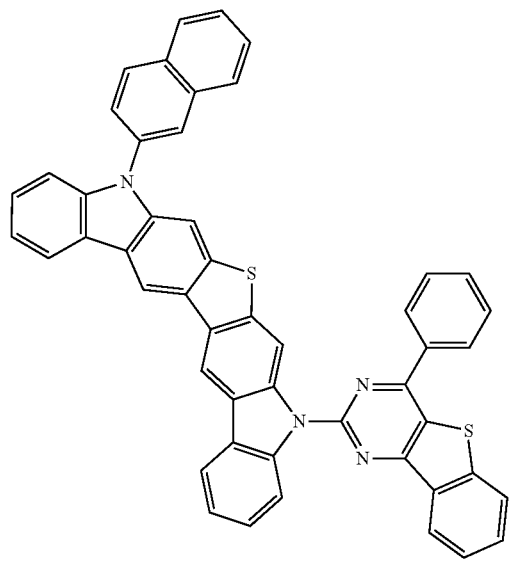
P-61
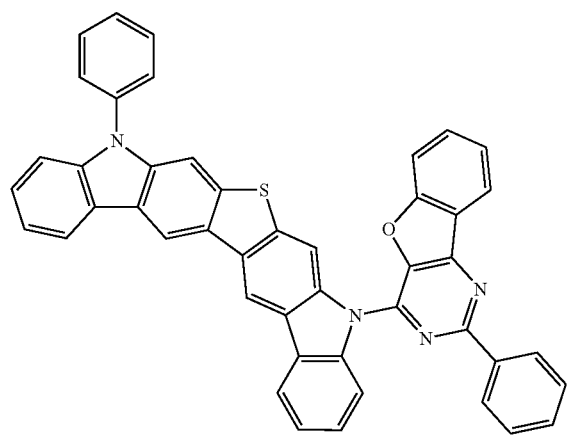
P-62
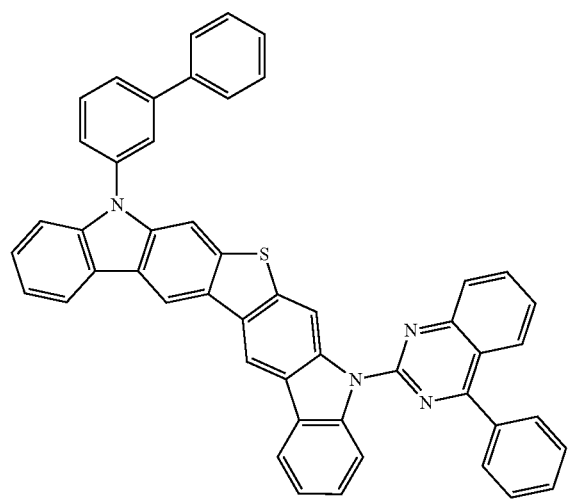
P-63
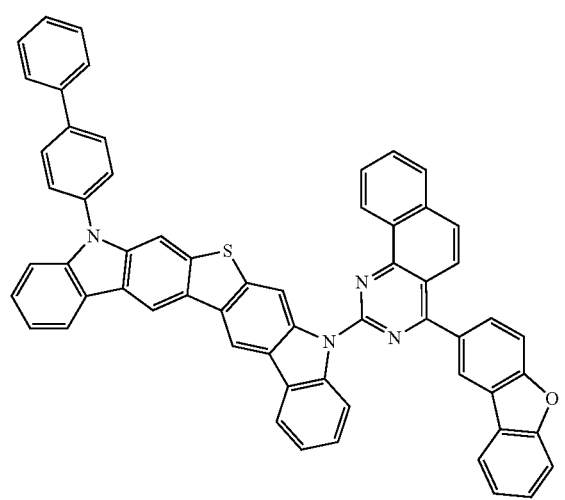
P-64
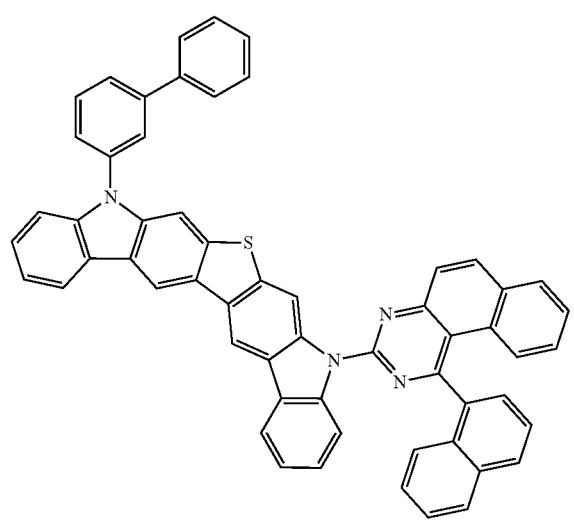

-continued
P-65
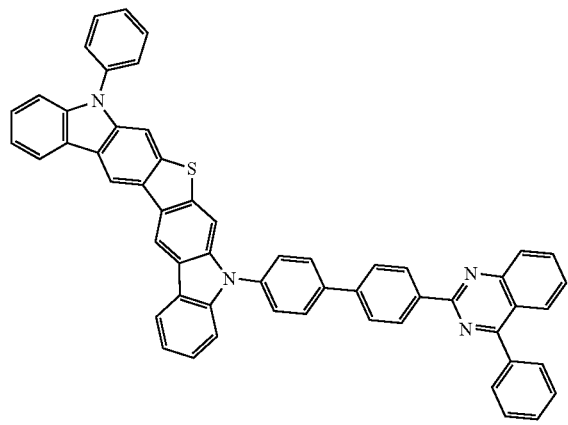
P-66
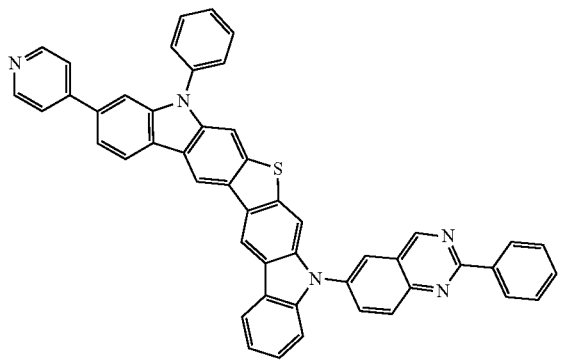
P-67
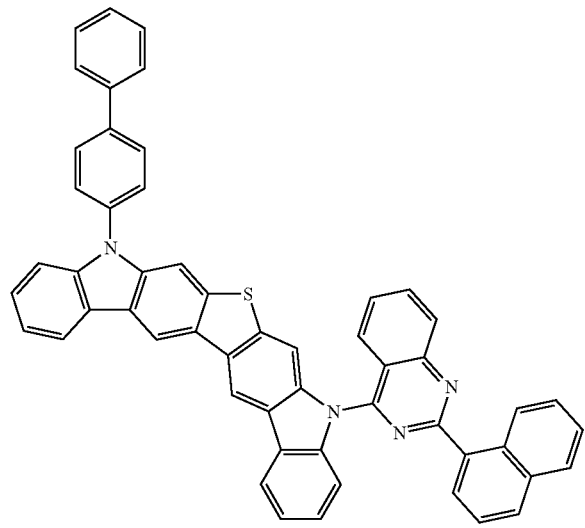
P-68
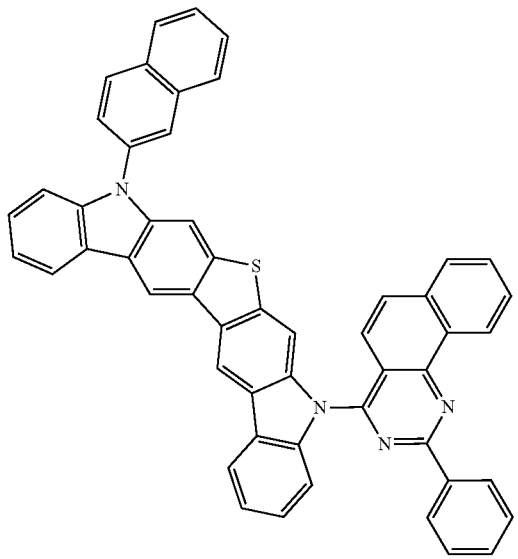
P-69
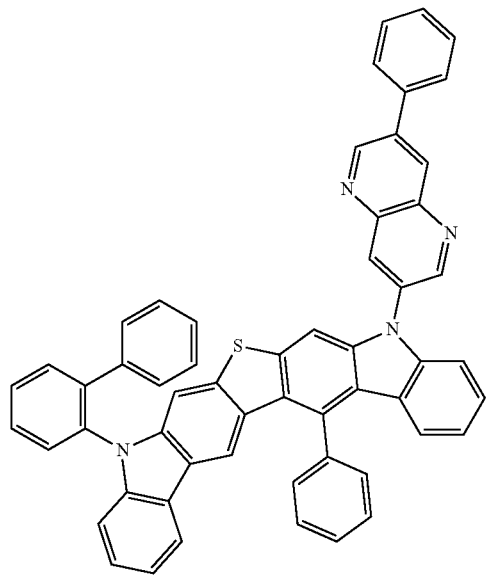
P-70
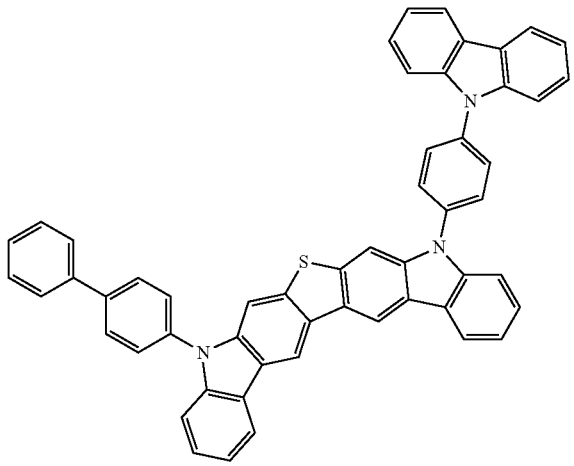

-continued
P-71
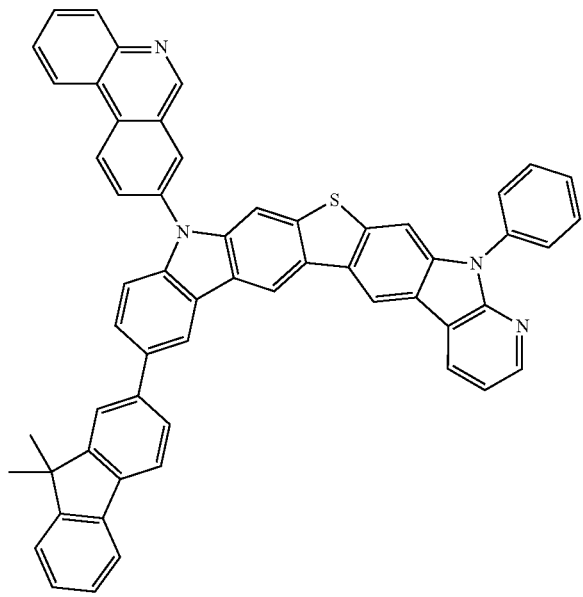
P-72
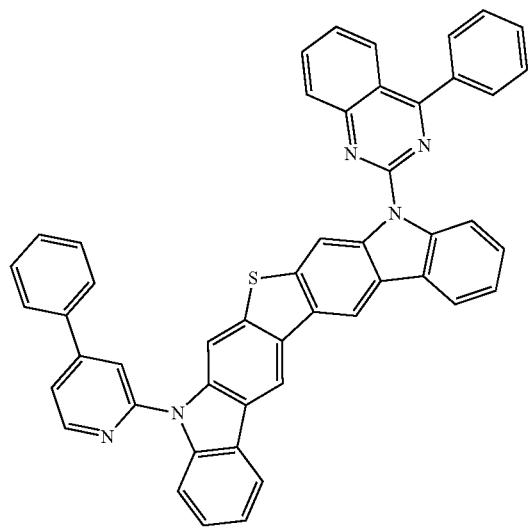
P-73
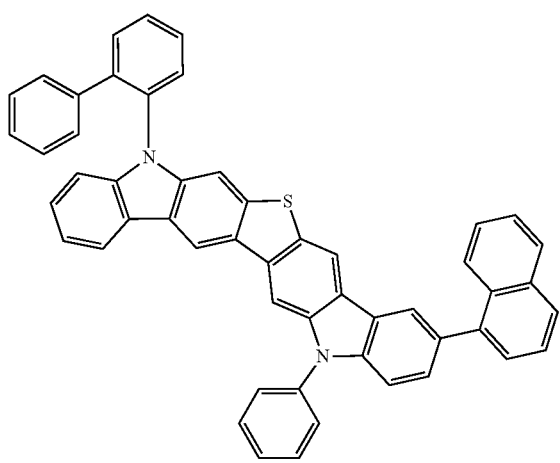
P-74
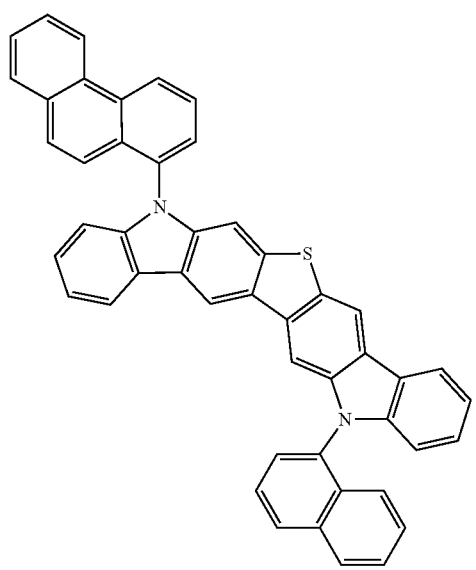

-continued
P-75
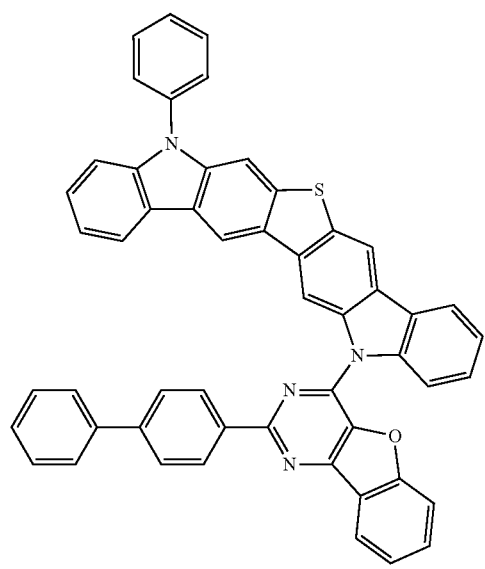
P-76
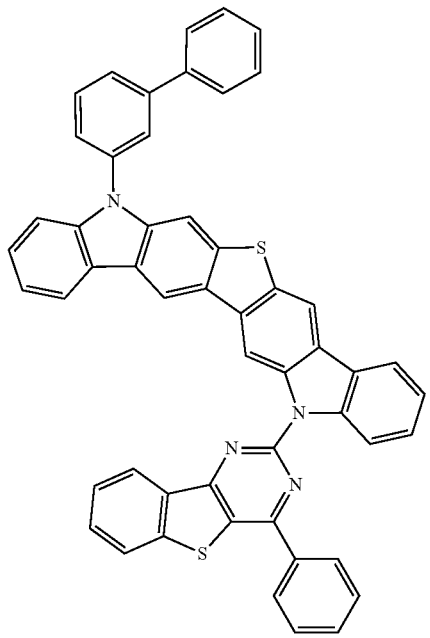
P-77
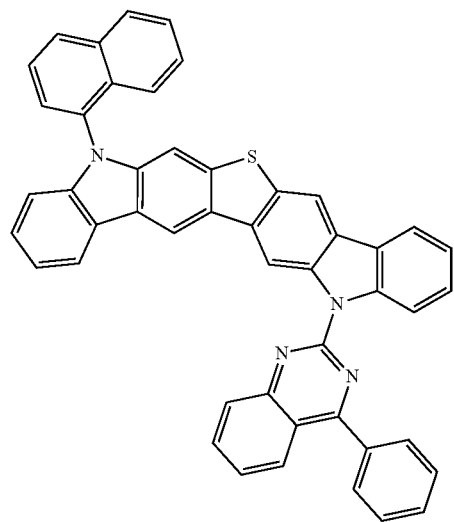
P-78
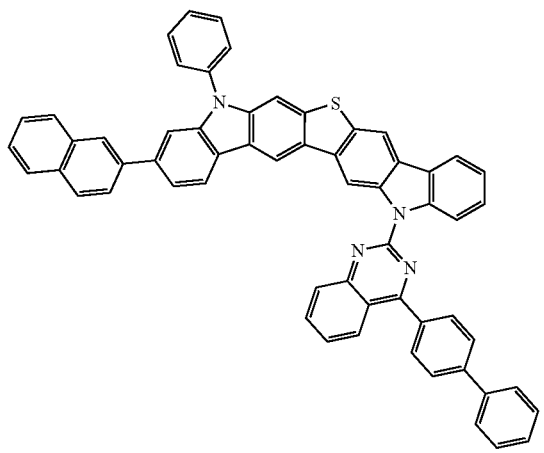

P-79
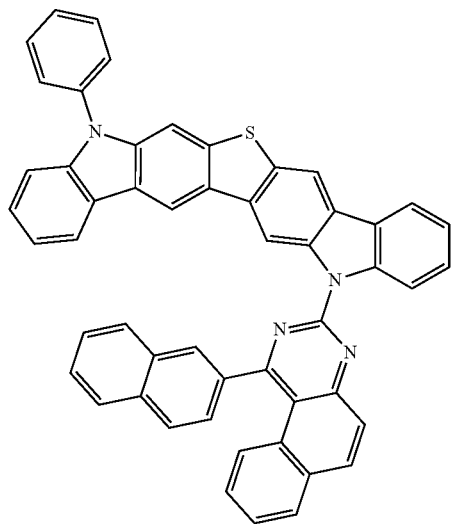
P-80
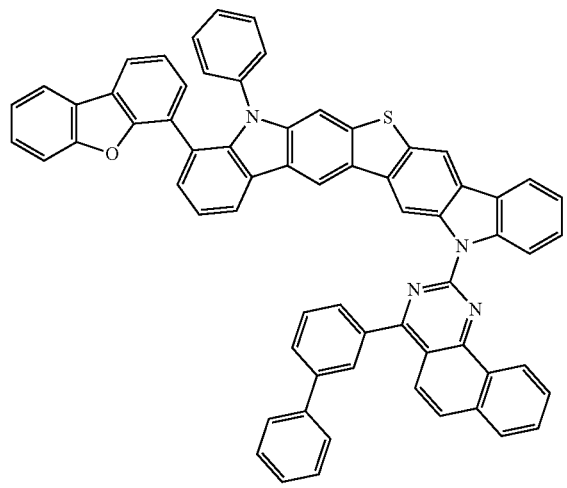
P-81
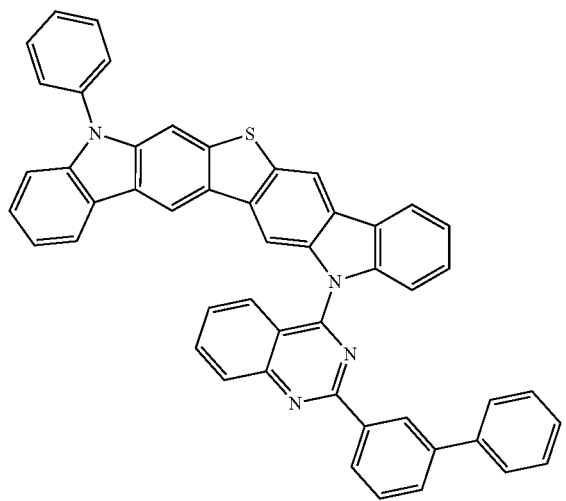
P-82
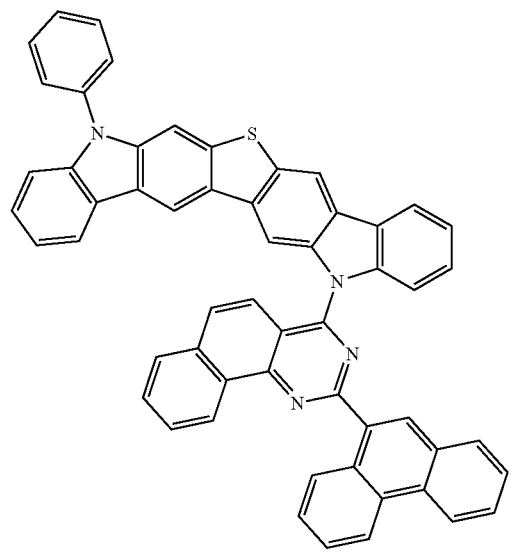

P-83
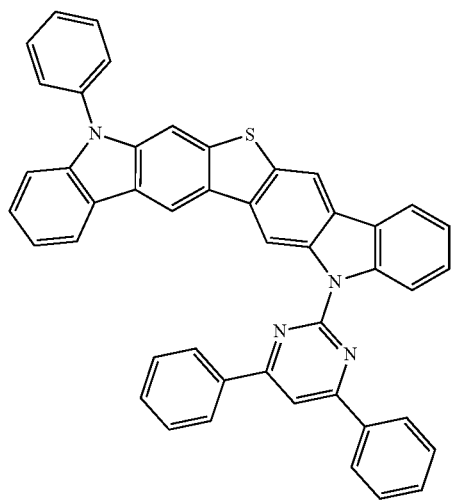
P-84
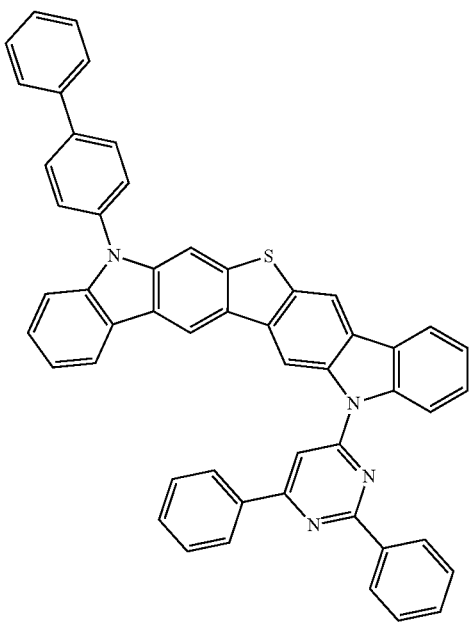
P-85
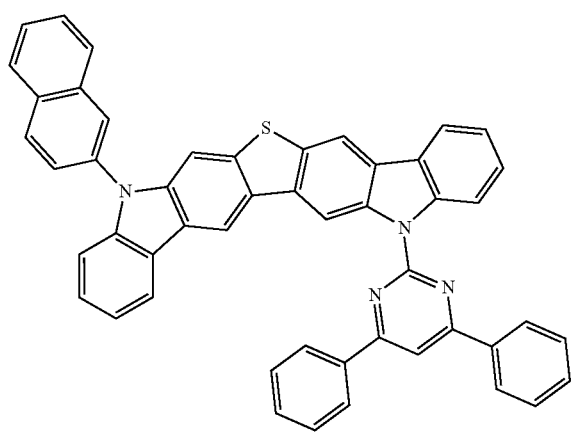
P-86
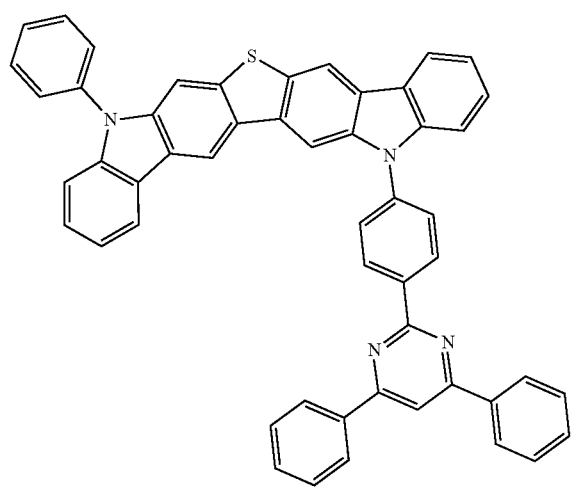

P-87
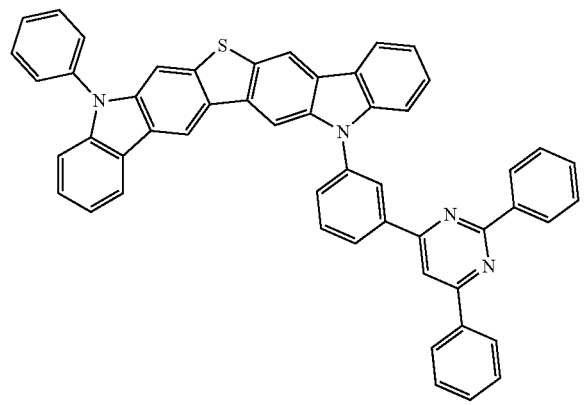
P-88
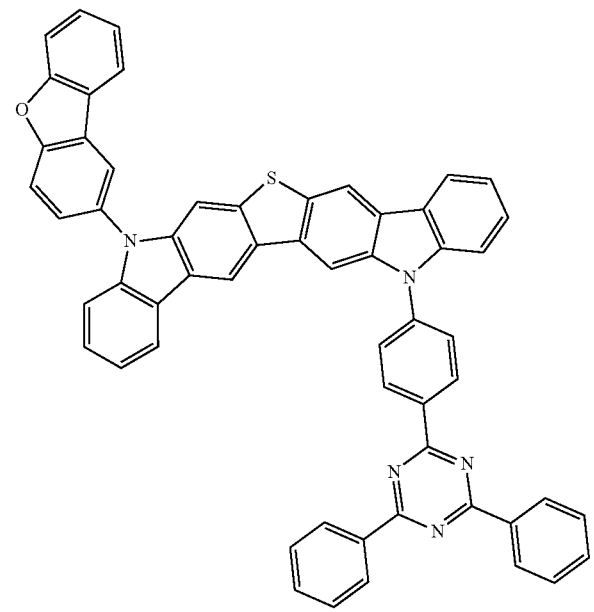
P-89
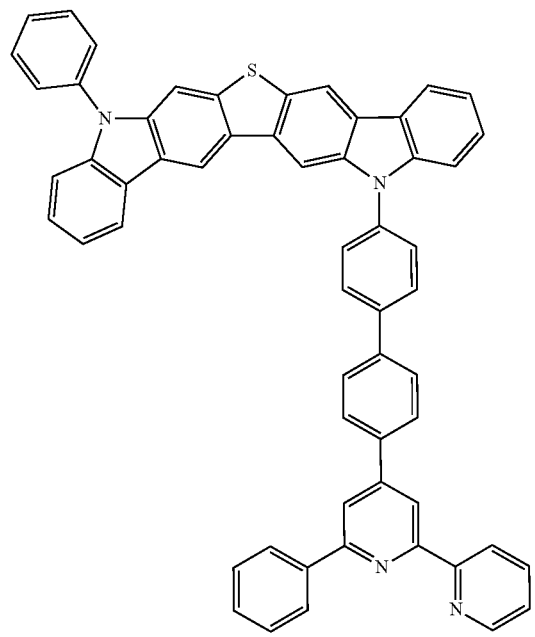
P-90
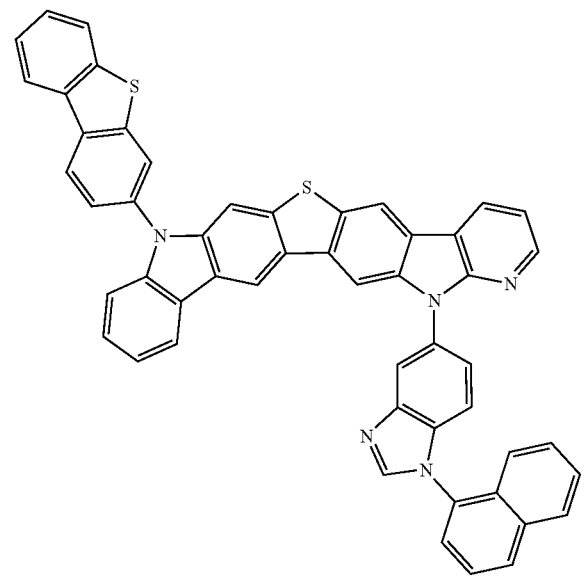

-continued
P-91
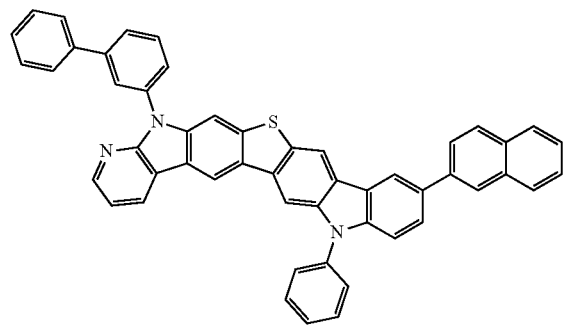
P-92
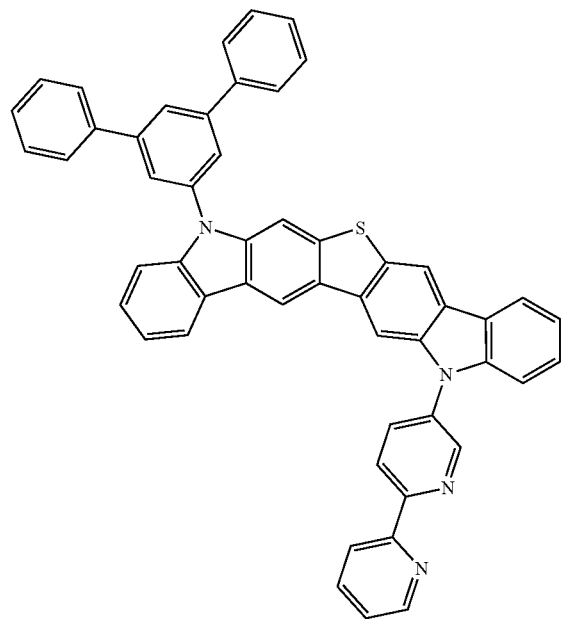
P-93
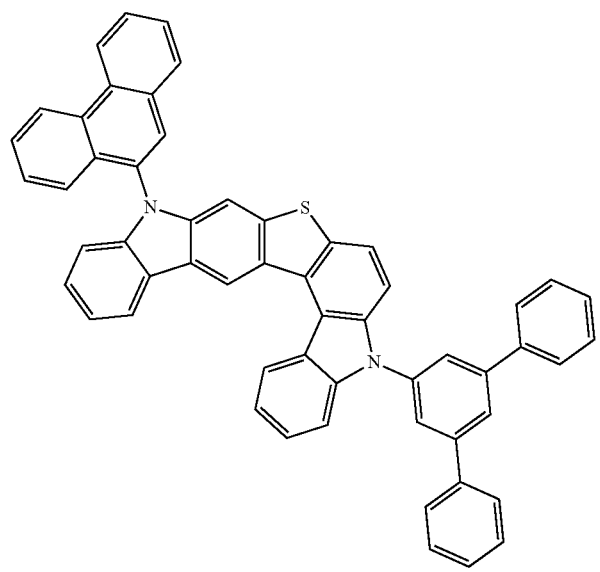
P-94
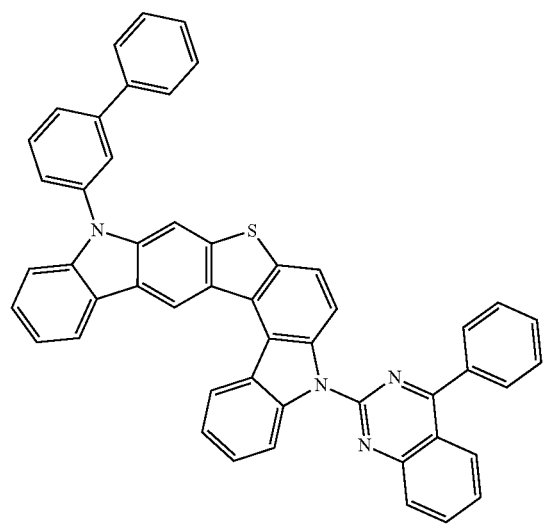

-continued
P-95
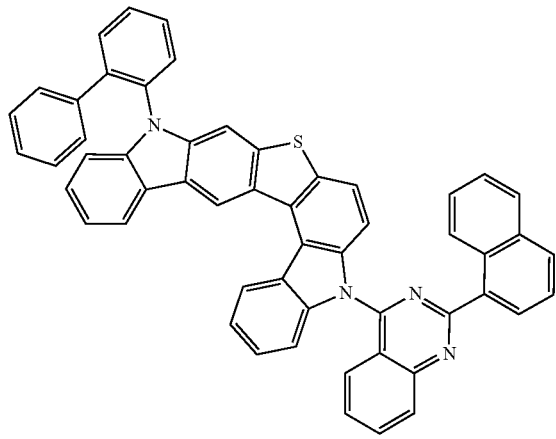
P-96
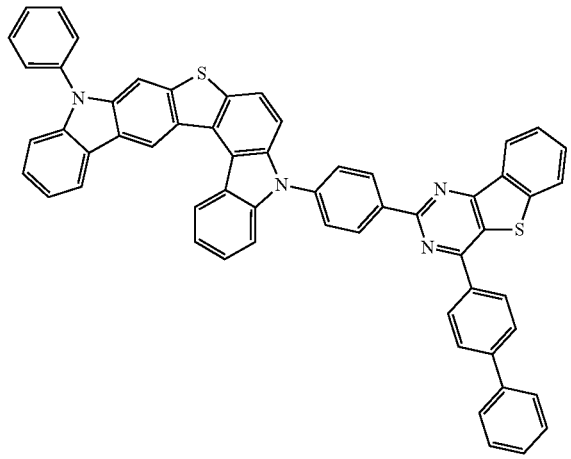
P-97
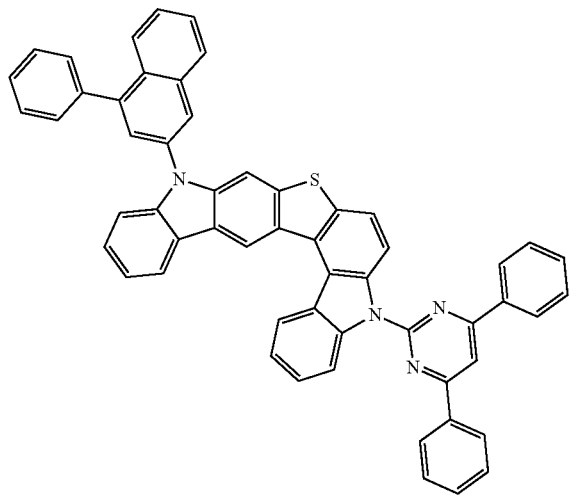
P-98
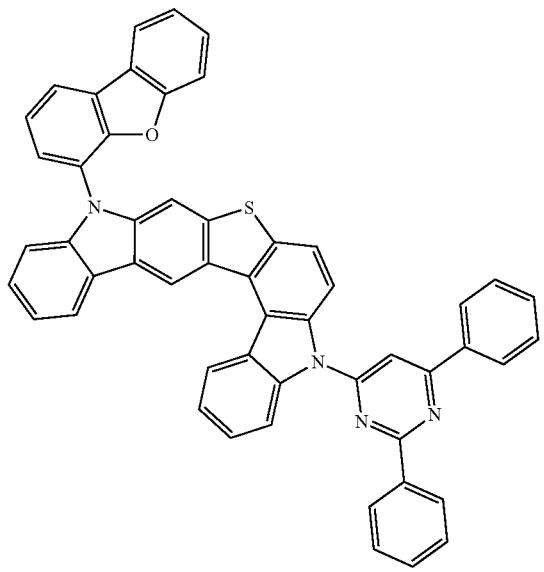
P-99
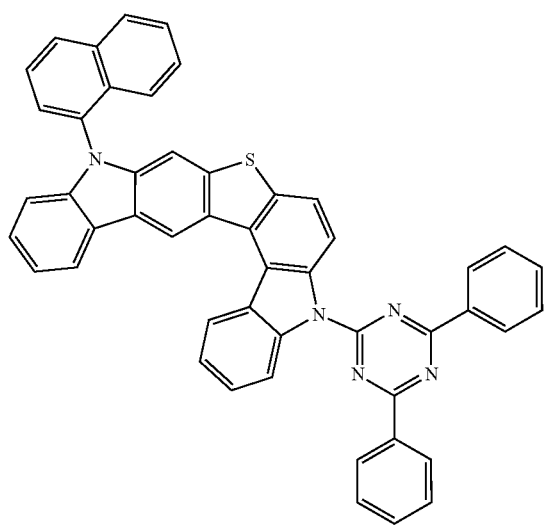
P-100
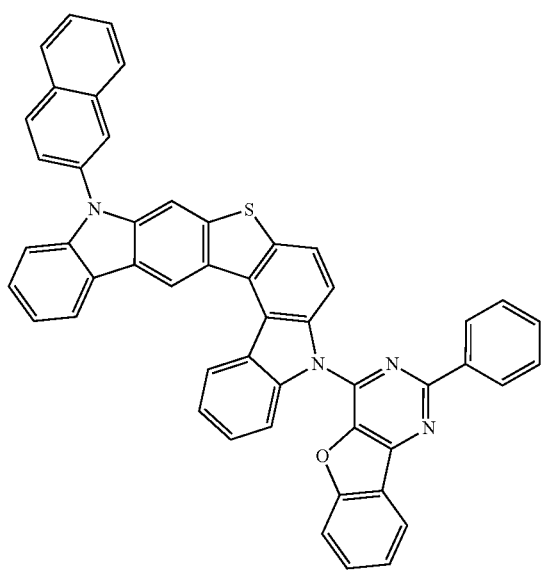

-continued
P-101
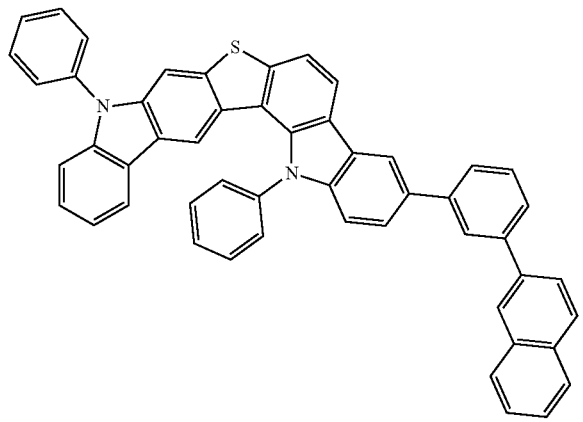
P-102
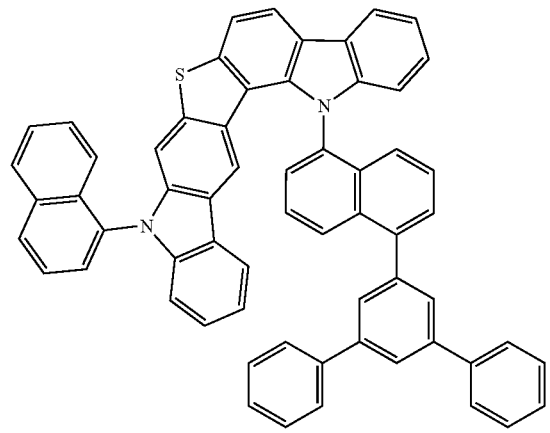
P-103
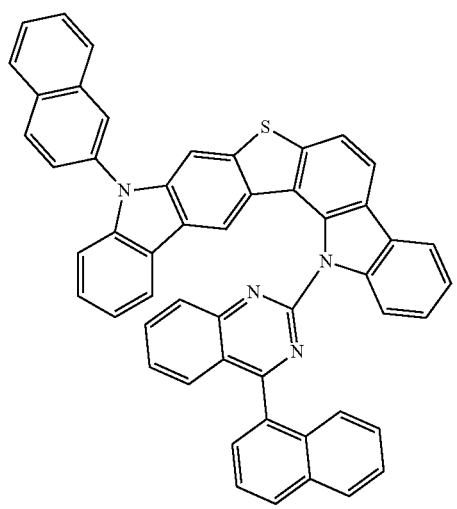
P-104
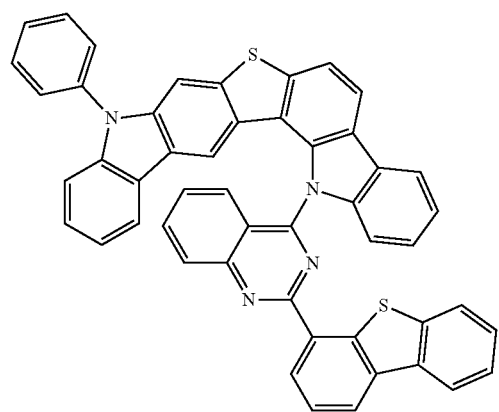
P-105
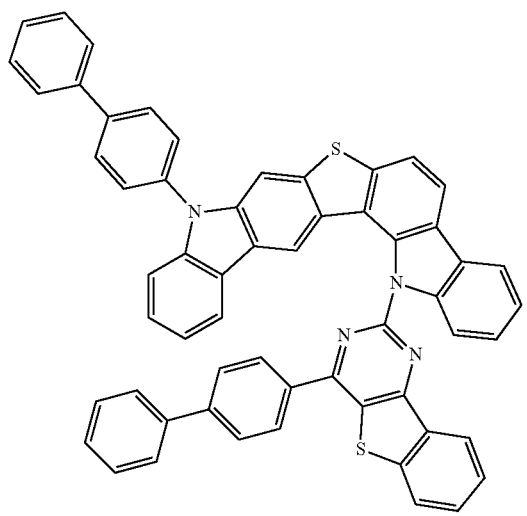
P-106
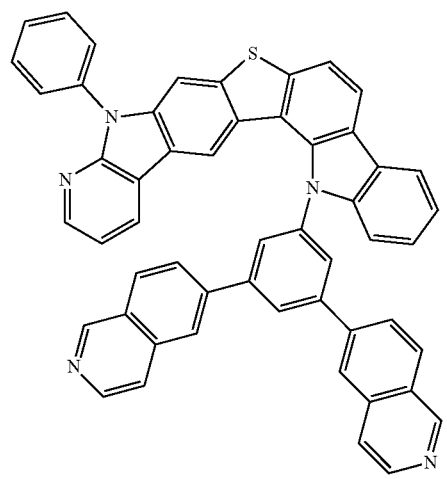

-continued
P-107
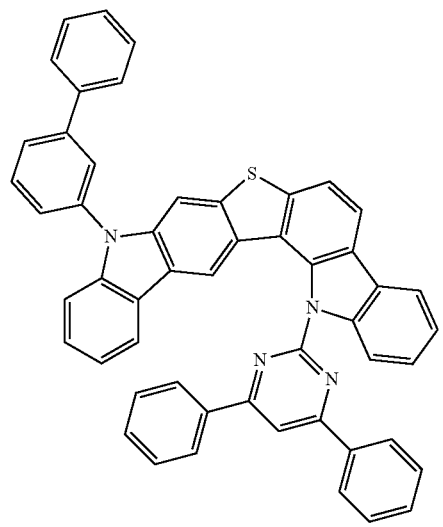
P-108
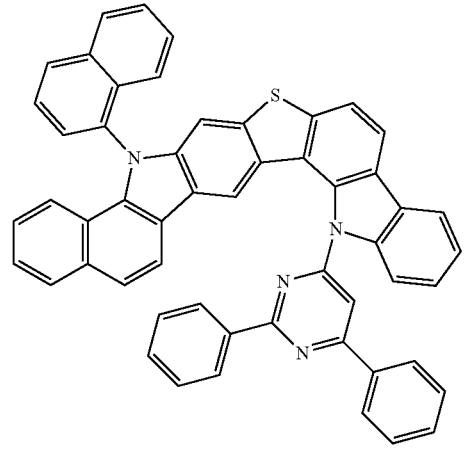
P-109
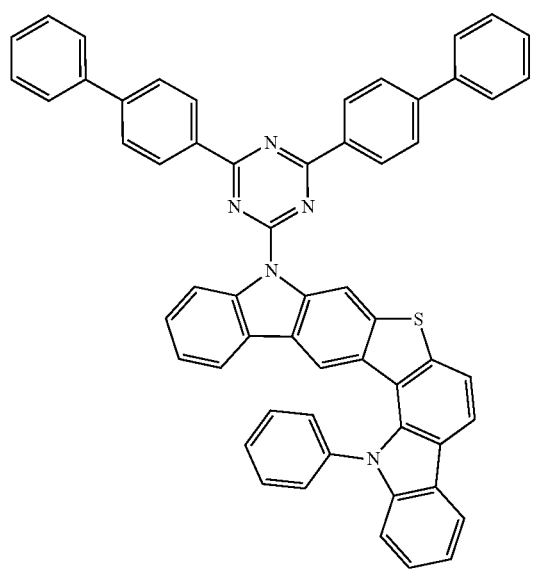
P-110
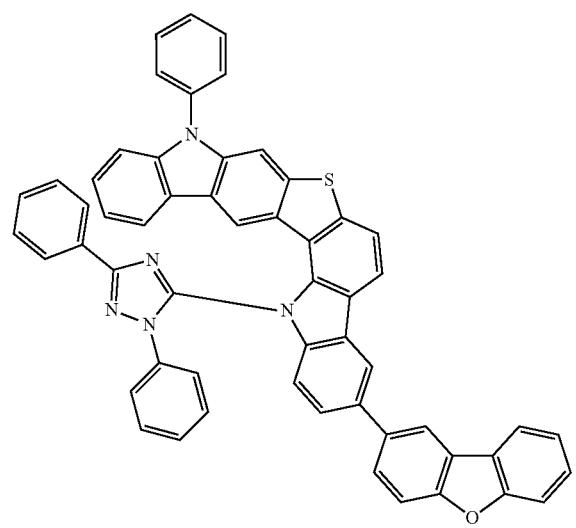
P-111
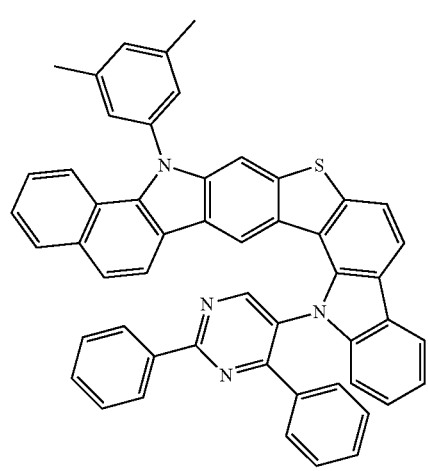
P-112
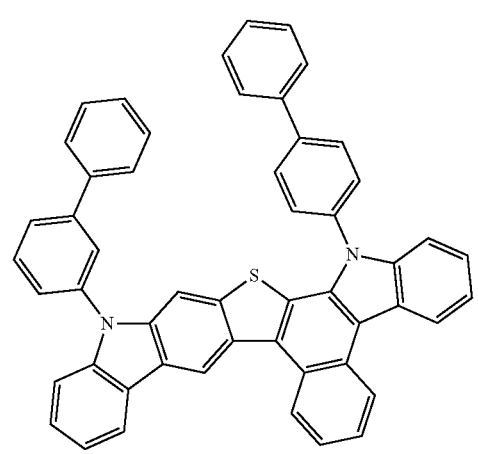

-continued
P-113
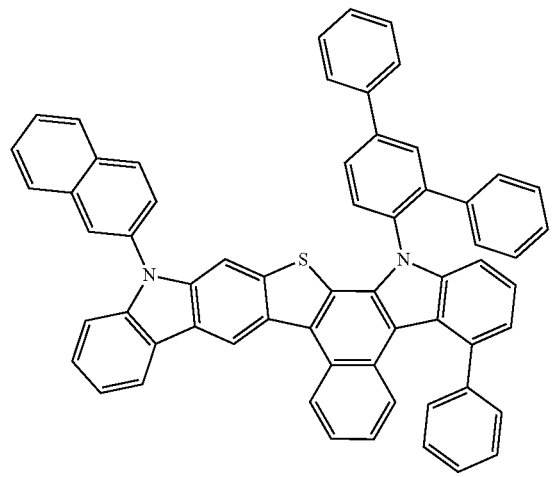
P-114
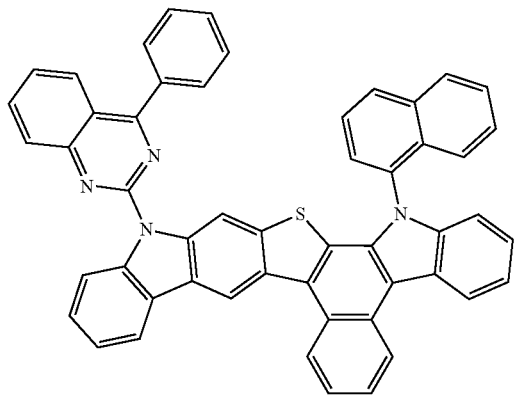
P-115
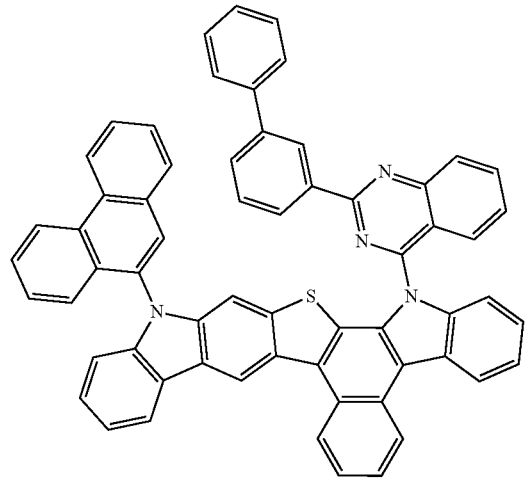
P-116
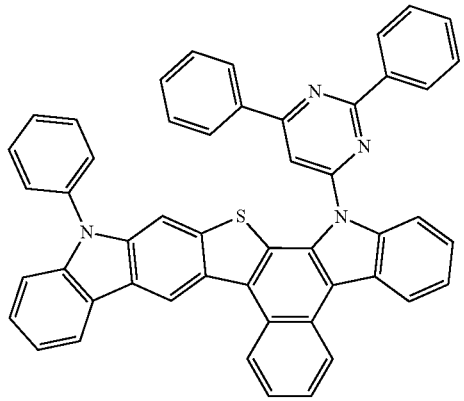
P-117
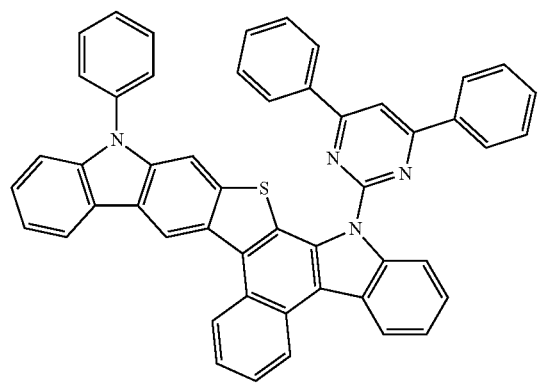
P-118
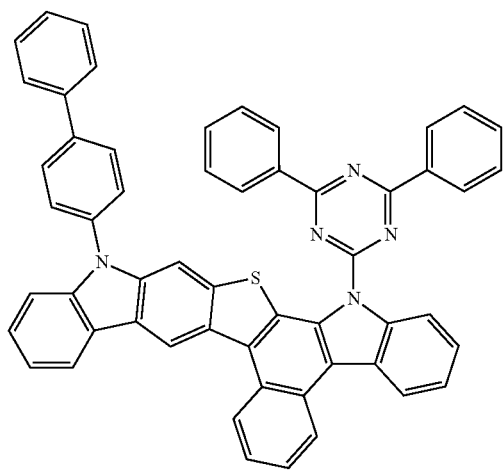

-continued
P-119
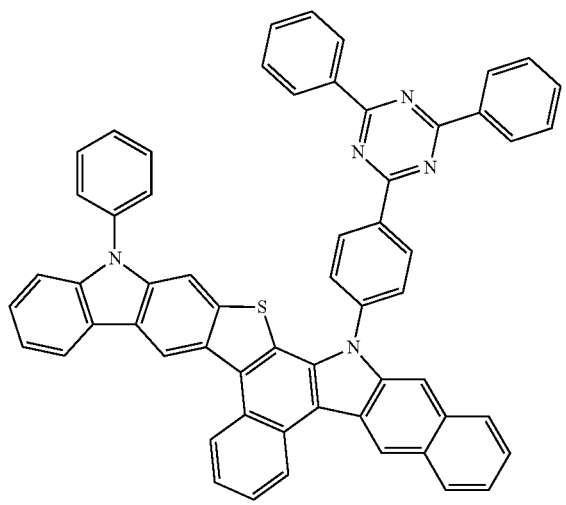
P-120
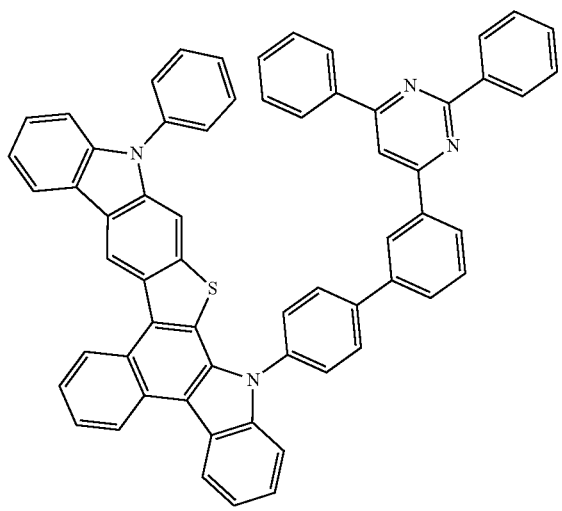
P-121
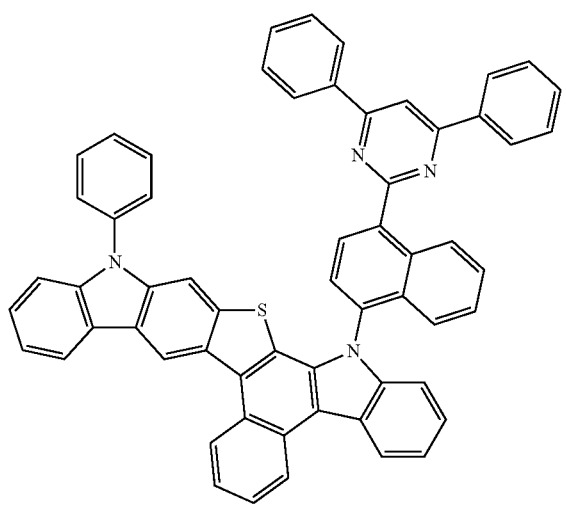
P-122
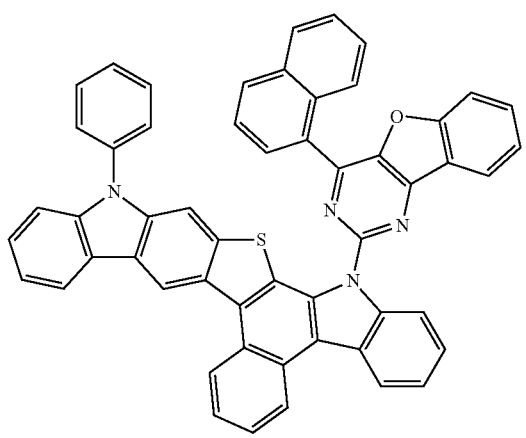
P-123
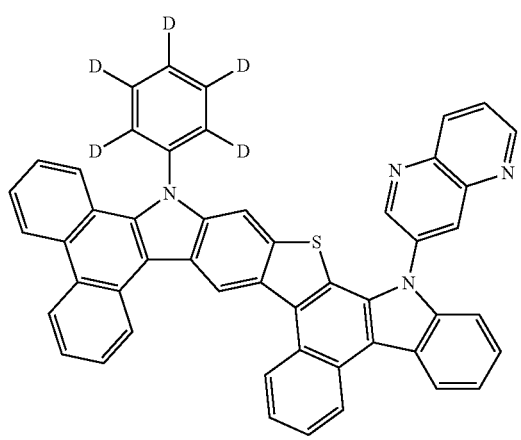
P-124
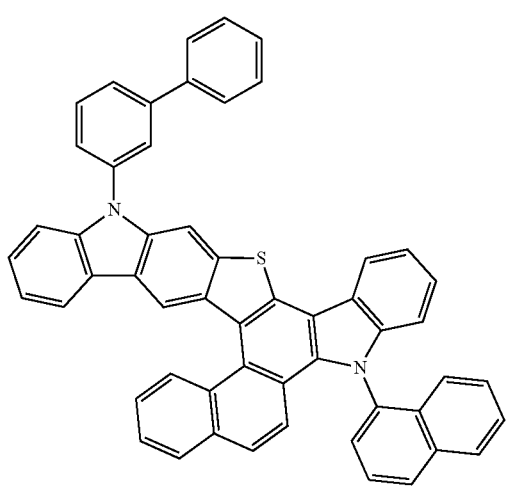

-continued
P-125
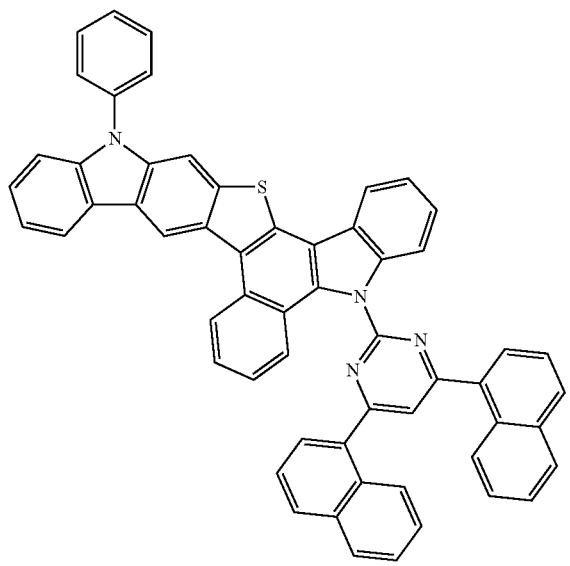
P-126
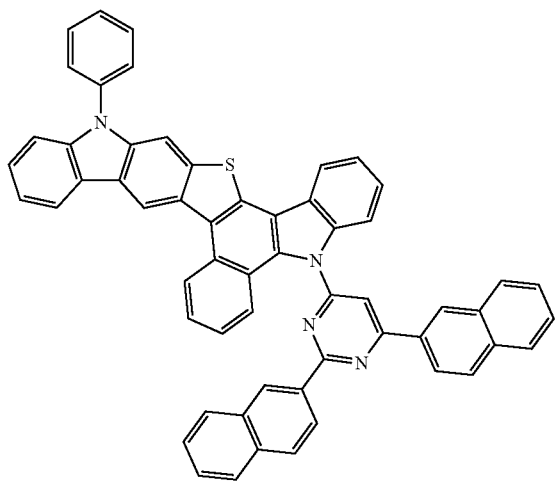
P-127
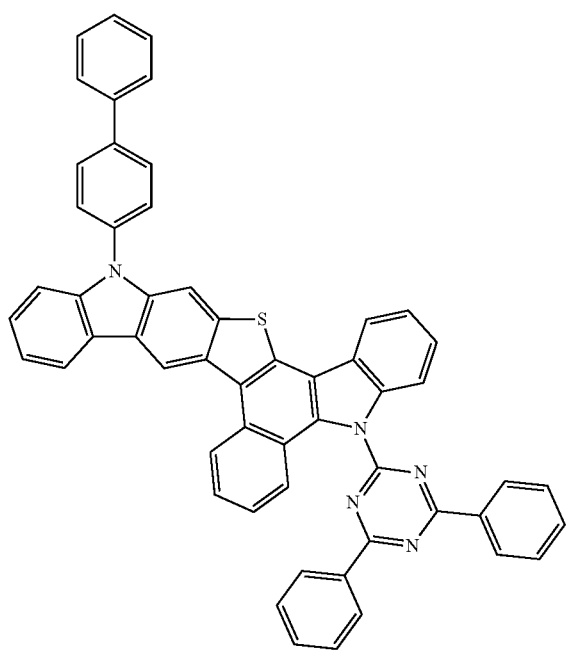
P-128
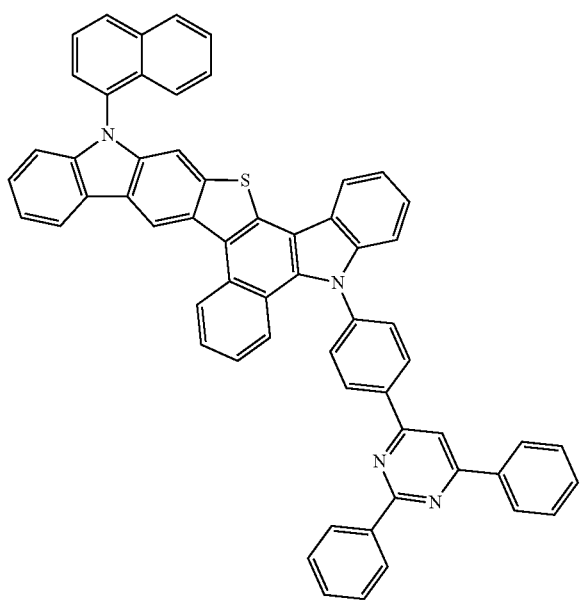

-continued
P-129
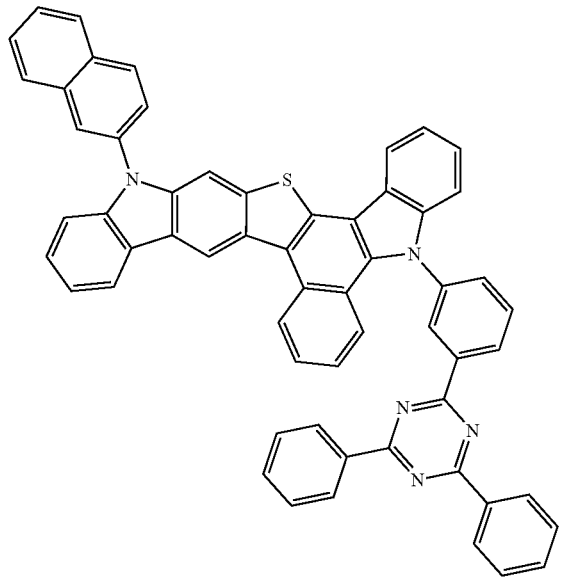
P-130
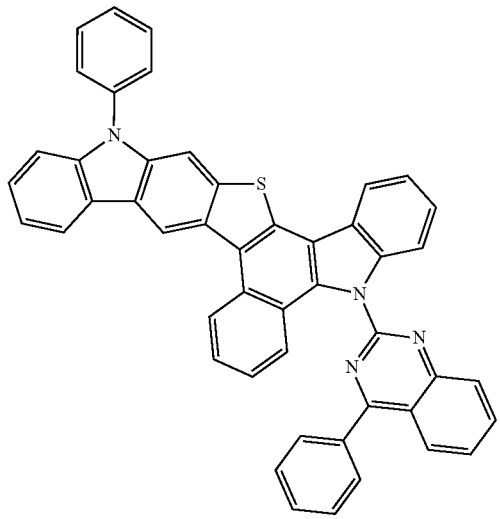
P-131
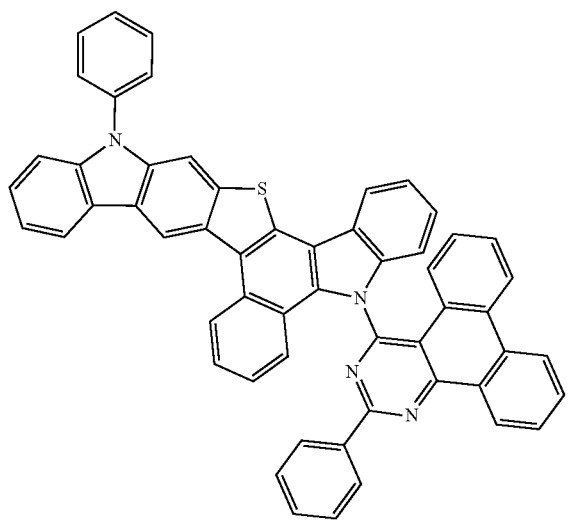
P-132
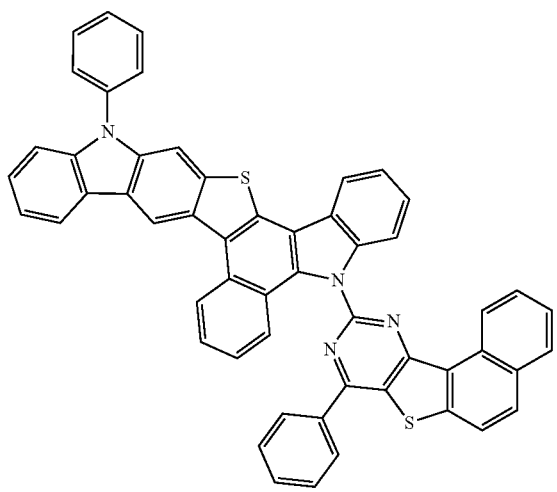
P-133
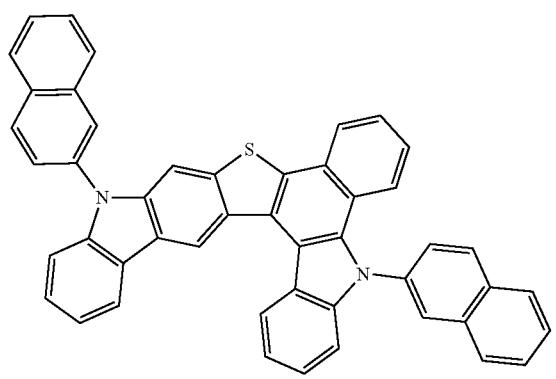
P-134
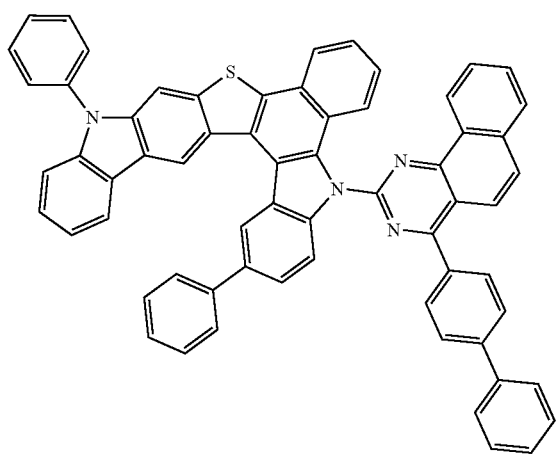

-continued
P-135
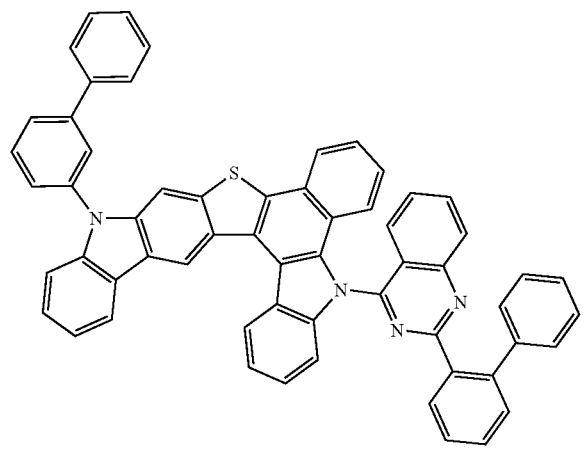
P-136
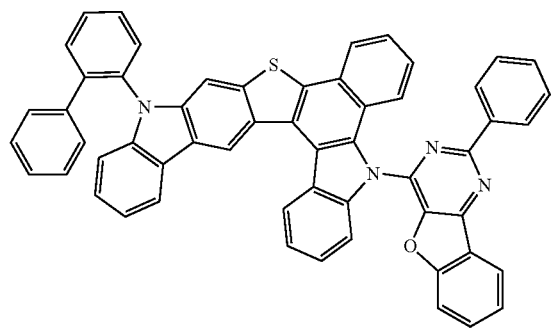
P-137
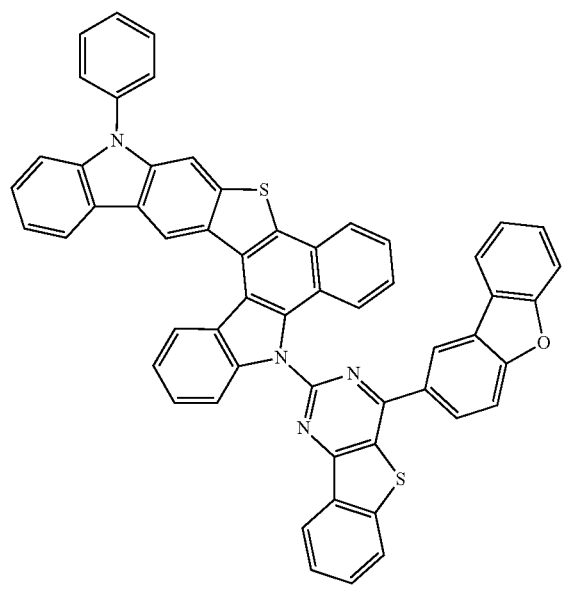
P-138
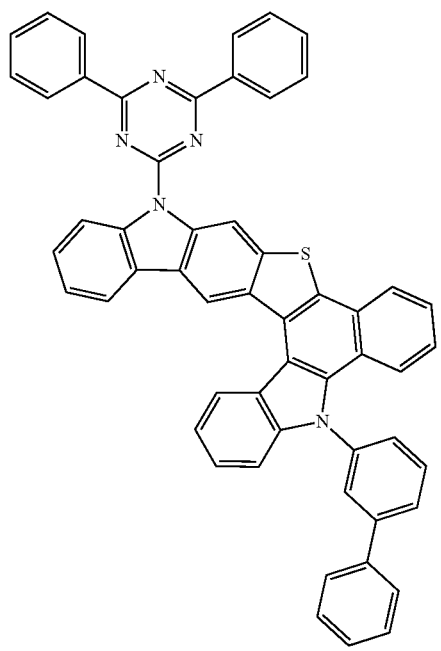

-continued
P-139
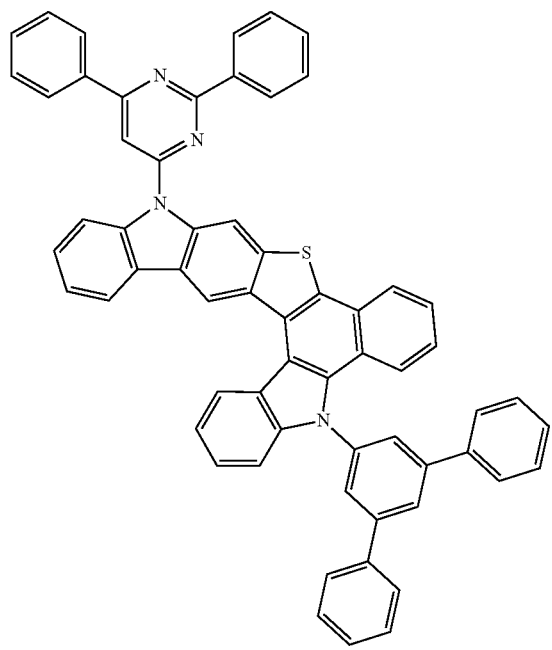
P-140
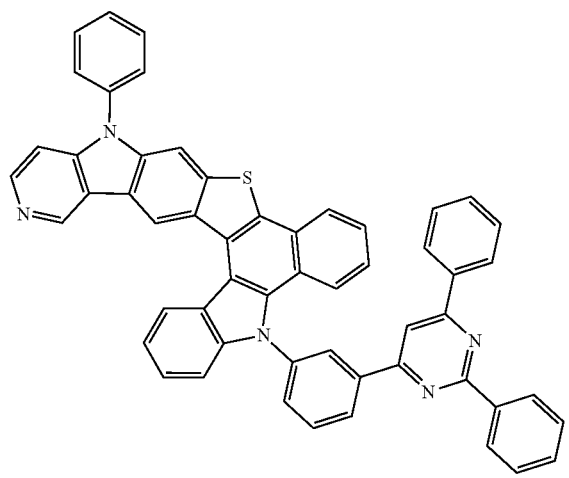
P-141
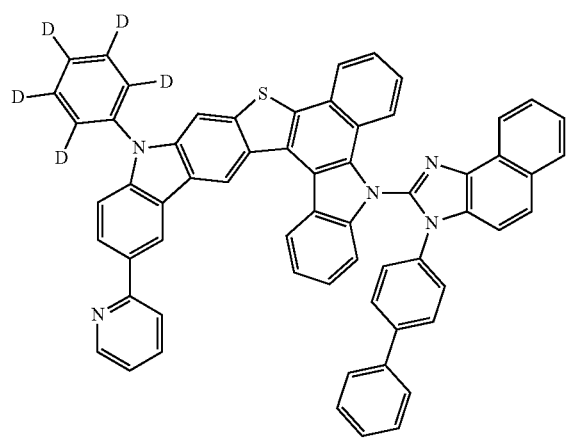
P-142
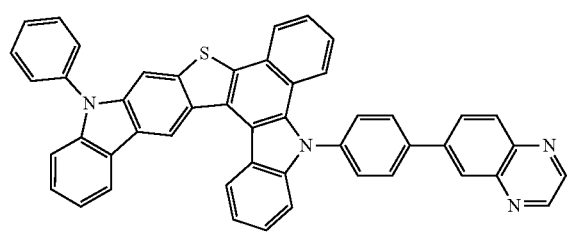
P-143
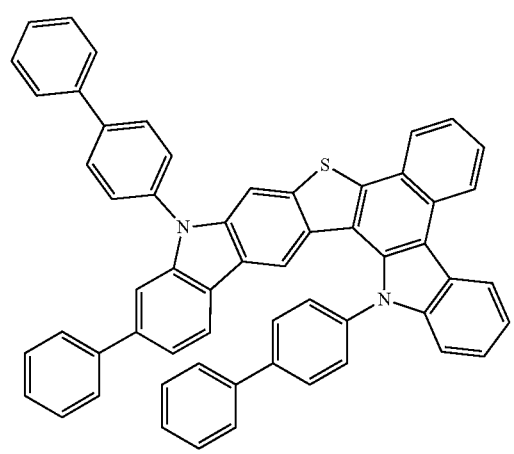
P-144
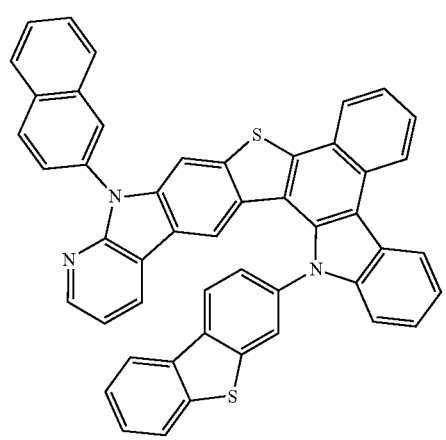

P-145
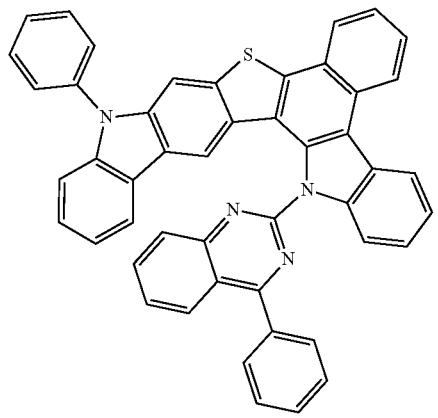
P-146
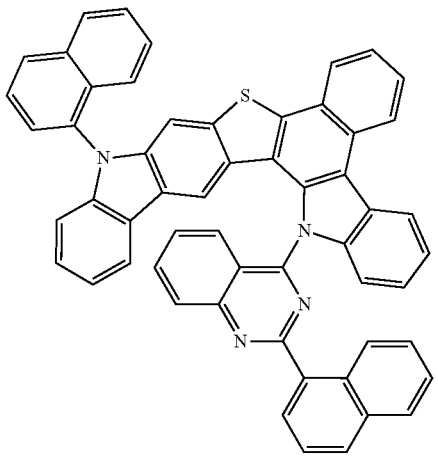
P-147
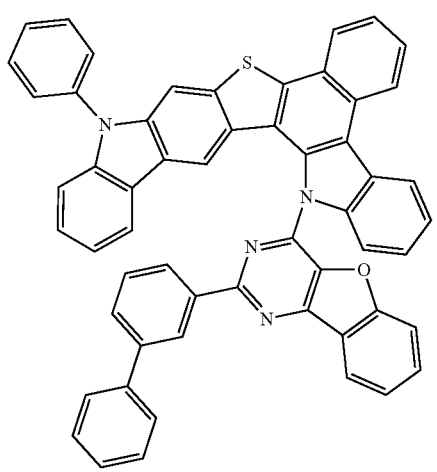
P-148
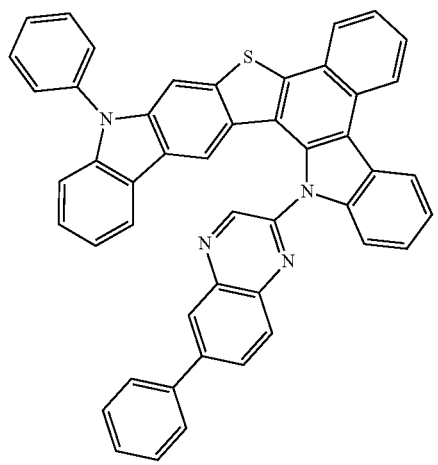
P-149
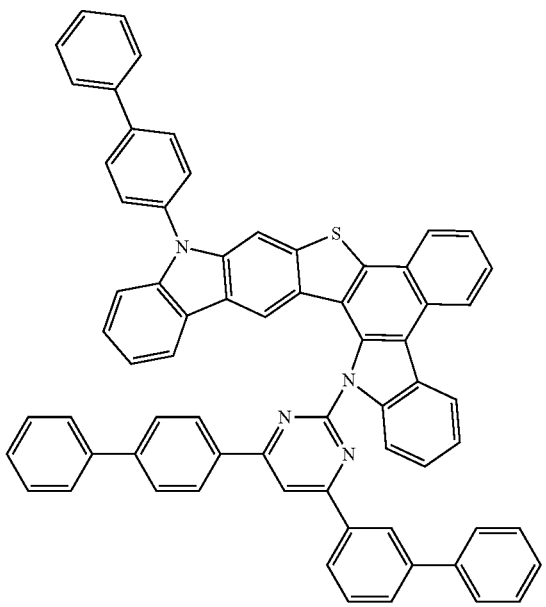

P-150
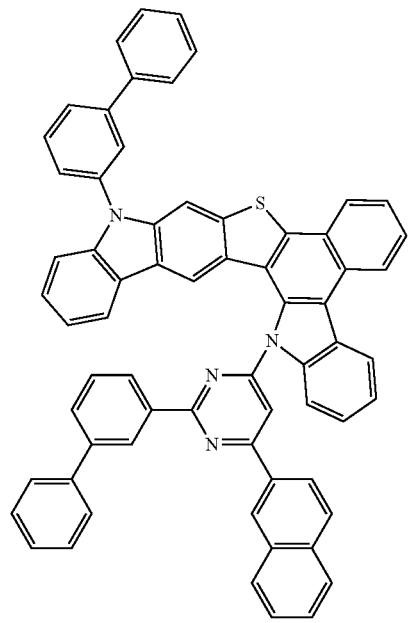
P-151
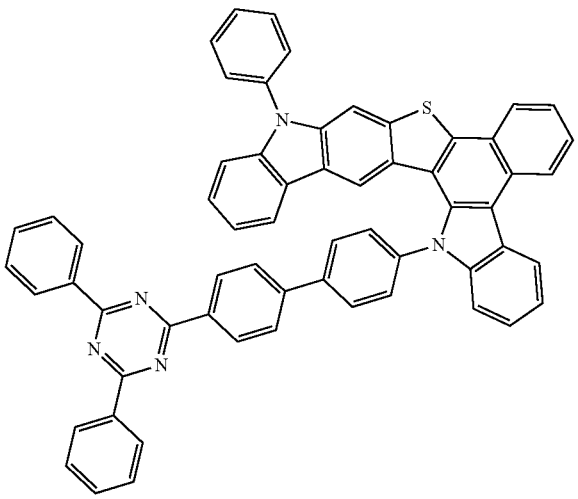
P-152
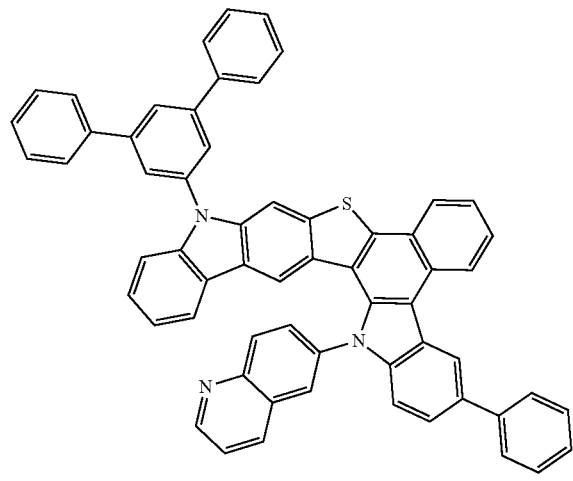
P-153
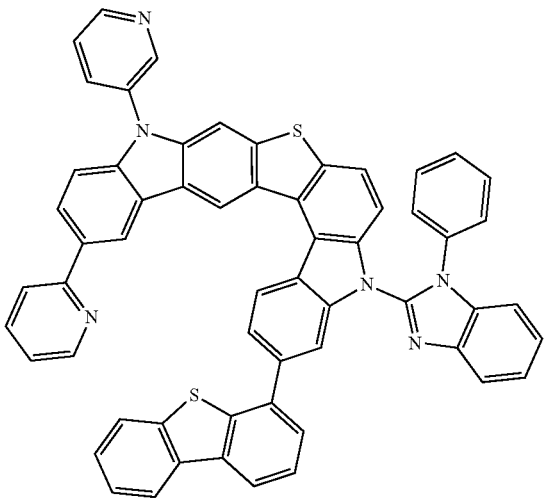

-continued
P-154
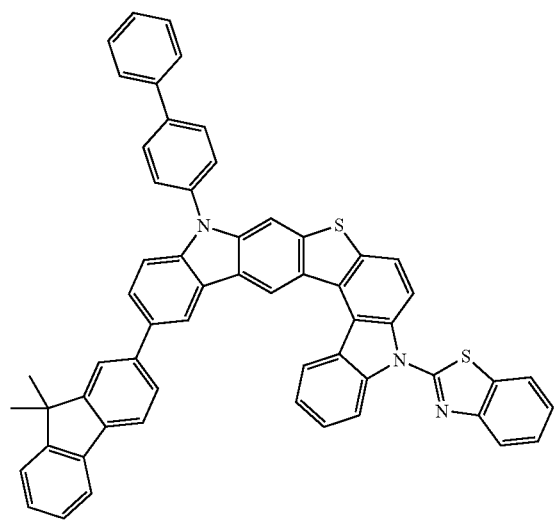
P-155
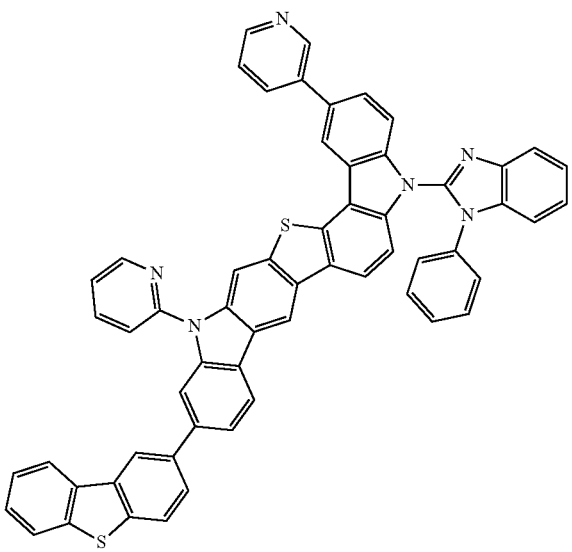
P-156
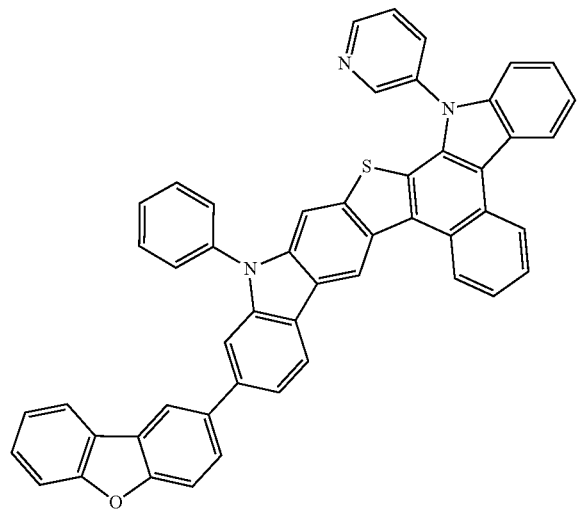
P-157
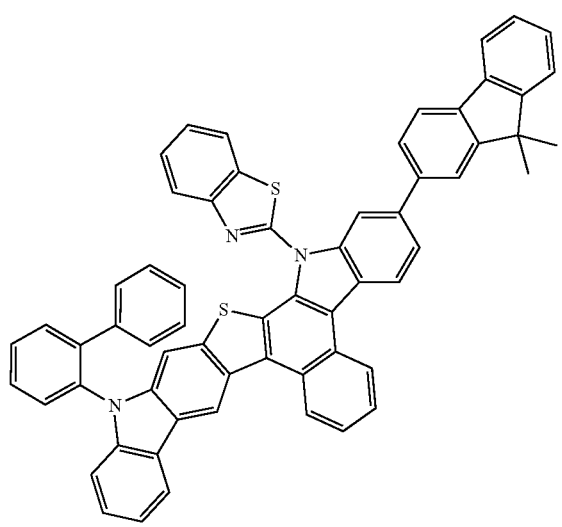

P-158
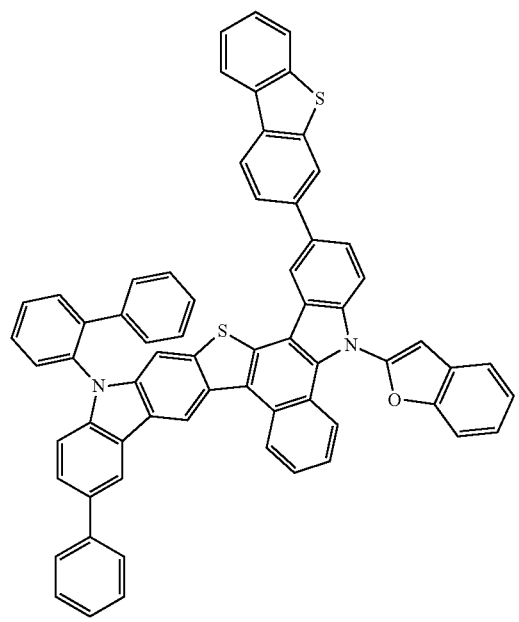
P-159
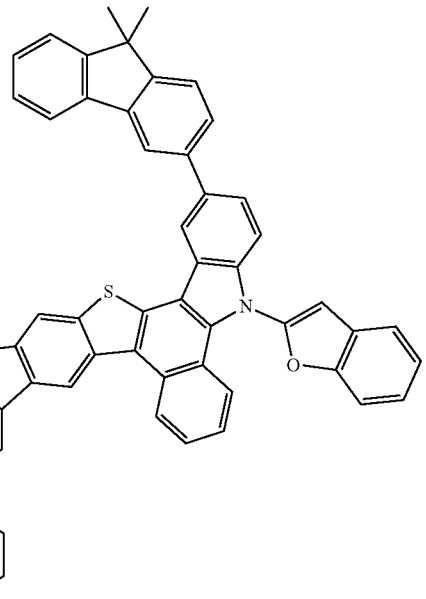
P-160
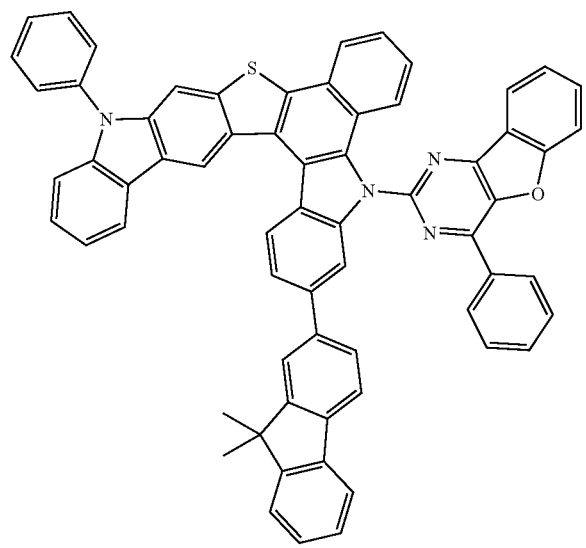
P-161
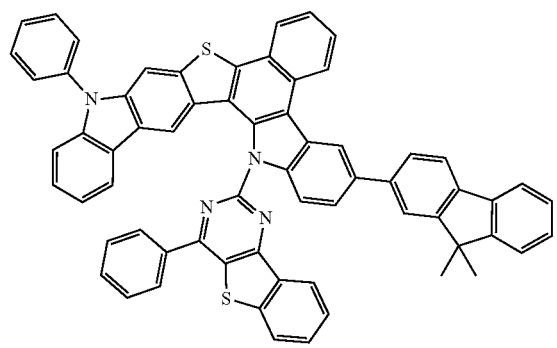

-continued
P-162
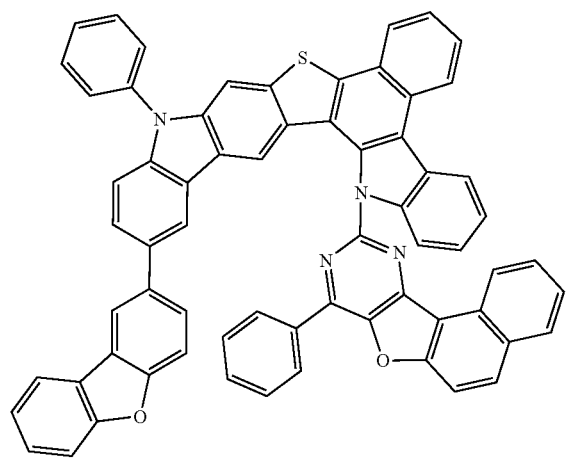
P-163
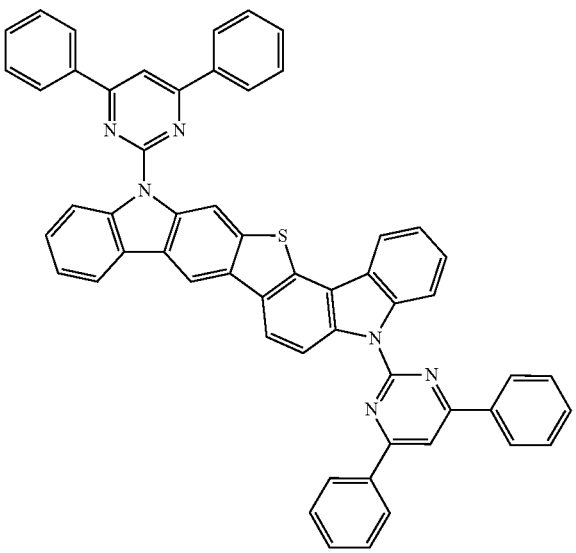
P-164
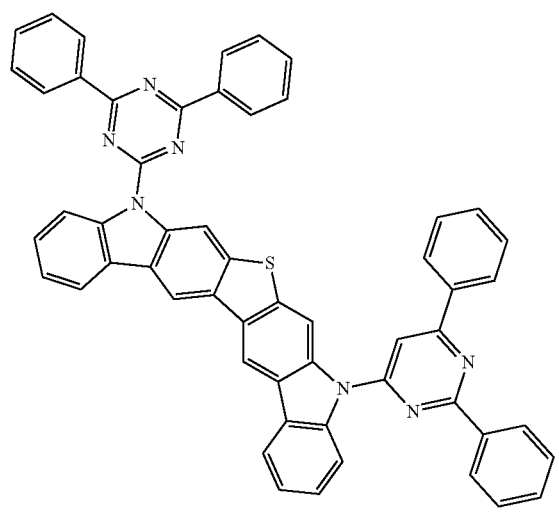
P-165
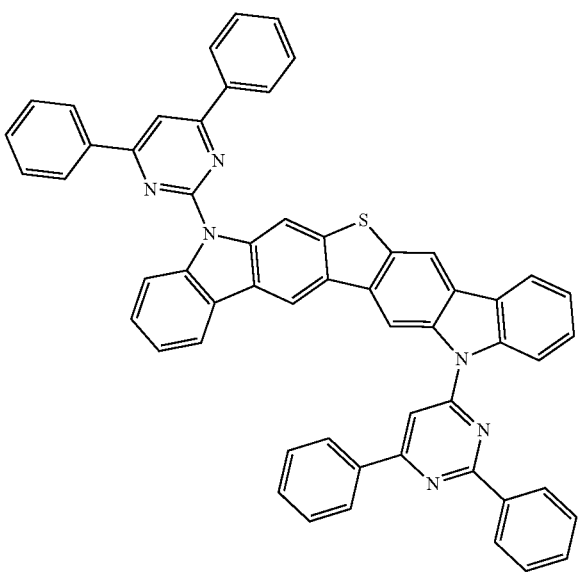

-continued
P-166
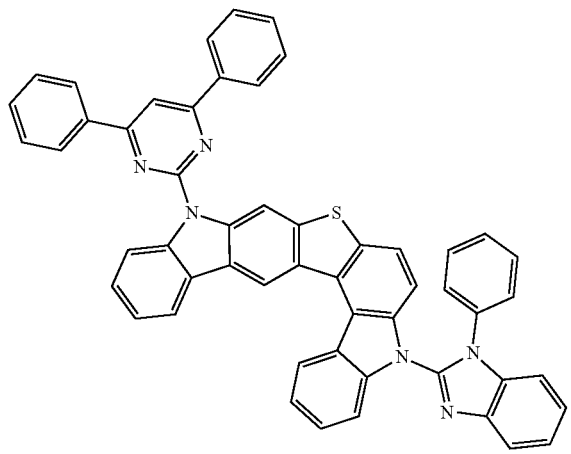
P-167
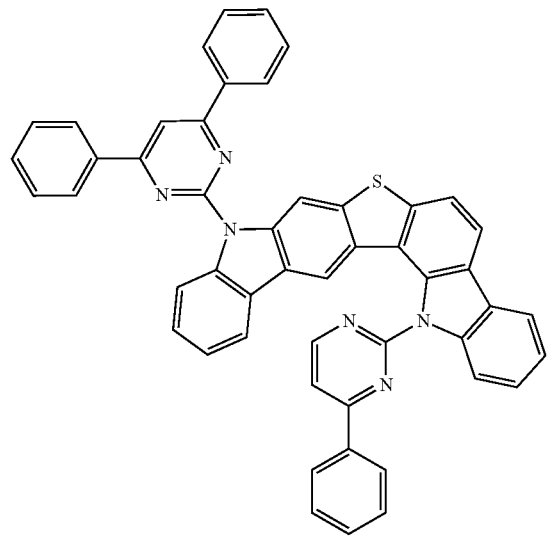
P-168
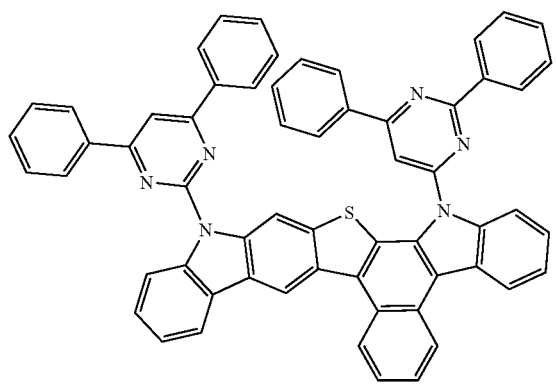
P-169
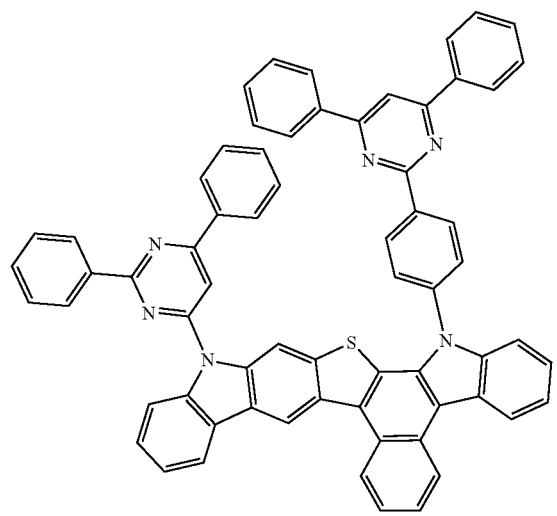
P-170
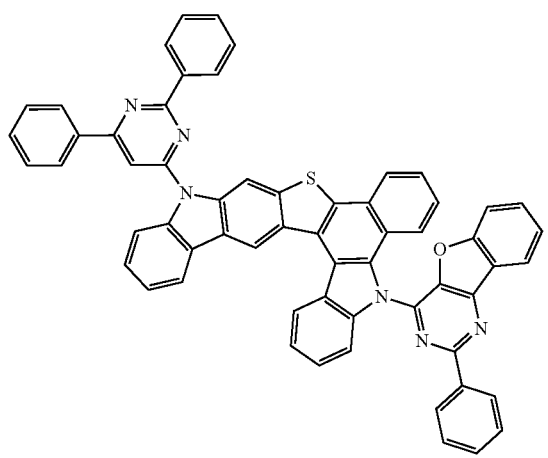
P-171
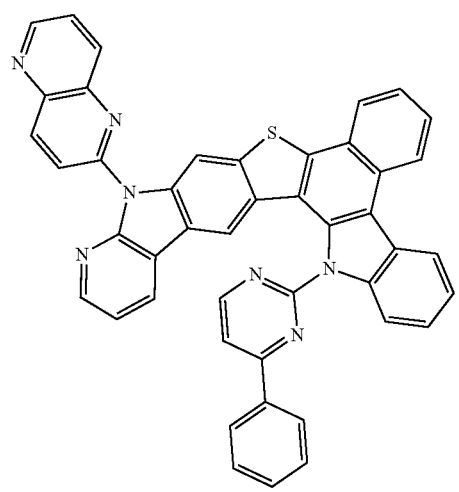

In another embodiment, the present invention provides a compound for an organic electronic element, represented by Formula 1.

In still another embodiment, the present invention provides an organic electronic element containing the compound represented by Formula 1.

Here, the organic electronic element may include: a first electrode; a second electrode; and an organic material layer positioned between the first electrode and the second electrode, wherein the organic material layer may contain a compound represented by Formula 1, and the compound represented by Formula 1 may be contained in at least one of a hole injection layer, a hole transport layer, an auxiliary light emitting layer, a light emitting layer, an electron transport layer, and an electron injection layer of an organic material layer. Especially, the compound represented by Formula 1 may be contained in the light emitting layer.

That is, the compound represented by Formula 1 may be used as a material for a hole injection layer, a hole transport layer, an auxiliary light emitting layer, a light emitting layer, an electron transport layer, or an electron injection layer. Especially, the compound represented by Formula 1 may be used as a material for the light emitting layer. The present invention provides, specifically, an organic electronic element including the organic material layer containing one of the compounds represented by Formulas 2 to 9, and more specifically, an organic electronic element including the organic material layer containing the compound represented by the above individual Formula (P-1 to P-171).

In still another embodiment, the present invention provides an organic electronic element, in which the compound is contained alone, two or more different kinds of the compounds are contained as a combination, or the compound is contained together with other compounds as a combination of two or more in at least one of the hole injection layer, the hole transport layer, the auxiliary light emitting layer, the light emitting layer, the electron transport layer, and the electron injection layer of the organic material layer. In other words, the compounds corresponding to Formulas 1 to 9 may be contained alone, a mixture of two or more kinds of compounds of Formulas 1 to 9 may be contained, or a mixture of the compound of claims 1 to 5 and a compound not corresponding to the present invention may be contained in each of the layers. Here, the compounds that do not correspond to the present invention may be a single compound or two or more kinds of compounds. Here, when the compound is contained together with other compounds as a combination of two or more kinds of compounds, the other compounds may be a compound that is already known for each organic material layer, or a compound to be developed in the future. Here, the compounds contained in the organic material layer may be composed of only the same kind of compounds, or a mixture of two or more kinds of different compounds represented by Formula 1.

In still another embodiment of the present invention, the present invention provides an organic electronic element further including a light efficiency improvement layer, which is formed on at least one of one side of one surface of the first electrode, which is opposite to the organic material layer, and one side of one surface of the second electrode, which is opposite to the organic material layer.

Hereinafter, synthesis examples of the compound represented by Formula 1 and manufacturing examples of the organic electronic element according to the present invention will be described in detail by way of example. However, the following examples are only for illustrative purposes and are not intended to limit the scope of the invention.

SYNTHESIS EXAMPLES

The compounds (final products) represented by Formula 1 according to the present invention are synthesized by a reaction of Sub 1 and Sub 2 as shown in Reaction Scheme 1 below, but are not limited thereto.

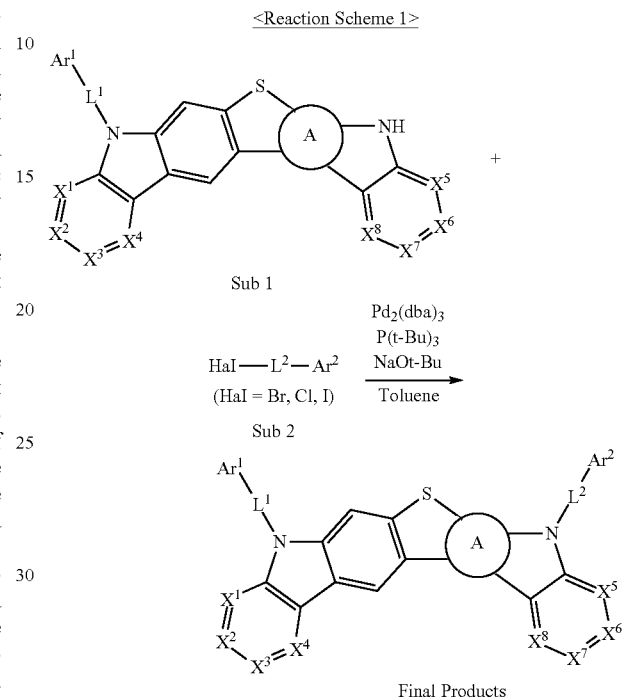

<Reaction Scheme 1>

Sub 1

Sub 2

Final Products ($X^1$ to $X^8$, $Ar^1$, $Ar^2$, $L^1$, $L^2$, and A each are the same as defined in Formula 1 above)

I. Synthesis Example of Sub 1

Sub 1 in Reaction Scheme 1 above may be synthesized by a reaction pathway of Reaction Scheme 2, but is not limited thereto.

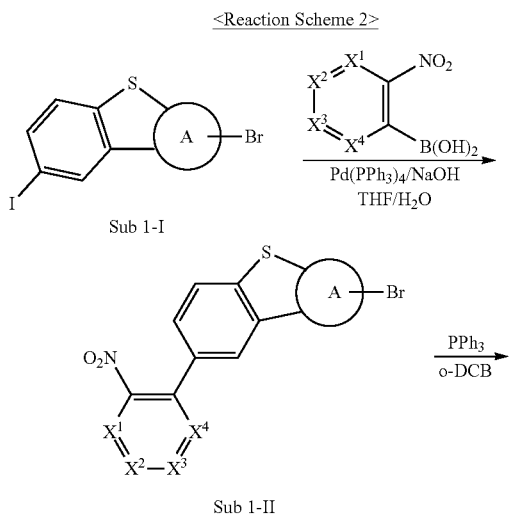

<Reaction Scheme 2>

Sub 1-I

Sub 1-II

-continued
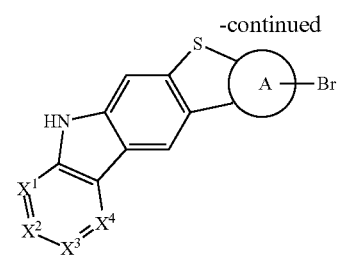
Sub 1-III
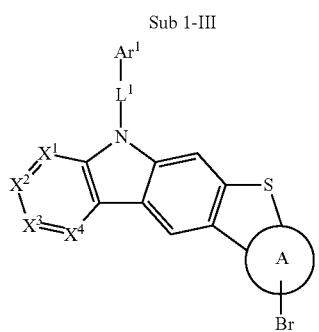
Sub 1-IV
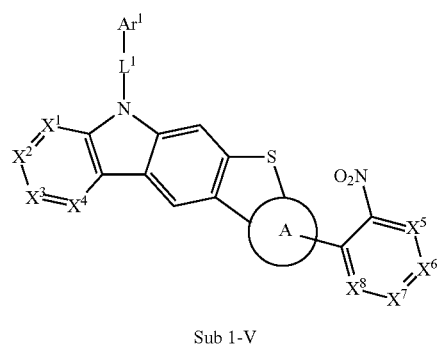
Sub 1-V
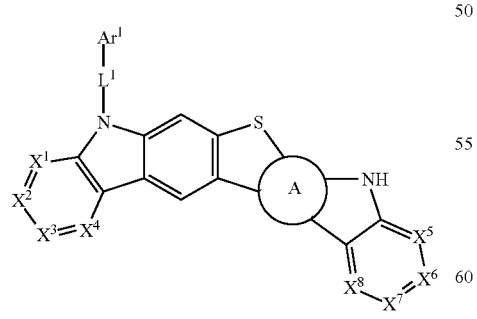
Sub 1
Synthesis examples of specific compounds pertaining to Sub 1 are as follows.
Synthesis of Sub 1-24
<Reaction Scheme 3>
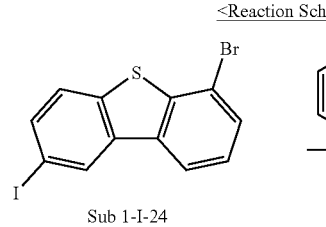
Sub 1-I-24
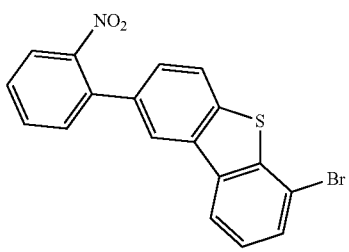
Sub-1-II-24
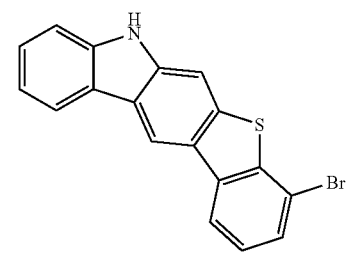
Sub-1-III-24
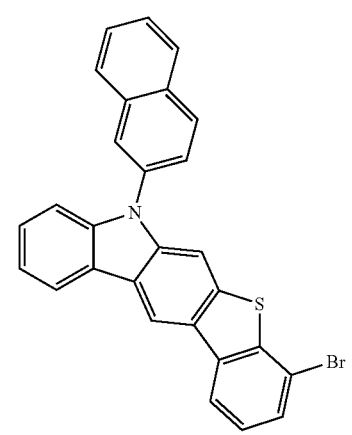
Sub-1-IV-24

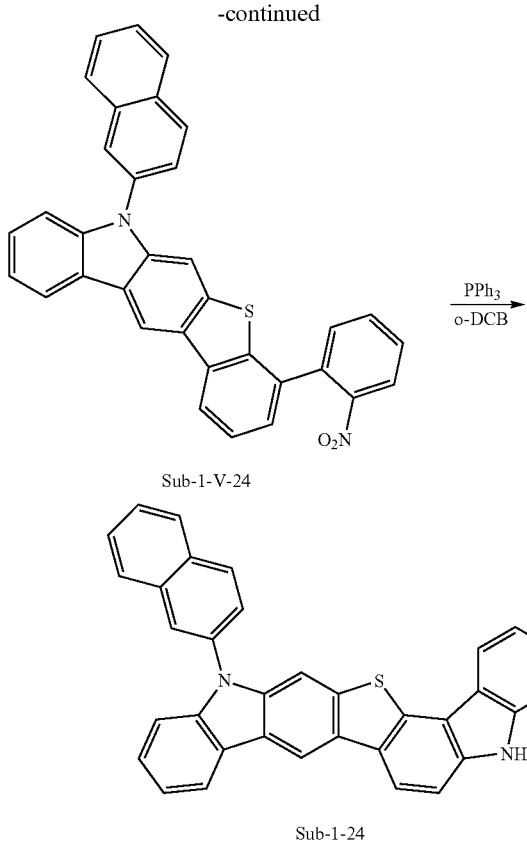

Sub-1-V-24

Sub-1-24

(1) Synthesis of Sub 1-II-24

In a round-bottom flask, Sub 1-I-24 (160 g, 151.9 mmol) was added, and then (2-nitrophenyl)boronic acid (86.1 g, 515.9 mmol), Pd(PPh$_3$)$_4$ (17.9 g, 15.5 mmol), NaOH (61.9 g, 1548 mmol), THF (2270 ml), and water (1134 ml) were added. Thereafter, the mixture was heated under reflux at 80-90° C. Upon completion of the reaction, the reaction product was diluted with distilled water at room temperature, followed by extraction with methylene chloride and water. The organic layer was dried over MgSO$_4$ and concentrated, and then the compound thus formed was subjected to silica gel column chromatography and recrystallization to give a product 152.6 g (yield: 77%).

(2) Synthesis of Sub 1-III-24

Sub 1-II-24 (151 g, 393.97 mmol) obtained in the above synthesis was dissolved in o-dichlorobenzene (1572 ml) in a round bottom flask, and then triphenylphosphine (309.2 g, 1179 mmol) was added, followed by stirring at 200° C. Upon completion of the reaction, o-dichlorobenzene was removed through distillation, followed by extraction with CH$_2$Cl$_2$ and water. The organic layer was dried over MgSO$_4$ and concentrated, and then the compound thus formed was subjected to silica gel column chromatography and recrystallization to give a product 59.5 g (yield: 43%).

(3) Synthesis of Sub 1-IV-24

Sub 1-III-24 (59 g, 167.5 mmol) was dissolved in nitrobenzene (838 ml) in a round bottom flask, and then 2-iodonaphthalene (46.8 g, 184.2 mmol), Na$_2$SO$_4$ (23.8 g, 167.5 mmol), K$_2$CO$_3$ (23.1 g, 167.5 mmol), and Cu (3.2 g, 50.2 mmol) were added, followed by stirring at 200° C. Upon completion of the reaction, nitrobenzene was removed through distillation, followed by extraction with CH$_2$Cl$_2$ and water. The organic layer was dried over MgSO$_4$ and concentrated, and then the compound thus formed was subjected to silica gel column chromatography and recrystallization to give a product 41.7 g (yield: 52%).

(4) Synthesis of Sub 1-V-24

In a round-bottom flask, Sub 1-IV-24 (40 g, 83.6 mmol) was added, and then (2-nitrophenyl)boronic acid (14 g, 83.6 mmol), Pd(PPh$_3$)$_4$ (2.9 g, 2.5 mmol), NaOH (10 g, 251 mmol), THF (368 ml), and water (184 ml) were added. Thereafter, the mixture was heated under reflux at 80-90° C. Upon completion of the reaction, the reaction product was diluted with distilled water at room temperature, followed by extraction with methylene chloride and water. The organic layer was dried over MgSO$_4$ and concentrated, and then the compound thus formed was subjected to silica gel column chromatography and recrystallization to give a product 34 g (yield: 78%).

(5) Synthesis of Sub 1-24

Sub 1-V-24 (28 g, 53.8 mmol) obtained in the above synthesis was dissolved in o-dichlorobenzene (215 ml) in a round bottom flask, and then triphenylphosphine (42.3 g, 161.4 mmol) was added, followed by stirring at 200° C. Upon completion of the reaction, o-dichlorobenzene was removed through distillation, followed by extraction with CH$_2$Cl$_2$ and water. The organic layer was dried over MgSO$_4$ and concentrated, and then the compound thus formed compound was subjected to silica gel column chromatography and recrystallization to give a product 16.6 g (yield: 63%).

2. Synthesis of Sub 1-36

<Reaction Scheme 4>

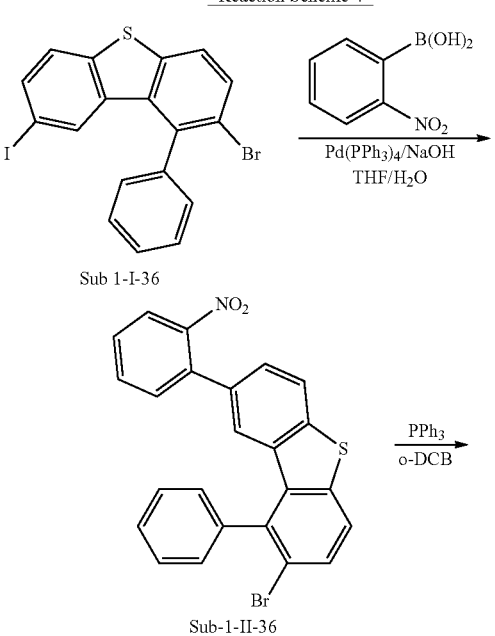

Sub 1-I-36

Sub-1-II-36

-continued

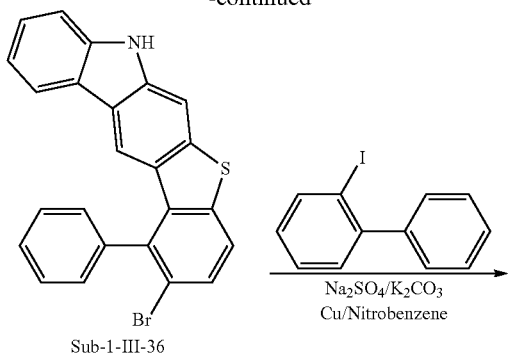
Sub-1-III-36

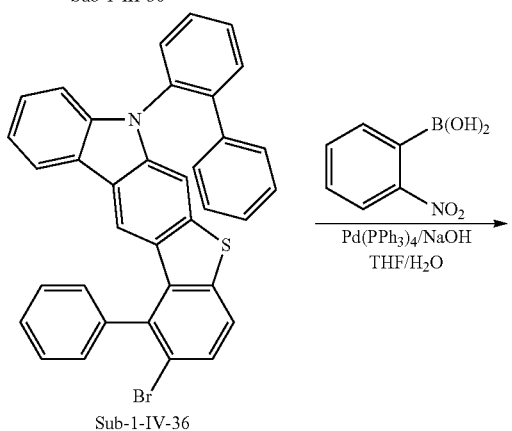
Sub-1-IV-36

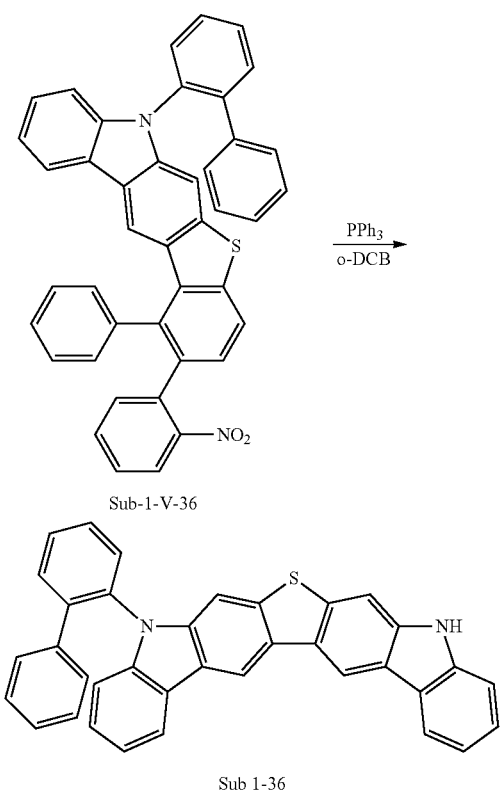

Sub-1-V-36

Sub 1-36

(1) Synthesis of Sub 1-II-36

The synthesis method for Sub 1-II-24 was employed using Sub 1-I-36 (241 g, 518.1 mmol), (2-nitrophenyl) boronic acid (86.5 g, 518.1 mmol), Pd(PPh$_3$)$_4$ (18 g, 15.5 mmol), NaOH (62.2 g, 1554 mmol), THF (2280 ml), and water (1140 ml) to give a product 188.4 g (yield: 79%).

(2) Synthesis of Sub 1-III-36

The synthesis method for Sub 1-III-24 was employed using Sub 1-II-36 (187 g, 406.2 mmol), o-dichlorobenzene (1645 ml), and triphenylphosphine (319.6 g, 1218.7 mmol) to give a product 71.3 g (yield: 41%).

(3) Synthesis of Sub 1-IV-36

The synthesis method for Sub 1-IV-24 was employed using Sub 1-III-36 (70.5 g, 164.6 mmol), nitrobenzene (823 ml), 2-iodo-1,1'-biphenyl (50.7 g, 181 mmol), Na$_2$SO$_4$ (23.4 g, 164.6 mmol), K$_2$CO$_3$ (22.7 g, 164.6 mmol), and Cu (3.1 g, 49.4 mmol) to give a product 48.6 g (yield: 49%).

(4) Synthesis of Sub 1-V-36

The synthesis method for Sub 1-V-24 was employed using Sub 1-IV-36 (46 g, 79.2 mmol), (2-nitrophenyl)boronic acid (13.2 g, 79.2 mmol), Pd(PPh$_3$)$_4$ (2.7 g, 2.4 mmol), NaOH (9.5 g, 238 mmol), THF (349 ml), and water (174 ml) to give a product 35.5 g (yield: 72%).

(5) Synthesis of Sub 1-36

The synthesis method for Sub 1-24 was employed using Sub 1-V-36 (33 g, 53 mmol) obtained from the synthesis above, o-dichlorobenzene (212 ml), and triphenylphosphine (41.7 g, 159 mmol) to give a product 16.4 g (yield: 60%).

3. Synthesis of Sub 1-59

<Reaction Scheme 5>

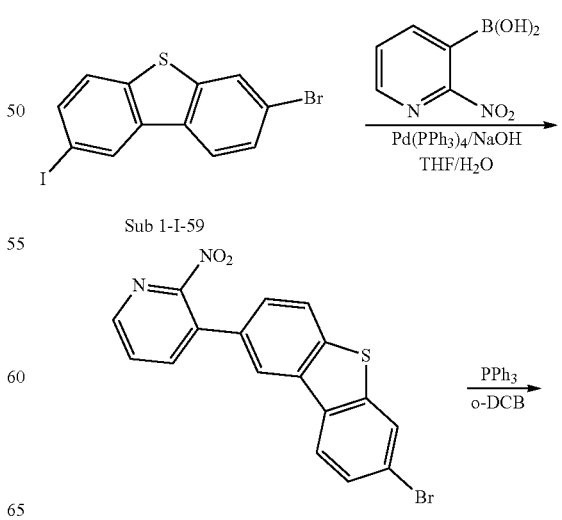
Sub 1-I-59

Sub-1-II-59

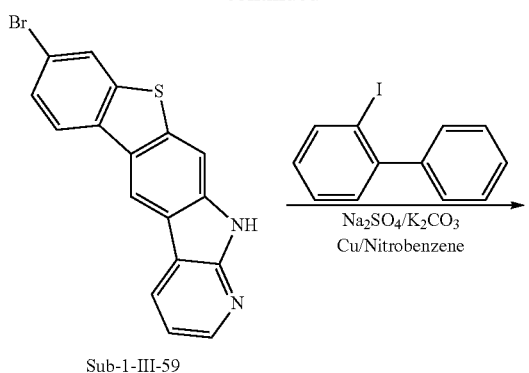

Sub-1-III-59

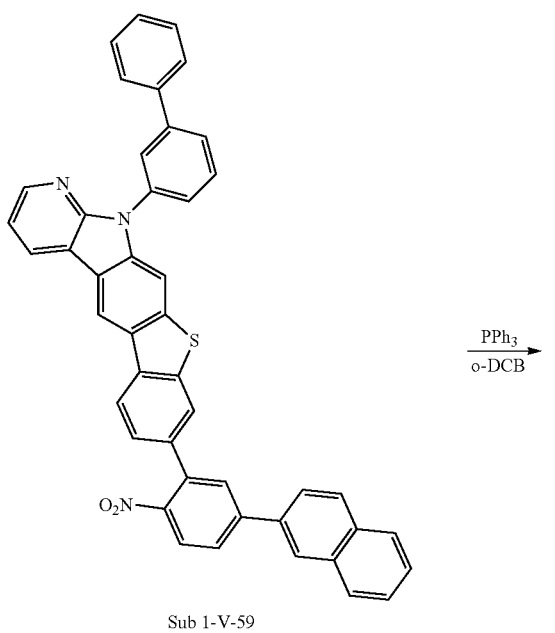

Sub-1-V-59

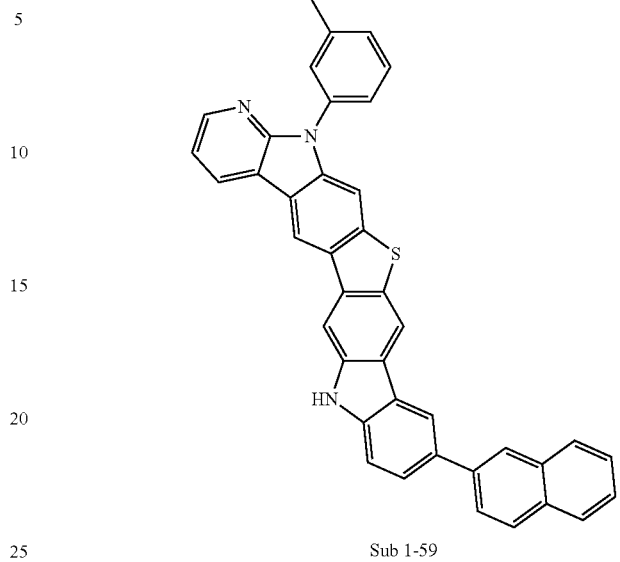

Sub 1-59

(1) Synthesis of Sub 1-II-59

The synthesis method for Sub 1-II-24 was employed using Sub 1-I-59 (357.5 g, 918.9 mmol), (2-nitropyridin-3-yl)boronic acid (154.3 g, 918.9 mmol), Pd(PPh$_3$)$_4$ (31.9 g, 27.6 mmol), NaOH (110.3 g, 2757 mmol), THF (4043 ml), and water (2021 ml) to give a product 215.9 g (yield: 61%).

(2) Synthesis of Sub 1-III-59

The synthesis method for Sub 1-III-34 was employed using Sub 1-II-59 (215.5 g, 559.4 mmol), o-dichlorobenzene (2237 ml), and triphenylphosphine (440.2 g, 1678.2 mmol) to give a product 84.97 g (yield: 43%).

(3) Synthesis of Sub 1-IV-59

The synthesis method for Sub 1-IV-24 was employed using Sub 1-III-59 (84.6 g, 239.5 mmol), nitrobenzene (1200 ml), 2-iodo-1,1'-biphenyl (73.8 g, 263.4 mmol), Na$_2$SO$_4$ (34 g, 239.5 mmol), K$_2$CO$_3$ (33.1 g, 239.5 mmol), Cu (4.6 g, 71.8 mmol) to give a product 50.8 (yield: 42%).

(4) Synthesis of Sub 1-V-59

The synthesis method for Sub 1-V-24 was employed using Sub 1-IV-59 (50 g, 98.9 mmol), (5-(naphthalen-2-yl)-2-nitrophenyl)boronic acid (29 g, 98.9 mmol), Pd(PPh$_3$)$_4$ (3.4 g, 2.97 mmol), NaOH (11.9 g, 297 mmol), THF (435 ml), and water (218 ml) to give a product 41.3 g (yield: 62%).

(5) Synthesis of Sub 1-59

The synthesis method for Sub 1-24 was employed using Sub 1-V-59 (40 g, 59.4 mmol) obtained from the synthesis above, o-dichlorobenzene (237 ml), and triphenylphosphine (46.7 g, 178 mmol) to give a product 16 g (yield: 42%).

4. Synthesis of Sub 1-71

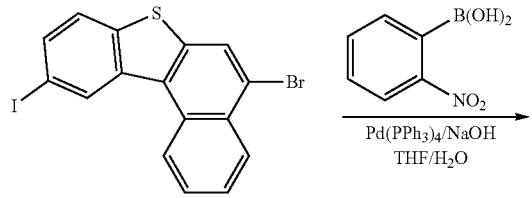

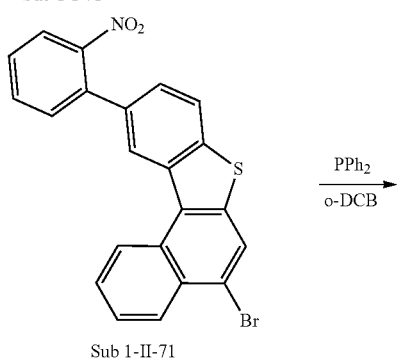

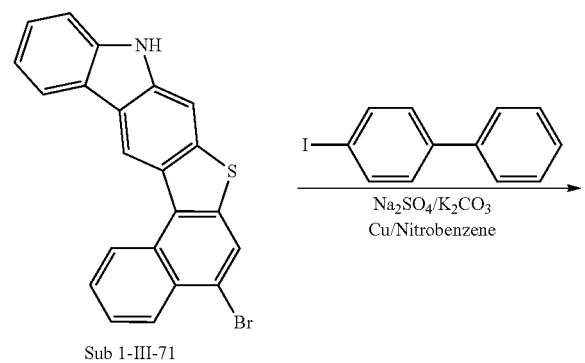

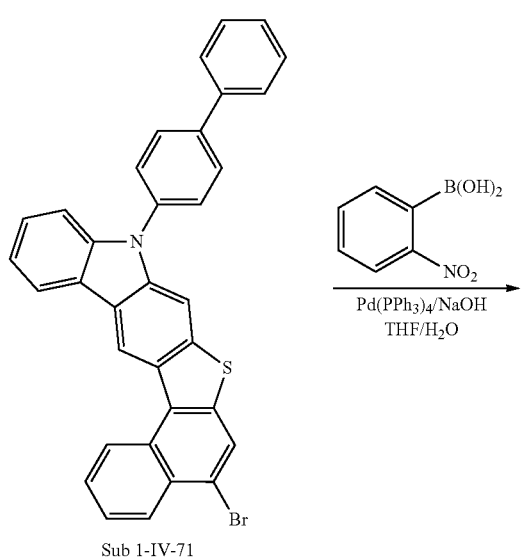

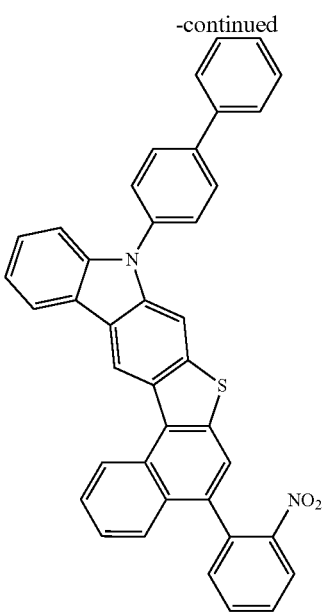

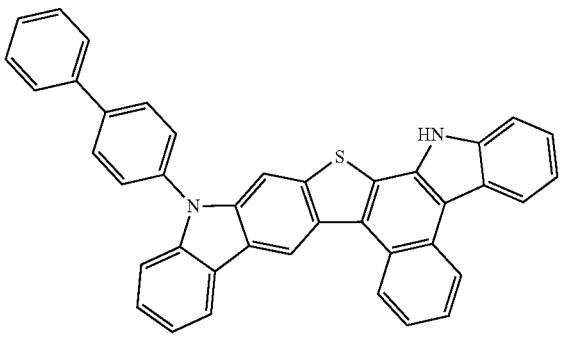

(1) Synthesis of Sub 1-II-71

The synthesis method for Sub 1-II-24 was employed using Sub 1-I-71 (308 g, 701.4 mmol), (2-nitrophenyl) boronic acid (117.1 g, 701.4 mmol), Pd(PPh$_3$)$_4$ (24.3 g, 21 mmol), NaOH (84.2 g, 2104 mmol), THF (3086 ml), and water (1543 ml) to give a product 219.3 g (yield: 72%).

(2) Synthesis of Sub 1-III-71

The synthesis method for Sub 1-III-34 was employed using Sub 1-II-71 (220 g, 506.5 mmol), o-dichlorobenzene (2,026 ml), and triphenylphosphine (398.6 g, 1519.7 mmol) to give a product 87.6 g (yield: 43%).

(3) Synthesis of Sub 1-IV-71

The synthesis method for Sub 1-IV-24 was employed using Sub 1-III-71 (79 g, 196.4 mmol), nitrobenzene (982 ml), 4-iodo-1,1'-biphenyl (60.5 g, 216 mmol), Na$_2$SO$_4$ (27.9 g, 196.4 mmol), K$_2$CO$_3$ (27.1 g, 196.4 mmol), and Cu (3.7 g, 58.9 mmol) to give a product 49 g (yield: 45%).

(4) Synthesis of Sub 1-V-71

The synthesis method for Sub 1-V-24 was employed using Sub 1-IV-71 (48 g, 86.6 mmol), (2-nitrophenyl)boronic acid (14.5 g, 86.6 mmol), Pd(PPh$_3$)$_4$ g, 2.6 mmol), NaOH (10.4 g, 259.7 mmol), THF (381 ml), and water (190 ml) to give a product 35.1 g (yield: 68%).

(5) Synthesis of Sub 1-71

The synthesis method for Sub 1-24 was employed using Sub 1-V-71 (31 g, 52 mmol) obtained from the synthesis above, o-dichlorobenzene (208 ml), and triphenylphosphine (40.9 g, 156 mmol) to give a product 13.2 g (yield: 45%).

5. Synthesis of Sub 1-63

<Reaction Scheme 7>

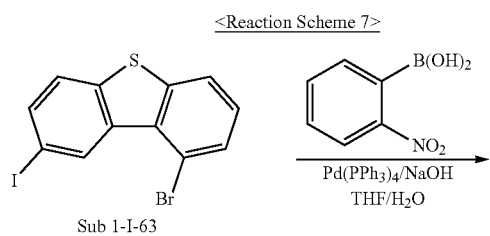

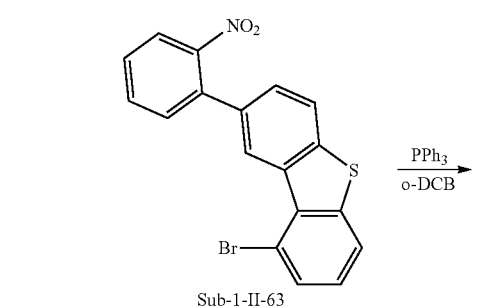

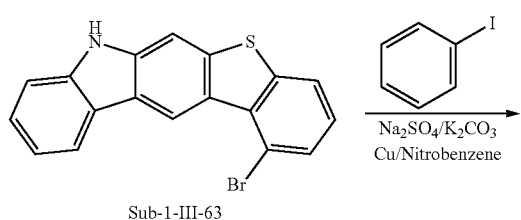

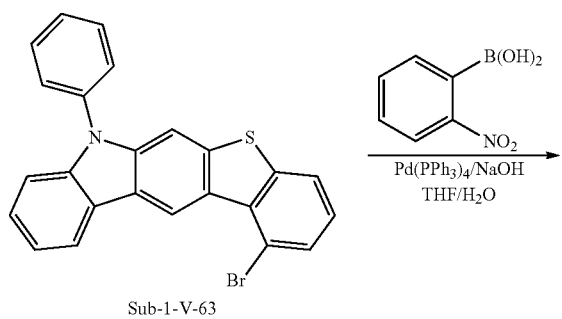

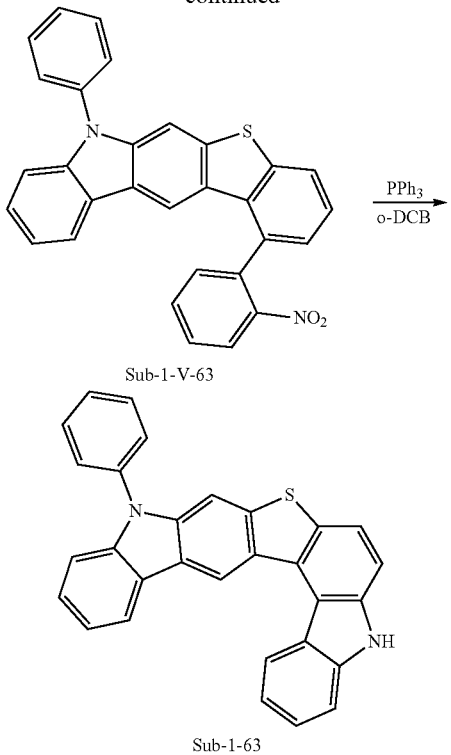

(1) Synthesis of Sub 1-II-63

The synthesis method for Sub 1-II-24 was employed using Sub 1-I-63 (251 g, 645.2 mmol), (2-nitrophenyl)boronic acid (107.7 g, 645.2 mmol), Pd(PPh$_3$)$_4$ (22.4 g, 19.4 mmol), NaOH (77.4 g, 1935 mmol), THF (2839 ml), and water (1419 ml) to give a product 188.4 g (yield: 76%).

(2) Synthesis of Sub 1-III-63

The synthesis method for Sub 1-III-24 was employed using Sub 1-II-63 (105 g, 273.3 mmol), o-dichlorobenzene (1093 ml), and triphenylphosphine (215 g, 819.8 mmol) to give a product 40.4 g (yield: 42%).

(3) Synthesis of Sub 1-IV-63

The synthesis method for Sub 1-IV-24 was employed using Sub 1-III-63 (38 g, 107.9 mmol), nitrobenzene (540 ml), iodobenzene (24.2 g, 118.7 mmol), Na$_2$SO$_4$ (15.3 g, 107.9 mmol), K$_2$CO$_3$ (14.9 g, 107.9 mmol), and Cu (2.1 g, 32.4 mmol) to give a product 31.9 g (yield: 69%).

(4) Synthesis of Sub 1-V-63

The synthesis method for Sub 1-V-24 was employed using Sub 1-IV-63 (31 g, 72.4 mmol), (2-nitrophenyl)boronic acid (12.1 g, 72.4 mmol), Pd(PPh$_3$)$_4$ (2.5 g, 2.2 mmol), NaOH (8.7 g, 217.1 mmol), THF (318 ml), and (159 ml) to give a product 26.9 g (yield: 79%).

(5) Synthesis of Sub 1-63

The synthesis method for Sub 1-24 was employed using Sub 1-V-63 (26 g, 55 mmol) obtained from the synthesis above, o-dichlorobenzene (221 ml), and triphenylphosphine (43.5 g, 166 mmol) to give a product 16.5 g (yield: 68%).

6. Synthesis of Sub 1-107

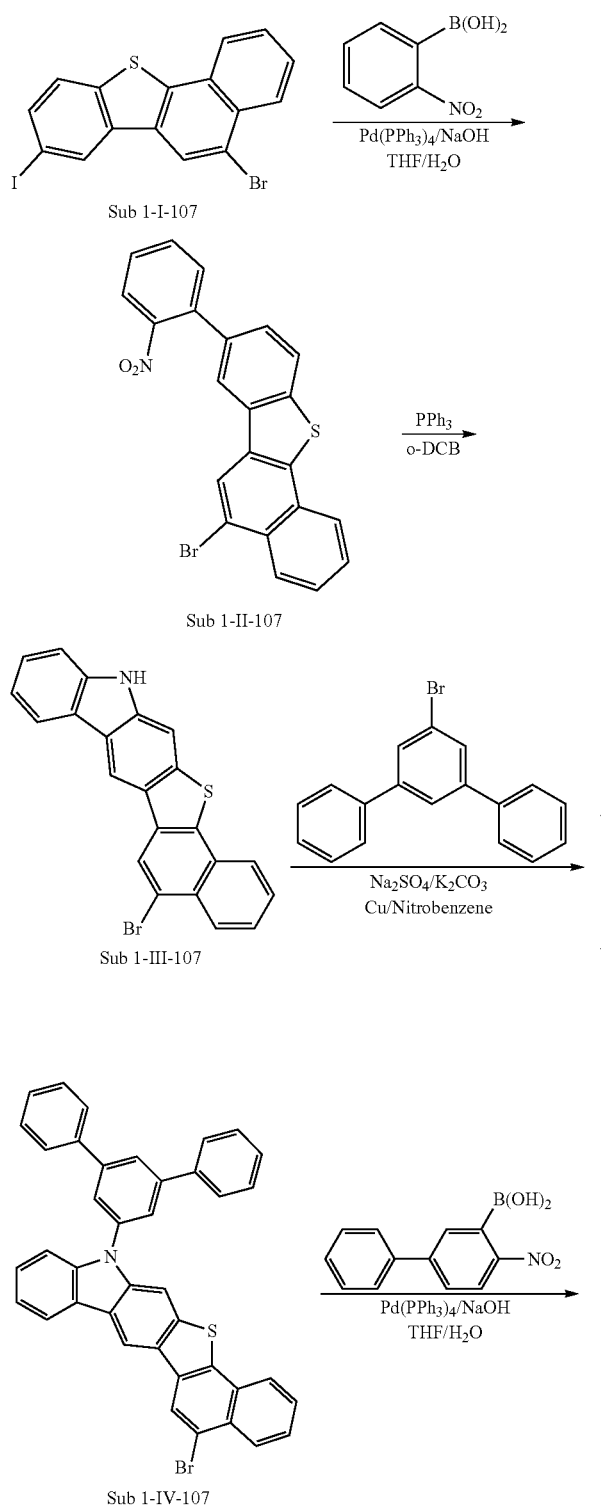

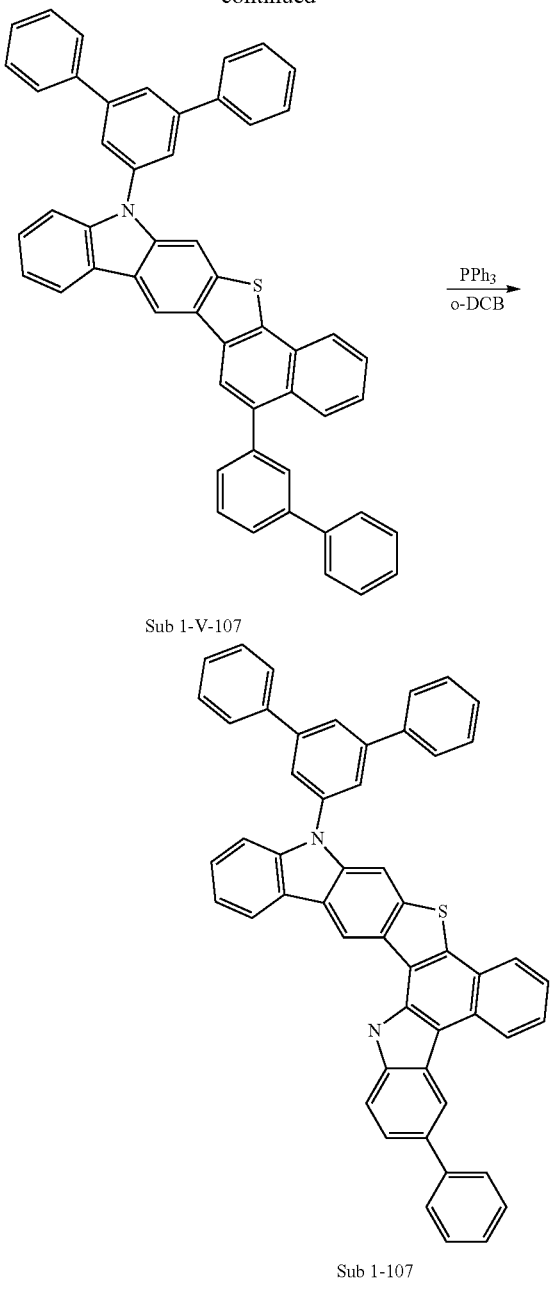

(1) Synthesis of Sub 1-II-107

The synthesis method for Sub 1-II-24 was employed using Sub 1-I-107 (275 g, 626.3 mmol), (2-nitrophenyl)boronic acid (104.5 g, 626.3 mmol), Pd(PPh$_3$)$_4$ (21.7 g, 18.8 mmol), NaOH (75.2 g, 1879 mmol), THF (2756 ml), and water (1378 ml) to give a product 190.4 g (yield: 70%).

(2) Synthesis of Sub 1-III-107

The synthesis method for Sub 1-III-24 was employed using Sub 1-II-107 (189.5 g, 436.3 mmol), o-dichlorobenzene (1745 ml), and triphenylphosphine (343.3 g, 1309 mmol) to give a product 82.5 g (yield: 47%).

(3) Synthesis of Sub 1-IV-107

The synthesis method for Sub 1-IV-24 was employed using Sub 1-III-107 (82.2 g, 204.3 mmol), nitrobenzene (1022 ml), 5'-bromo-1,1':3',1''-terphenyl (69.5 g, 224.8 mmol), Na$_2$SO$_4$ (29 g, 204.3 mmol), K$_2$CO$_3$ (28.2 g, 204.3 mmol), and Cu (3.9 g, 61.3 mmol) to give a product 60.6 g (yield: 47%).

(4) Synthesis of Sub 1-V-107

The synthesis method for Sub 1-V-24 was employed using Sub 1-IV-107 (60 g, 95.1 mmol), (4-nitro-[1,1'-biphenyl]-3-yl)boronic acid (23.1 g, 95.1 mmol), Pd(PPh$_3$)$_4$ (3.3 g, 2.9 mmol), NaOH (11.4 g, 285.4 mmol), THF (419 ml), and water (209 ml) to give a product 36.3 g (yield: 51%).

(5) Synthesis of Sub 1-107

The synthesis method for Sub 1-24 was employed using Sub 1-V-107 (35 g, 46.7 mmol) obtained from the synthesis above, o-dichlorobenzene (187 ml), and triphenylphosphine (36.8 g, 140 mmol) to give a product 16.4 g (yield: 49%).

Meanwhile, the compounds pertaining to Sub 1 may be compounds below, but are not limited thereto. Table 1 below shows FD-MS values of the compounds pertaining to Sub 1.

Sub 1-1

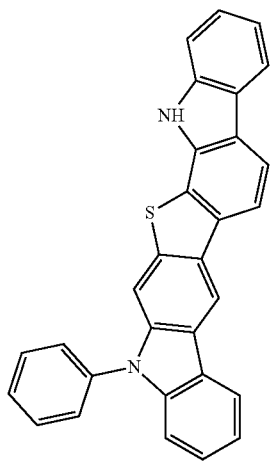

Sub 1-2

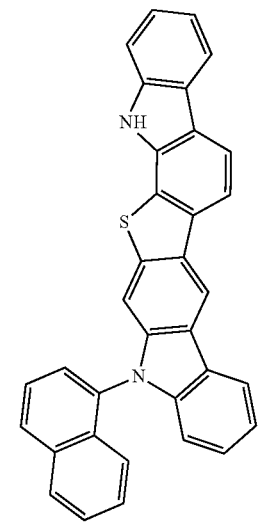

-continued

Sub 1-3

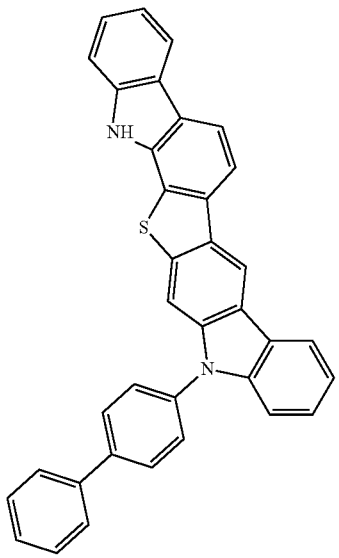

Sub 1-4

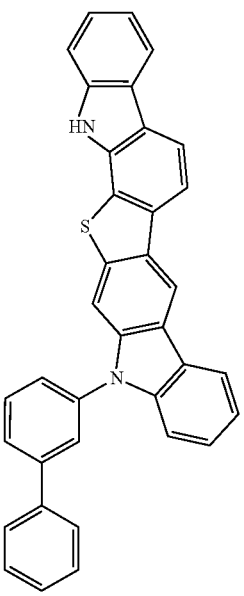

Sub 1-5
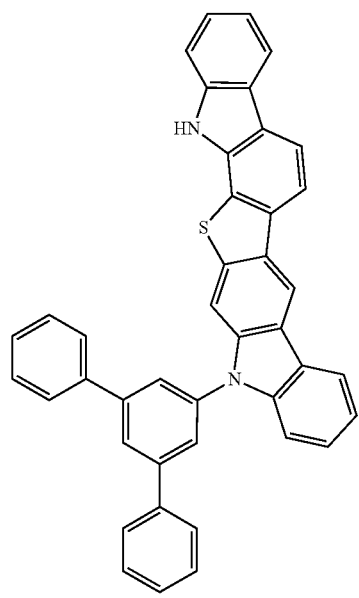
Sub 1-6
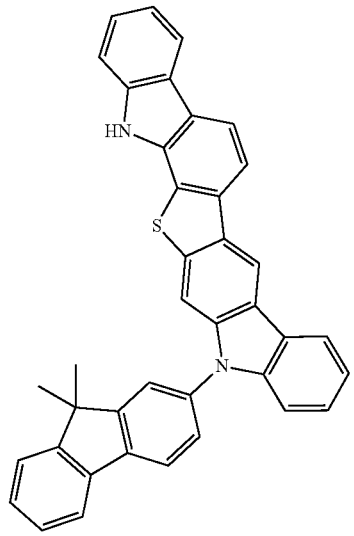
Sub 1-7
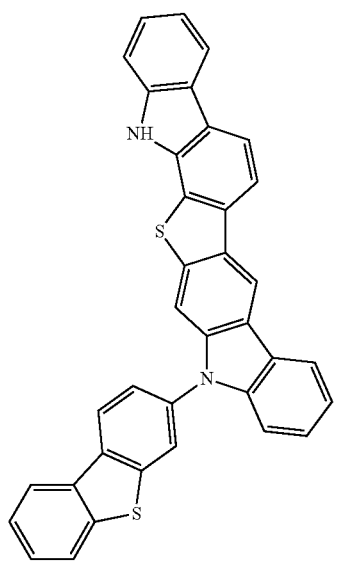
Sub 1-8
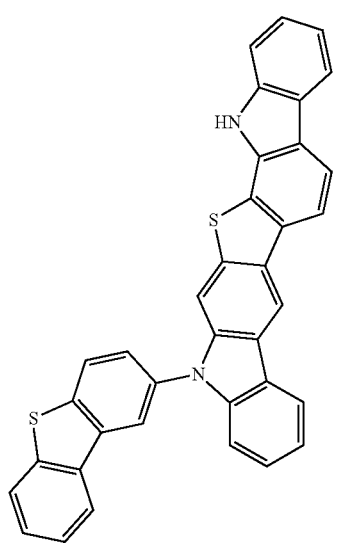
Sub 1-9
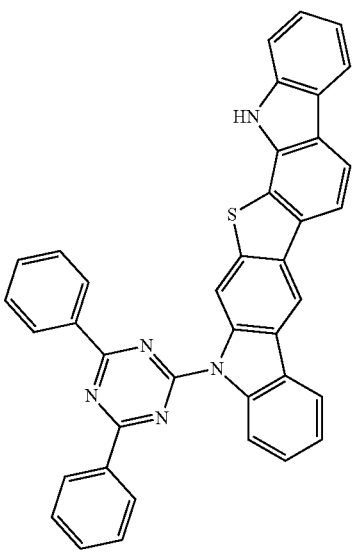

Sub 1-10
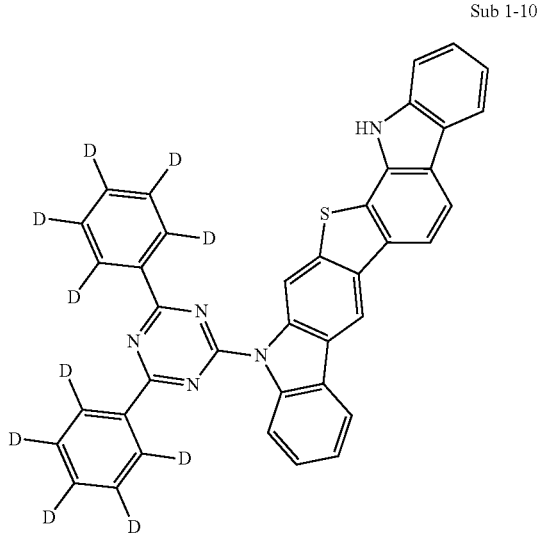
Sub 1-11
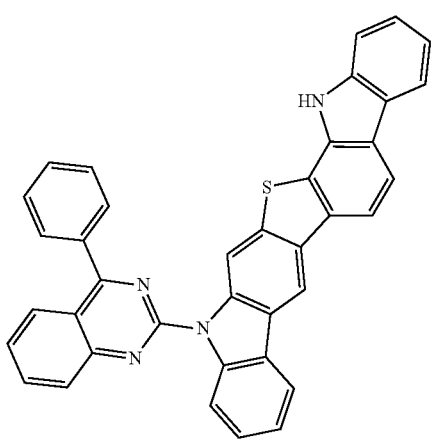
Sub 1-12
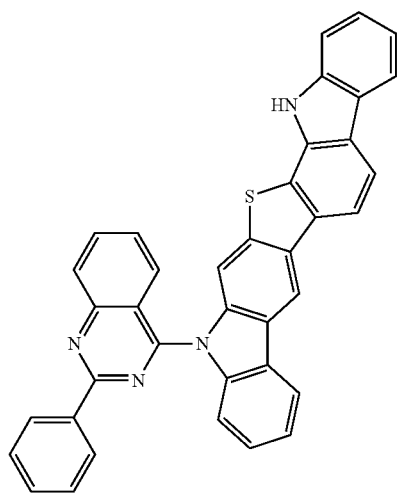
Sub 1-13
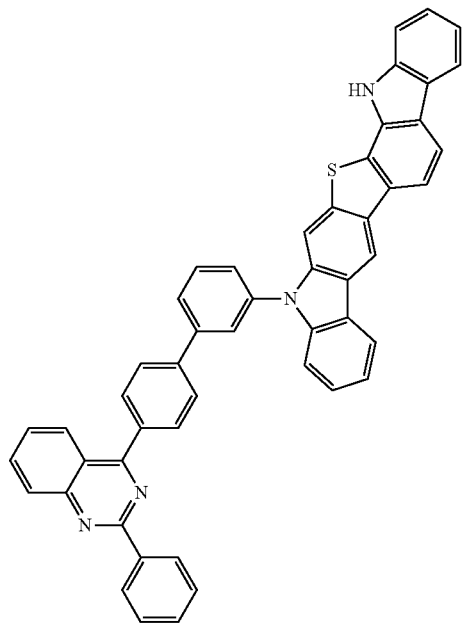
Sub 1-14
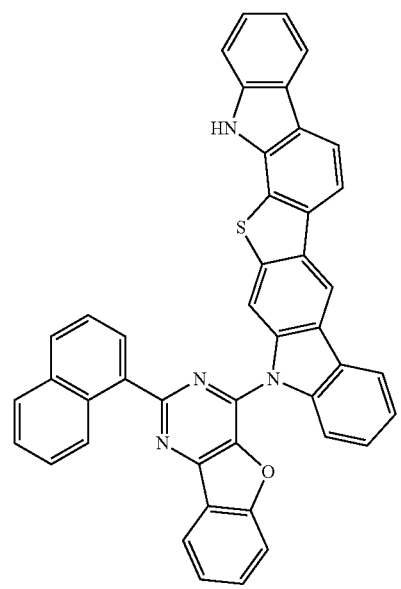

Sub 1-15
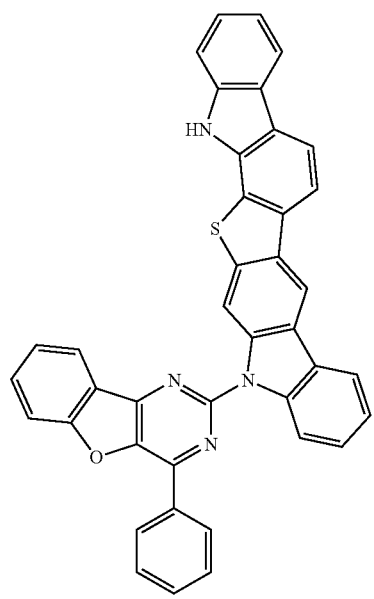
Sub 1-16
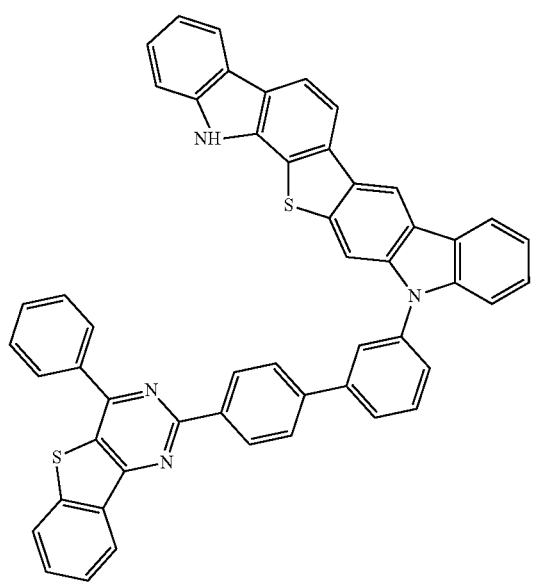
Sub 1-17
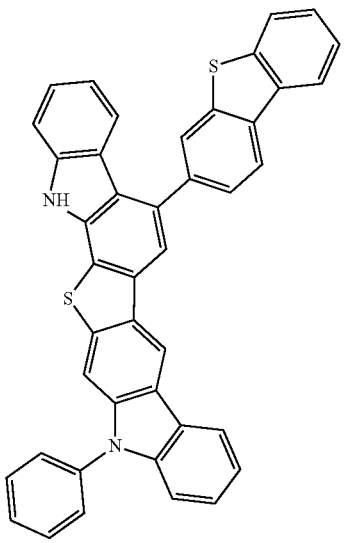
Sub 1-18
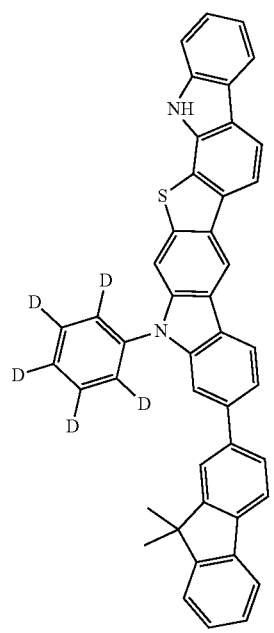

Sub 1-19
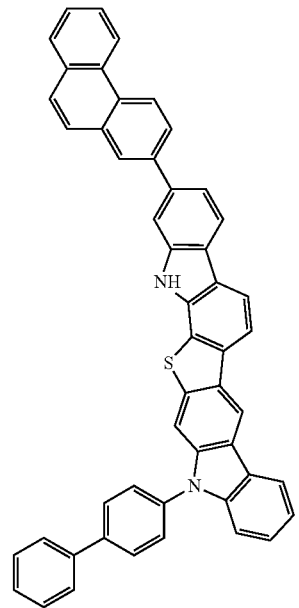
Sub 1-20
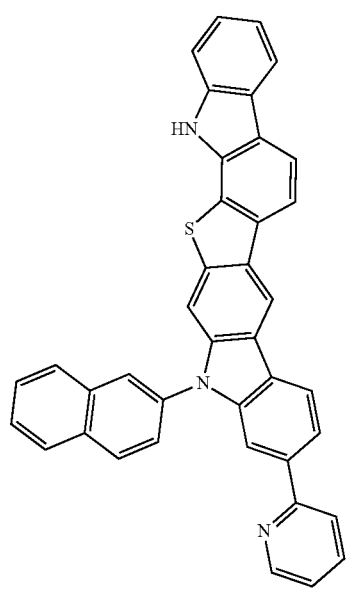
Sub 1-21
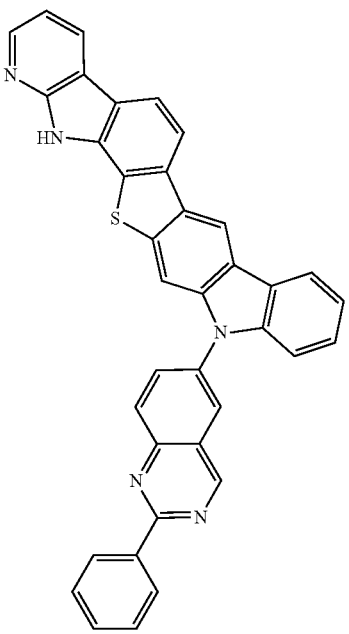
Sub 1-22
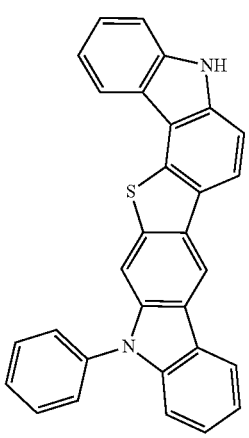
Sub 1-23
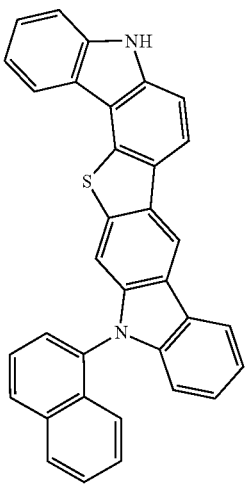

Sub 1-24
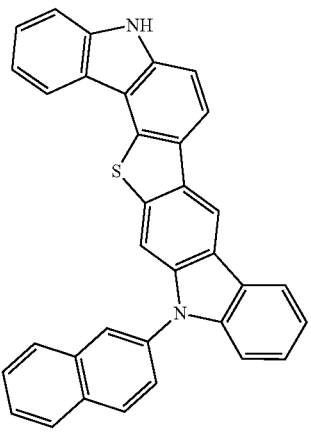
Sub 1-25
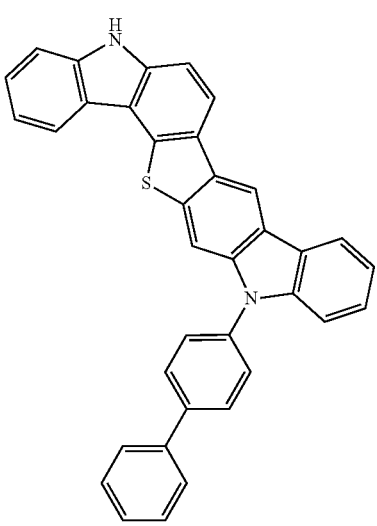
Sub 1-26
Sub 1-27
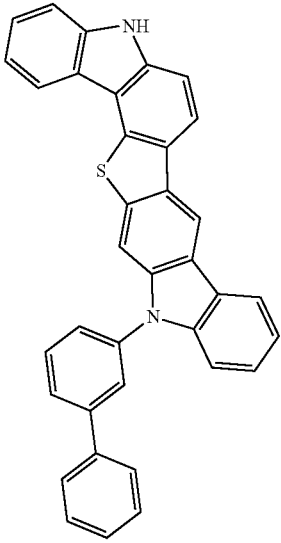
Sub 1-28
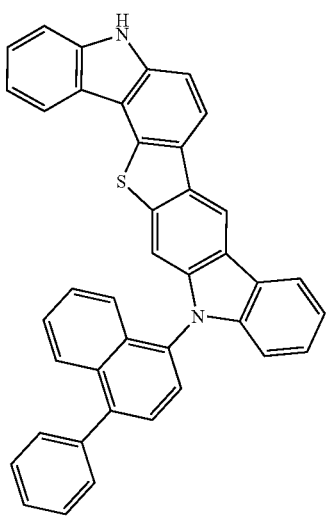
Sub 1-29
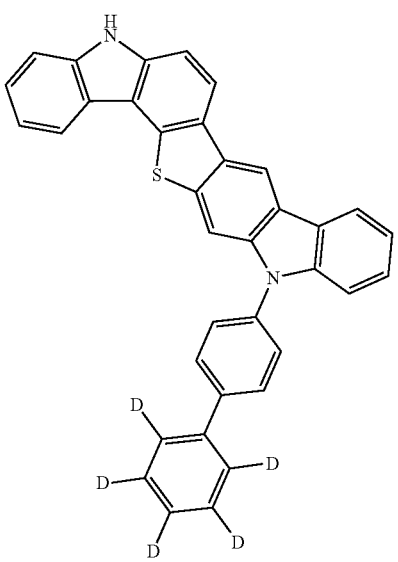

Sub 1-30
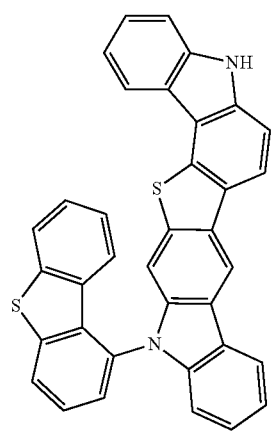
Sub 1-31
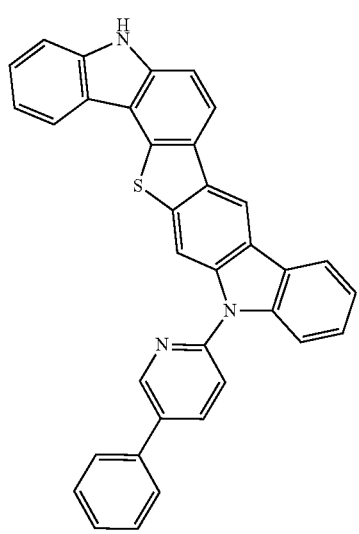
Sub 1-32
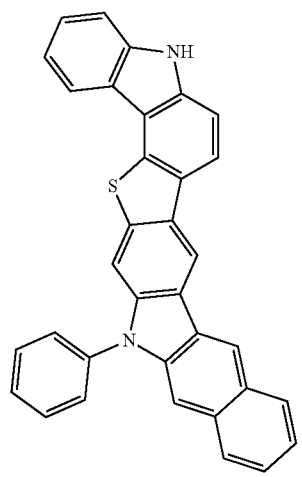
Sub 1-33
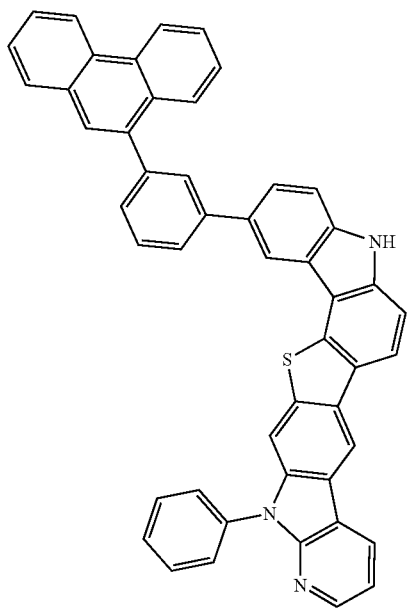
Sub 1-34
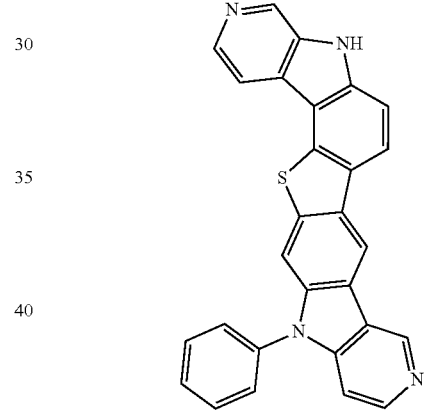
Sub 1-35
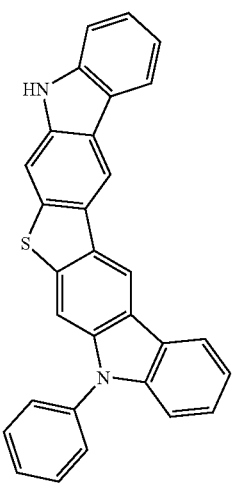

Sub 1-36
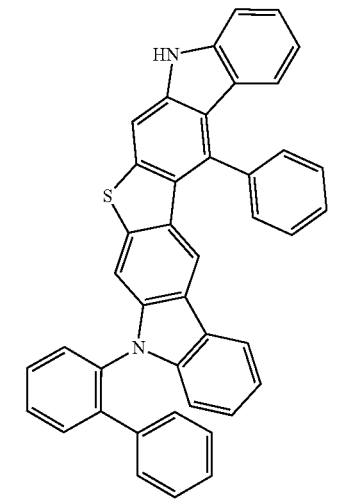
Sub 1-37
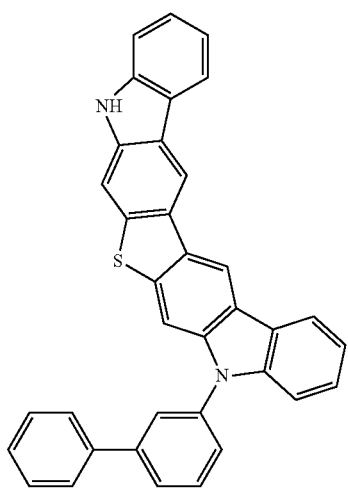
Sub 1-38
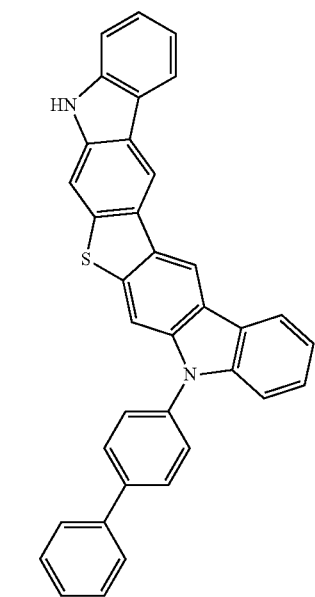
Sub 1-39
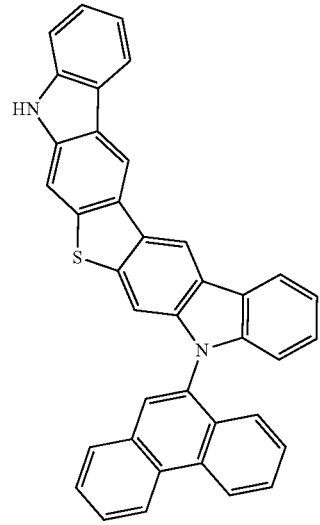
Sub 1-40
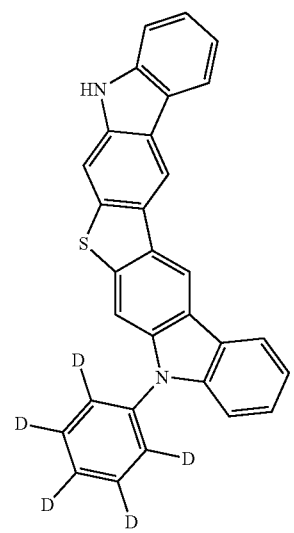
Sub 1-41
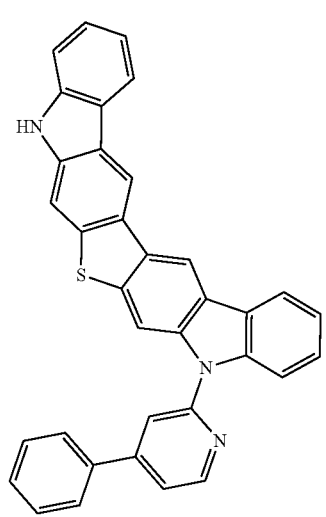

Sub 1-42
Sub 1-43
Sub 1-44
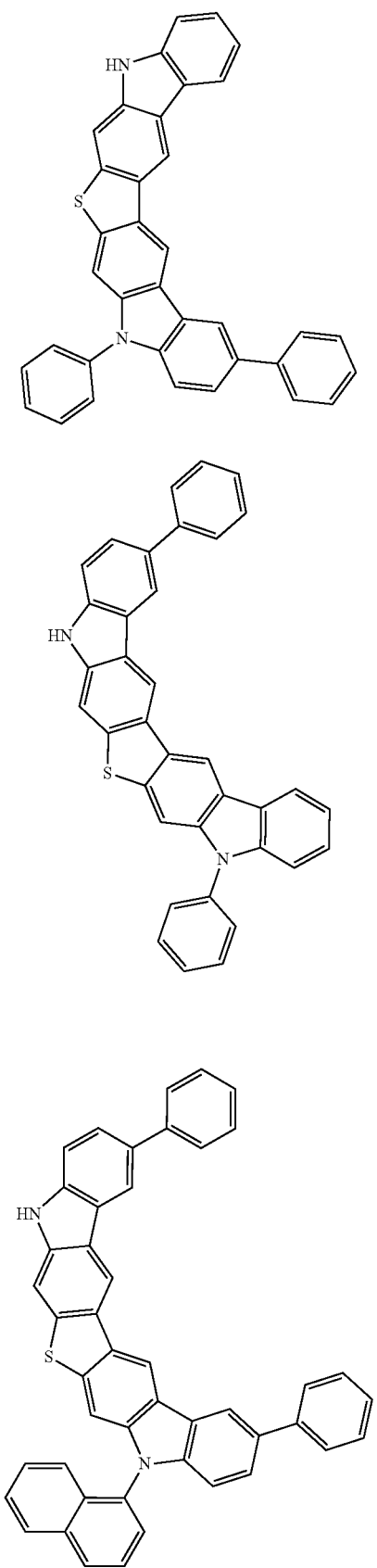
Sub 1-45
Sub 1-46
Sub 1-47
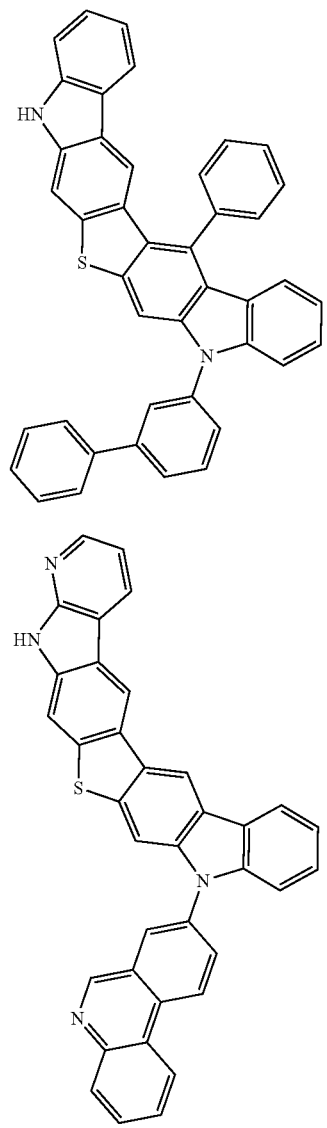

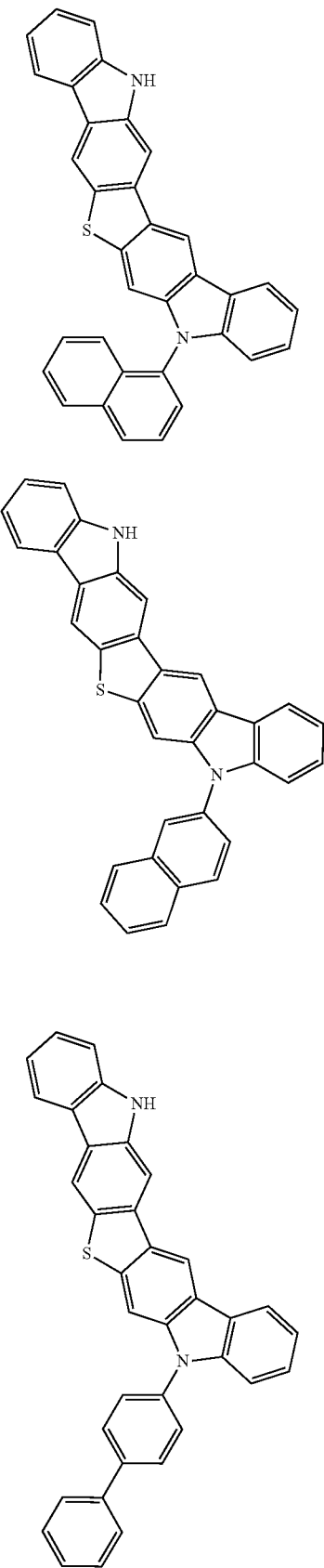
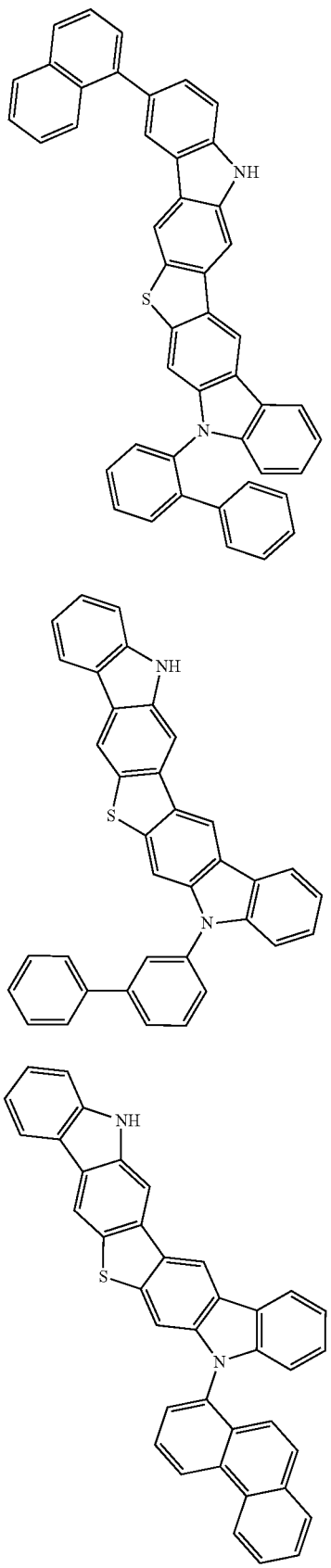
Sub 1-48
Sub 1-49
Sub 1-50
Sub 1-51
Sub 1-52
Sub 1-53

-continued
Sub 1-54
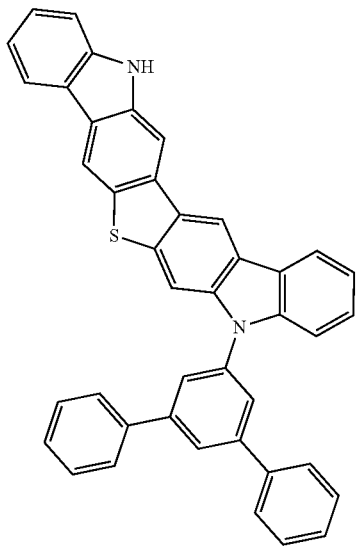
Sub 1-55
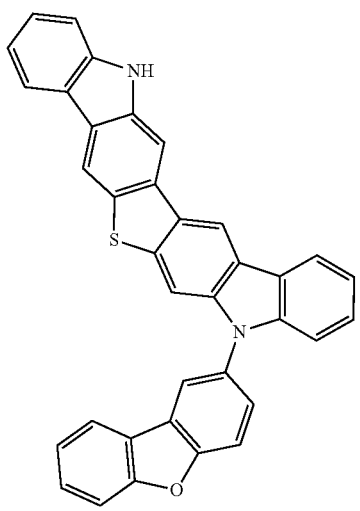
Sub 1-56
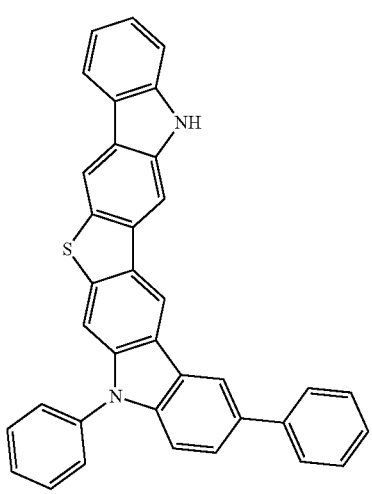
Sub 1-57
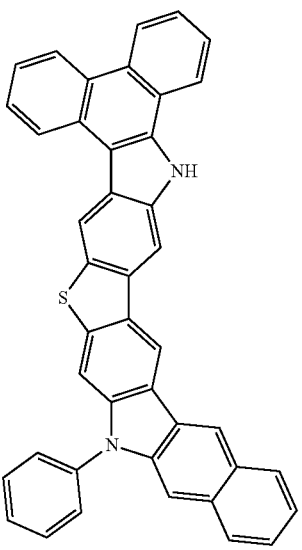
Sub 1-58
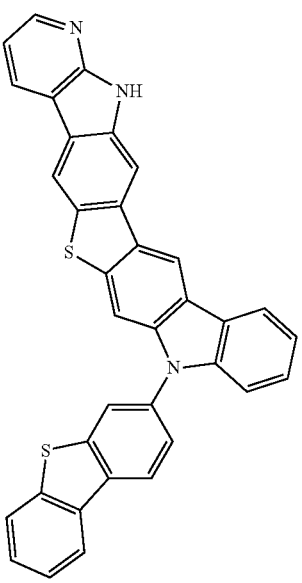

Sub 1-59
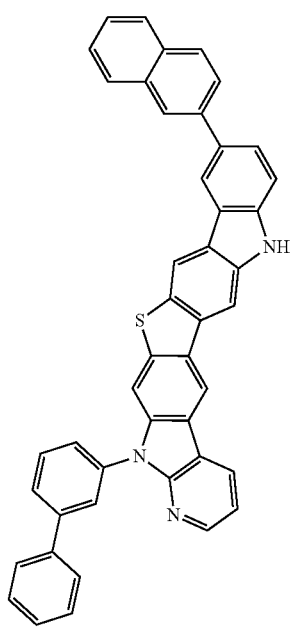
Sub 1-60
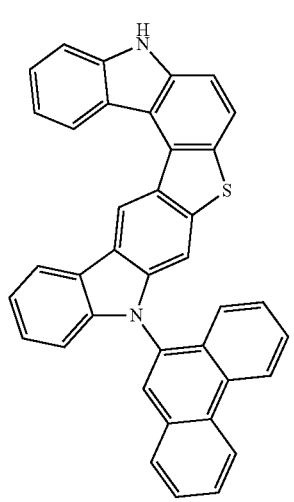
Sub 1-61
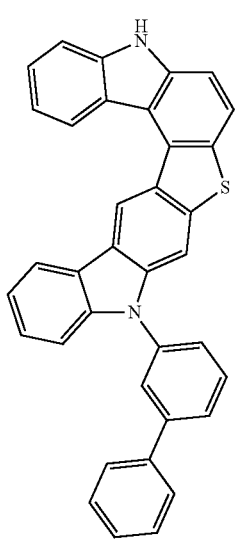
Sub 1-62
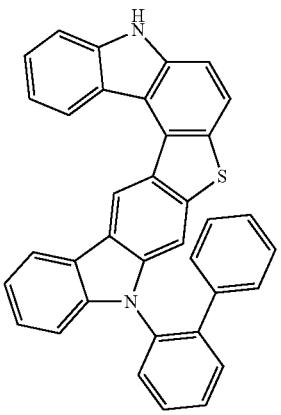
Sub 1-63
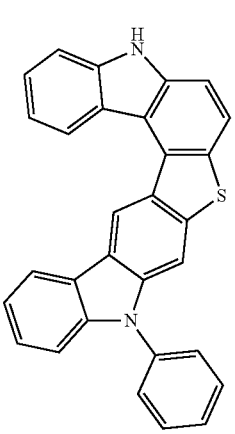
Sub 1-64
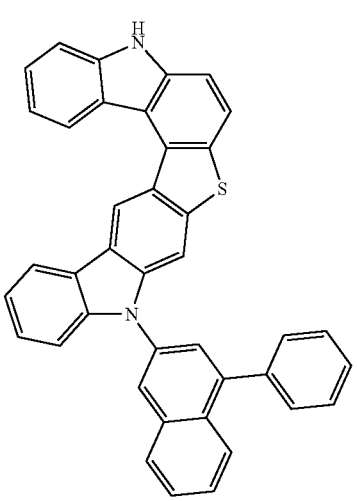

Sub 1-65
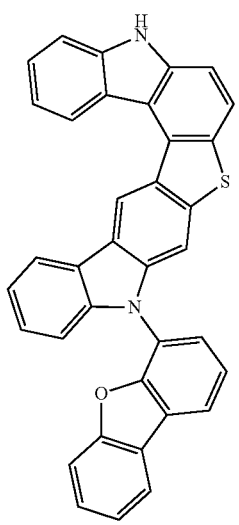
Sub 1-68
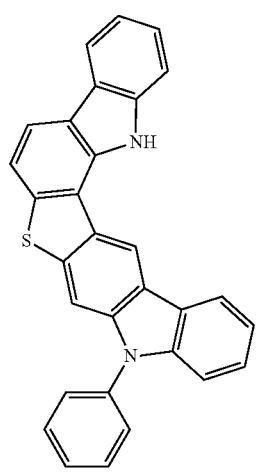
Sub 1-66
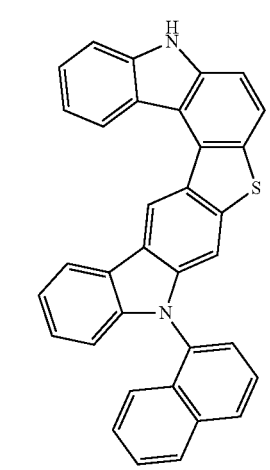
Sub 1-69
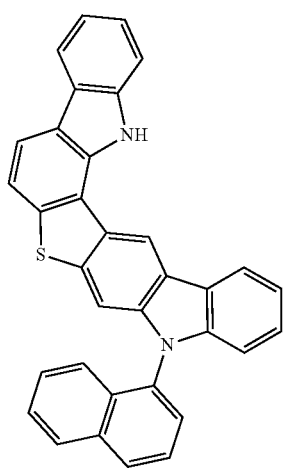
Sub 1-67
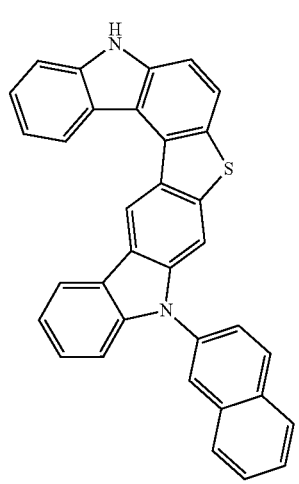
Sub 1-70
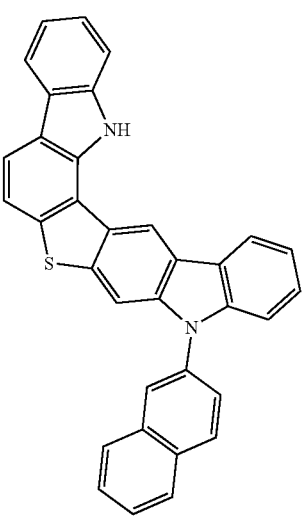

-continued
Sub 1-71
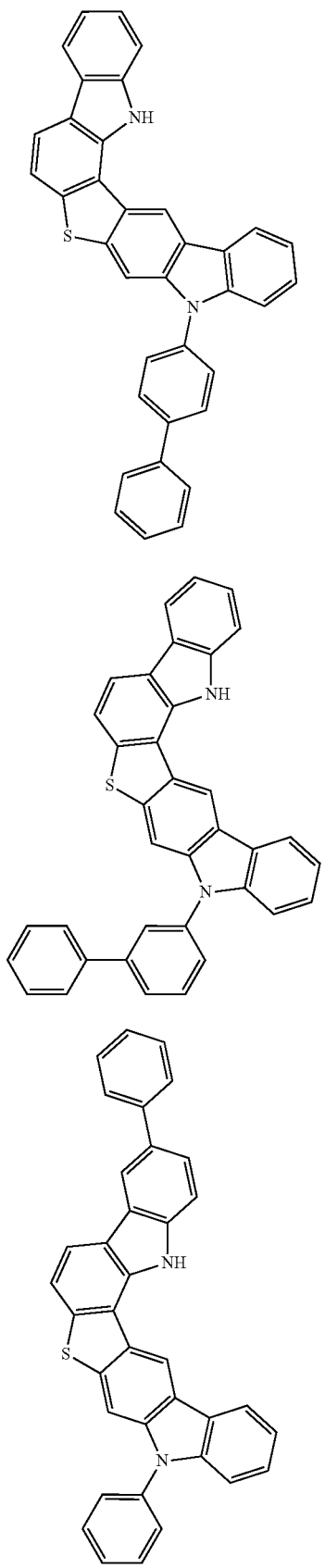
Sub 1-72
Sub 1-73
-continued
Sub 1-74
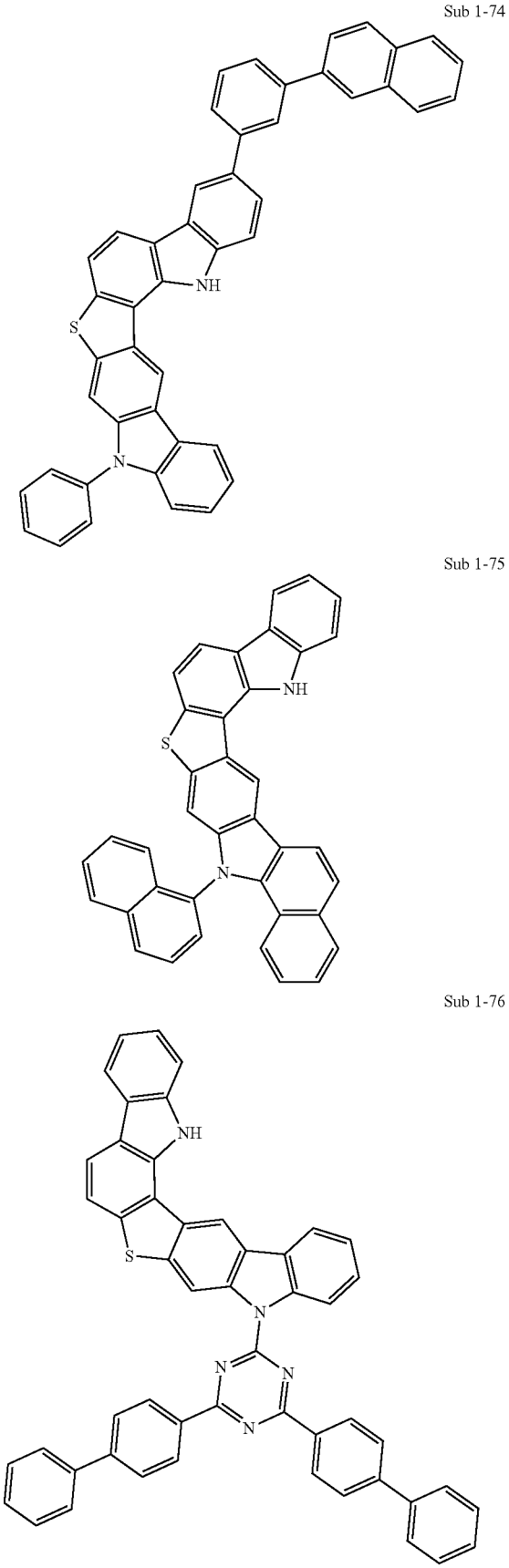
Sub 1-75
Sub 1-76

-continued
Sub 1-77
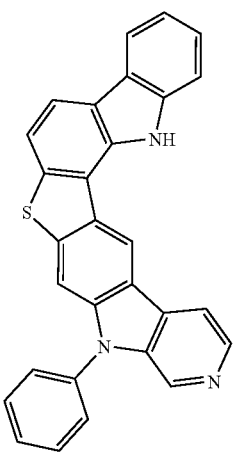
Sub 1-78
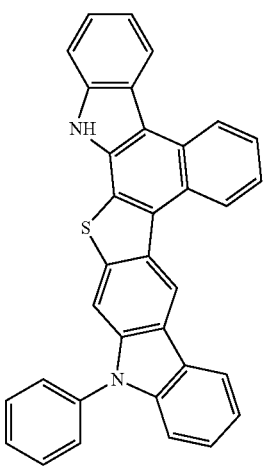
Sub 1-79
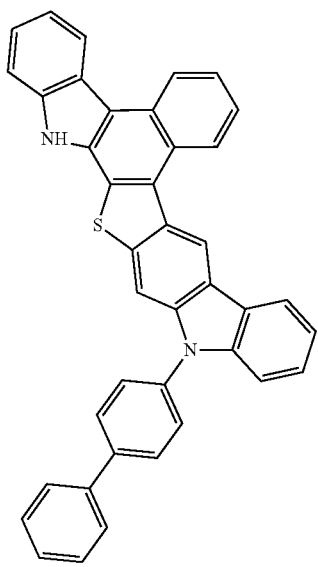
-continued
Sub 1-80
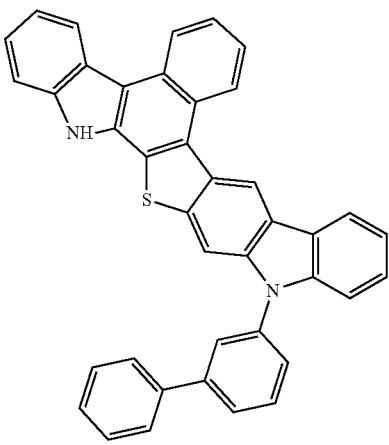
Sub 1-81
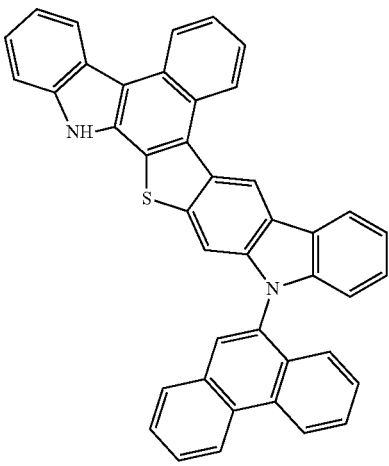
Sub 1-82
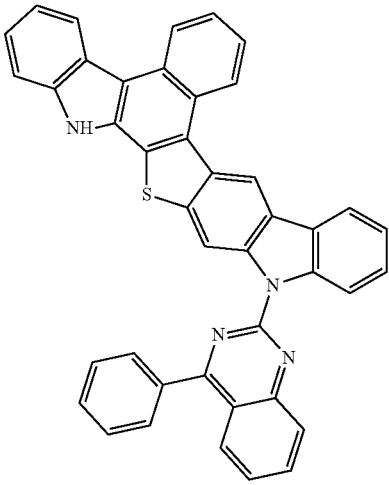

Sub 1-83
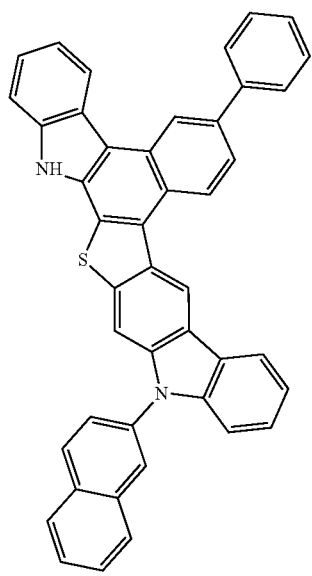
Sub 1-86
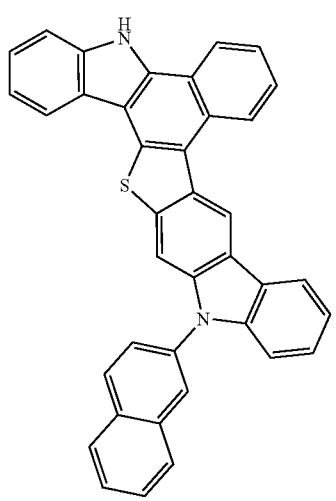
Sub 1-84
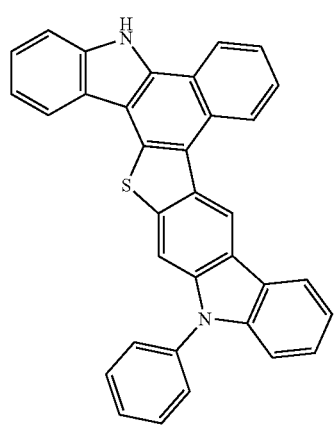
Sub 1-87
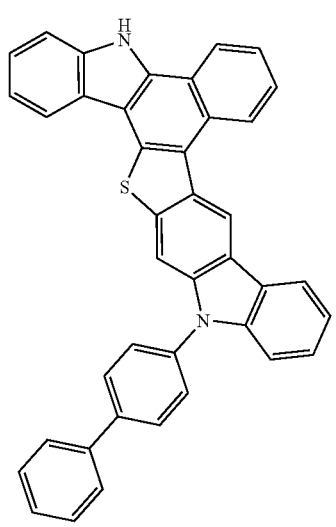
Sub 1-85
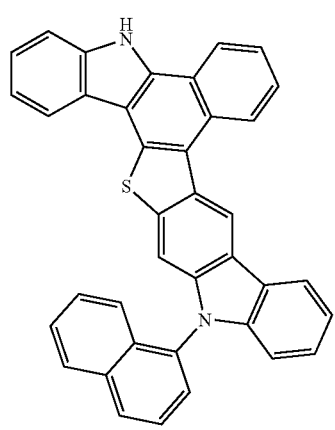
Sub 1-88
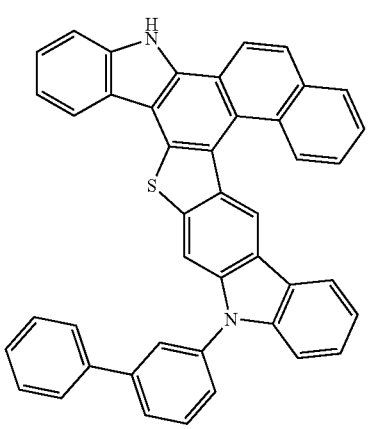

Sub 1-89
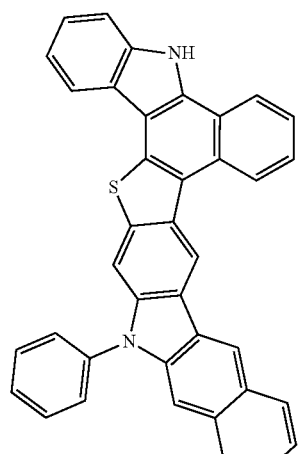
Sub 1-90
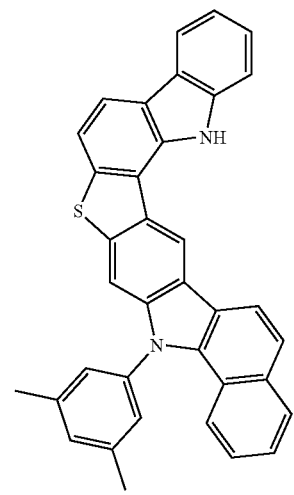
Sub 1-91
Sub 1-92
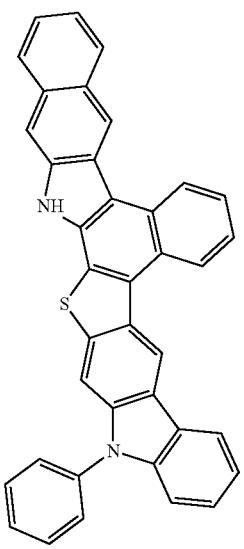
Sub 1-93
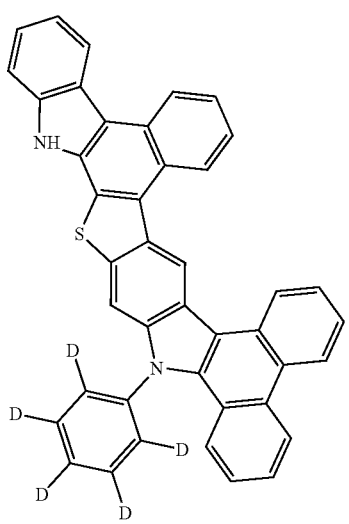
Sub 1-94
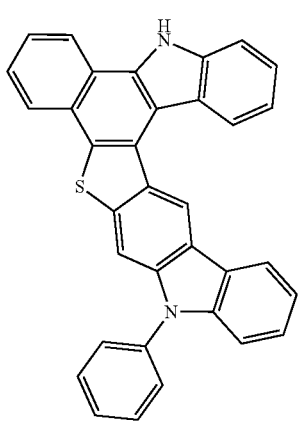

Sub 1-95
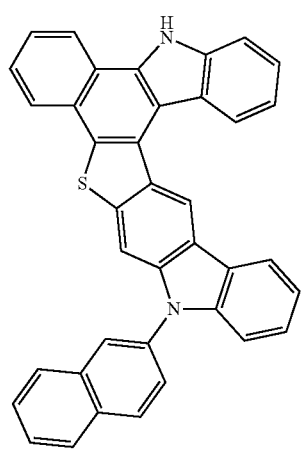
Sub 1-98
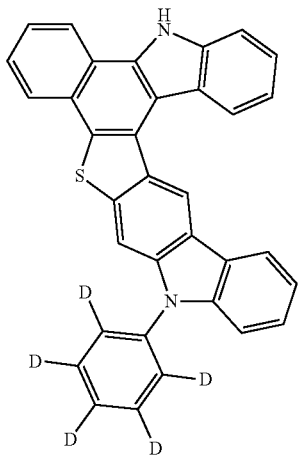
Sub 1-96
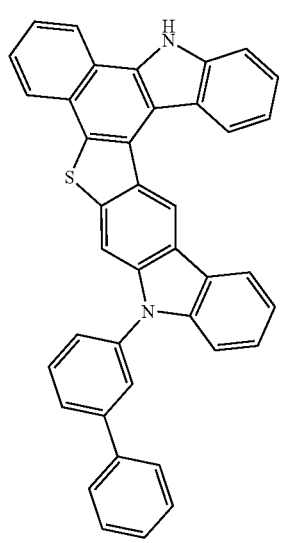
Sub 1-99
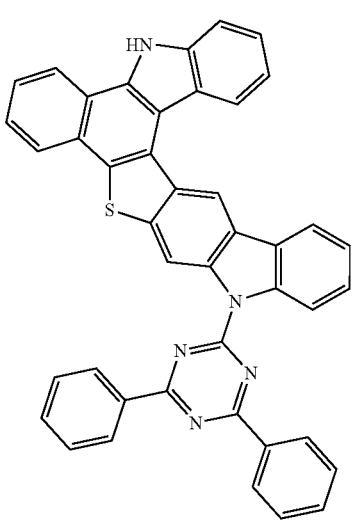
Sub 1-97
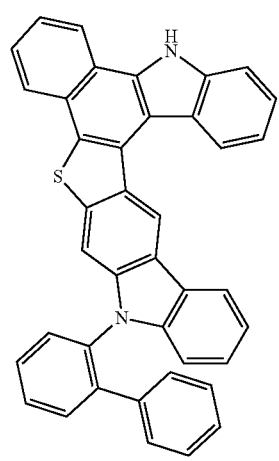
Sub 1-100
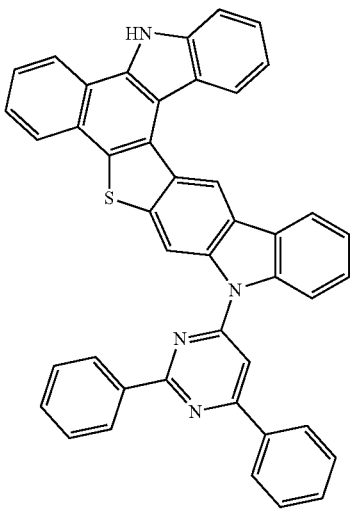

Sub 1-101
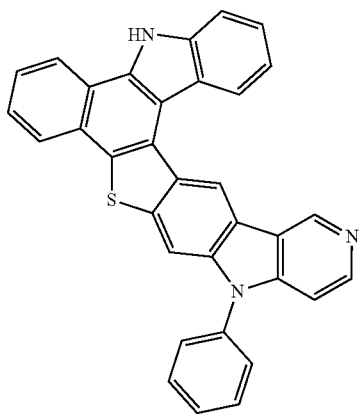
Sub 1-102
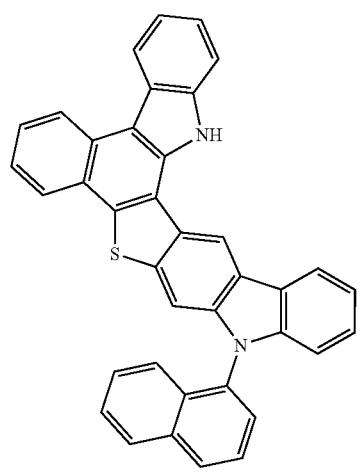
Sub 1-103
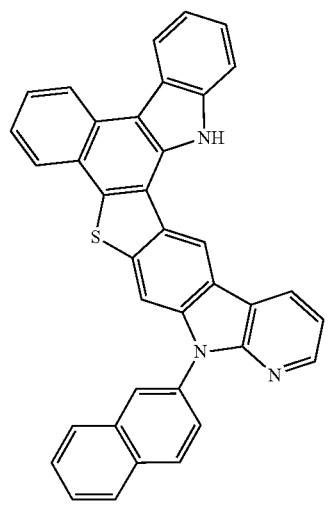
Sub 1-104
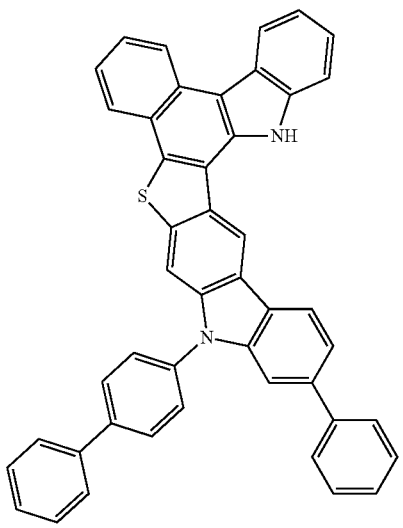
Sub 1-105
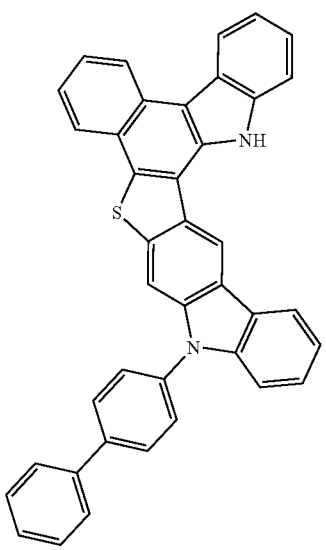
Sub 1-106
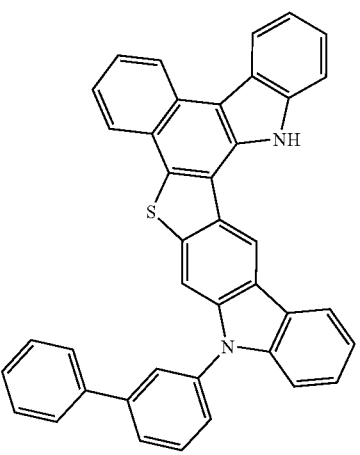

Sub 1-107

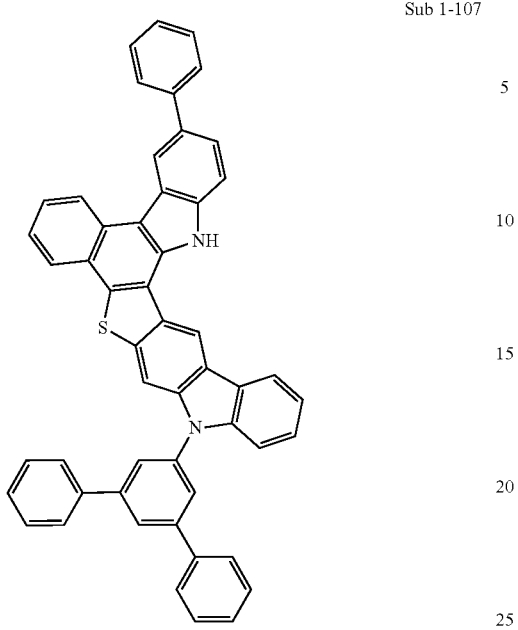

TABLE 1

| Compound | FD-MS | Compound | FD-MS |
| --- | --- | --- | --- |
| Sub 1-1 | m/z = 438.12 ($C_{30}H_{18}N_2S$ = 438.54) | Sub 1-2 | m/z = 488.13 ($C_{34}H_{20}N_2S$ = 488.60) |
| Sub 1-3 | m/z = 514.15 ($C_{30}H_{22}N_2S$ = 514.64) | Sub 1-4 | m/z = 514.15 ($C_{36}H_{22}N_2S$ = 514.64) |
| Sub 1-5 | m/z = 590.18 ($C_{42}H_{26}N_2S$ = 590.73) | Sub 1-6 | m/z = 554.18 ($C_{39}H_{26}N_2S$ = 554.70) |
| Sub 1-7 | m/z = 544.11 ($C_{36}H_{20}N_2S_2$ = 544.69) | Sub 1-8 | m/z = 544.11 ($C_{36}H_{20}N_2S_2$ = 544.69) |
| Sub 1-9 | m/z = 593.17 ($C_{39}H_{23}N_5S$ = 593.70) | Sub 1-10 | m/z = 603.23 ($C_{39}H_{13}D_{10}N_5S$ = 603.76) |
| Sub 1-11 | m/z = 566.16 ($C_{38}H_{22}N_4S$ = 566.67) | Sub 1-12 | m/z = 566.16 ($C_{38}H_{22}N_4S$ = 566.67) |
| Sub 1-13 | m/z = 718.22 ($C_{50}H_{30}N_4S$ = 718.87) | Sub 1-14 | m/z = 656.17 ($C_{44}H_{24}N_4OS$ = 656.75) |
| Sub 1-15 | m/z = 622.13 ($C_{40}H_{22}N_4S_2$ = 622.76) | Sub 1-16 | m/z = 774.19 ($C_{52}H_{30}N_4S_2$ = 774.95) |
| Sub 1-17 | m/z = 620.14 ($C_{42}H_{24}N_2S_2$ = 620.78) | Sub 1-18 | m/z = 635.24 ($C_{45}H_{25}D_5N_2S$ = 635.83) |
| Sub 1-19 | m/z = 690.21 ($C_{50}H_{30}N_2S$ = 690.85) | Sub 1-20 | m/z = 565.16 ($C_{39}H_{23}N_3S$ = 565.69) |
| Sub 1-21 | m/z = 567.15 ($C_{37}H_{21}N_5S$ = 567.66) | Sub 1-22 | m/z = 438.12 ($C_{30}H_{18}N_2S$ = 438.54) |
| Sub 1-23 | m/z = 488.13 ($C_{34}H_{20}N_2S$ = 488.60) | Sub 1-24 | m/z = 488.13 ($C_{34}H_{20}N_2S$ = 488.60) |
| Sub 1-25 | m/z = 514.15 ($C_{36}H_{22}N_2S$ = 514.64) | Sub 1-26 | m/z = 514.15 ($C_{36}H_{22}N_2S$ = 514.64) |
| Sub 1-27 | m/z = 514.16 ($C_{36}H_{22}N_2S$ = 514.64) | Sub 1-28 | m/z = 564.17 ($C_{40}H_{24}N_2S$ = 564.70) |
| Sub 1-29 | m/z = 519.18 ($C_{36}H_{17}D_5N_2S$ = 519.67) | Sub 1-30 | m/z = 544.11 ($C_{36}H_{20}N_2S_2$ = 544.69) |
| Sub 1-31 | m/z = 515.15 ($C_{35}H_{21}N_3S$ = 515.63) | Sub 1-32 | m/z = 488.13 ($C_{34}H_{20}N_2S$ = 488.60) |
| Sub 1-33 | m/z = 691.21 ($C_{49}H_{29}N_3S$ = 691.84) | Sub 1-34 | m/z = 440.11 ($C_{28}H_{16}N_4S$ = 440.52) |
| Sub 1-35 | m/z = 438.12 ($C_{30}H_{18}N_2S$ = 438.54) | Sub 1-36 | m/z = 590.18 ($C_{42}H_{26}N_2S$ = 590.73) |
| Sub 1-37 | m/z = 514.15 ($C_{36}H_{22}N_2S$ = 514.64) | Sub 1-38 | m/z = 514.15 ($C_{36}H_{22}N_2S$ = 514.64) |
| Sub 1-39 | m/z = 538.15 ($C_{38}H_{22}N_2S$ = 538.66) | Sub 1-40 | m/z = 443.15 ($C_{30}H_{13}D_5N_2S$ = 443.57) |
| Sub 1-41 | m/z = 515.15 ($C_{35}H_{21}N_3S$ = 515.63) | Sub 1-42 | m/z = 514.15 ($C_{36}H_{22}N_2S$ = 514.64) |
| Sub 1-43 | m/z = 514.15 ($C_{36}H_{22}N_2S$ = 514.64) | Sub 1-44 | m/z = 640.20 ($C_{46}H_{28}N_2S$ = 640.79) |
| Sub 1-45 | m/z = 590.18 ($C_{42}H_{26}N_2S$ = 590.73) | Sub 1-46 | m/z = 540.14 ($C_{36}H_{20}N_4S$ = 540.64) |
| Sub 1-47 | m/z = 438.12 ($C_{30}H_{18}N_2S$ = 438.54) | Sub 1-48 | m/z = 488.13 ($C_{34}H_{20}N_2S$ = 488.60) |
| Sub 1-49 | m/z = 488.13 ($C_{34}H_{20}N_2S$ = 488.60) | Sub 1-50 | m/z = 514.15 ($C_{36}H_{22}N_2S$ = 514.64) |
| Sub 1-51 | m/z = 640.20 ($C_{46}H_{28}N_2S$ = 640.79) | Sub 1-52 | m/z = 514.15 ($C_{36}H_{22}N_2S$ = 514.64) |
| Sub 1-53 | m/z = 538.15 ($C_{38}H_{22}N_2S$ = 538.66) | Sub 1-54 | m/z = 590.18 ($C_{42}H_{26}N_2S$ = 590.73) |
| Sub 1-55 | m/z = 528.13 ($C_{36}H_{20}N_2OS$ = 528.62) | Sub 1-56 | m/z = 514.15 ($C_{36}H_{22}N_2S$ = 514.64) |
| Sub 1-57 | m/z = 588.17 ($C_{42}H_{24}N_2S$ = 588.72) | Sub 1-58 | m/z = 545.10 ($C_{35}H_{19}N_3S_2$ = 545.68) |
| Sub 1-59 | m/z = 641.19 ($C_{45}H_{27}N_3S$ = 641.78) | Sub 1-60 | m/z = 538.15 ($C_{38}H_{22}N_2S$ = 538.66) |
| Sub 1-61 | m/z = 514.15 ($C_{36}H_{22}N_2S$ = 514.64) | Sub 1-62 | m/z = 514.15 ($C_{36}H_{22}N_2S$ = 514.64) |
| Sub 1-63 | m/z = 438.12 ($C_{30}H_{18}N_2S$ = 438.54) | Sub 1-64 | m/z = 564.17 ($C_{40}H_{24}N_2S$ = 564.70) |
| Sub 1-65 | m/z = 528.13 ($C_{36}H_{20}N_2OS$ = 528.62) | Sub 1-66 | m/z = 488.13 ($C_{34}H_{20}N_2S$ = 488.60) |
| Sub 1-67 | m/z = 488.13 ($C_{34}H_{20}N_2S$ = 488.60) | Sub 1-68 | m/z = 438.12 ($C_{30}H_{18}N_2S$ = 438.54) |
| Sub 1-69 | m/z = 488.13 ($C_{34}H_{20}N_2S$ = 488.60) | Sub 1-70 | m/z = 488.13 ($C_{34}H_{20}N_2S$ = 488.60) |
| Sub 1-71 | m/z = 514.15 ($C_{36}H_{22}N_2S$ = 514.64) | Sub 1-72 | m/z = 514.15 ($C_{36}H_{22}N_2S$ = 514.64) |
| Sub 1-73 | m/z = 514.15 ($C_{36}H_{22}N_2S$ = 514.64) | Sub 1-74 | m/z = 640.20 ($C_{46}H_{28}N_2S$ = 640.79) |
| Sub 1-75 | m/z = 538.15 ($C_{38}H_{22}N_2S$ = 538.66) | Sub 1-76 | m/z = 745.23 ($C_{51}H_{31}N_5S$ = 745.89) |
| Sub 1-77 | m/z = 439.11 ($C_{29}H_{17}N_3S$ = 439.53) | Sub 1-78 | m/z = 488.13 ($C_{34}H_{20}N_2S$ = 488.60) |
| Sub 1-79 | m/z = 564.17 ($C_{40}H_{24}N_2S$ = 564.70) | Sub 1-80 | m/z = 564.17 ($C_{40}H_{24}N_2S$ = 564.70) |
| Sub 1-81 | m/z = 588.17 ($C_{42}H_{24}N_2S$ = 588.72) | Sub 1-82 | m/z = 616.17 ($C_{42}H_{24}N_4S$ = 616.73) |
| Sub 1-83 | m/z = 614.18 ($C_{44}H_{26}N_2S$ = 614.76) | Sub 1-84 | m/z = 488.13 ($C_{34}H_{20}N_2S$ = 488.60) |
| Sub 1-85 | m/z = 538.15 ($C_{38}H_{22}N_2S$ = 538.66) | Sub 1-86 | m/z = 538.15 ($C_{30}H_{22}N_2S$ = 538.66) |
| Sub 1-87 | m/z = 564.17 ($C_{40}H_{24}N_2S$ = 564.70) | Sub 1-88 | m/z = 614.18 ($C_{44}H_{26}N_2S$ = 614.76) |

TABLE 1-continued

| Compound | FD-MS | Compound | FD-MS |
|---|---|---|---|
| Sub 1-89 | m/z = 538.15 ($C_{38}H_{22}N_2S$ = 538.66) | Sub 1-90 | m/z = 514.15 ($C_{36}H_{22}N_2S$ = 514.64) |
| Sub 1-91 | m/z = 516.17 ($C_{36}H_{24}N_2S$ = 516.65) | Sub 1-92 | m/z = 538.15 ($C_{38}H_{22}N_2S$ = 538.66) |
| Sub 1-93 | m/z = 593.20 ($C_{42}H_{19}D_5N_2S$ = 593.75) | Sub 1-94 | m/z = 488.13 ($C_{34}H_{20}N_2S$ = 488.60) |
| Sub 1-95 | m/z = 538.15 ($C_{38}H_{22}N_2S$ = 538.66) | Sub 1-96 | m/z = 564.17 ($C_{40}H_{24}N_2S$ = 564.70) |
| Sub 1-97 | m/z = 564.17 ($C_{40}H_{24}N_2S$ = 564.70) | Sub 1-98 | m/z = 493.17 ($C_{34}H_{15}D_5N_2S$ = 493.63) |
| Sub 1-99 | m/z = 643.18 ($C_{43}H_{25}N_5S$ = 643.76) | Sub 1-100 | m/z = 642.19 ($C_{44}H_{26}N_4S$ = 642.77) |
| Sub 1-101 | m/z = 489.13 ($C_{33}H_{19}N_3S$ = 489.59) | Sub 1-102 | m/z = 538.15 ($C_{38}H_{22}N_2S$ = 538.66) |
| Sub 1-103 | m/z = 539.15 ($C_{37}H_{21}N_3S$ = 539.65) | Sub 1-104 | m/z = 640.20 ($C_{46}H_{28}N_2S$ = 640.79) |
| Sub 1-105 | m/z = 564.17 ($C_{40}H_{24}N_2S$ = 564.70) | Sub 1-106 | m/z = 564.17 ($C_{40}H_{24}N_2S$ = 564.70) |
| Sub 1-107 | m/z = 716.23 ($C_{52}H_{32}N_2S$ = 716.89) | | |

II. Synthesis of Sub 2

Sub 2 of Reaction Scheme 1 above may be synthesized by a reaction pathway of Reaction Scheme 9, but is not limited thereto.

Synthesis of Sub 2-18

<Reaction Scheme 9>

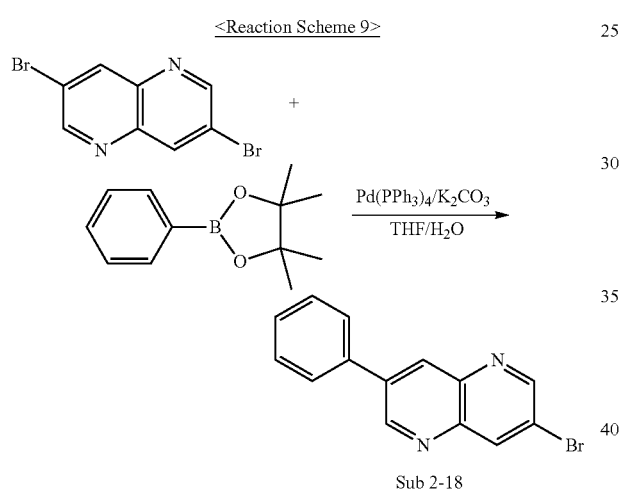

Sub 2-18

After phenylboronic acid pinacol ester (26 g, 90.4 mmol) was dissolved in THF (398 ml), 3,7-dibromo-1,5-naphthyridine (18 g, 90.4 mmol), Pd(PPh₃)₄ (3.1 g, 2.7 mmol), K₂CO₃ (37.5 g, 271 mmol), and water (200 ml), followed by stirring at 90° C. Upon completion of the reaction, the reaction product was extracted with ether and water. The organic layer was dried over MgSO₄ and concentrated, and then the resulting organic material was subjected to silica gel column chromatography and recrystallization to give a product 12.4 g (yield: 48%).

2. Synthesis of Sub 2-21

<Reaction Scheme 10>

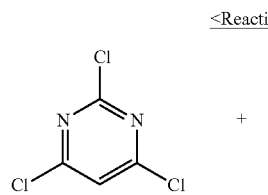

+

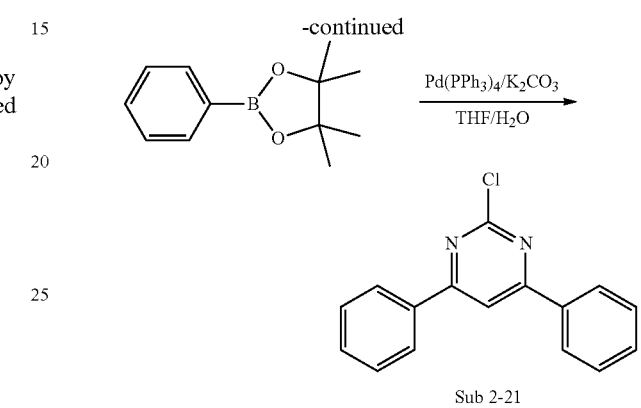

Sub 2-21

The synthesis method for Sub 2-18 was employed using Phenylboronic acid pinacol ester (31.2 g, 152.7 mmol), THF (336 ml), 2,4,6-trichloropyrimidine (14 g, 76 mmol), Pd(PPh₃)₄ (5.3 g, 4.58 mmol), K₂CO₃ (63.3 g, 458 mmol), and (168 ml) to give a product 13.2 g (yield: 65%).

3. Synthesis of Sub 2-33

<Reaction Scheme 11>

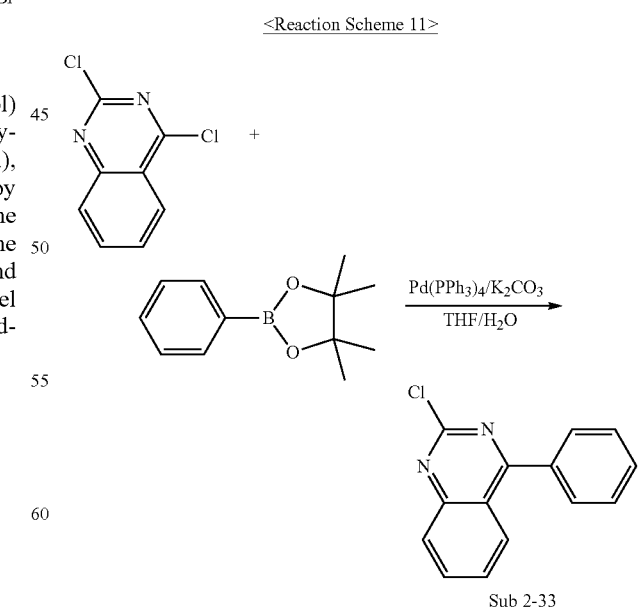

Sub 2-33

The synthesis method for Sub 2-18 was employed using phenylboronic acid pinacol ester (24.6 g, 120.5 mmol), THF (531 ml), 2,4-dichloroquinazoline (24 g, 120.5 mmol), Pd(PPh$_3$)$_4$ (4.2 g, 3.62 mmol), K$_2$CO$_3$ (50 g, 361.7 mmol), and water (265.3 ml) to give a product 13.93 g (yield: 48%).

4. Synthesis of Sub 2-53

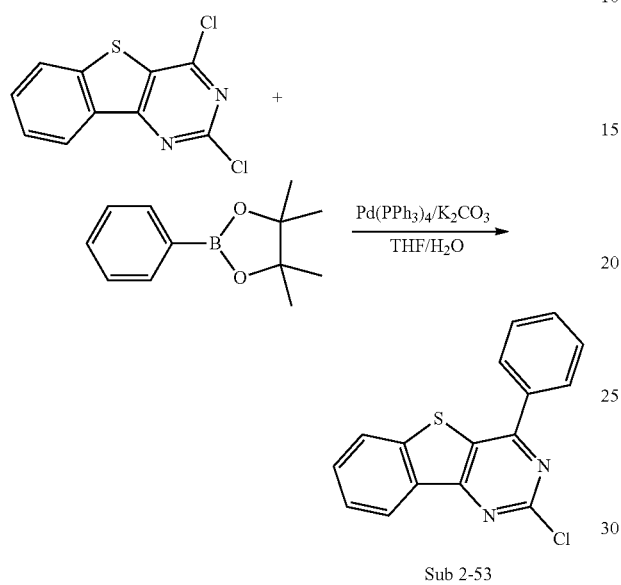

Sub 2-53

The synthesis method for Sub 2-18 was employed using phenylboronic acid pinacol ester (21.6 g, 106 mmol), THF (466 ml), 2,4-dichlorobenzo[4,5]thieno[3,2-d]pyrimidine (27 g, 106 mmol), Pd(PPh$_3$)$_4$ (3.7 g, 3.18 mmol), K$_2$CO$_3$ (43.9 g, 317.5 mmol), and (233 ml) to give a product 13.8 g (yield: 44%).

Meanwhile, the compounds pertaining to Sub 2 may be compounds below, but are not limited thereto. Table 2 below shows FD-MS values of the compounds pertaining to Sub 2.

Sub 2-1

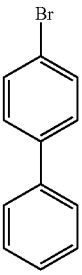

Sub 2-2

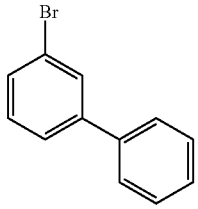

Sub 2-3

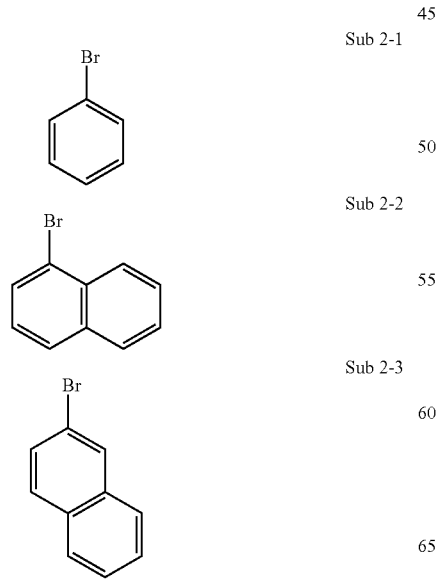

Sub 2-4

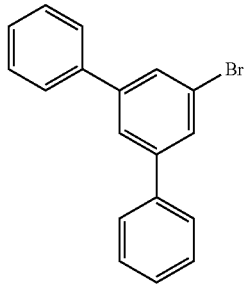

Sub 2-5

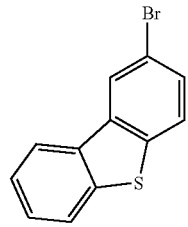

Sub 2-6

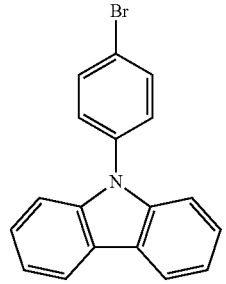

Sub 2-7

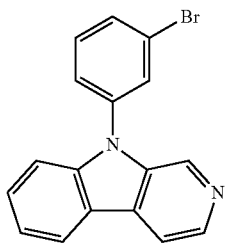

Sub 2-8

Sub 2-9

-continued
Sub 2-10
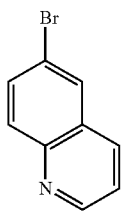
Sub 2-11
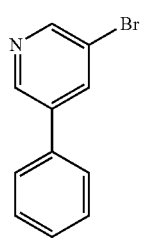
Sub 2-12
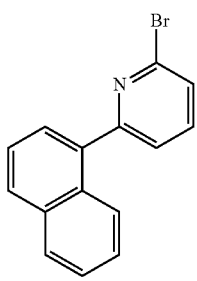
Sub 2-13
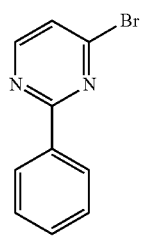
Sub 2-14
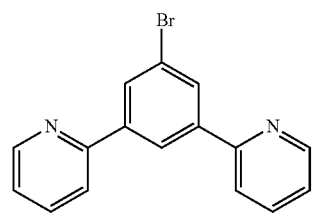
Sub 2-15
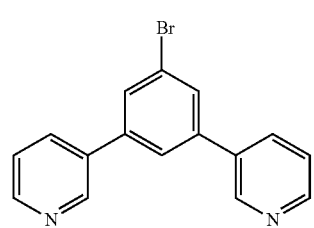
-continued
Sub 2-16
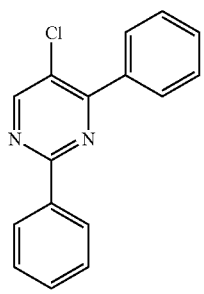
Sub 2-17
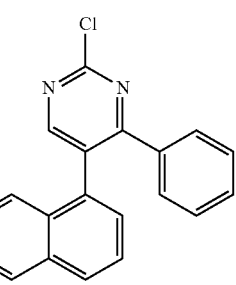
Sub 2-18
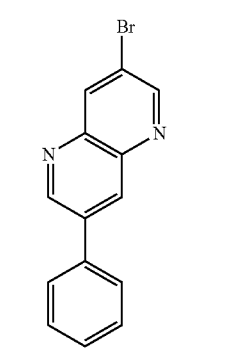
Sub 2-19
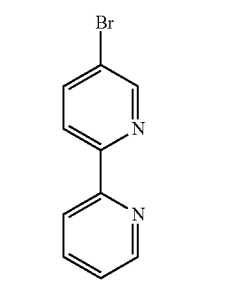
Sub 2-20
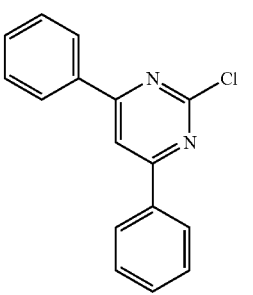

Sub 2-21
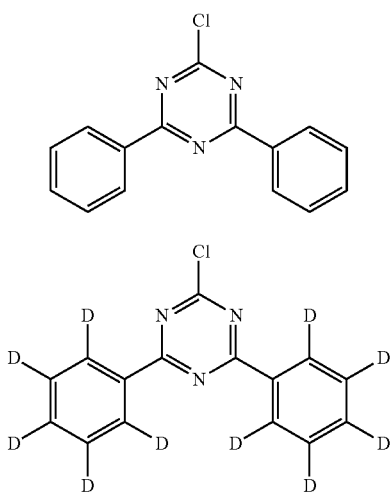
Sub 2-22
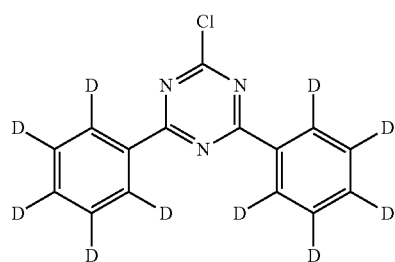
Sub 2-23
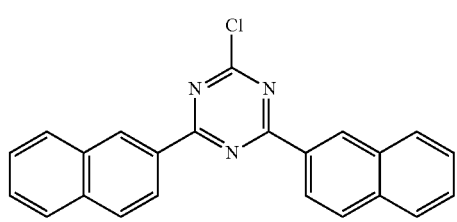
Sub 2-24
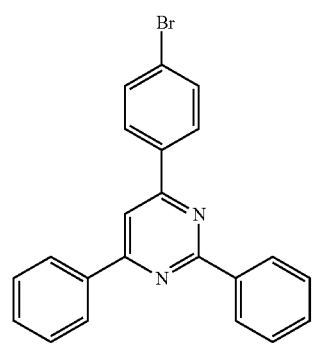
Sub 2-25
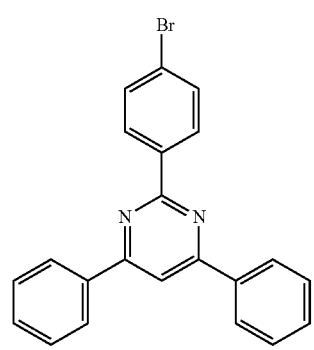
Sub 2-26
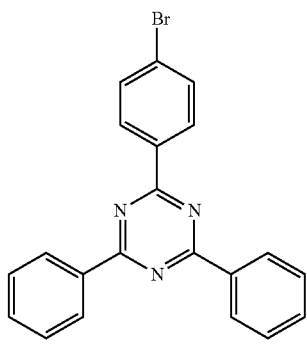
Sub 2-27
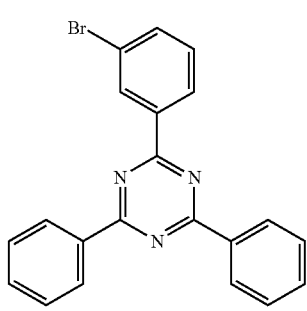
Sub 2-28
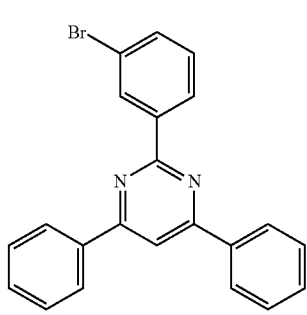
Sub 2-29
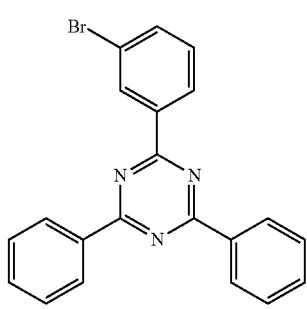

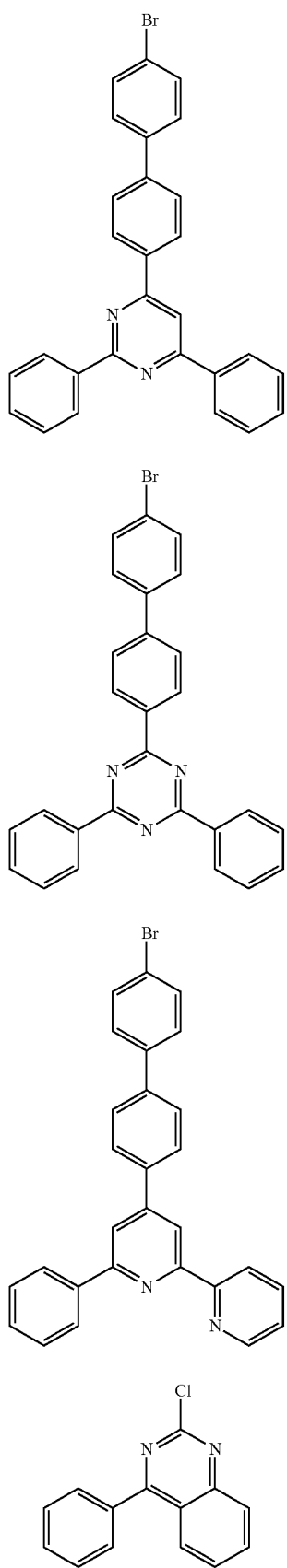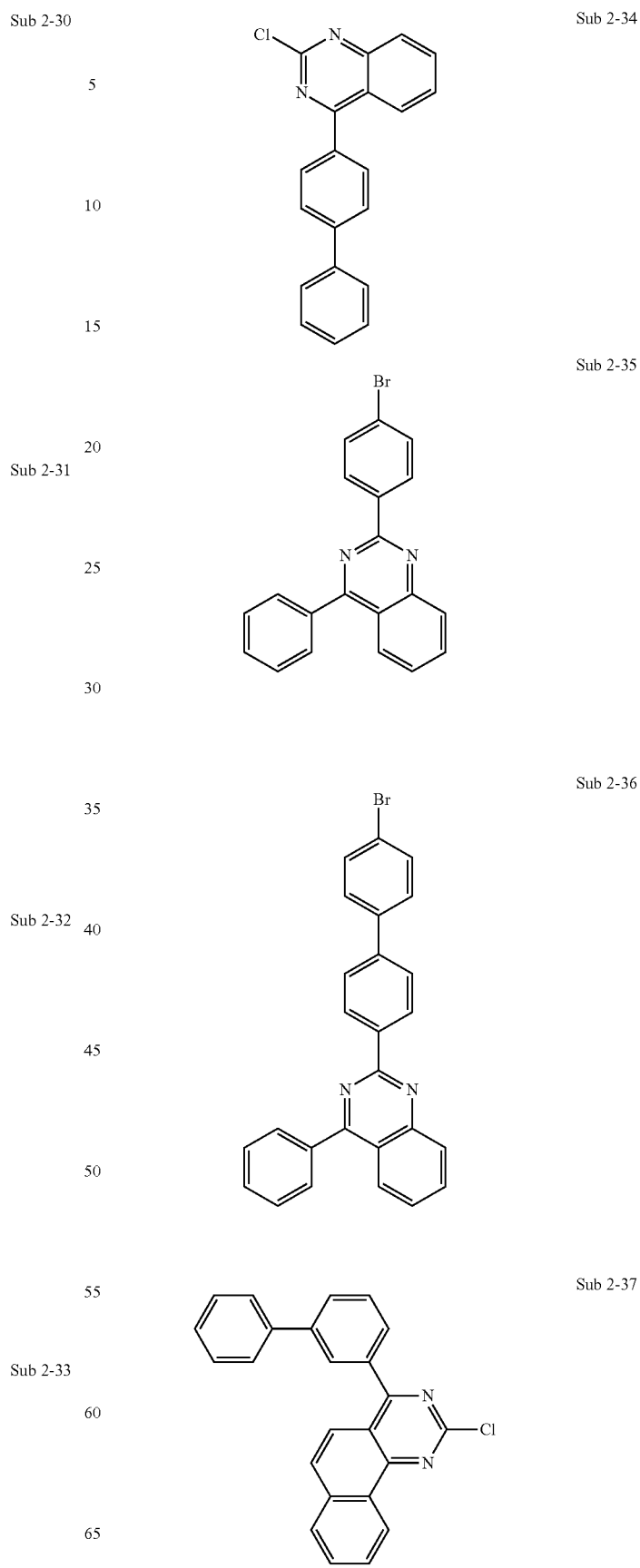

Sub 2-38
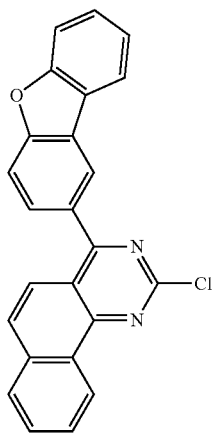
Sub 2-39
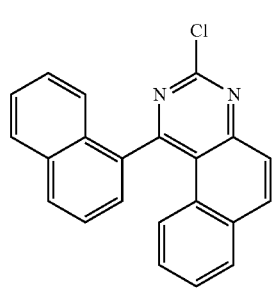
Sub 2-40
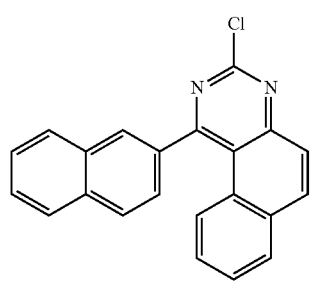
Sub 2-41
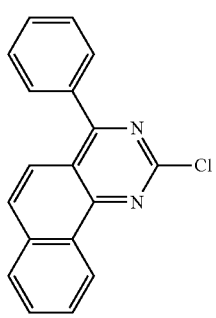
Sub 2-42
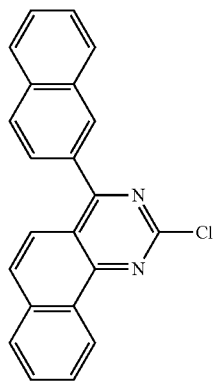
Sub 2-43
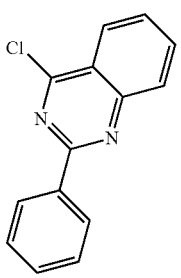
Sub 2-44
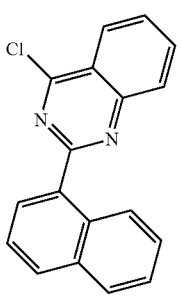
Sub 2-45
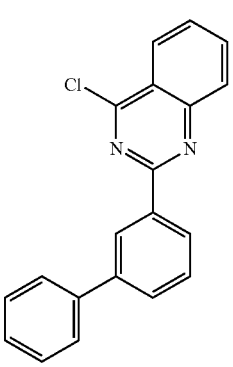
Sub 2-46
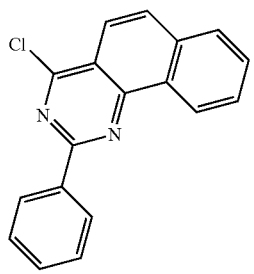

-continued
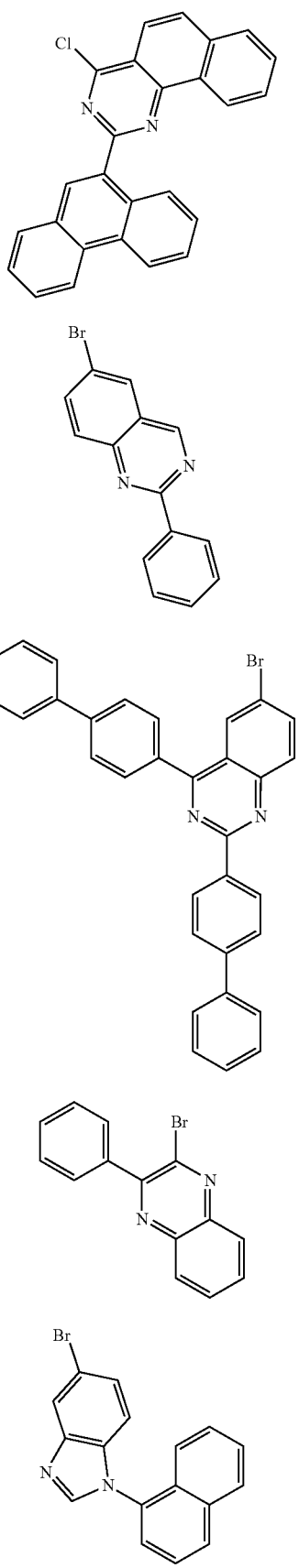
Sub 2-47
Sub 2-48
Sub 2-49
Sub 2-50
Sub 2-51
-continued
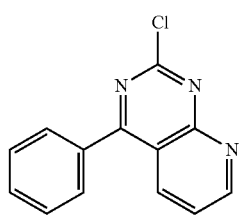
Sub 2-52
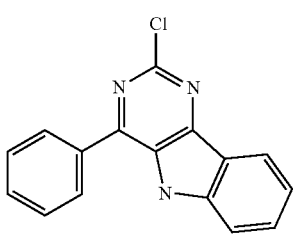
Sub 2-53
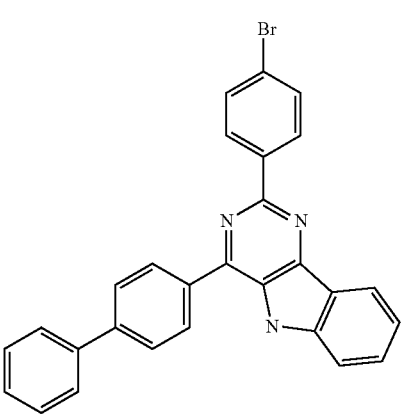
Sub 2-54
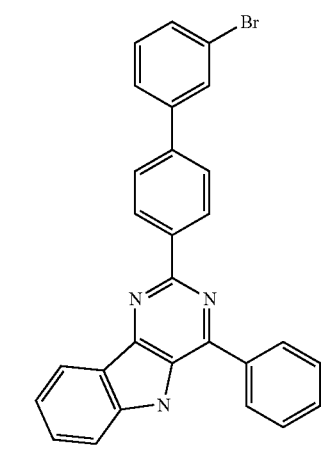
Sub 2-55
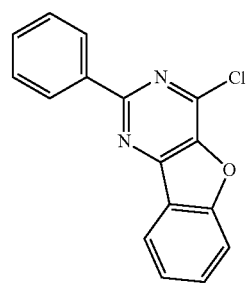
Sub 2-56

-continued

Sub 2-57

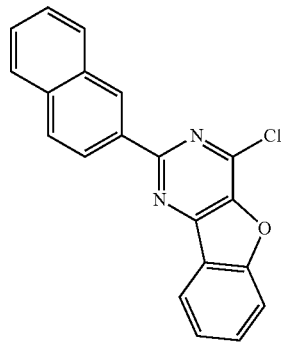

Sub 2-58

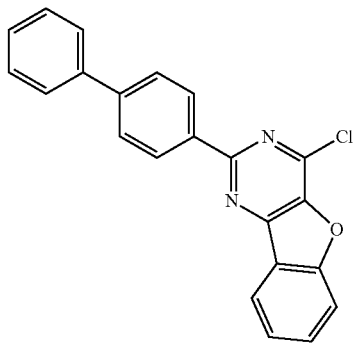

III. Synthesis of Final Product

Sub 1 compound (1.1 eq.), Sub 2 compound (1 eq.), $Pd_2(dba)_3$ (0.05 eq.), $P(t-Bu)_3$ (0.1 eq.), NaOt-Bu (3 eq.), and toluene (10.5 mL/1 mmol) were added in a round-bottom flask, followed by a reaction at 100° C. Upon completion of the reaction, the reaction product was extracted with ether and water. The organic layer was dried over $MgSO_4$ and concentrated, and then the resulting organic material was subjected to silica gel column chromatography and recrystallization to give a product.

Synthesis of P-31

<Reaction Scheme 13>

Sub 1-24

TABLE 2

| Compound | FD-MS | Compound | FD-MS |
|---|---|---|---|
| Sub 2-1 | m/z = 155.96 ($C_6H_5Br$ = 157.01) | Sub 2-2 | m/z = 205.97 ($C_{10}H_7Br$ = 207.07) |
| Sub 2-3 | m/z = 205.97 ($C_{10}H_7Br$ = 207.07) | Sub 2-4 | m/z = 231.99 ($C_{12}H_9Br$ = 233.10) |
| Sub 2-5 | m/z = 231.99 ($C_{12}H_9Br$ = 233.10) | Sub 2-6 | m/z = 308.02 ($C_{18}H_{13}Br$ = 309.20) |
| Sub 2-7 | m/z = 261.95 ($C_{12}H_7BrS$ = 263.15) | Sub 2-8 | m/z = 321.02 ($C_{18}H_{12}BrN$ = 322.20) |
| Sub 2-9 | m/z = 322.01 ($C_{17}H_{11}BrN_2$ = 323.19) | Sub 2-10 | m/z = 206.97 ($C_9H_6BrN$ = 208.05) |
| Sub 2-11 | m/z = 232.98 ($C_{11}H_8BrN$ = 234.09) | Sub 2-12 | m/z = 283.00 ($C_{15}H_{10}BrN$ = 284.15) |
| Sub 2-13 | m/z = 233.98 ($C_{10}H_7BrN_2$ = 235.08) | Sub 2-14 | m/z = 310.01 ($C_{16}H_{11}BrN_2$ = 311.18) |
| Sub 2-15 | m/z = 310.01 ($C_{16}H_{11}BrN_2$ = 311.18) | Sub 2-16 | m/z = 266.06 ($C_{16}H_{11}ClN_2$ = 266.72) |
| Sub 2-17 | m/z = 316.08 ($C_{20}H_{13}ClN_2$ = 316.78) | Sub 2-18 | m/z = 283.99 ($C_{14}H_9BrN_2$ = 285.14) |
| Sub 2-19 | m/z = 233.98 ($C_{10}H_7BrN_2$ = 235.08) | Sub 2-20 | m/z = 266.06 ($C_{16}H_{11}ClN_2$ = 266.72) |
| Sub 2-21 | m/z = 267.06 ($C_{16}H_{11}ClN_2$ = 267.71) | Sub 2-22 | m/z = 277.12 ($C_{15}D_{10}ClN_3$ = 277.77) |
| Sub 2-23 | m/z = 367.09 ($C_{23}H_{14}ClN_3$ = 367.83) | Sub 2-24 | m/z = 386.04 ($C_{22}H_{15}BrN_2$ = 387.27) |
| Sub 2-25 | m/z = 386.04 ($C_{22}H_{15}BrN_2$ = 387.27) | Sub 2-26 | m/z = 387.04 ($C_{21}H_{14}BrN_3$ = 388.26) |
| Sub 2-27 | m/z = 386.04 ($C_{22}H_{15}BrN_2$ = 387.27) | Sub 2-28 | m/z = 386.04 ($C_{22}H_{15}BrN_2$ = 387.27) |
| Sub 2-29 | m/z = 387.04 ($C_{21}H_{14}BrN_3$ = 388.26) | Sub 2-30 | m/z = 462.07 ($C_{28}H_{19}BrN_2$ = 463.37) |
| Sub 2-31 | m/z = 463.07 ($C_{27}H_{18}BrN_3$ = 464.36) | Sub 2-32 | m/z = 462.07 ($C_{28}H_{19}BrN_2$ = 463.37) |
| Sub 2-33 | m/z = 240.05 ($C_{14}H_9ClN_2$ = 240.69) | Sub 2-34 | m/z = 316.08 ($C_{20}H_{13}ClN_2$ = 316.78) |
| Sub 2-35 | m/z = 360.03 ($C_{20}H_{13}BrN_2$ = 361.23) | Sub 2-36 | m/z = 436.06 ($C_{26}H_{17}BrN_2$ = 437.33) |
| Sub 2-37 | m/z = 366.09 ($C_{24}H_{15}ClN_2$ = 366.84) | Sub 2-38 | m/z = 380.07 ($C_{24}H_{13}ClN_2O$ = 380.83) |
| Sub 2-39 | m/z = 340.08 ($C_{22}H_{13}ClN_2$ = 340.81) | Sub 2-40 | m/z = 340.08 ($C_{22}H_{13}ClN_2$ = 340.81) |
| Sub 2-41 | m/z = 290.06 ($C_{18}H_{11}ClN_2$ = 290.75) | Sub 2-42 | m/z = 340.08 ($C_{22}H_{13}ClN_2$ = 340.81) |
| Sub 2-43 | m/z = 240.05 ($C_{14}H_9ClN_2$ = 240.69) | Sub 2-44 | m/z = 290.06 ($C_{18}H_{11}ClN_2$ = 290.75) |
| Sub 2-45 | m/z = 316.08 ($C_{20}H_{13}ClN_2$ = 316.78) | Sub 2-46 | m/z = 290.06 ($C_{18}H_{11}ClN_2$ = 290.75) |
| Sub 2-47 | m/z = 390.09 ($C_{26}H_{15}ClN_2$ = 390.86) | Sub 2-48 | m/z = 283.99 ($C_{14}H_9BrN_2$ = 285.14) |
| Sub 2-49 | m/z = 512.09 ($C_{32}H_{21}BrN_2$ = 513.43) | Sub 2-50 | m/z = 283.99 ($C_{14}H_9BrN_2$ = 285.14) |
| Sub 2-51 | m/z = 322.01 ($C_{17}H_{11}BrN_2$ = 323.19) | Sub 2-52 | m/z = 241.04 ($C_{13}H_8ClN_3$ = 241.68) |
| Sub 2-53 | m/z = 296.02 ($C_{16}H_9ClN_2S$ = 296.77) | Sub 2-54 | m/z = 492.03 ($C_{28}H_{17}BrN_2S$ = 493.42) |
| Sub 2-55 | m/z = 476.05 ($C_{28}H_{17}BrN_2O$ = 477.35) | Sub 2-56 | m/z = 280.04 ($C_{16}H_9ClN_2O$ = 280.71) |
| Sub 2-57 | m/z = 330.06 ($C_{20}H_{11}ClN_2O$ = 330.77) | Sub 2-58 | m/z = 356.07 ($C_{22}H_{13}ClN_2O$ = 356.80) |

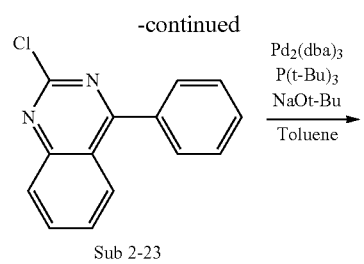

Sub 2-23

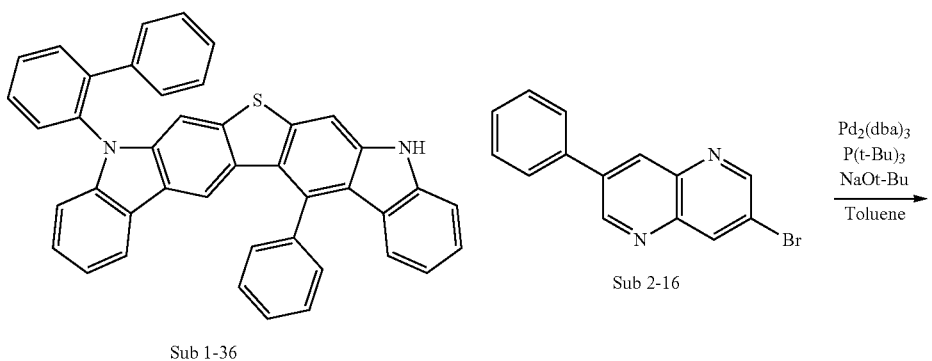

Sub 1-24 (14 g, 28.7 mmol), Sub 2-33 (7.6 g, 31.5 mmol), $Pd_2(dba)_3$ (1.3 g, 1.4 mmol), $P(t-Bu)_3$ (0.6 g, 2.87 mmol), NaOt-Bu (8.3 g, 86 mmol), and toluene (301 ml) were added in a round-bottom flask, followed by a reaction at 100° C. Upon completion of the reaction, the reaction product was extracted with ether and water. The organic layer was dried over $MgSO_4$ and concentrated, and then the resulting organic material was subjected to silica gel column chromatography and recrystallization to give a product 11 g (yield: 55%).

2. Synthesis of P-69

<Reaction Scheme 14>

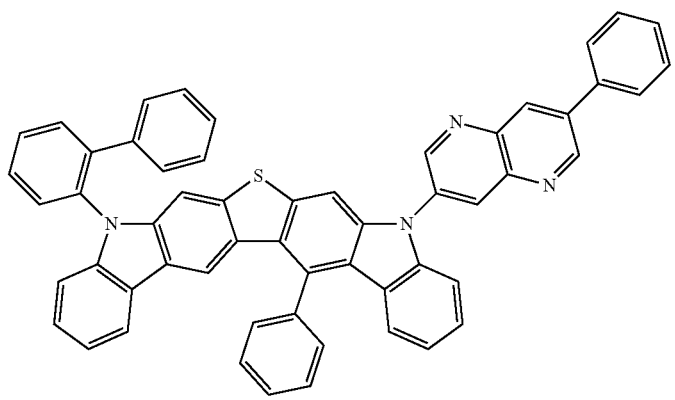

Sub 1-69

The synthesis method for P-31 was employed using Sub 1-36 (14 g, 23.7 mmol), Sub 2-18 (7.4 g, 26 mmol), Pd$_2$(dba)$_3$ (1.1 g, 1.2 mmol), P(t-Bu)$_3$ (0.5 g, 2.4 mmol), NaOt-Bu (6.8 g, 71 mmol), and toluene (250 ml) to give a product 10.9 g (yield: 58%).

3. Synthesis of P-91

<Reaction Scheme 15>

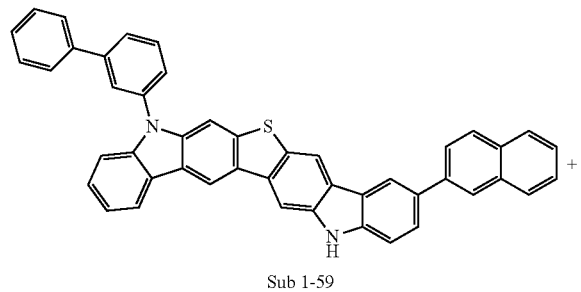

Sub 1-59

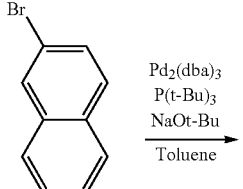

Sub 2-3

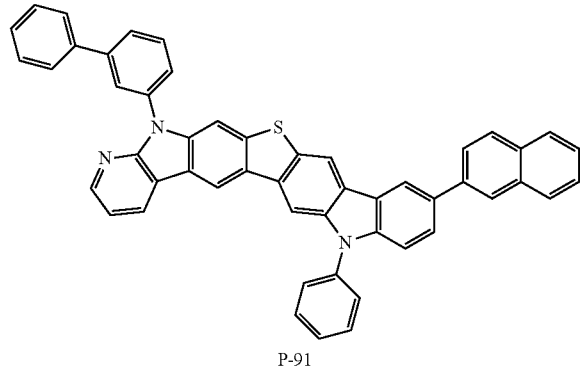

P-91

4. Synthesis of P-118

<Reaction Scheme 16>

Sub 1-79

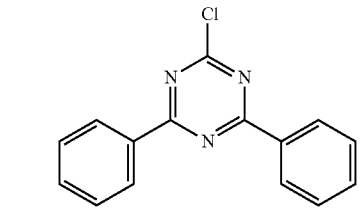

Sub 2-21

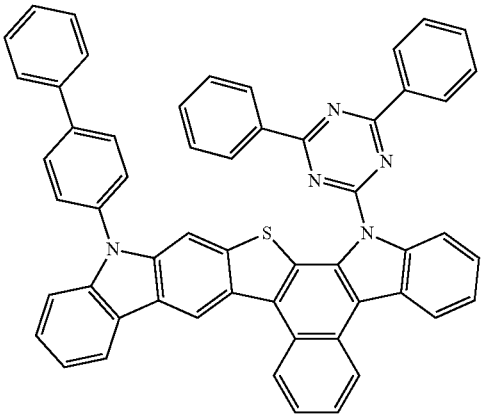

P-118

The synthesis method for P-31 was employed using Sub 1-59 (15 g, 23.4 mmol), Sub 2-3 (5.3 g, 25.7 mmol), Pd$_2$(dba)$_3$ (1.1 g, 1.17 mmol), P(t-Bu)$_3$ (0.5 g, 2.3 mmol), NaOt-Bu (6.7 g, 70 mmol), and toluene (245 ml) to give a product 10.4 g (yield: 62%).

The synthesis method for P-31 was employed using Sub 1-79 (12 g, 21.3 mmol), Sub 2-21 (6.3 g, 23.4 mmol), Pd$_2$(dba)$_3$ (1 g, 1.1 mmol), P(t-Bu)$_3$ (0.4 g, 2.1 mmol), NaOt-Bu (6.1 g, 63.8 mmol), and toluene (223 ml) in a round-bottom flask, to give a product 12.2 g (yield: 72%).

5. Synthesis of P-96

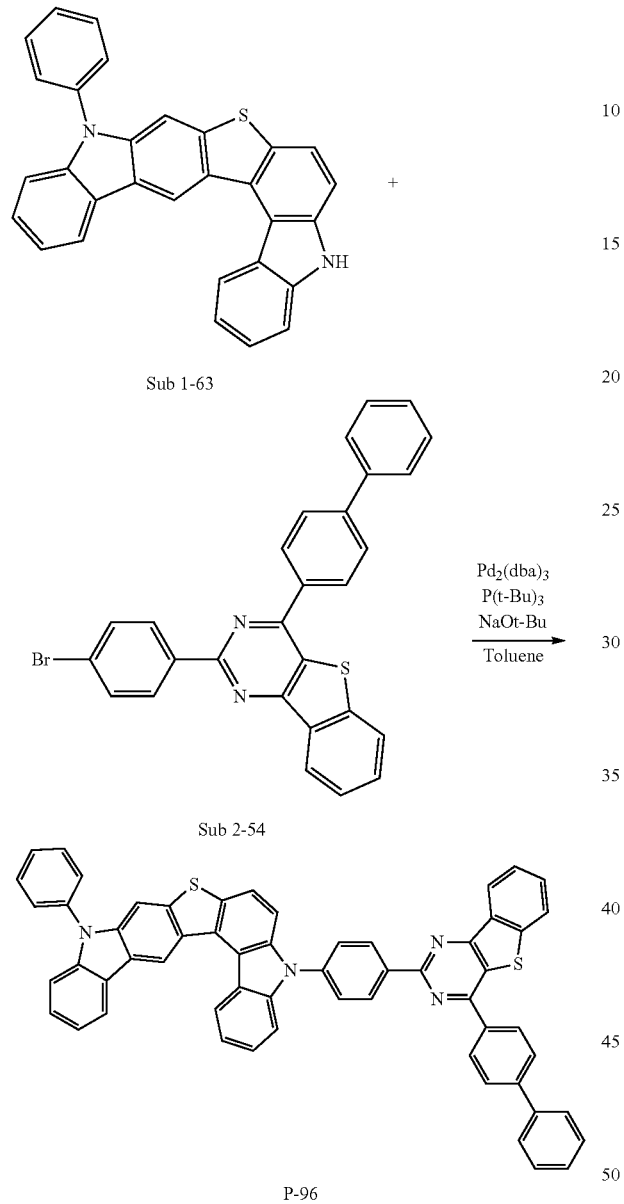

6. Synthesis of P-152

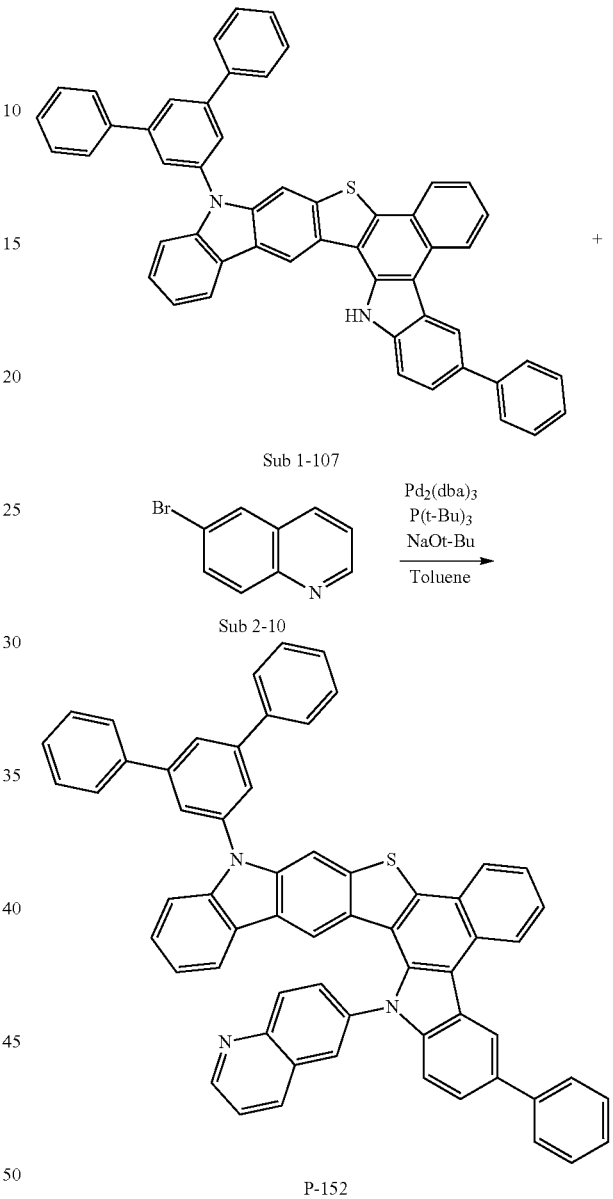

The synthesis method for P-31 was employed using Sub 1-63 (10 g, 22.8 mmol), Sub 2-54 (12.4 g, 25.1 mmol), Pd$_2$(dba)$_3$ (1 g, 1.1 mmol), P(t-Bu)$_3$ (0.5 g, 2.3 mmol), NaOt-Bu (6.6 g, 68.4 mmol), and toluene (240 ml) to give a product 14.2 g (yield: 73%).

The synthesis method for P-31 was employed using Sub 1-107 (14 g, 19.5 mmol), Sub 2-10 (4.5 g, 21.5 mmol), Pd$_2$(dba)$_3$ (0.9 g, 0.98 mmol), P(t-Bu)$_3$ (0.4 g, 1.95 mmol), NaOt-Bu (5.6 g, 58.6 mmol), and toluene (205 ml) to give a product 10.55 g (yield: 64%).

TABLE 3

| Compound | FD-MS | Compound | FD-MS |
|---|---|---|---|
| P-1 | m/z = 564.17 ($C_{40}H_{24}N_2S$ = 564.70) | P-2 | m/z = 640.20 ($C_{46}H_{28}N_2S$ = 640.79) |
| P-3 | m/z = 747.18 ($C_{51}H_{29}N_3S_2$ = 747.93) | P-4 | m/z = 748.18 ($C_{50}H_{28}N_4S_2$ = 748.91) |
| P-5 | m/z = 808.23 ($C_{56}H_{32}N_4OS$ = 808.94) | P-6 | m/z = 900.24 ($C_{62}H_{36}N_4S_2$ = 901.11) |
| P-7 | m/z = 668.20 ($C_{46}H_{28}N_4S$ = 688.81) | P-8 | m/z = 668.20 ($C_{46}H_{28}N_4S$ = 688.81) |
| P-9 | m/z = 755.29 ($C_{51}H_{21}D_{10}N_5S$ = 755.95) | P-10 | m/z = 669.20 ($C_{45}H_{27}N_5S$ = 669.79) |
| P-11 | m/z = 744.23 ($C_{52}H_{32}N_4S$ = 744.90) | P-12 | m/z = 745.23 ($C_{51}H_{31}N_5S$ = 745.89) |

TABLE 3-continued

| Compound | FD-MS | Compound | FD-MS |
|---|---|---|---|
| P-13 | m/z = 820.27 ($C_{58}H_{36}N_4S$ = 821.00) | P-14 | m/z = 784.27 ($C_{55}H_{36}N_4S$ = 784.97) |
| P-15 | m/z = 820.27 ($C_{58}H_{36}N_4S$ = 821.00) | P-16 | m/z = 642.19 ($C_{44}H_{26}N_4S$ = 642.77 ) |
| P-17 | m/z = 794.25 ($C_{56}H_{34}N_4S$ = 794.96) | P-18 | m/z = 798.19 ($C_{54}H_{30}N_4S_2$ = 798.97) |
| P-19 | m/z = 718.22 ($C_{54}H_{30}N_4S_2$ = 718.87) | P-20 | m/z = 718.22 ($C_{50}H_{30}N_4S$ = 718.87) |
| P-21 | m/z = 794.25 ($C_{56}H_{34}N_4S$ = 794.96) | P-22 | m/z = 642.19 ($C_{44}H_{26}N_4S$ = 642.77 ) |
| P-23 | m/z = 840.31 ($C_{58}H_{32}D_5N_5S$ = 841.04) | P-24 | m/z = 766.24 ($C_{56}H_{34}N_2S$ = 766.95) |
| P-25 | m/z = 748.18 ($C_{50}H_{28}N_4S_2$ = 748.91) | P-26 | m/z = 807.25 ($C_{56}H_{33}N_5S$ = 807.96) |
| P-27 | m/z = 643.18 ($C_{43}H_{25}N_5S$ = 643.76) | P-28 | m/z = 823.25 ($C_{55}H_{33}N_7S$ = 823.96) |
| P-29 | m/z = 614.18 ($C_{44}H_{26}N_2S$ = 614.76) | P-30 | m/z = 716.23 ($C_{52}H_{32}N_2S$ = 716.89) |
| P-31 | m/z = 692.20 ($C_{48}H_{28}N_4S$ = 692.83) | P-32 | m/z = 692.20 ($C_{48}H_{28}N_4S$ = 692.83) |
| P-33 | m/z = 870.28 ($C_{62}H_{38}N_4S$ = 871.06) | P-34 | m/z = 668.20 ($C_{46}H_{28}N_4S$ = 668.81) |
| P-35 | m/z = 718.22 ($C_{50}H_{30}N_4S$ = 718.87) | P-36 | m/z = 845.26 ($C_{59}H_{35}N_5S$ = 846.01) |
| P-37 | m/z = 774.19 ($C_{52}H_{30}N_4S_2$ = 774.95) | P-38 | m/z = 808.23 ($C_{56}H_{32}N_4OS$ = 808.94) |
| P-39 | m/z = 834.25 ($C_{58}H_{34}N_4OS$ = 834.98) | P-40 | m/z = 729.28 ($C_{40}H_{19}D_{10}N_5S$ = 729.91) |
| P-41 | m/z = 744.23 ($C_{52}H_{32}N_4S$ = 744.90) | P-42 | m/z = 870.28 ($C_{62}H_{38}N_4S$ = 871.06) |
| P-43 | m/z = 718.22 ($C_{50}H_{30}N_4S$ = 718.87) | P-44 | m/z = 673.23 ($C_{46}H_{23}D_5N_4S$ = 673.84) |
| P-45 | m/z = 824.21 ($C_{56}H_{32}N_4S_2$ = 825.01) | P-46 | m/z = 767.24 ($C_{55}H_{33}N_3S$ = 767.94) |
| P-47 | m/z = 859.30 ($C_{62}H_{41}N_3S$ = 860.07) | P-48 | m/z = 668.20 ($C_{46}H_{28}N_4S$ = 668.81) |
| P-49 | m/z = 666.21 ($C_{48}H_{30}N_2S$ = 666.83) | P-50 | m/z = 671.24 ($C_{48}H_{25}D_5N_2S$ = 671.86) |
| P-51 | m/z = 696.17 ($C_{48}H_{28}N_2S_2$ = 696.88) | P-52 | m/z = 717.22 ($C_{51}H_{31}N_3S$ = 717.88) |
| P-53 | m/z = 768.23 ($C_{54}H_{32}N_4S$ = 768.92) | P-54 | m/z = 668.20 ($C_{46}H_{28}N_4S$ = 668.81) |
| P-55 | m/z = 669.20 ($C_{45}H_{27}N_5S$ = 669.79) | P-56 | m/z = 744.23 ($C_{52}H_{32}N_4S$ = 744.90) |
| P-57 | m/z = 744.23 ($C_{52}H_{32}N_4S$ = 000.00) | P-58 | m/z = 897.29 ($C_{63}H_{39}N_5S$ = 898.08) |
| P-59 | m/z = 668.20 ($C_{46}H_{28}N_4S$ = 668.81) | P-60 | m/z = 748.18 ($C_{50}H_{28}N_4S_2$ = 748.91) |
| P-61 | m/z = 682.18 ($C_{46}H_{26}N_4OS$ = 682.79) | P-62 | m/z = 718.22 ($C_{50}H_{30}N_4S$ = 718.87) |
| P-63 | m/z = 858.25 ($C_{60}H_{34}N_4OS$ = 859.00) | P-64 | m/z = 818.25 ($C_{58}H_{34}N_4S$ = 818.98) |
| P-65 | m/z = 794.25 ($C_{56}H_{34}N_4S$ = 794.96) | P-66 | m/z = 719.2 ($C_{49}H_{29}N_5S$ = 719.85) |
| P-67 | m/z = 768.23 ($C_{54}H_{32}N_4S$ = 768.92) | P-68 | m/z = 742.22 ($C_{52}H_{30}N_4S$ = 742.89) |
| P-69 | m/z = 794.25 ($C_{56}H_{34}N_4S$ = 794.96) | P-70 | m/z = 755.24 ($C_{54}H_{33}N_3S$ = 755.92) |
| P-71 | m/z = 808.27 ($C_{57}H_{36}N_4S$ = 808.99) | P-72 | m/z = 719.21 ($C_{49}H_{29}N_5S$ = 719.85) |
| P-73 | m/z = 716.23 ($C_{52}H_{32}N_2S$ = 716.89) | P-74 | m/z = 664.20 ($C_{48}H_{28}N_2S$ = 664.81) |
| P-75 | m/z = 758.21 ($C_{52}H_{30}N_4OS$ = 758.89) | P-76 | m/z = 774.19 ($C_{52}H_{30}N_4S_2$ = 774.95) |
| P-77 | m/z = 692.20 ($C_{48}H_{28}N_4S$ = 692.83) | P-78 | m/z = 844.27 ($C_{60}H_{36}N_4S$ = 845.02) |
| P-79 | m/z = 742.22 ($C_{52}H_{30}N_4S$ = 742.89) | P-80 | m/z = 934.28 ($C_{66}H_{38}N_4OS$ = 935.10) |
| P-81 | m/z = 718.22 ($C_{50}H_{30}N_4S$ = 718.87) | P-82 | m/z = 792.23 ($C_{56}H_{32}N_4S$ = 792.95) |
| P-83 | m/z = 668.20 ($C_{46}H_{28}N_4S$ = 668.81) | P-84 | m/z = 744.23 ($C_{52}H_{32}N_4S$ = 744.90) |
| P-85 | m/z = 719.21 ($C_{49}H_{29}N_5S$ = 719.85) | P-86 | m/z = 744.23 ($C_{52}H_{32}N_4S$ = 744.90) |
| P-87 | m/z = 744.23 ($C_{52}H_{32}N_4S$ = 744.90) | P-88 | m/z = 835.24 ($C_{57}H_{33}N_5OS$ = 835.97) |
| P-89 | m/z = 820.27 ($C_{58}H_{36}N_4S$ = 821.00) | P-90 | m/z = 787.19 ($C_{52}H_{29}N_5S_2$ = 787.95) |
| P-91 | m/z = 717.22 ($C_{51}H_{31}N_3S$ = 717.88) | P-92 | m/z = 744.23 ($C_{52}H_{32}N_4S$ = 744.90) |
| P-93 | m/z = 766.24 ($C_{56}H_{34}N_2S$ = 766.95) | P-94 | m/z = 718.22 ($C_{50}H_{30}N_4S$ = 718.87) |
| P-95 | m/z = 768.23 ($C_{54}H_{32}N_4S$ = 768.92) | P-96 | m/z = 850.22 ($C_{58}H_{34}N_4S_2$ = 851.05) |
| P-97 | m/z = 794.25 ($C_{56}H_{34}N_4S$ = 794.96) | P-98 | m/z = 758.21 ($C_{52}H_{30}N_4OS$ = 758.89) |
| P-99 | m/z = 719.21 ($C_{49}H_{29}N_5S$ = 719.85) | P-100 | m/z = 732.20 ($C_{50}H_{28}N_2OS$ = 732.85) |
| P-101 | m/z = 716.23 ($C_{52}H_{32}N_2S$ = 716.89) | P-102 | m/z = 842.28 ($C_{62}H_{38}N_2S$ = 843.04) |
| P-103 | m/z = 742.22 ($C_{52}H_{30}N_4S$ = 742.89) | P-104 | m/z = 748.18 ($C_{50}H_{28}N_4S_2$ = 748.91) |
| P-105 | m/z = 850.22 ($C_{58}H_{34}N_4S_2$ = 851.05) | P-106 | m/z = 769.23 ($C_{53}H_{31}N_5S$ = 769.91) |
| P-107 | m/z = 744.23 ($C_{52}H_{32}N_4S$ = 744.90) | P-108 | m/z = 768.23 ($C_{54}H_{32}N_4S$ = 768.92) |
| P-109 | m/z = 821.26 ($C_{57}H_{35}N_5S$ = 821.99) | P-110 | m/z = 823.24 ($C_{56}H_{33}N_5OS$ = 823.96) |
| P-111 | m/z = 746.25 ($C_{52}H_{34}N_4S$ = 746.92) | P-112 | m/z = 716.23 ($C_{52}H_{32}N_2S$ = 716.89) |
| P-113 | m/z = 842.28 ($C_{62}H_{38}N_2S$ = 843.04) | P-114 | m/z = 742.22 ($C_{52}H_{30}N_4S$ = 742.89) |
| P-115 | m/z = 868.27 ($C_{62}H_{36}N_4S$ = 869.04) | P-116 | m/z = 718.22 ($C_{50}H_{30}N_4S$ = 718.87) |
| P-117 | m/z = 718.22 ($C_{50}H_{30}N_4S$ = 718.87) | P-118 | m/z = 795.25 ($C_{55}H_{33}N_5S$ = 795.95) |
| P-119 | m/z = 845.26 ($C_{59}H_{35}N_5S$ = 846.01) | P-120 | m/z = 870.28 ($C_{62}H_{38}N_4S$ = 871.06) |
| P-121 | m/z = 844.27 (C60H36N = 845.02) | P-122 | m/z = 782.21 ($C_{54}H_{30}N_4OS$ = 782.91) |
| P-123 | m/z = 721.23 ($C_{50}H_{23}D_5N_4S$ = 721.88) | P-124 | m/z = 740.23 ($C_{54}H_{32}N_2S$ = 740.91) |
| P-125 | m/z = 818.25 ($C_{58}H_{34}N_4S$ = 818.98) | P-126 | m/z = 818.25 ($C_{58}H_{34}N_4S$ = 818.98) |
| P-127 | m/z = 795.25 ($C_{55}H_{33}N_5S$ = 795.95) | P-128 | m/z = 844.27 ($C_{60}H_{36}N_4S$ = 845.02) |
| P-129 | m/z = 845.26 ($C_{59}H_{35}N_5S$ = 846.01) | P-130 | m/z = 692.20 ($C_{48}H_{28}N_4S$ = 692.83) |
| P-131 | m/z = 792.23 ($C_{56}H_{32}N_4S$ = 792.95) | P-132 | m/z = 848.21 ($C_{58}H_{32}N_4S_2$ = 849.03) |
| P-133 | m/z = 664.20 ($C_{48}H_{28}N_2S$ = 664.81) | P-134 | m/z = 894.28 ($C_{64}H_{38}N_4S$ = 895.08) |
| P-135 | m/z = 844.27 ($C_{60}H_{36}N_4S$ = 845.02) | P-136 | m/z = 808.23 ($C_{56}H_{32}N_4OS$ = 808.94) |
| P-137 | m/z = 838.19 ($C_{56}H_{30}N_4OS_2$ = 838.99) | P-138 | m/z = 795.25 ($C_{55}H_{33}N_5S$ = 795.95) |
| P-139 | m/z = 870.28 ($C_{62}H_{38}N_4S$ = 871.06) | P-140 | m/z = 795.25 ($C_{55}H_{33}N_5S$ = 795.95) |
| P-141 | m/z = 888.31 ($C_{67}H_{32}D_5N_5S$ = 889.09) | P-142 | m/z = 692.20 ($C_{48}H_{28}N_4S$ = 692.83) |
| P-143 | m/z = 792.26 ($C_{58}H_{36}N_2S$ = 792.98) | P-144 | m/z = 721.16 ($C_{49}H_{27}N_3S_2$ = 721.89) |
| P-145 | m/z = 692.20 ($C_{48}H_{28}N_4S$ = 692.83) | P-146 | m/z = 792.23 ($C_{56}H_{32}N_4S$ = 792.95) |
| P-147 | m/z = 808.23 ($C_{56}H_{32}N_4OS$ = 808.94) | P-148 | m/z = 692.20 ($C_{48}H_{28}N_4S$ = 692.83) |
| P-149 | m/z = 946.31 ($C_{68}H_{42}N_4S$ = 947.15) | P-150 | m/z = 920.30 ($C_{66}H_{40}N_4S$ = 921.12) |
| P-151 | m/z = 871.28 ($C_{61}H_{37}N_5S$ = 872.04) | P-152 | m/z = 843.27 ($C_{61}H_{37}N_3S$ = 844.03) |
| P-153 | m/z = 890.23 ($C_{61}H_{37}N_5S$ = 891.07) | P-154 | m/z = 839.24 ($C_{61}H_{37}N_5S$ = 840.06) |
| P-155 | m/z = 890.23 ($C_{61}H_{37}N_5S$ = 891.07) | P-156 | m/z = 731.20 ($C_{61}H_{37}N_5S$ = 731.86) |
| P-157 | m/z = 889.26 ($C_{61}H_{37}N_5S$ = 890.12) | P-158 | m/z = 938.24 ($C_{61}H_{37}N_5S$ = 939.15) |
| P-159 | m/z = 887.30 ($C_{61}H_{37}N_5S$ = 888.08) | P-160 | m/z = 924.29 ($C_{65}H_{40}N_4OS$ = 1002.19) |
| P-161 | m/z = 940.27 ($C_{65}H_{40}N_4S_2$ = 941.17) | P-162 | m/z = 964.23 ($C_{66}H_{36}N_4OS_2$ = 965.15) |
| P-163 | m/z = 822.26 ($C_{56}H_{34}N_6S$ = 822.97) | P-164 | m/z = 823.25 ($C_{55}H_{33}N_7S$ = 823.96) |
| P-165 | m/z = 822.26 ($C_{56}H_{34}N_6S$ = 822.97) | P-165 | m/z = 784.24 ($C_{53}H_{32}N_6S$ = 784.93) |
| P-167 | m/z = 746.23 ($C_{50}H_{30}N_6S$ = 746.88) | P-166 | m/z = 872.27 ($C_{60}H_{36}N_6S$ = 873.03) |

TABLE 3-continued

| Compound | FD-MS | Compound | FD-MS |
|---|---|---|---|
| P-169 | m/z = 948.30 ($C_{66}H_{40}N_6S$ = 949.13) | P-170 | m/z = 885.26 ($C_{61}H_{35}N_5OS$ = 886.03) |
| P-171 | m/z = 695.19 ($C_{45}H_{25}N_7S$ = 695.79) | | |

Although the exemplary synthesis examples of the present invention represented by Formula 1 have been described above, the synthesis examples are on the basis of a Suzuki cross-coupling reaction, a Diazotization-Thiocyanation reaction (Org. Biomol. Chem. 2011, 9, 6066), an MW(Microwave)-assisted cyclization reaction (Org. Biomol. Chem. 2011, 9, 6066), a PPh3-mediated reductive cyclization reaction (J. Org. Chem. 2005, 70, 5014.), ab Ullmann reaction and a Buchwald-Hartwig cross coupling reaction. A person skilled in the art could easily understand that the above reactions proceed even though, besides the substituents specified in the specific synthesis examples, the other substituents ($Ar^1$, $Ar^2$, $R^1$, $R^2$, $R^3$, $L^1$, $L^2$, and $X^1$ to $X^8$) defined in Formula 1 are bound.

Manufacturing and Evaluation of Organic Electronic Element

[Example 1] Green Organic Light Emitting Diode (Phosphorescent Host)

An organic electronic light emitting diode was manufactured by an ordinary method using the compound obtained through the synthesis as a light emitting host material for a light emitting layer. First, a film of $N^1$-(naphthalen-2-yl)-$N^4,N^4$-bis(4-(naphthalen-2-yl (phenyl)amino)phenyl)-$N^1$-phenylbenzene-1,4-diamine (hereinafter, abbreviated as "2-TNATA") was vacuum-deposited with a thickness of 60 nm on an ITO layer (anode) formed on a galas substrate. Then, 4,4-bis[N-(1-naphthyl)-N-phenylamino]biphenyl (hereinafter, abbreviated as "NPD") as a hole transport compound was vacuum-deposited with a thickness of 60 nm on the film, to form a hole transport layer. Subsequently, a light emitting layer with a thickness of 30 nm was deposited on the auxiliary light emitting layer by doping, on the hole transport layer, compound P-4 of the present invention as a host and Ir(ppy)₃ [tris(2-phenylpyridine)-iridium] as a dopant at a weight ratio of 95:5. Then, (1,1'-bisphenyl)-4-olato)bis(2-methyl-8-quinolinolato)aluminum (hereinafter abbreviated as "BAlq") was vacuum-deposited with a thickness of 10 nm for a hole blocking layer, and tris(8-quinolinol) aluminum (hereinafter abbreviated as "$Alq_3$") was formed with a thickness of 40 for an electron injection layer. Thereafter, LiF as halogenated alkali metal was deposited with a thickness of 0.2 nm, and subsequently Al was deposited with a thickness of 150 nm, thereby using this Al/LiF as a negative electrode. In this way, an organic electronic light emitting diode was manufactured.

[Example 2] to [Example 21] Green Organic Light Emitting Diode (Phosphorescent Host)

Organic light emitting diodes were manufactured by the same method as in Example 1 except that, instead of inventive compound P-4, the inventive compounds shown in table 4 below were used as a host material for a light emitting layer.

[Comparative Examples 1] to [Comparative Example 5]

<Comparative Compound A>

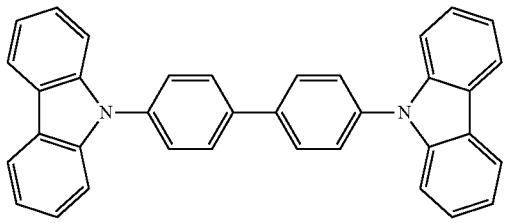

<Comparative Compound B>

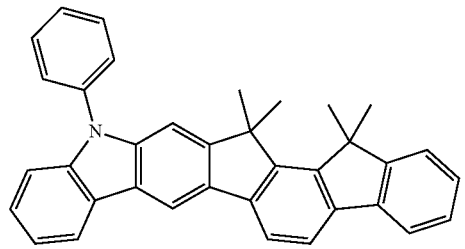

<Comparative Compound C>

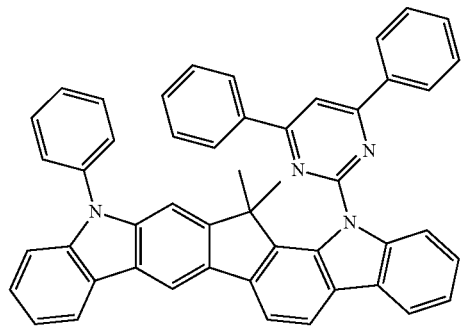

<Comparative Compound D>

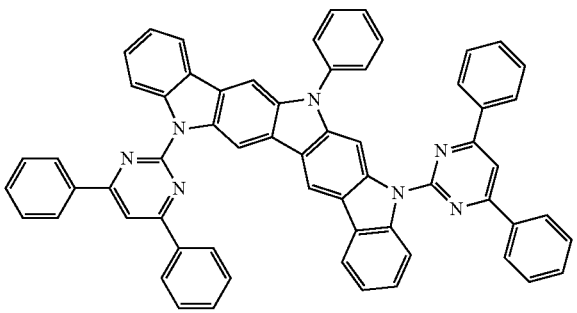

<Comparative Compound E>

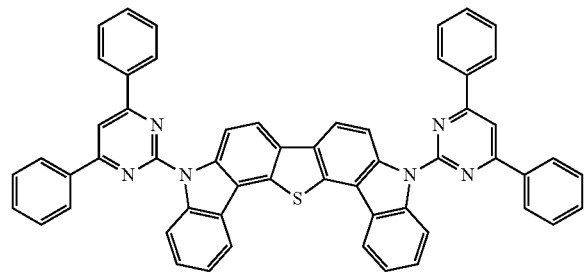

Organic light emitting diodes were manufactured by the same method as in Example 1 except that, instead of inventive compound P-4, comparative compounds A to E were used as a host material for a light emitting layer.

A forward bias DC voltage was applied to each of the organic light emitting diodes manufactured in Examples I1 to 21 and Comparative Examples I to 5 to measure electroluminescent (EL) characteristics thereof by PR-650 (Photoresearch). Also, the T95 lifetime was measured by the lifetime measurement equipment (Mcscience) at reference brightness of 5000 cd/m². The measurement results are shown in Table 4 below.

TABLE 4

|  | Compound | Voltage | Current Density (mA/cm2) | Brightness (cd/m2) | Efficiency (cd/A) | T (95) | CIE X | CIE Y |
|---|---|---|---|---|---|---|---|---|
| Comparative Example (1) | Comparative Compound A | 6.3 | 21.2 | 5000 | 23.6 | 68.5 | 0.33 | 0.62 |
| Comparative Example (2) | Comparative Compound B | 6.2 | 24.2 | 5000 | 20.7 | 57.8 | 0.33 | 0.62 |
| Comparative Example (3) | Comparative Compound C | 5.9 | 22.1 | 5000 | 22.6 | 62.2 | 0.33 | 0.61 |
| Comparative Example (4) | Comparative Compound D | 6 | 14.4 | 5000 | 31.8 | 94.1 | 0.33 | 0.61 |
| Comparative Example (5) | Comparative Compound E | 5.7 | 10.8 | 5000 | 36.2 | 84.7 | 0.33 | 0.62 |
| Example (1) | Compound (P-4) | 5.2 | 10.6 | 5000 | 47.3 | 138.6 | 0.33 | 0.62 |
| Example (2) | Compound (P-5) | 5.1 | 10.6 | 5000 | 47.0 | 140.7 | 0.33 | 0.62 |
| Example (3) | Compound (P-7) | 5.0 | 10.3 | 5000 | 47.9 | 143.6 | 0.33 | 0.62 |
| Example (4) | Compound (P-8) | 5.1 | 10.0 | 5000 | 48.2 | 143.2 | 0.33 | 0.62 |
| Example (5) | Compound (P-9) | 5.0 | 10.1 | 5000 | 49.6 | 144.9 | 0.33 | 0.62 |
| Example (6) | Compound (P-10) | 5.0 | 10.4 | 5000 | 50.2 | 145.8 | 0.33 | 0.61 |
| Example (7) | Compound (P-11) | 5.1 | 11.0 | 5000 | 45.6 | 138.4 | 0.33 | 0.62 |
| Example (8) | Compound (P-12) | 5.2 | 10.8 | 5000 | 46.3 | 140.1 | 0.33 | 0.61 |
| Example (9) | Compound (P-13) | 5.1 | 11.1 | 5000 | 45.1 | 140.9 | 0.33 | 0.61 |
| Example (10) | Compound (P-15) | 5.2 | 10.5 | 5000 | 47.5 | 136.4 | 0.33 | 0.61 |
| Example (11) | Compound (P-28) | 5.2 | 12.3 | 5000 | 40.8 | 125.6 | 0.33 | 0.61 |
| Example (12) | Compound (P-34) | 5.1 | 10.8 | 5000 | 46.5 | 138.4 | 0.33 | 0.61 |
| Example (13) | Compound (P-35) | 5.2 | 10.7 | 5000 | 45.6 | 135.8 | 0.33 | 0.62 |
| Example (14) | Compound (P-36) | 5.1 | 11.0 | 5000 | 46.9 | 139.4 | 0.33 | 0.61 |
| Example (15) | Compound (P-37) | 5.3 | 11.6 | 5000 | 43.0 | 133.1 | 0.33 | 0.61 |
| Example (16) | Compound (P-39) | 5.3 | 12.3 | 5000 | 40.8 | 127.4 | 0.33 | 0.61 |
| Example (17) | Compound (P-41) | 5.2 | 11.4 | 5000 | 43.8 | 132.8 | 0.33 | 0.61 |
| Example (18) | Compound (P-42) | 5.1 | 11.7 | 5000 | 42.8 | 134.9 | 0.33 | 0.61 |
| Example (19) | Compound (P-49) | 5.3 | 11.4 | 5000 | 44.1 | 128.9 | 0.33 | 0.61 |
| Example (20) | Compound (P-53) | 5.1 | 10.2 | 5000 | 50.1 | 146.3 | 0.33 | 0.61 |
| Example (21) | Compound (P-54) | 5.2 | 10.1 | 5000 | 50.6 | 146.5 | 0.33 | 0.62 |
| Example (22) | Compound (P-55) | 5.2 | 10.2 | 5000 | 50.2 | 144.3 | 0.33 | 0.62 |
| Example (23) | Compound (P-56) | 5.2 | 11.0 | 5000 | 46.7 | 140.2 | 0.33 | 0.61 |

TABLE 4-continued

| | Compound | Voltage | Current Density (mA/cm2) | Brightness (cd/m2) | Efficiency (cd/A) | T (95) | CIE X | CIE Y |
|---|---|---|---|---|---|---|---|---|
| Example (24) | Compound (P-57) | 5.2 | 10.9 | 5000 | 47.1 | 140.7 | 0.33 | 0.62 |
| Example (25) | Compound (P-58) | 5.3 | 10.8 | 5000 | 47.6 | 137.6 | 0.33 | 0.61 |
| Example (26) | Compound (P-60) | 5.2 | 10.7 | 5000 | 48.1 | 139.2 | 0.33 | 0.62 |
| Example (27) | Compound (P-61) | 5.2 | 11.1 | 5000 | 46.3 | 137.3 | 0.33 | 0.62 |
| Example (28) | Compound (P-73) | 5.4 | 12.5 | 5000 | 39.9 | 117.6 | 0.33 | 0.62 |
| Example (29) | Compound (P-75) | 5.1 | 11.8 | 5000 | 42.3 | 128.5 | 0.33 | 0.61 |
| Example (30) | Compound (P-76) | 5.2 | 12.1 | 5000 | 41.3 | 126.7 | 0.33 | 0.62 |
| Example (31) | Compound (P-83) | 5.2 | 11.5 | 5000 | 43.4 | 130.2 | 0.33 | 0.61 |
| Example (32) | Compound (P-84) | 5.1 | 11.3 | 5000 | 44.4 | 134.4 | 0.33 | 0.62 |
| Example (33) | Compound (P-85) | 5.0 | 11.6 | 5000 | 43.2 | 134.7 | 0.33 | 0.62 |
| Example (34) | Compound (P-86) | 5.1 | 12.1 | 5000 | 41.2 | 126.7 | 0.33 | 0.62 |
| Example (35) | Compound (P-87) | 5.3 | 11.8 | 5000 | 42.4 | 128.7 | 0.33 | 0.62 |
| Example (36) | Compound (P-88) | 5.1 | 12.0 | 5000 | 41.5 | 123.1 | 0.33 | 0.62 |
| Example (37) | Compound (P-90) | 5.5 | 12.4 | 5000 | 40.3 | 121.6 | 0.33 | 0.62 |
| Example (38) | Compound (P-96) | 5.4 | 12.5 | 5000 | 40.0 | 107.9 | 0.33 | 0.61 |
| Example (39) | Compound (P-97) | 5.4 | 11.9 | 5000 | 42.1 | 124.7 | 0.33 | 0.61 |
| Example (40) | Compound (P-98) | 5.5 | 12.7 | 5000 | 39.3 | 117.9 | 0.33 | 0.62 |
| Example (41) | Compound (P-99) | 5.5 | 11.8 | 5000 | 42.2 | 127.4 | 0.33 | 0.61 |
| Example (42) | Compound (P-105) | 5.4 | 12.9 | 5000 | 38.9 | 114.4 | 0.33 | 0.62 |
| Example (43) | Compound (P-106) | 5.5 | 12.7 | 5000 | 39.3 | 120.6 | 1.33 | 0.62 |
| Example (44) | Compound (P-107) | 5.5 | 12.0 | 5000 | 41.6 | 132.9 | 0.33 | 0.62 |
| Example (45) | Compound (P-109) | 5.5 | 13.0 | 5000 | 38.3 | 101.5 | 0.33 | 0.61 |

As can be seen from the results of table 4 above, it was verified that, when comparing comparative compound B, C, D, and E, which are hepta-cyclic compound similar to the present inventive compounds, and comparative compound A, which is generally widely used, comparative compound E had the highest efficiency and comparative compound D had the longest lifetime.

Especially, as a result of investigating the lifetimes of comparative compounds B and C, it was verified that the hepta-cyclic compound showed a shortened lifetime when it contains fluorene, and furthermore, comparative compound B having two fluorenes showed a longer lifetime than comparative compound C having one fluorene.

It was confirmed from table 4 that the present inventive compounds, which have a similar fused position to the core of compound compound D and have a type of N—S—N, similar to that of comparative compound E, showed the higher efficiency and longer lifetime than comparative compounds D and E.

This indicates that, although the hepta-cyclic compounds have the same N—S—N type heteroatoms therein, the compounds have varied lifetimes depending on the fused position and may have varied efficiency characteristics depending on the kind and arrangement of heteroatoms contained therein.

Therefore, it is considered that the efficiency and lifetime of a hepta-cyclic compound is not easy to predict due to the difference in the fused position and the differences in the kind and arrangement of heteroatoms in the compound.

[Example 22] Red Organic Light Emitting Diode (Phosphorescent Host)

An organic electronic light emitting diode was manufactured by an ordinary method using the compound obtained through the synthesis as a light emitting host material for a light emitting layer. First, a film of 2-TNATA was vacuum-deposited on an ITO layer (anode) formed on a galas substrate to form a hole injection layer with a thickness of 60 nm, and then, a film of NPD as a hole transport compound was vacuum-deposited with a thickness of 60 nm on the hole injection layer to form a hole transport layer. Then, a light emitting layer with a thickness of 30 nm was deposited on the hole transport layer by doping inventive compound P-16 as a host material and (piq)$_2$Ir(acac) as a dopant material at a weight ratio of 95:5. Then, BAlq was vacuum-deposited with a thickness of nm as a hole blocking layer, and a film of Alq₃ was formed with a thickness of 40 nm for an electron transport layer. Thereafter, LiF as halogenated alkali metal was deposited to a thickness of 0.2 nm for an electron injection layer, and then Al was deposited to a thickness of 150 nm and used as a cathode, and ultimately, an organic light emitting diode was manufactured.

[Example 23] to [Example 42] Red Organic Light Emitting Diode (Phosphorescent Host)

Organic light emitting diodes were manufactured by the same method as in Example 22 except that, instead of inventive compound P-16, the inventive compounds shown in table 5 below were used as a host material for a light emitting layer.

[Comparative Examples 6] to [Comparative Example 9]

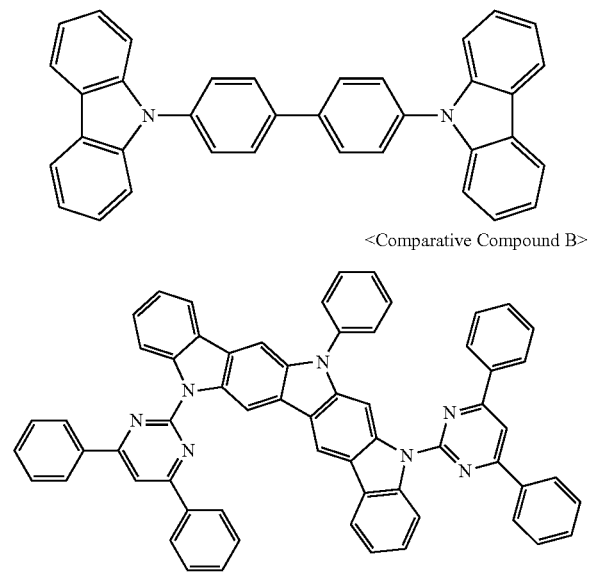

Organic light emitting diode was manufactured by the same method as in Example 22 except that, instead of inventive compound P-16, comparative compound A, D, F, or G was used as a host material for a light emitting layer.

A forward bias DC voltage was applied to each of the organic light emitting diodes manufactured in Examples to 42 and Comparative Examples 6 to 9 to measure electroluminescent (EL) characteristics thereof by PR-650 (Photoresearch). Also, the T95 lifetime was measured by the lifetime measurement equipment (Mcscience) at reference brightness of 2500 cd/m². The measurement results are shown in Table 5 below.

TABLE 5

|  | Compound | Voltage | Current Density (mA/cm2) | Brightness (cd/m2) | Efficiency (cd/A) | T (95) | CIE X | |
|---|---|---|---|---|---|---|---|---|
| Comparative Example (6) | Comparative Compound A | 6.5 | 34.7 | 2500 | 7.2 | 60.3 | 0.66 | 0.32 |
| Comparative Example (7) | Comparative Compound D | 6.7 | 29.4 | 2500 | 8.5 | 98.7 | 0.66 | 0.32 |
| Comparative Example (8) | Comparative Compound F | 6.4 | 27.2 | 2500 | 9.2 | 57.2 | 0.66 | 0.33 |
| Comparative Example (9) | Comparative Compound G | 6.1 | 20.2 | 2500 | 12.4 | 87.4 | 0.66 | 0.33 |
| Example (46) | Compound (P-16) | 5.9 | 17.1 | 2500 | 14.7 | 148.9 | 0.66 | 0.33 |
| Example (47) | Compound (P-19) | 6.0 | 18.0 | 2500 | 13.9 | 141.8 | 0.66 | 0.32 |
| Example (48) | Compound (P-20) | 6.0 | 17.2 | 2500 | 14.5 | 146.2 | 0.66 | 0.32 |
| Example (49) | Compound (P-21) | 5.9 | 18.0 | 2500 | 13.9 | 141.7 | 0.66 | 0.32 |

TABLE 5-continued

| | Compound | Voltage | Current Density (mA/cm2) | Brightness (cd/m2) | Efficiency (cd/A) | T (95) | CIE X | |
|---|---|---|---|---|---|---|---|---|
| Example (50) | Compound (P-27) | 5.9 | 18.1 | 2500 | 13.8 | 142.8 | 0.66 | 0.32 |
| Example (51) | Compound (P-31) | 5.9 | 18.9 | 2500 | 13.2 | 144.1 | 0.66 | 0.33 |
| Example (52) | Compound (P-32) | 6.1 | 18.9 | 2500 | 13.3 | 142.5 | 0.66 | 0.32 |
| Example (53) | Compound (P-45) | 5.9 | 19.7 | 2500 | 12.7 | 139.5 | 0.66 | 0.33 |
| Example (54) | Compound (P-62) | 5.9 | 16.7 | 2500 | 15.0 | 150.0 | 0.66 | 0.33 |
| Example (55) | Compound (P-63) | 5.9 | 20.5 | 2500 | 12.2 | 138.2 | 0.66 | 0.32 |
| Example (56) | Compound (P-65) | 6.0 | 18.8 | 2500 | 13.3 | 143.7 | 0.66 | 0.32 |
| Example (57) | Compound (P-67) | 5.8 | 16.8 | 2500 | 14.9 | 147.9 | 0.66 | 0.33 |
| Example (58) | Compound (P-77) | 6.0 | 19.3 | 2500 | 13.0 | 139.3 | 0.66 | 0.33 |
| Example (59) | Compound (P-81) | 5.8 | 19.2 | 2500 | 13.0 | 140.5 | 0.66 | 0.32 |
| Example (60) | Compound (P-94) | 6.1 | 20.5 | 2500 | 12.2 | 136.7 | 0.66 | 0.33 |
| Example (61) | Compound (P-95) | 6.1 | 19.5 | 2500 | 12.8 | 135.7 | 0.66 | 0.32 |
| Example (62) | Compound (P-103) | 6.2 | 24.1 | 2500 | 10.4 | 126.6 | 0.66 | 0.33 |
| Example (63) | Compound (P-104) | 6.1 | 24.1 | 2500 | 10.4 | 125.2 | 0.66 | 0.32 |
| Example (64) | Compound (P-114) | 5.8 | 17.4 | 2500 | 14.4 | 151.2 | 0.66 | 0.33 |
| Example (65) | Compound (P-115) | 5.8 | 16.7 | 2500 | 14.9 | 150.3 | 0.66 | 0.32 |
| Example (66) | Compound (P-130) | 6.0 | 18.7 | 2500 | 13.4 | 147.1 | 0.66 | 0.32 |
| Example (67) | Compound (P-135) | 5.8 | 18.7 | 2500 | 13.4 | 146.9 | 0.66 | 0.32 |
| Example (68) | Compound (P-145) | 5.9 | 19.3 | 2500 | 13.0 | 142.5 | 0.66 | 0.32 |

As can be seen from the results of table 5 above, it was verified that, when comparing comparative compound D, F, and G, which are hepta-cyclic compound similar to the present inventive compounds, and comparative compound A, which is generally widely used, comparative compound G had the highest efficiency and comparative compound D had the longest lifetime.

Similarly, as a result of investigating the lifetime of comparative compound F, it was verified that the hepta-cyclic compound showed a shortened lifetime when it contains fluorene, and furthermore, and it was confirmed from table 5 that the present inventive compounds, which have a similar fused position to the core of compound compound D and have a type of N—S—N, similar to that of comparative compound G, showed the higher efficiency and longer lifetime than comparative compounds D and G.

This indicates that, although the hepta-cyclic compounds have the same N—S—N type heteroatoms therein, the compounds have varied lifetimes depending on the fused position and may have varied efficiency characteristics depending on the kind and arrangement of heteroatoms contained therein.

Therefore, it is considered that the efficiency and lifetime of a hepta-cyclic compound is not easy to predict due to the difference in the fused position and the differences in the kind and arrangement of heteroatoms in the compound.

In addition, the characteristics of elements have been described in view of a light emitting layer with reference to the foregoing evaluation results of the manufacture of elements, but the materials used for a light emitting layer may be ordinarily used alone or in a mixture with other materials, for the foregoing organic material layer for an organic electronic element, such as an electron transport layer, an electron injection layer, a hole injection layer, a hole transport layer, and an auxiliary light emitting layer. Therefore, for the foregoing reasons, the compounds of the present invention may be used alone or in a mixture with other materials, for the other layers for an organic material layer, excluding the light emitting layer, for example, an electron transport layer, an electron injection layer, a hole injection layer, a hole transport layer, and an auxiliary light emitting layer.

Although exemplary embodiments of the present invention have been described for illustrative purposes, a person skilled in the art will appreciate that various modifications, additions, and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

EXPLANATION OF NUMERICAL REFERENCES

100: organic electronic element
110: substrate
120: first electrode
130: hole injection layer
140: hole transport layer
141: buffer layer
150: light emitting layer
151: auxiliary light emitting layer
160: electron transport layer
170: electron injection layer
180: second electrode

What is claimed is:

1. A compound represented by Formula 1:

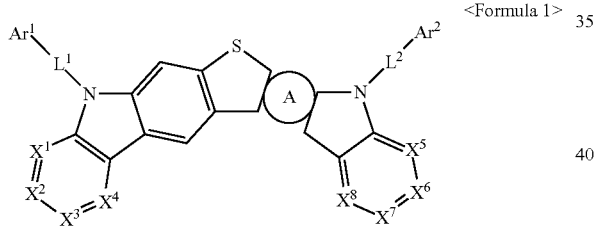
<Formula 1> wherein in Formula 1, $Ar^1$ and $Ar^2$ each are independently selected from the group consisting of a $C_6$-$C_{60}$ aryl group, a fluorenyl group, a fused ring group of a $C_3$-$C_{60}$ aliphatic group and a $C_6$-$C_{60}$ aromatic group, a $C_2$-$C_{60}$ heterocyclic group containing at least one heteroatom of O, N, S, Si, and P, a $C_1$-$C_{50}$ alkyl group, and —N(R')(R") wherein at least one of $Ar^1$ and $Ar^2$ is not the heterocyclic group;

R' and R" each are independently selected from the group consisting of a $C_6$-$C_{60}$ aryl group, a fluorenyl group, a $C_2$-$C_{60}$ heterocyclic group containing at least one heteroatom of O, N, S, Si, and P, and a $C_1$-$C_{50}$ alkyl group;

$L^1$ and $L^2$ each are selected from the group consisting of a single bond, a $C_6$-$C_{60}$ arylene group, a fluorenylene group, a $C_2$-$C_{60}$ bivalent heterocyclic group containing at least one heteroatom of O, N, S, Si, and P, a fused ring group of a $C_3$-$C_{60}$ bivalent aliphatic group and a $C_6$-$C_{60}$ bivalent aromatic group, and a bivalent aliphatic hydrocarbon group, each of which (excluding the single bond) may be substituted with at least one substituent selected from the group consisting of deuterium, a nitro group, a nitrile group, a halogen group, a $C_1$-$C_{50}$ alkyl group, a $C_6$-$C_{20}$ aryl group, a $C_2$-$C_{20}$ heterocyclic group, a $C_1$-$C_{20}$ alkoxy group, and an amino group;

$X^1$ to $X^8$ each are independently $CR^1$ or N;

i) $R^1$ is selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a fused ring group of a $C_6$-$C_{60}$ aromatic group and a $C_3$-$C_{60}$ aliphatic group, a $C_1$-$C_{60}$ alkyl group, a $C_2$-$C_{20}$ alkenyl group, a $C_1$-$C_{30}$ alkoxy group, and a $C_6$-$C_{30}$ aryloxy group, or ii) in the presence of a plurality of $R^1$'s, the plurality of $R^1$'s are different from or the same as each other and adjacent $R^1$'s may be linked to each other to form at least one ring (provided that $R^1$ forming no ring is the same as defined in i) above);

the aryl group, fluorenyl group, heterocyclic group, fused ring group, alkyl group, alkenyl group, alkoxy group, and aryloxy group each may be substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, a $C_8$-$C_{20}$ arylalkenyl group, and —N($R^a$)($R^b$);

$R^a$ and $R^b$ each are independently selected from the group consisting of a $C_6$-$C_{60}$ aryl group, a fluorenyl group, a $C_2$-$C_{60}$ heterocyclic group containing at least one heteroatom of O, N, S, Si, and P, and a $C_1$-$C_{50}$ alkyl group; and ring A is represented by one of the formulas below:

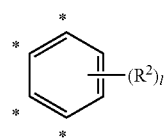
A2

173

-continued

A3 wherein in A2 and A3,

*'s are binding positions at which any one side of each of rings (thiophene and pyrrole) adjacent to ring A is shared and condensed;

l is an integer of 0 to 2, and m is an integer of 0 to 4;

$R^2$ and $R^3$ are i) selected from the group consisting of deuterium, halogen, a $C_6$-$C_{60}$ aryl group, a fluorenyl group, a $C_2$-$C_{60}$ heterocyclic group containing at least one heteroatom of O, N, S, Si, and P, a fused ring group of a $C_6$-$C_{60}$ aromatic group and a $C_3$-$C_{60}$ aliphatic group, a $C_2$-$C_{20}$ alkenyl group, a $C_1$-$C_{30}$ alkoxy group, and a $C_6$-$C_{30}$ aryloxy group, or ii) in the presence of a plurality of $R^2$'s and $R^3$'s, the plurality of $R^2$'s or $R^3$'s are different from or the same as each other and adjacent $R^2$'s or $R^3$'s may be linked to each other to form at least one ring (provided that $R^2$ and $R^3$ forming no ring are the same as defined in i) above); and the aryl group, fluorenyl group, heterocyclic group, fused ring group, alkyl group, alkenyl group, alkoxy group, and aryloxy group each may be substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group;

wherein the compound is represented by one of the formulas below:

<Formula 4>

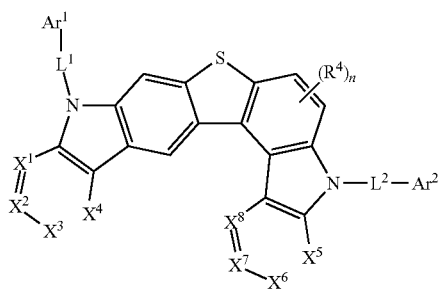

174

-continued

<Formula 5>

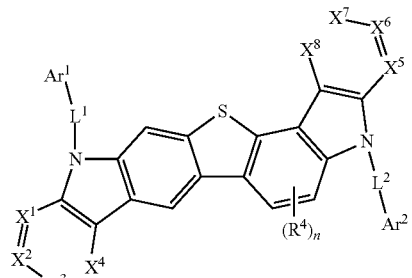

<Formula 6>

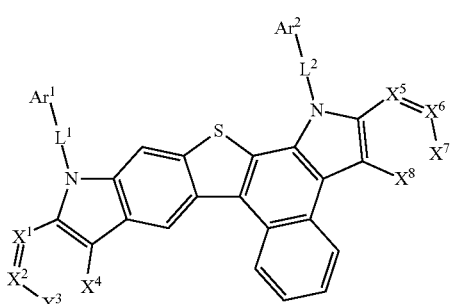

<Formula 8>

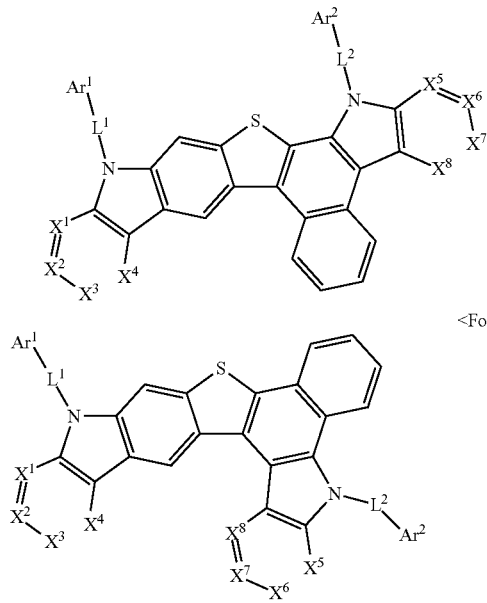

<Formula 9>

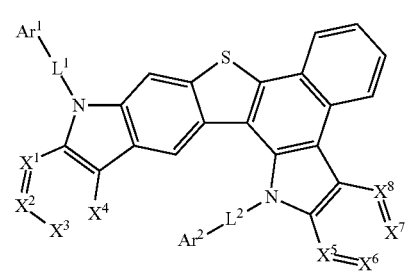

wherein in Formula 4, 5, 6, 8 and 9;

n is an integer of 0 to 2;

i) $R^4$ is selected from the group consisting of deuterium, halogen, a $C_6$-$C_{60}$ aryl group, a fluorenyl group, a $C_2$-$C_{60}$ heterocyclic group containing at least one heteroatom of O, N, S, Si, and P, a halogen group, a $C_1$-$C_{50}$ alkyl group, a fused ring group of a $C_6$-$C_{60}$ aromatic group and a $C_3$-$C_{60}$ aliphatic group, a $C_2$-$C_{20}$ alkenyl group, a $C_1$-$C_{30}$ alkoxy group, and a $C_6$-$C_{30}$ aryloxy group, or ii) in the presence of a plurality of $R^4$'s, the plurality of $R^4$'s each are different from or the same as each other and adjacent $R^4$'s may be linked to each other to form at least one ring (provided that $R^4$ forming no ring are the same as defined in i) above); and $X^1$ to $X^8$, $Ar^1$, $Ar^2$, $L^1$, and $L^2$ are the same as $X^1$ to $X^8$, $Ar^1$, $Ar^2$, $L^1$, and $L^2$ defined in Formula 1 above.

2. The compound of claim 1, wherein the compound is one of the compounds below:

P-93
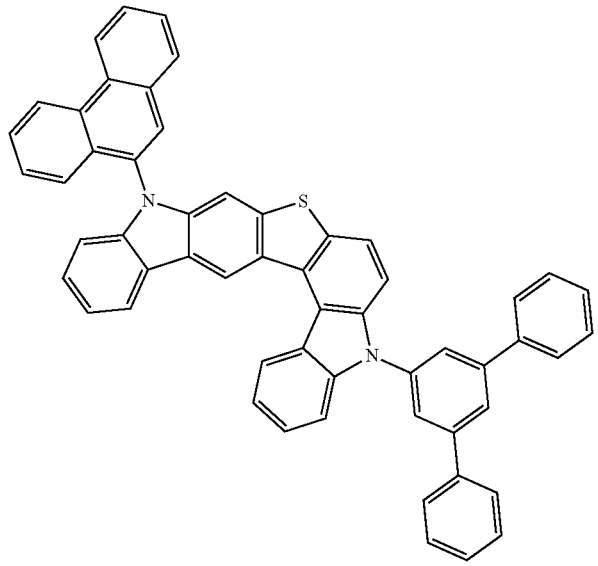
P-94
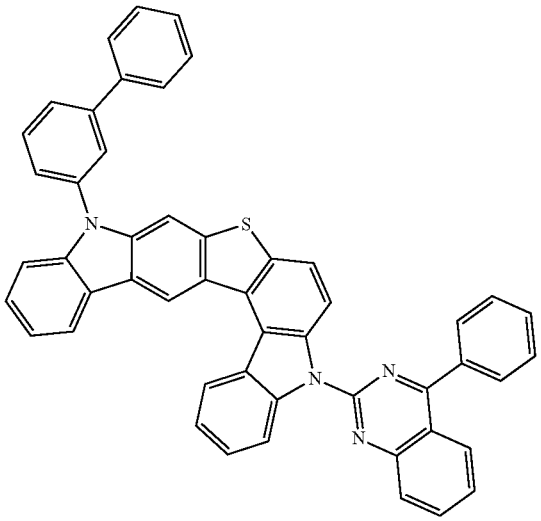
P-95
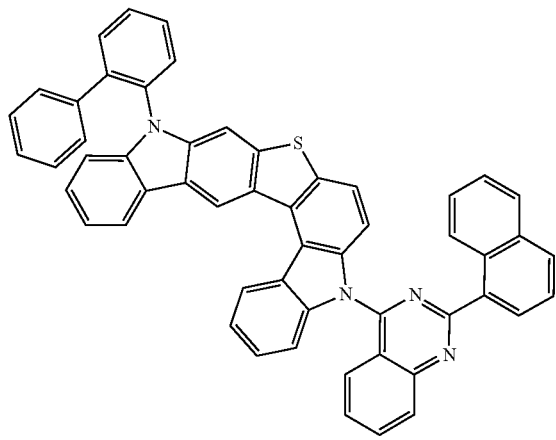
P-96
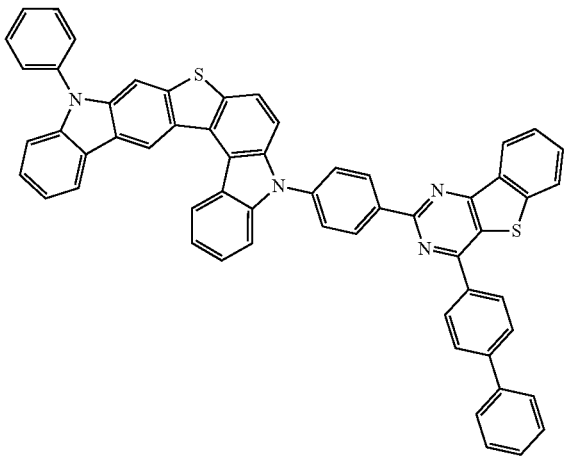
P-97
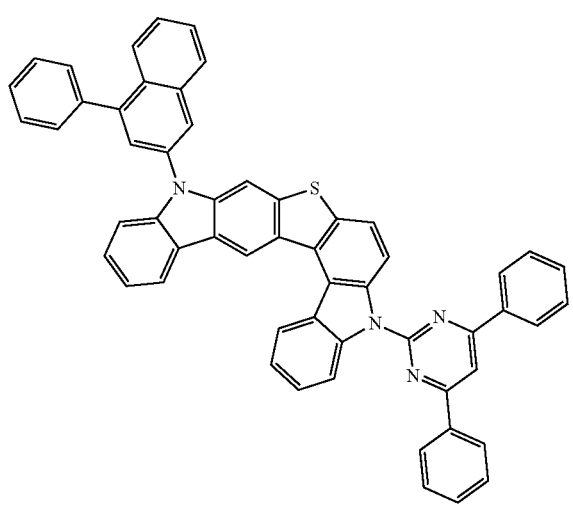

-continued
P-99
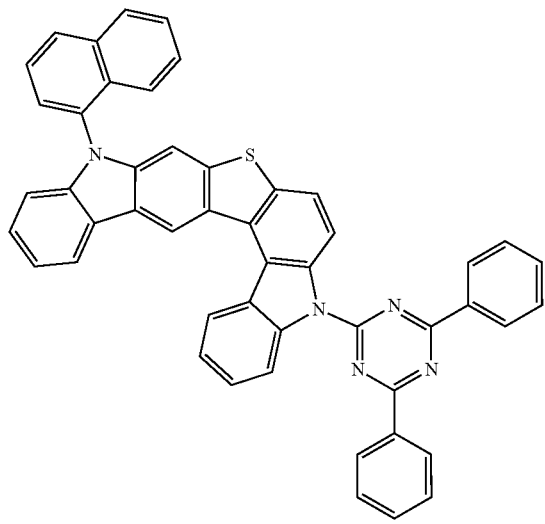
P-100
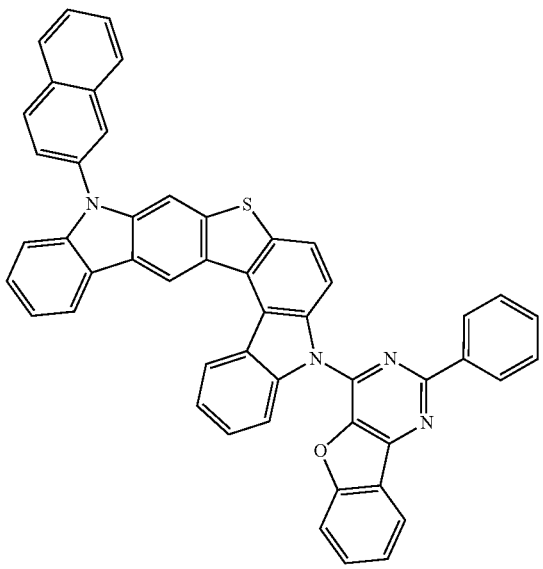
P-101
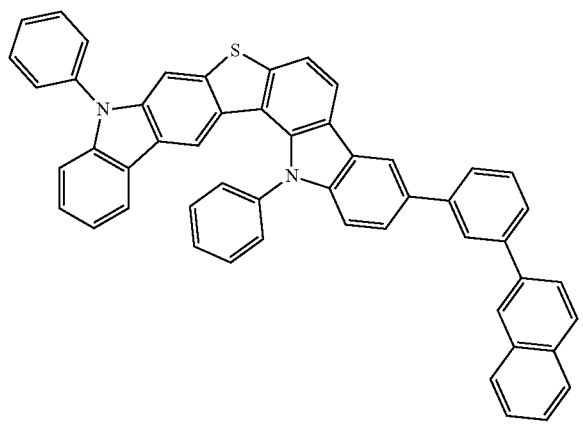
P-102
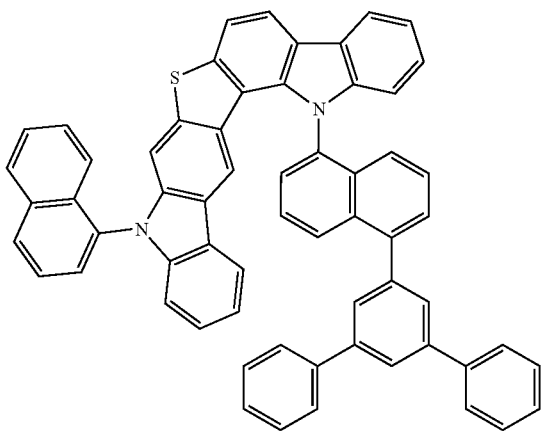
P-103
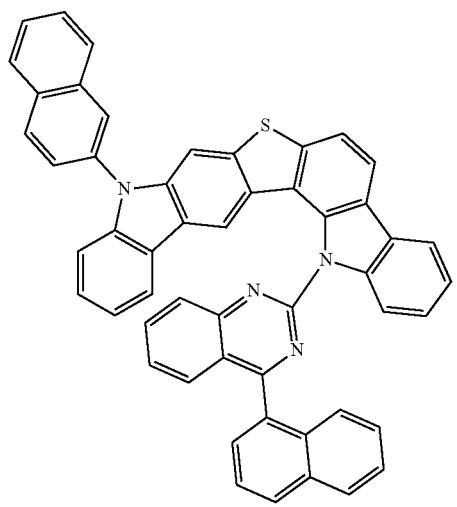
P-104
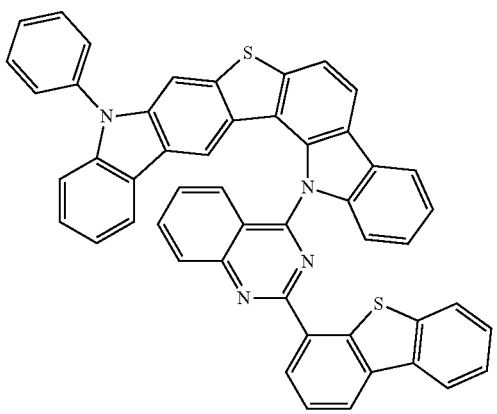

-continued
P-105
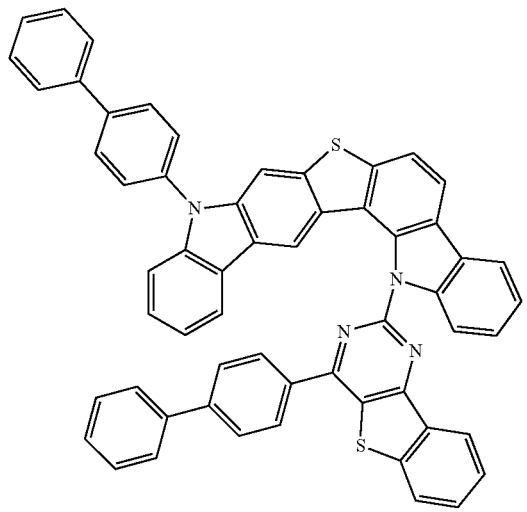
P-106
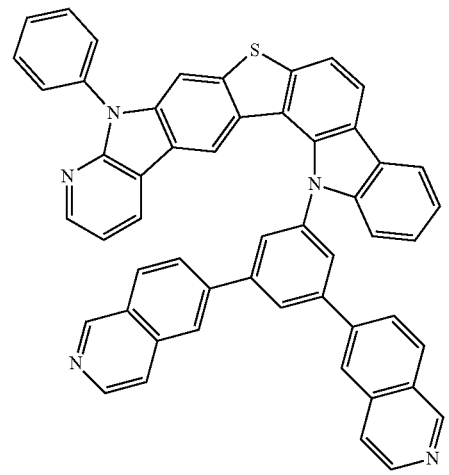
P-107
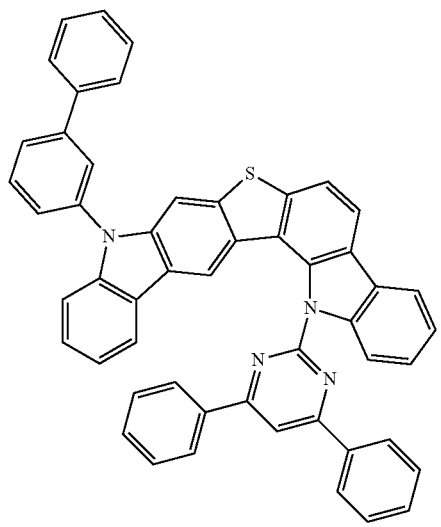
P-108
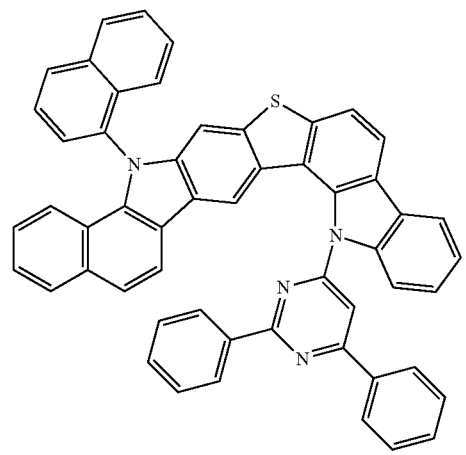
P-109
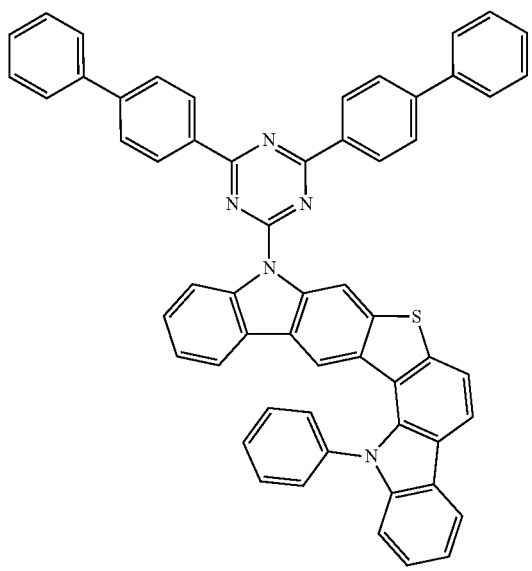
P-110
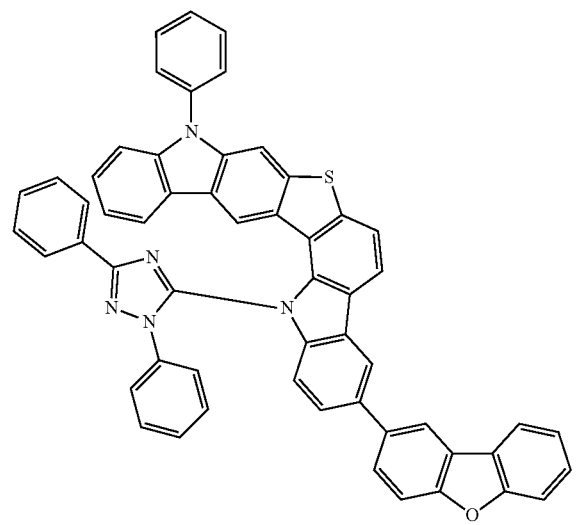

-continued
P-111
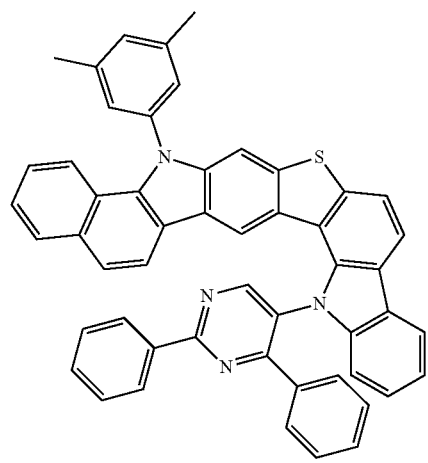
P-112
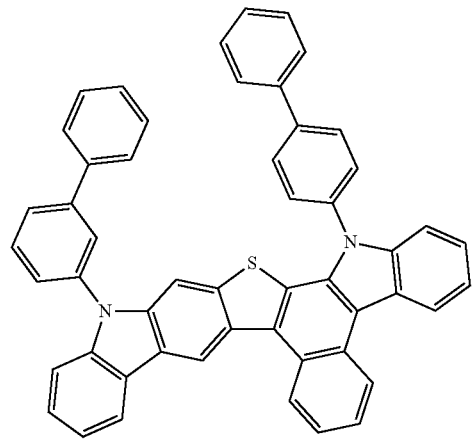
P-113
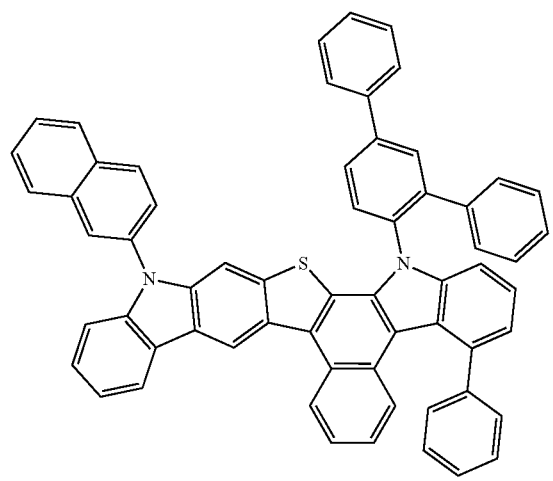
P-114
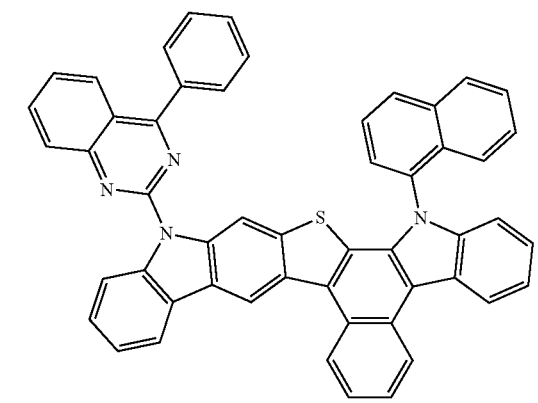
P-115
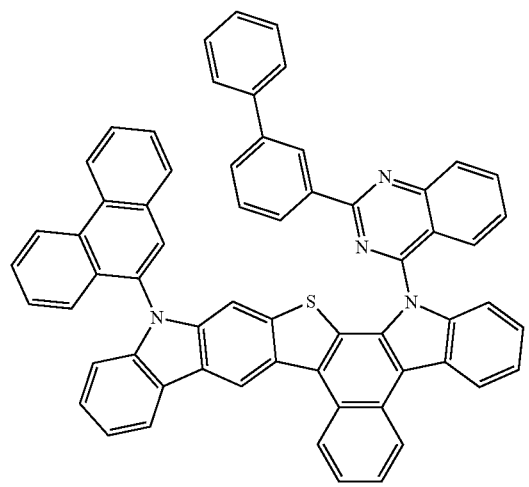
P-116
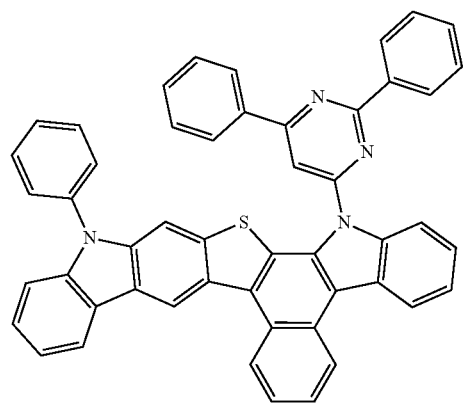

-continued
P-117
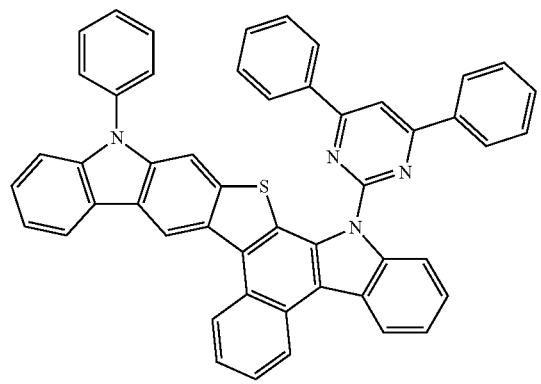
P-118
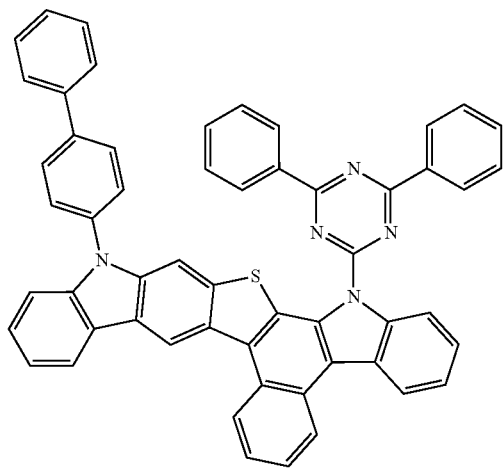
P-119
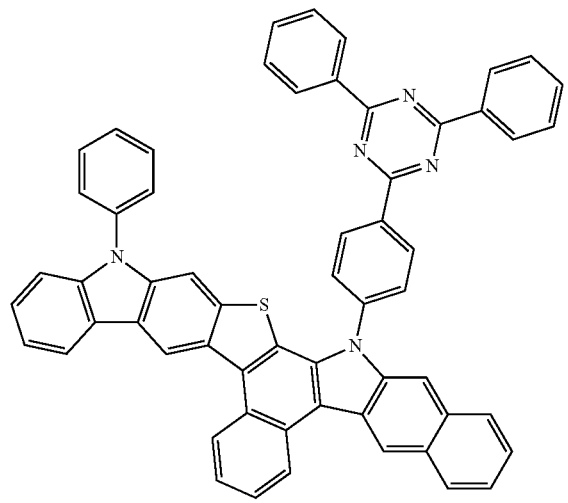
P-120
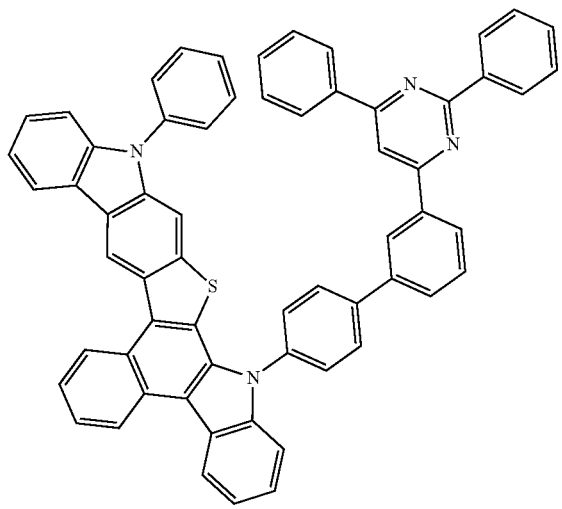
P-121
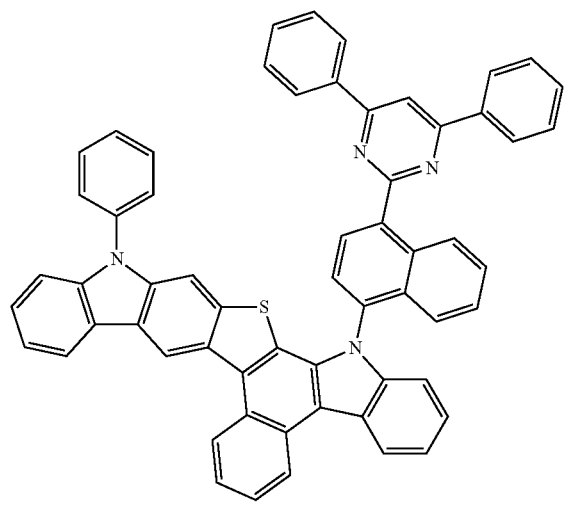
P-122
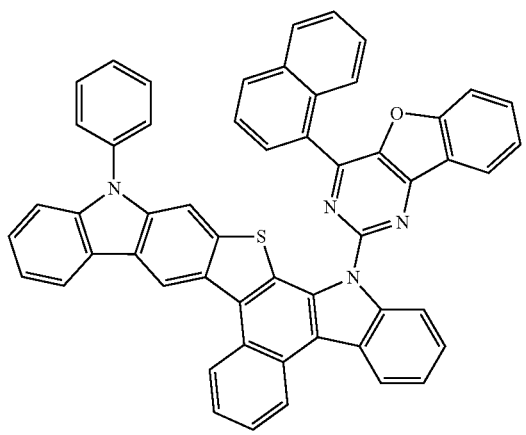

-continued
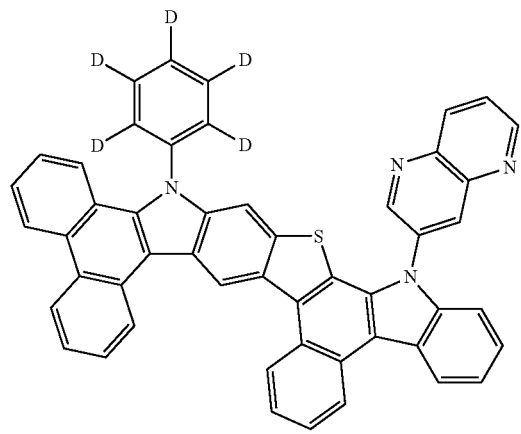
P-123
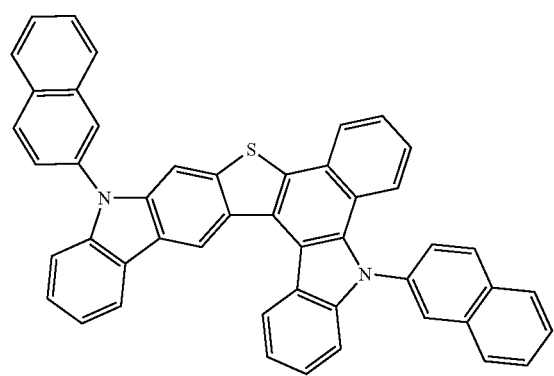
P-133
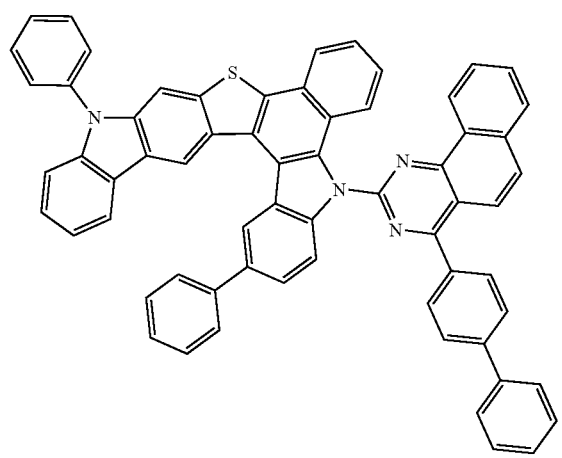
P-134
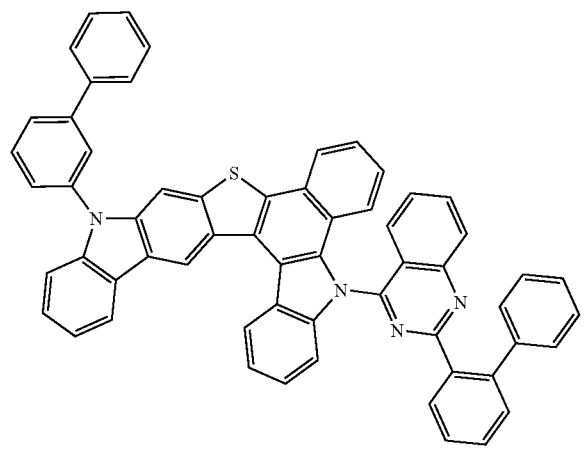
P-135
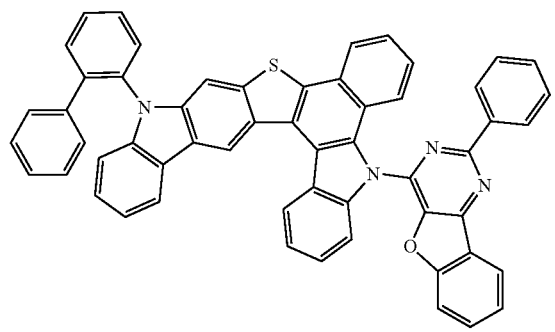
P-136

P-137
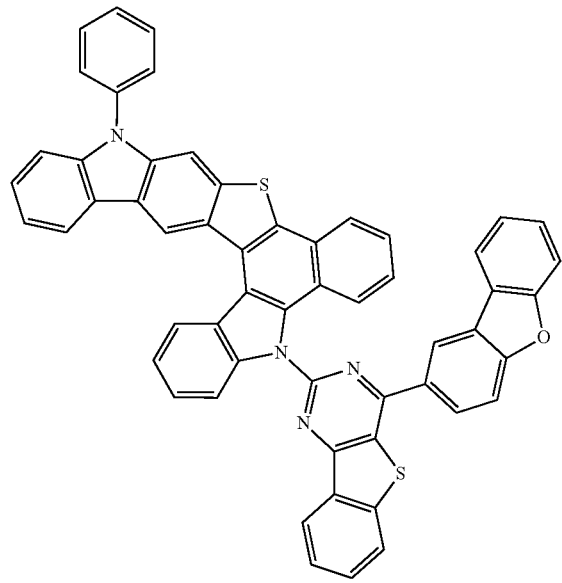
P-138
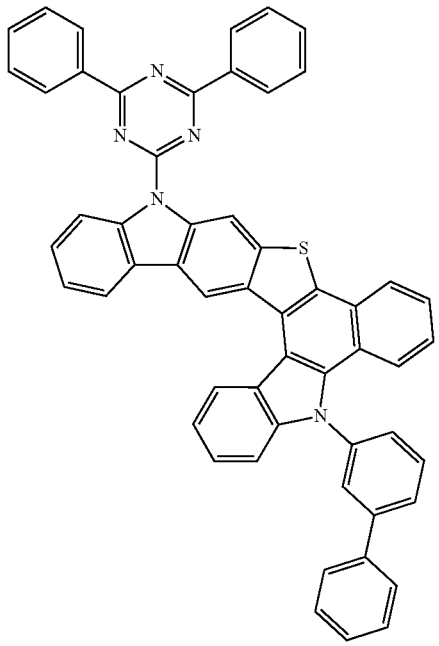
P-139
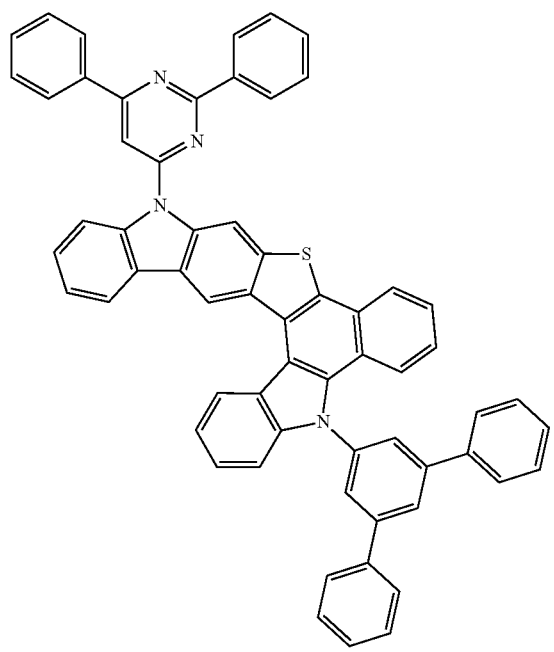
P-140
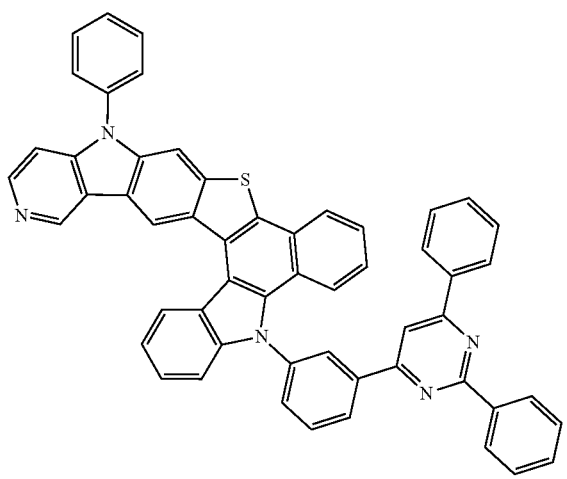

-continued
P-141
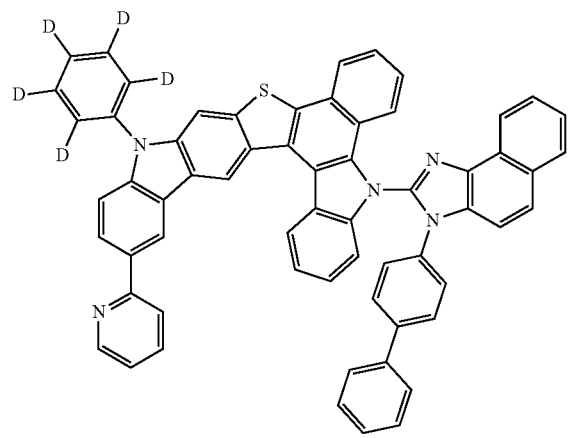
P-142
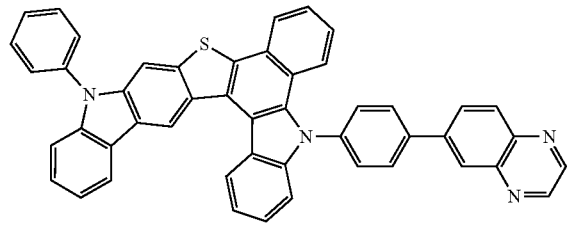
P-143
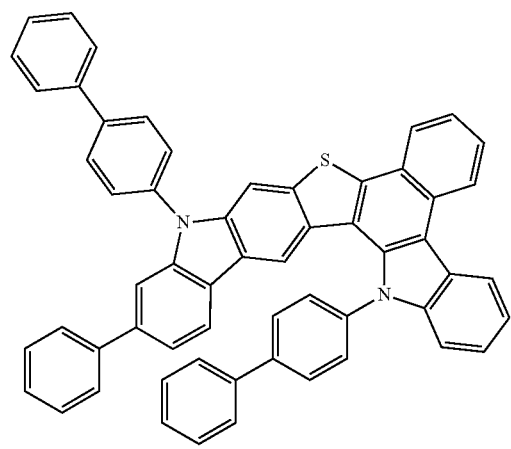
P-144
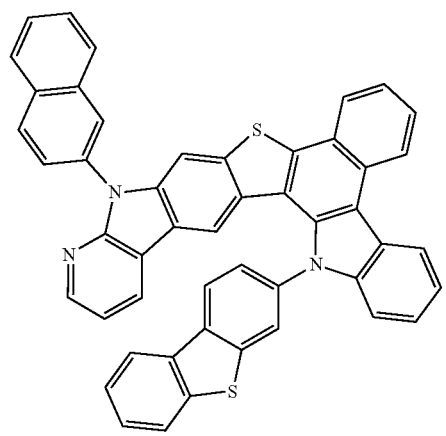
P-145
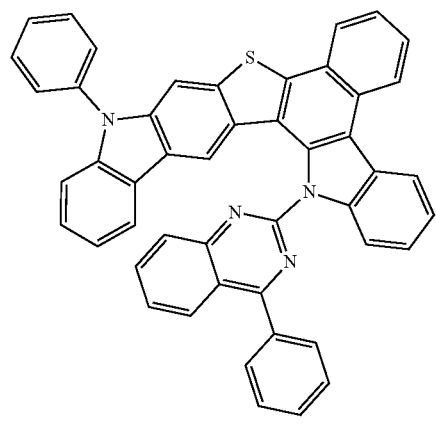
P-146
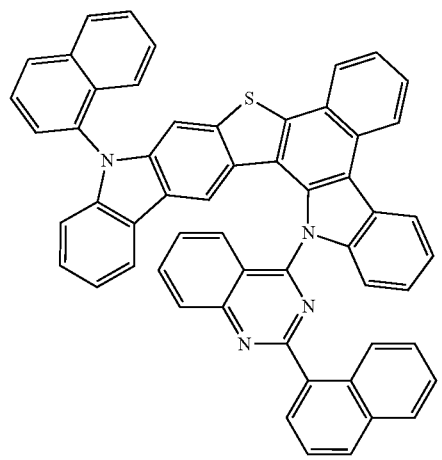

-continued
P-147
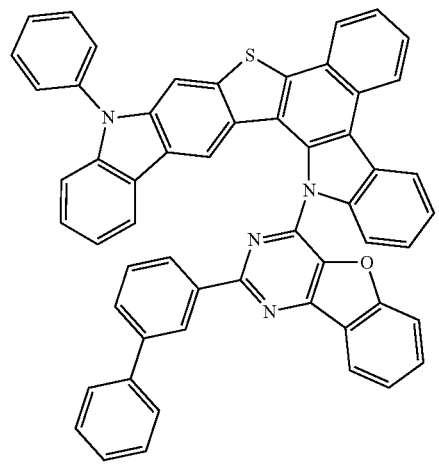
P-148
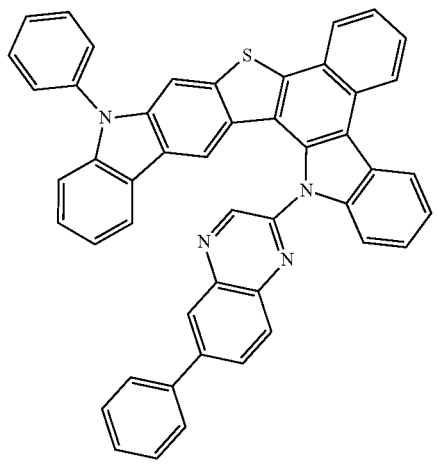
P-149
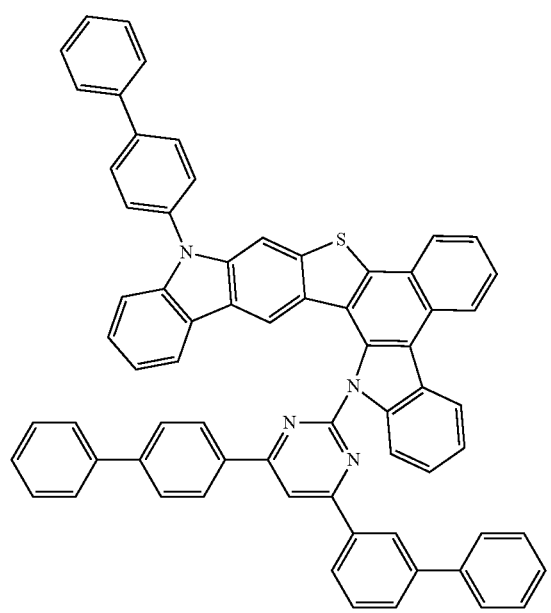
P-150
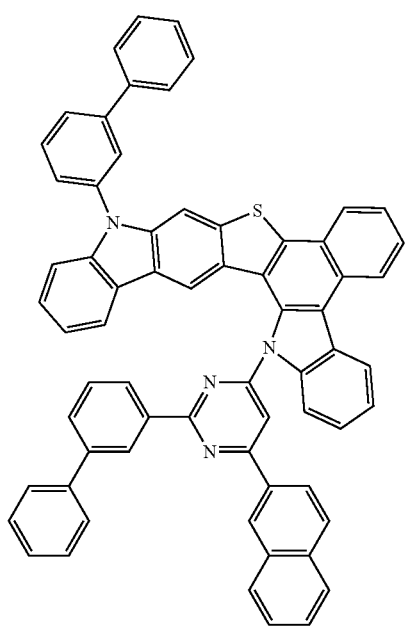
P-151
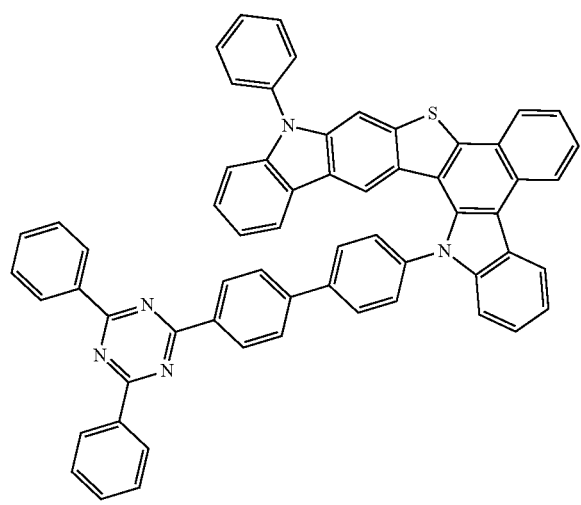
P-152
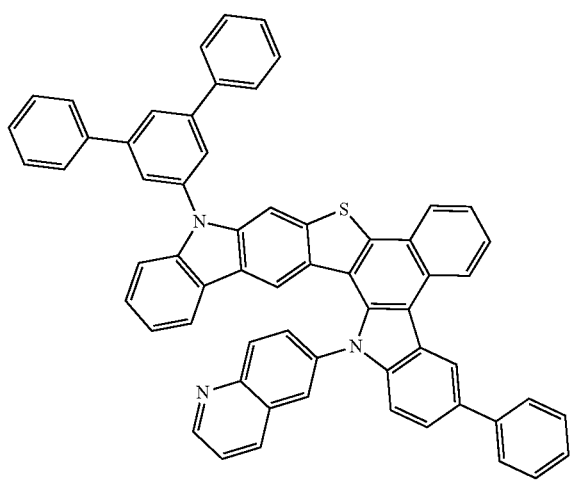

-continued

P-154

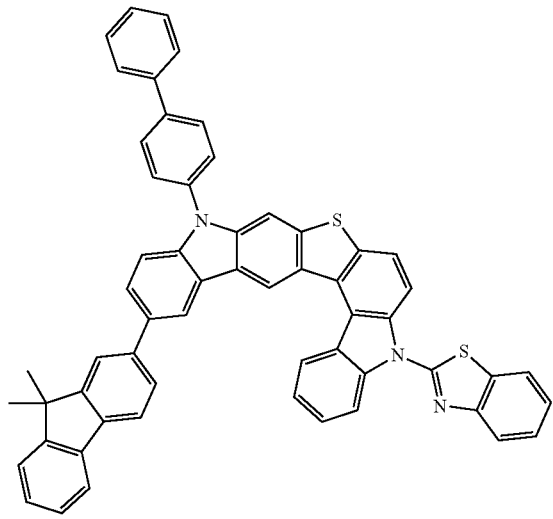

P-169

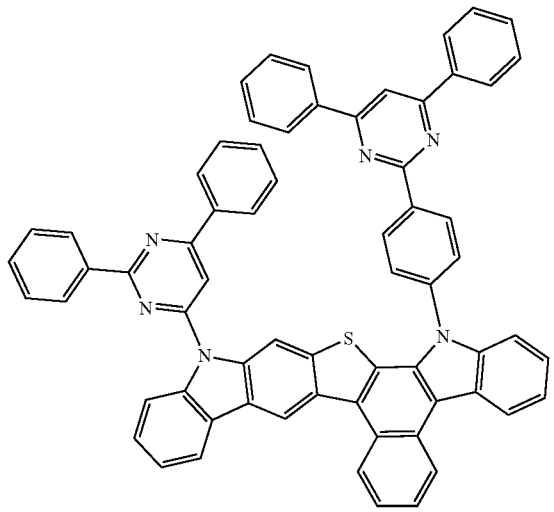

P-170

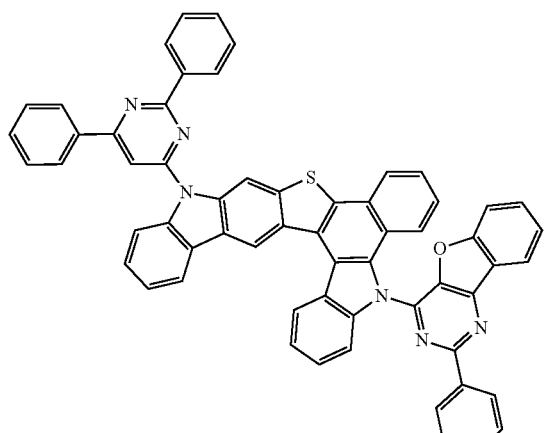

P-171

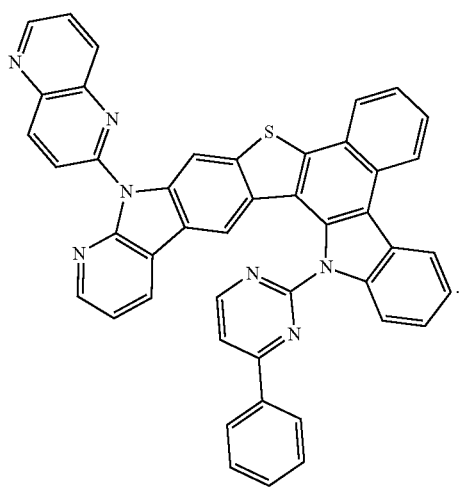

3. An organic electronic element comprising:
a first electrode;
a second electrode; and
an organic material layer positioned between the first electrode and the second electrode,
wherein the organic material layer contains a compound of claim 1.

4. The organic electronic element of claim 3, wherein the organic material layer contains a mixture of two or more compounds according to claim 1.

5. The organic electronic element of claim 3, further comprising a light efficiency improving layer formed on at least one of one surface of the first electrode and one of the second electrode, which is opposite to the organic material layer.

6. The organic electronic element of claim 3, wherein the organic material layer is formed by a spin coating process, a nozzle printing process, an inkjet printing process, a slot coating process, a dip coating process, or a roll-to-roll process.

7. An electronic device comprising:
a display device comprising the organic electronic element of claim 3; and
a controller driving the display device.

8. The electronic device of claim 7, wherein the organic electric element is one of an organic light emitting diode, an organic solar cell, an organic photo conductor, an organic transistor, and an element for a monochromatic or white illumination.

* * * * *